(12) United States Patent
Frohberg et al.

(10) Patent No.: US 8,558,060 B2
(45) Date of Patent: Oct. 15, 2013

(54) METHODS AND MEANS FOR THE MANUFACTURE OF HYALURONAN

(75) Inventors: Claus Frohberg, Kleinmachnow (DE); Rainhard Koch, Kleinmachnow (DE)

(73) Assignee: Bayer Cropscience AG, Monheim am Rhein (DE)

( * ) Notice: Subject to any disclaimer, the term of this patent is extended or adjusted under 35 U.S.C. 154(b) by 2008 days.

(21) Appl. No.: 11/233,089

(22) Filed: Sep. 23, 2005

(65) Prior Publication Data

US 2006/0115545 A1    Jun. 1, 2006

Related U.S. Application Data

(60) Provisional application No. 60/612,344, filed on Sep. 23, 2004.

(30) Foreign Application Priority Data

Sep. 23, 2004   (EP) ..................................... 04090373

(51) Int. Cl.
*A01H 1/00*      (2006.01)
*C12N 15/05*     (2006.01)
*C07H 21/04*     (2006.01)
*C12N 15/82*     (2006.01)

(52) U.S. Cl.
USPC ............ 800/295; 435/6.1; 435/468; 435/419; 435/320.1; 435/183; 530/350; 536/23.2; 800/278

(58) Field of Classification Search
USPC .............. 435/6, 69.1, 468, 419, 252.3, 320.1, 435/183, 6.1; 530/370, 350; 536/23.6, 23.2; 800/278, 295
See application file for complete search history.

(56) References Cited

U.S. PATENT DOCUMENTS

| 4,956,282 A * | 9/1990 | Goodman et al. .......... 435/69.51 |
| 6,492,150 B1 * | 12/2002 | McDonald et al. ........... 435/183 |
| 7,547,819 B2 | 6/2009 | Shibatani et al. |
| 2006/0168690 A1 * | 7/2006 | Shibatani et al. ............. 800/284 |

FOREIGN PATENT DOCUMENTS

| CN | 1498626 | 5/2004 |
| WO | WO 95/33067 A1 | 12/1995 |
| WO | WO 99/23227 A2 | 5/1999 |
| WO | WO 03/054163 A2 | 7/2003 |
| WO | WO 2005/012529 | 2/2005 |

OTHER PUBLICATIONS

P.L. DeAngelis, "Hyaluronan Synthases: Fascinating Glycosytransferases from Vertebrates, Bacterial Pathogens, and Algal Viruses", Cellular and Molecular Life Sciences, vol. 56, pp. 670-682, 1999.
Paul L. DeAngelis, et al., "Hyaluronan Synthase of Chlorella Virus PBCV-1", Science, vol. 278, pp. 1800-1803, Dec. 5, 1997.
Graves, et al., "Hyaluronan Synthesis in Virus PBCV-1 Infected Chlorella-Like Green Algae", Virology, vol. 257, pp. 15-23, 1999.
Jing, et al., "Synchronized Chemoenzymatic Synthesis of Monodisperse Hyaluronan Polymers", The Journal of Biological Chemistry, vol. 279, No. 40, pp. 42345-42349, Oct. 1, 2004.

* cited by examiner

*Primary Examiner* — Phuong Bui
(74) *Attorney, Agent, or Firm* — Hunton & Williams LLP

(57) ABSTRACT

The present invention relates to plant cells and plants which synthesize hyaluronan and to methods for preparing such plants, and also to methods for preparing hyaluronan with the aid of these plant cells or plants. Furthermore, the present invention relates to the use of plants for preparing hyaluronan and to food or feed which comprises hyaluronan.

26 Claims, 3 Drawing Sheets

METHODS AND MEANS FOR THE MANUFACTURE OF HYALURONAN

CROSS REFERENCE TO RELATED APPLICATIONS

This application claims the benefit of U.S. Provisional Application No. 60/612,344, filed on Sep. 23, 2004, and European Application No. 04090373.4, filed on Sep. 23, 2004, the disclosures of each of which are herein incorporated by reference in their entireties.

BACKGROUND OF THE INVENTION (1) Field of the Invention

The present invention relates to plant cells and plants which synthesize hyaluronan, and to methods for preparing such plants, and also to methods for preparing hyaluronan with the aid of these plant cells or plants. Furthermore, the present invention relates to the use of plants for preparing hyaluronan and hyaluronan-containing food or feed.

(2) Description of the Related Art

Hyaluronan is a naturally occurring unbranched, linear mucopolysaccharide (glucosaminoglucan) which is constructed of alternating molecules of glucuronic acid and. N-acetyl-glucosamine. The basic building block of hyaluronan consists of the disaccharide glucuronic acid-beta-1,3-N-acetyl-glucosamine. In hyaluronan, these repeating units are attached to one another by beta-1,4 linkages.

In pharmacy, use is frequently made of the term hyaluronic acid. Since hyaluronan is in most cases present as polyanion and not as free acid, hereinbelow, the term hyaluronan is preferably used, but each term is to be understood as embracing both molecular forms.

Hyaluronan has unusual physical chemical properties, such as, for example, properties of polyelectrolytes, viscoelastic properties, a high capacity to bind water, properties of gel formation, which, in addition to further properties of hyaluronan, are described in a review article by Lapcik et al. (1998, Chemical Reviews 98(8), 2663-2684). The specific properties of hyaluronan are determined inter alia by the molecular weight and the molecular weight distribution of the hyaluronan in question.

Hyaluronan is a component of extracellular connective tissue and bodily fluids of vertebrates. In humans, hyaluronic acid is synthesized by the cell membrane of all body cells, especially mesenchymal cells, and ubiquitously present in the body with a particularly high concentration in the connective tissues, the extracellular matrix, the umbilical cord, the joint fluid, the cartilageous tissue, the skin and the vitreous body of the eye (Bernhard Gebauer, 1998, Inaugural-Dissertation, Virchow-Klinikum Medizinische Fakultät Charité der Humboldt Universität zu Berlin; Fraser et al., 1997, Journal of Internal Medicine 242, 27-33).

Recently, hyaluronan was also found in animal non-vertebrate organisms (molluscs) (Volpi and Maccari, 2003, Biochimie 85, 619-625).

Furthermore, some pathogenic gram-positive bacteria (*Streptococcus* group A and C) and gram-negative bacteria (*Pasteurella*) synthesize hyaluronan as exopolysaccharides which protect these bacteria against attack by the immune system of their host, since hyaluronan is a non-immunogenic substance.

Viruses which infect single-cell green algae of the genus *Chlorella*, some of which are present as endosymbionts in *Paramecium* species, bestow upon the single-cell green algae the ability to synthesize hyaluronan after infection by the virus (Graves et al., 1999, Virology 257, 15-23). Hitherto, this is the only example from the systematic kingdom of the plants where the synthesis of hyaluronan was demonstrated. However, the ability to synthesize hyaluronan is not a feature which characterizes the algae in question. The ability of the algae to synthesize hyaluronan is mediated by an infection with a virus whose genome has a sequence coding for hyaluronan synthase (DeAngelis, 1997, Science 278, 1800-1803). Furthermore, the virus genome contains sequences coding for a UDP-glucose dehydrogenase (UDP-Glc-DH) and a glutamine: fructose 6-phosphate amidotransferase (GFTA). UDP-Glc-DH catalyses the synthesis of UDP-glucuronic acid used as substrate by hyaluronan synthase. GFTA converts fructose 6-phosphate into glucosamine 6-phosphate which is an important metabolite in the metabolic pathway for hyaluronan synthesis. Both genes encode active proteins which, like the hyaluronan synthase of the virus, are transcribed simultaneously in the early phase of the viral infection (DeAngelis et al., 1997, Science 278, 1800-1803, Graves et al., 1999, Virology 257, 15-23). Plants themselves do not have any nucleic acids in their genome which code for proteins catalysing the synthesis of hyaluronan and, although a large number of plant carbohydrates have been described and characterized, it has hitherto not been possible to detect hyaluronan or molecules related to hyaluronan in non-infected plants (Graves et al., 1999, Virology 257, 15-23).

The catalysis of the hyaluronan synthesis is effected by a single membrane-integrated or membrane-associated enzyme, hyaluronan synthase. The hyaluronan synthases which have hitherto been studied can be classified into two groups: hyaluronan synthases of Class I and hyaluronan synthases of Class II (DeAngelis, 1999, CMLS, Cellular and Molecular Life Sciences 56, 670-682).

The hyaluronan synthases of vertebrates are further distinguished by the identified isoenzymes. The different isoenzymes are referred to in the order of their identification using Arabic numbers (for example, hsHAS1, hsHAS2, hsHAS3).

The unusual properties of hyaluronan offer a wealth of possibilities for application in various fields, such as, for example, pharmacy, the cosmetics industry, in the production of food and feed, in technical applications (for example as lubricants), etc. The most important applications where hyaluronan is currently being used are in the medicinal and cosmetics field (see, for example, Lapcik et al., 1998, Chemical Reviews 98(8), 2663-2684, Goa and Benfield, 1994, Drugs 47(3), 536-566).

In the medical field, hyaluronan-containing products are currently used for the intraarticular treatment of arthrosis and in ophthalmics used for eye surgery. Hyaluronan is also used for treating joint disorders in racehorses. In addition, hyaluronic acid is a component of some rhinologics which, for example in the form of eye drops and nasalia, serve to moisten dry mucous membranes. Hyaluronan-containing solutions for injection are used as analgesics and antirheumatics. Patches comprising hyaluronan or derivatized hyaluronan are employed in wound healing. As dermatics, hyaluronan-containing gel implants are used for correcting skin deformations in plastic surgery.

For pharmacological applications, preference is given to using hyaluronan having a high molecular weight.

In cosmetic medicine, hyaluronan preparations are among the most suitable skin filler materials. By injecting hyaluronan, for a limited period of time, it is possible to smooth wrinkles or to increase the volume of lips.

In cosmetic products, in particular in skin creams and lotions, hyaluronan is frequently used as moisturizer by virtue of its high water-binding capacity.

Further possibilities of application in the medicinal and cosmetics field, such as, for example, the use of hyaluronan as carrier for active compounds which ensures a controlled release of the active compound over a long period of time, as carrier for active compounds which transports the active compounds in a targeted manner into the lymphatic system or as active compound which, after application as an ointment, ensures that the active compound remains in the skin for a relatively long period of time, are described in Lapcik et al. (1998, Chemical Reviews 98(8), 2663-2684). The use of hyaluronan derivatives in the medicinal field requires further research efforts; however, first results have already revealed a large potential (Lapcik et al. 1998, Chemical Reviews 98(8), 2663-2684).

Furthermore, hyaluronan-containing preparations are sold as so-called nutraceuticals (food supplements) which can also be used in animals (for example dogs, horses) for the prophylaxis and alleviation of arthrosis.

Hyaluronan used for commercial purposes is currently isolated from animal tissues (rooster combs) or prepared fermentatively using bacterial cultures.

U.S. Pat. No. 4,141,973 describes a process for isolating hyaluronan from rooster combs or alternatively from umbilical cords. In addition to hyaluronan, animal tissues (for example rooster combs, umbilical cords) also contain further mucopolysaccharides related to hyaluronan, such as chondroitin sulphate, dermatan sulphate, keratan sulphate, heparan sulphate and heparin. Furthermore, animal organisms contain proteins (hyaladherins) which bind specifically to hyaluronan and which are required for the most different functions in the organism, such as, for example, the degradation of hyaluronan in the liver, the function of hyaluronan as lead structure for cell migration, the regulation of endocytosis, the anchoring of hyaluronan on the cell surface or the formation of hyaluronan networks (Turley, 1991, Adv Drug Delivery Rev 7, 257 ff.; Laurent and Fraser, 1992, FASEB J. 6, 183 ff.; Stamenkovic and Aruffo, 1993, Methods Enzymol. 245, 195 ff; Knudson and Knudson, 1993, FASEB 7, 1233 ff.).

The *Streptococcus* strains used for the bacterial production of hyaluronan are exclusively pathogenic bacteria. During cultivation, too, these bacteria produce (pyrogenic) exotoxins and haemolysins (streptolysin, (in particular alpha- and beta-haemolysin) (Kilian, M.: *Streptococcus* and *Enterococcus*. In: *Medical Microbiology*. Greenwood, D.; Slack, R C A; Peutherer, J. F. (Eds.). Chapter 16. Churchill Livingstone, Edinburgh, UK: pp. 174-188, 2002, ISBN 0443070776) which are released into the culture medium. This renders purification and isolation of the hyaluronan prepared with the aid of *Streptococcus* strains more difficult. In particular for pharmaceutical application, the presence of exotoxins and haemolysins in the preparation is a problem.

U.S. Pat. No. 4,801,539 describes the preparation of hyaluronan by fermentation of a mutagenized bacterial strain (*Streptococcus zooedemicus*). The mutagenized bacteria strain used no longer synthesizes beta-haemolysin. The yield achieved was 3.6 g of hyaluronan per liter of culture.

EP 0694616 describes a method for cultivating *Streptococcus zooedemicus* or *Streptococcus equi*, where, under the culture conditions employed, no streptolysin, but increased amounts of hyaluronan are synthesized. The yield achieved was 3.5 g of hyaluronan per liter of culture.

During cultivation, *Streptococcus* strains release the enzyme hyaluronidase into the culture medium, as a consequence of which, in this production system, too, the molecular weight is reduced during purification. The use of hyaluronidase-negative *Streptococcus* strains or of methods for the production of hyaluronan where the production of hyaluronidase during cultivation is inhibited are described in U.S. Pat. No. 4,782,046. The yield achieved was up to 2.5 g of hyaluronan per liter of culture, and the maximum mean molecular weight achieved was $3.8 \times 10^6$ Da, at a molecular weight distribution of from $2.4 \times 10^6$ to $4.0 \times 10^6$.

US 20030175902 and WO 03 054163 describe the preparation of hyaluronan with the aid of heterologous expression of a hyaluronan synthase from *Streptococcus equisimilis* in *Bacillus subtilis*. To achieve the production of sufficient amounts of hyaluronan, in addition to heterologous expression of a hyaluronan synthase, simultaneous expression of an UDP-glucose dehydrogenase in the *Bacillus* cells is also required. US 20030175902 and WO 03 054163 do not state the absolute amount of hyaluronan obtained in the production with the aid of *Bacillus subtilis*. The maximum mean molecular weight achieved was about $4.2 \times 10^6$. However, this mean molecular weight was only achieved for the recombinant *Bacillus*. strain where a gene coding for the hyaluronan synthase gene from *Streptococcus equisimilis* and the gene coding for the UDP-glucose dehydrogenase from *Bacillus subtilis* were integrated into the *Bacillus subtilis* genome under the control of the amyQ promoter, where at the same time the *Bacillus subtilis*-endogenous cxpY gene (which codes for a cytochrome P450 oxidase) was inactivated.

The production of hyaluronan by fermentation of bacteria strains is associated with high costs, since the bacteria have to be fermented in sealed sterile containers under expensive controlled culture conditions (see, for example, U.S. Pat. No. 4,897,349). Furthermore, the amount of hyaluronan which can be produced by fermentation of bacteria strains is limited by the production facilities present in each case. Here, it also has to be taken into account that fermenters, as a consequence of physical laws, cannot be built for excessively large culture volumes. Particular mention may be made here of homogeneous mixing of the substances fed in from the outside (for example essential nutrient sources for bacteria, reagents for regulating the pH, oxygen) with the culture medium required for efficient production, which, in large fermenters, can be ensured only with great technical expenditure, if at all.

The purification of hyaluronan from animal organisms is complicated owing to the presence, in animal tissues, of other mucopolysaccharides and proteins which specifically bind to hyaluronan. In patients, the use of hyaluronan-containing medicinal preparations contaminated by animal proteins can result in unwanted immunological reactions of the body (U.S. Pat. No. 4,141,973), in particular if the patient is allergic to animal proteins (for example chicken egg white). Furthermore, the amounts (yields) of hyaluronan which can be obtained from animal tissues in satisfactory quality and purity are low (rooster comb: 0.079% w/w, EP 0144019, U.S. Pat. No. 4,782,046), which necessitates the processing of large amounts of animal tissues. A further problem in the isolation of hyaluronan from animal tissues consists in effect that the molecular weight of hyaluronan during purification is reduced since animal tissues also contain a hyaluronan-degrading enzyme (hyaluronidase).

In addition to the hyaluronidases and exotoxins mentioned, *Streptococcus* strains also produce endotoxins which, when present in pharmacological products, pose risks for the health of the patient. In a scientific study, it was shown that even hyaluronan-containing medicinal products on the market contain detectable amounts of bacterial endotoxins (Dick et al., 2003, Eur J Opthalmol. 13(2), 176-184). A further disadvantage of the hyaluronan produced with the aid of *Streptococcus* strains is the fact that the isolated hyaluronan has a lower molecular weight than hyaluronan isolated from rooster combs (Lapcik et al. 1998, Chemical Reviews 98(8), 2663-2684). US 20030134393 describes the use of a *Streptococcus* strain for producing hyaluronan which synthesizes a particularly pronounced hyaluronan capsule (supercapsulated). The hyaluronan isolated after fermentation had a molecular weight of $9.1 \times 10^6$. However, the yield was only 350 mg per liter.

Although hyaluronan has unusual properties, it is, owing to its scarcity and the high price, rarely, if at all, used for industrial applications.

SUMMARY AND OBJECTS OF THE INVENTION

Accordingly, it is an object of the present invention to provide means and methods which permit the provision of hyaluronan in sufficient amounts and quality and which make it possible to provide hyaluronan even for industrial applications and applications in the field of food and feed.

This object is achieved by the embodiments disclosed herein.

Thus, the present invention relates to a plant cell or a plant, characterized in that it has, stably integrated into its genome, a nucleic acid molecule coding for a hyaluronan synthase.

The present invention also provides plant cells or plants which synthesize hyaluronan. A preferred embodiment are plant cells according to the invention or plants according to the invention which synthesize hyaluronan.

DETAILED DESCRIPTION OF THE PREFERRED EMBODIMENTS

Figure 1:
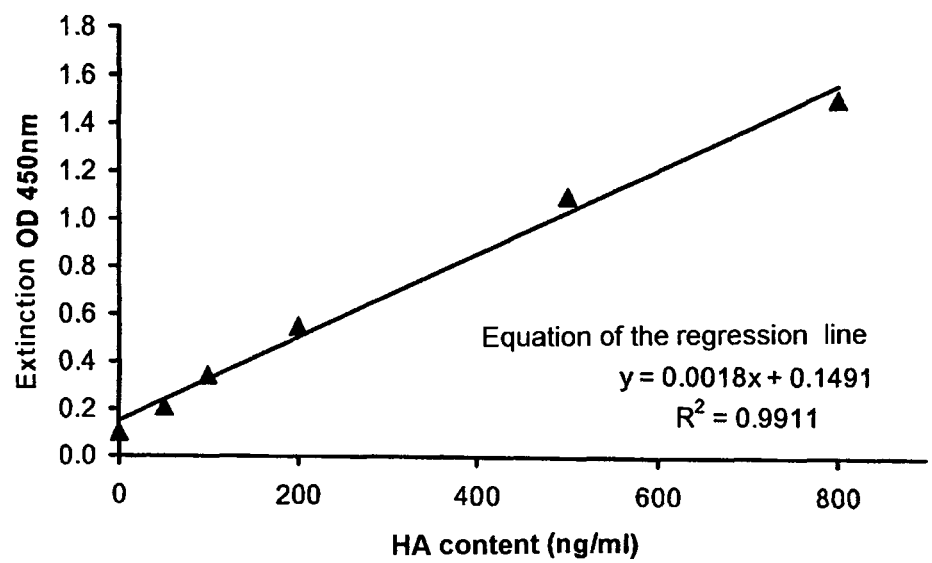
FIG. 1: shows a calibration line and the associated equation of the regression line used for calculating the hyaluronan content in plant tissue. The calibration line was drawn using the commercial test kit (hyaluronic acid (HA) test kit from Corgenix, Inc., Colorado, USA, Prod. No. 029-001) and the standard solutions contained therein.

Hyaluronan can be isolated from plant cells according to the invention or plants according to the invention. Accordingly, plant cells according to the invention or plants according to the invention offer, compared to the prior art, the advantage that they can be cultivated on large areas for producing hyaluronan at little expense. This leads to the possibility to provide hyaluronan in sufficient amounts even for industrial application where it is currently not used owing to its scarcity and the high price. The only plant organisms which have hitherto been described for synthesis of hyaluronan, virus-infected algae of the genus *Chlorella*, are unsuitable for producing relatively large amounts of hyaluronan. In the production of hyaluronan, virus-infected algae have the disadvantage that the genes required for hyaluronan synthase are not stably integrated into their genome (Van Etten and Meints, 1999, Annu. Rev. Microbiol. 53, 447-494), so that, for producing hyaluronan, there have to be repeated virus infections. Accordingly, it is not possible to isolate individual *Chlorella* cells which synthesize continuously the desired quality and quantity of hyaluronan. Furthermore, in virus-infected *Chlorella* algae, hyaluronan is only produced for a limited period of time, and as a result of the lysis caused by the virus, the algae are killed only about 8 hours after the infection (Van Etten et al., 2002, Arch Virol 147, 1479-1516). In contrast, the present invention offers the advantage that the plants or plant cells according to the invention can be propagated in an unlimited manner vegetatively or sexually and that they produce hyaluronan continuously.

A further advantage of the present invention compared to the prior art is based on the fact that the plants according to the invention are autotrophic organisms, whereas currently, exclusively heterotrophic organisms are used for producing hyaluronan. As is known, the energy balance of heterotrophic organisms is considerably less efficient than in the case of autotrophic organisms, resulting in higher costs, at least in the production of hyaluronan by fermentation.

In the context of the present invention, the term "hyaluronan" is to be understood as meaning both a free acid (hyaluronic acid) and the polyanion form of a linear glucosamine comprising a plurality of basic building blocks of the disaccharide glucuronic acid beta-1,3-N-acetyl-glucosamine attached by beta-1,4 linkages.

In the context of the present invention, the term "hyaluronan synthase" (EC 2.4.1.212) is to be understood as meaning a protein which synthesizes hyaluronan from the substrates UDP-glucuronic acid (UDP-GlcA) and N-acetyl-glucosamine (UDP-GlcNAc). The hyaluronan synthesis is catalysed according to the reaction schemes below:

Nucleic acid molecules and corresponding protein sequences coding for hyaluronan synthases have been described, inter alia, for the following organisms: rabbit (*Oryctolagus cuniculus*) ocHas2 (EMBL AB055978.1, US 20030235893), ocHas3 (EMBL AB055979.1, US 20030235893); baboon (*Papio anubis*) paHas1 (EMBL AY463695.1); frog (*Xenopus laevis*) xlHas1 (EMBL M22249.1, US 20030235893), xlHas2 (DG42) (EMBL AF168465.1), xlHas3 (EMBL AY302252.1); human (*Homo sapiens*) hsHAS1 (EMBL D84424.1, US 20030235893), hsHAS2 (EMBL U54804.1, US 20030235893), hsHAS3 (EMBL AF232772.1, US 20030235893); mouse (*Mus musculus*), mmHas1 (EMBL D82964.1, US 20030235893), mmHAS2 (EMBL U52524.2, US 20030235893), mmHas3 (EMBL U86408.2, US 20030235893); cattle (*Bos taurus*) btHas2 (EMBL AJ004951.1, US 20030235893); chicken (*Gallus gallus*) ggHas2 (EMBL AF106940.1, US 20030235893); rat (*Rattus norvegicus*) rnHas 1 (EMBL AB097568.1, Itano et al., 2004, J. Biol. Chem. 279(18) 18679-18678), rnHas2 (EMBL AF008201.1); rnHas 3 (NCBI NM_172319.1, Itano et al., 2004, J. Biol. Chem. 279(18) 18679-18678), horse (*Equus caballus*) ecHAS2 (EMBL AY056582.1, GI:23428486), pig (*Sus scrofa*) sscHAS2 (NCBI NM_214053.1, GI:47522921), sscHas 3 (EMBLAB159675), zebra fish (*Danio rerio*) brHas1 (EMBL AY437407), brHas2 (EMBL AF190742.1) brHas3 (EMBL AF190743.1); *Pasteurella multocida* pmHas (EMBL AF036004.2); *Streptococcus pyogenes* spHas (EMBL, L20853.1, L21187.1, U.S. Pat. No. 6,455,304, US 20030235893); *Streptococcus equis* seHas (EMBL AF347022.1, AY173078.1), *Streptococcus uberis* suHasA (EMBL AJ242946.2, US 20030235893), *Streptococcus equisimilis* seqHas (EMBL AF023876.1, US 20030235893); *Sulfolobus solfataricus* ssHAS (US 20030235893), *Sulfolobus tokodaii* stHas (AP000988.1), *Paramecium bursaria Chlorella* virus 1, cvHAS (EMBL U42580.3, PB42580, US 20030235893).

In the context of the present invention, the term "genome" is to be understood as meaning the entire genetic material present in a plant cell. It is known to the person skilled in the art that, in addition to the nucleus, other compartments (for example plastids, mitochondria) also contain genetic material.

In the context of the present invention, the term "stably integrated nucleic acid molecule" is to be understood as meaning the integration of a nucleic acid molecule into the genome of the plant. A stably integrated nucleic acid molecule is characterized in that, during the replication of the corresponding integration site, it is multiplied together with the nucleic acid sequences of the host which border on the integration site, so that the integration site in the replicated DNA strand is surrounded by the same nucleic acid sequences as on the strand which serves as a matrix for the replication. Preferably, the nucleic acid molecule is stably integrated into the genome of the nucleus.

A stable integration of a nucleic acid molecule into the genome of a plant cell or plant can be demonstrated by genetic methods and/or methods of molecular biology. A stable integration of a nucleic acid molecule into the genome of a plant cell or the genome of a plant is characterized in that in the progeny which has inherited said nucleic acid molecule, the stably integrated nucleic acid molecule is present in the same genomic environment as in the parent generation. The presence of a stable integration of a nucleic acid sequence in the genome of a plant cell or in the genome of a plant can be demonstrated using methods known to the person skilled in the art, inter alia with the aid of southern blot analysis of the RFLP analysis (Restriction Fragment Length Polymorphism) (Nam et al., 1989, The Plant Cell 1, 699-705; Leister and Dean, 1993, The Plant Journal 4 (4), 745-750), with methods based on PCR, such as, for example, the analysis of differences in length in the amplified fragment (Amplified Fragment Length Polymorphism, AFLP) (Castiglioni et al., 1998, Genetics 149, 2039-2056; Meksem et al., 2001, Molecular Genetics and Genomics 265, 207-214; Meyer et al., 1998, Molecular and General Genetics 259, 150-160) or using amplified fragments cleaved using restriction endonucleases (Cleaved Amplified Polymorphic Sequences, CAPS) (Konieczny and Ausubel, 1993, The Plant Journal 4, 403-410; Jarvis et al., 1994, Plant Molecular Biology 24, 685-687; Bachem et al., 1996, The Plant Journal 9 (5), 745-753).

A further embodiment of the present invention relates to plant cells of a green terrestrial plant or green terrestrial plants which synthesize hyaluronan.

In the context of the present invention, the term "green terrestrial plant (Embryophyta)" is to be understood as defined in Strasburger, "Lehrbuch der Botanik" [textbook of botany], 34. ed., Spektrum Akad. Verl., 1999, (ISBN 3-8274-0779-6).

A preferred embodiment of the present invention relates to plant cells according to the invention of multicellular plants or plants according to the invention which are multicellular organisms. Accordingly, this embodiment relates to plant cells or plants which do not originate from single-cell plants (protists) or which are not protists.

In a further preferred embodiment, the present invention relates to plant cells according to the invention or plants according to the invention where the nucleic acid molecule coding for hyaluronan synthase is characterized in that it codes for a hyaluronan synthase Class I.

The hyaluronan synthases which have hitherto been investigated can be classified into two groups: hyaluronan synthases of Class I and hyaluronan synthases of Class II (DeAngelis, 1999, CMLS, Cellular-and Molecular Life Sciences 56, 670-682). This classification is based essentially on biochemical studies of the reaction mechanism and the analysis of the amino acid sequences coding for the hyaluronan synthases in question. Class I includes inter alia the hyaluronan synthases from *Streptococcus pyogenes* (spHas), *Streptococcus equisimilis* (seHas), *Paramecium bursaria Chlorella* virus 1 (cvHas) and the known hyaluronan synthases of the vertebrates (*Xenopus laevis*, xlHas; *Homo sapiens*; hsHAS, *Mus musculus*, mmHas). Class I hyaluronan synthases have an amino acid sequence of from 417 to 588 amino acids. Class I hyaluronan synthases are proteins which are integrated into a membrane of the cytoplasm and have multiple (five to seven) membrane-associated regions. Lengthening of the hyaluronan with further molecular building blocks probably takes place at a reducing end of the polymer. Suitable acceptor molecules used by hyaluronan synthases of Class I have hitherto not been disclosed.

To date, the hyaluronan synthase from *Pasteurella* is the only known representative of Class II hyaluronan synthases. Its protein sequence has 972 amino acids. It is a soluble protein which, on its C-terminus, contains amino acid sequences responsible for localization at the cytoplasma membrane (Jing and DeAngelis, 2000, Glycobiology 10, 883-889). Interaction probably takes place via molecules associated with the cytoplasma membrane. In the case of the enzyme of Class II, the hyaluronan is synthesized by extension at the non-reducing end (DeAngelis, 1999, J. Biol. Chem 274, 26557-26562). The synthesis of hyaluronan by the Class II enzyme does not require an acceptor molecule; however, it was shown that hyaluronan oligomers (DP4) are used as acceptor and the rate of synthesis is increased by adding the acceptors (DeAngelis, 1999, J. Biol. Chem 274, 26557-26562).

In a preferred embodiment, the present invention relates to plant cells according to the invention or plants according to the invention where the nucleic acid molecule coding for hyaluronan synthase is characterized in that it codes for a hyaluronan synthase from vertebrates or a viral hyaluronan synthase. Preferably, the nucleic acid molecule coding for the hyaluronan synthase codes for a hyaluronan synthase from mammals or a hyaluronan synthase of a virus which infects algae.

With regard to a virus which infects algae, the nucleic acid molecule coding for hyaluronan synthase particularly preferably codes for a hyaluronan synthase of a *Chlorella*-infecting virus, especially preferably a hyaluronan synthase of a *Paramecium bursaria Chlorella* virus 1.

With regard to the nucleic acid molecule which codes for a hyaluronan synthase from mammals, preference is given to a human hyaluronan synthase, in particular human hyaluronan synthase 3.

In a further preferred embodiment, the present invention relates to plant cells according to the invention or plants according to the invention where the nucleic acid molecule coding for hyaluronan synthase is characterized in that the codons of the nucleic acid molecule coding for a hyaluronan synthase are modified compared to the codons of the nucleic acid molecule coding for the hyaluronan synthase of the parent organism of the hyaluronan synthase. Particularly preferably, the codons of the hyaluronan synthase are modified such that they are adapted to the frequency of the use of the codons of the plant cell or plant into whose genome they are integrated.

Owing to the degeneration of the genetic code, amino acids can be encoded by one or more codons. In different organisms, the codons coding for an amino acid are used at different frequencies. Adapting the codon of a coding nucleic acid sequence to the frequency of their use in the plant cell or in the plant into whose genome the sequence to be expressed is to be integrated may contribute to an increased amount of translated protein and/or to the stability of the mRNA in question in the particular plant cells or plants. The frequency of use of codons in the plant cells or plants in question can be determined by the person skilled in the art by examining as many coding nucleic acid sequences of the organism in question as possible for the frequency with which certain codons are used for coding for a certain amino acid. The frequency of the use of codons of certain organisms is known to the person skilled in the art and can be determined in a simple and rapid manner using computer programs. Suitable computer programs are publicly accessible and provided for free inter alia on the Internet (for example, the graphical codon usage analyzer available on the internet at gcua.schoedl.de/; the codon usage database available on the world wide web at kazusa.or.jp/codon/ the Entelechon website).

Adapting the codons of a coding nucleic acid sequence to the frequency of their use in the plant cell or in the plant into whose genome the sequence to be expressed is to be integrated can be carried out by in vitro mutagenesis or, preferably, by de novo synthesis of the gene sequence. Methods for the de novo synthesis of nucleic acid sequences are known to the person skilled in the art. A de novo synthesis can be carried out, for example, by initially synthesizing individual nucleic acid oligonucleotides, hybridizing these with oligonucleotides complementary thereto, so that they form a DNA double strand, and then ligating the individual double-stranded oligonucleotides such that the desired nucleic acid sequence is obtained. The de novo synthesis of nucleic acid sequences including the adaptation of the frequency with which the codons are used to a certain target organism can also be sourced out to companies offering this service (for example Entelechon GmbH, Regensburg, Germany).

In a further preferred embodiment, the present invention relates to plant cells according to the invention or plants according to the invention where the nucleic acid molecule coding for hyaluronan synthase is characterized in that it codes for a hyaluronan synthase having the amino acid sequence shown under SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 20, SEQ ID NO 22, SEQ ID NO 24, SEQ ID NO 26, SEQ ID NO 28, SEQ ID NO 30, SEQ ID NO 32, SEQ ID NO 34, SEQ ID NO 36, SEQ ID NO 38, SEQ ID NO 40, SEQ ID NO 42, SEQ ID NO 44, SEQ ID NO 46, SEQ ID NO 48, SEQ ID NO 50, SEQ ID NO 52, SEQ ID NO 54, SEQ ID NO 56, SEQ ID NO 58, SEQ ID NO 60 or SEQ ID NO 62. Particularly preferably, the nucleic acid molecule coding for the hyaluronan synthase is characterized in that it codes for a hyaluronan synthase having the amino acid sequence shown under SEQ ID NO 2 or SEQ ID NO 6, especially preferably a hyaluronan synthase having the amino acid sequence shown under SEQ ID NO 4 or SEQ ID NO 8.

In a further preferred embodiment, the present invention relates to plant cells according to the invention or plants according to the invention where the nucleic acid molecule coding for the hyaluronan synthase is characterized in that it comprises a nucleic acid sequence shown under SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 19, SEQ ID NO 21, SEQ ID NO 23, SEQ ID NO 25, SEQ ID NO 27, SEQ ID NO 29, SEQ ID NO 31, SEQ ID NO 33, SEQ ID NO 35, SEQ ID NO 37, SEQ ID NO 39, SEQ ID NO 41, SEQ ID NO 43, SEQ ID NO 45, SEQ ID NO 47, SEQ ID NO 49, SEQ ID NO 51, SEQ ID NO 53, SEQ ID NO 55, SEQ ID NO 57, SEQ ID NO 59 or SEQ ID NO 61. Particularly preferably, the nucleic acid molecule coding for the hyaluronan synthase is characterized in that it comprises a nucleic acid sequence shown under SEQ ID NO 1 or SEQ ID NO 5, especially preferably a hyaluronan synthase having the nucleic acid sequence shown under SEQ ID NO 3 or SEQ ID NO 7.

The plasmid IC 341-222, which comprises a synthetic nucleic acid molecule coding for a *Paramecium bursaria Chlorella* virus hyaluronan synthase and the plasmid IC 362-237 which comprises a synthetic nucleic acid molecule coding for a *Homo sapiens* hyaluronan synthase 3 were deposited at the Deutsche Sammlung von Mikroorganismen und Zellkulturen GmbH, Mascheroder Weg 1b, 38124 Brunswick, Germany, on 25.08.2004 under the numbers DSM16664 and DSM16665, respectively. The amino acid sequence shown in SEQ ID NO 4 can be derived from the coding region of the nucleic acid sequence integrated into the plasmid IC 341-222 and codes for a *Paramecium bursaria Chlorella* virus hyaluronan synthase. The amino acid sequence shown in SEQ ID NO 8 can be derived from the coding region of the cDNA sequence integrated into plasmid IC 362-237 and codes for a *Homo sapiens* hyaluronan synthase 3.

Accordingly, the present invention also relates to plant cells according to the invention or plants according to the invention where the nucleic acid molecule coding for the hyaluronan synthase is characterized in that it codes for a protein whose amino acid sequence can be derived from the coding region of the nucleic acid sequence inserted into plasmid DSM16664 or DSM16665.

A large number of techniques are available for stably integrating nucleic acid molecules into a host plant cell. These techniques include the transformation of plant cells with T-DNA using *Agrobacterium tumefaciens* or *Agrobacterium rhizogenes* as means for the transformation, the fusion of protoplasts, injection, the electroporation of DNA, the introduction of DNA using a biolisic approach and further options (reviewed in "Transgenic Plants", Leandro ed., Humana Press 2004, ISBN 1-59259-827-7).

The use of agrobacteria-mediated transformation of plant cells has been studied intensively and is described in sufficient detail in EP 120516; Hoekema, Ind.: The Binary Plant Vector System, Offsetdrukkerij Kanters B. V. Alblasserdam (1985), Chapter V; Fraley et al., Crit. Rev. Plant Sci. 4, 1-46 and in An et al. EMBO J. 4, (1985), 277-287. For the transformation of potato, see, for example, Rocha-Sosa et al., EMBO J. 8, (1989), 29-33, for the transformation of tomato plants see, for example, U.S. Pat. No. 5,565,347.

Also described is the transformation of monocotyledonous plants using vectors based on *Agrobacterium* transformation (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et al., Biol/Technology 13, (1995), 486-492; Conner and Domisse, Int. J. Plant Sci. 153 (1992), 550-555; Ritchie et al, Transgenic Res. 2, (1993), 252-265). An alternative system for transforming monocotyledonous plants is the transformation using the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), the protoplast transformation, the electroporation of partially permeabilized cells or the introduction of DNA using glass fibres. In particular the transformation of maize has been described repeatedly in the literature (cf., for example, WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726).

Successful transformations of other cereal species have likewise already been described, for example for barley (Wan and Lemaux, see above; Ritala et al., see above; Krens et al., Nature 296, (1982), 72-74) and for wheat (Nehra et al., Plant J. 5, (1994), 285-297; Becker et al., 1994, Plant Journal 5, 299-307). All of the above methods are suitable in the context of the present invention.

Plant cells according to the invention and plants according to the invention having a nucleic acid molecule coding for a hyaluronan synthase stably integrated into their genome can be identified inter alia by the fact that they have at least one copy of a nucleic acid molecule coding for a hyaluronan synthase stably integrated into their genome. This can be checked, for example, by a southern blot analysis.

Furthermore, the plant cells according to the invention and the plants according to the invention preferably have at least one of the following distinguishing features: the plant cells according to the invention or plants according to the invention have transcripts of the nucleic acid molecules stably integrated into the genome and coding for a hyaluronan synthase. These can be identified, for example, by northern blot analysis or by RT-PCR (Reverse Transcription Polymerase Chain Reaction). Preferably, the plant cells according to the invention and the plants according to the invention contain a protein which is encoded by nucleic acid molecules stably integrated into the genome coding for a hyaluronan synthase. This can be checked, for example, by immunological methods, in particular by a western blot analysis.

Methods for preparing antibodies which react specifically with a certain protein, i.e. which bind specifically to said protein, are known to the person skilled in the art (see, for example, Lottspeich and Zorbas (Eds.), 1998, Bioanalytik [bioanalysis], Spektrum akad. Verlag, Heidelberg, Berlin, ISBN 3-8274-0041-4). Some companies (for example Eurogentec, Belgium) offer the preparation of such antibodies as a service. Antibodies which specifically recognize hyaluronan synthases are described, for example, in Jacobson et al., 2000, Biochem J. 348, 29-35.

Plant cells according to the invention or plants according to the invention which synthesize hyaluronan can be identified by isolating the hyaluronan that is synthesized by them and proving its structure.

Since plant tissue has the advantage that it does not contain hyaluronidases, a simple and rapid isolation method can be used for confirming the presence of hyaluronan in plant cells according to the invention or plants according to the invention. To this end, water is added to the plant tissue to be examined and the plant tissue is then comminuted mechanically (with the aid of, for example, a bead mill, a Warring blender, a juice extractor, etc.). If required, more water may then be added to the suspension, and cell debris and water-insoluble components are then removed by centrifugation. The presence of hyaluronan in the supernatant obtained after centrifugation can then be demonstrated using, for example, a protein which binds specifically to hyaluronan. A method for detecting hyaluronan with the aid of a protein that binds specifically to hyaluronan is described, for example, in U.S. Pat. No. 5,019,498. Test kits (for example the hyaluronic acid (HA) test kit from Corgenix, Inc., Colorado, USA, Prod. No. 029-001) for carrying out the method described in U.S. Pat. No. 5,019,498 are commercially available (for example the hyaluronic acid (HA) test kit from Corgenix, Inc., Colorado, USA, Prod. No. 029-001; see also General Methods item 6.). In parallel, it is possible to initially digest an aliquot of the centrifugation supernatant obtained with a hyaluronidase and then to confirm the presence of hyaluronan with the aid of a protein which specifically binds to hyaluronan, as described above. By the action of the hyaluronidase in the parallel batch, the hyaluronan present therein is degraded, so that after complete digestion it is no longer possible to detect significant amounts of hyaluronan.

The presence of hyaluronan in the centrifugation supernatant can furthermore also be confirmed using other analysis methods, such as, for example, IR, NMR or mass spectroscopy.

The present invention furthermore provides plant cells according to the invention or plants according to the invention characterized in that the nucleic acid molecule stably integrated into the genome of the plant and coding for a hyaluronan synthase is linked to regulatory elements initiating the transcription in plant cells (promoters). In a preferred embodiment, the promoters are tissue-specific promoters, particularly preferably promoters initiating transcription specifically in tuber, fruit or seed cells of plants.

For the expression of nucleic acid molecules according to the invention coding for hyaluronan synthase, these are preferably linked to regulatory DNA sequences which ensure transcription in plant cells. These include in particular promoters. Suitable for expression are, in general, all promoters active in plant cells.

The promoter may be chosen such that the expression takes place constitutively or only in a certain tissue, at a certain point in time in the development of the plant or at a point in time determined by external factors. The promoter may be homologous or heterologous, both with respect to the plant and with respect to the nucleic acid molecule.

Suitable promoters are, for example, the promoter of the 35S RNA of the cauliflower mosaic virus and the ubiquitin promoter from maize for constitutive expression, the patatin gene promoter B33 (Rocha-Sosa et al., EMBO J. 8 (1989), 23-29) for tuber-specific expression in potatoes or a fruit-specific promoter for tomato, such as, for example, the polygalacturonase promoter (Montgomery et al., 1993, Plant Cell 5, 1049-1062) or the E8 promoter (Metha et al., 2002, Nature Biotechnol. 20(6), 613-618), or a promoter which ensured expression only in photosynthetically active tissues, for example the ST-LS1 promoter (Stockhaus et al., Proc. Natl. Acad. Sci. USA 84 (1987), 7943-7947; Stockhaus et al., EMBO J. 8 (1989), 2445-2451) or, for an endosperm-specific expression, the HMWG promoter from wheat, the USP promoter, the phaseolin promoter, promoters of zein genes from maize (Pedersen et al., Cell 29 (1982), 1015-1026; Quatroccio et al., Plant Mol. Biol. 15 (1990), 81-93), the glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218) or shrunken-1 promoter (Werr et al., EMBO J. 4 (1985), 1373-1380). However, it is also possible to use promoters which are only activated at a point in time determined by external factors (see, for example, WO 9307279). Here, promoters of heat-shock proteins, which permit simple induction, may be of particular interest. Furthermore, it may be possible to use seed-specific promoters, such as, for example, the USP promoter from *Vicia faba*, which ensures seed-specific expression in *Vicia faba* and other plants (Fiedler et al., Plant Mol. Biol. 22 (1993), 669-679; Bäumlein et al., Mol. Gen. Genet. 225 (1991), 459-467).

The use of promoters present in the genome of algae-infecting viruses is also possible for expressing nucleic acid sequences in plants (Mitra et al., 1994, Biochem. Biophys Res Commun 204(1), 187-194; Mitra and Higgins, 1994, Plant Mol Biol 26(1), 85-93, Van Etten et al., 2002, Arch Virol 147, 1479-1516).

In the context of the present invention, the term "tissue specific" is to be understood as meaning the restriction of a feature (for example initiation of transcription) predominantly to a certain tissue.

In the context of the present invention, the terms "tuber, fruit or seed cell" are to be understood as meaning all cells contained in a tuber, fruit and seed, respectively.

It is furthermore possible for a termination sequence (polyandenylation signal) to be present, which serves to add a poly-A tail to the transcript. It is thought that the poly-A tail has a function in stabilizing the transcripts. Such elements are described in the literature (cf. Gielen et al., EMBO J. 8 (1989), 23-29) and are interchangeable.

It is also possible for intron sequences to be present between the promoter and the coding region. Such intron sequences may stabilize the expression and lead to a higher expression in plants (Callis et al., 1987, Genes Devel. 1, 1183-1200; Luehrsen, and Walbot, 1991, Mol. Gen. Genet. 225, 81-93; Rethmeier et al., 1997; Plant Journal 12(4), 895-899; Rose and Beliakoff, 2000, Plant Physiol. 122 (2), 535-542; Vasil et al., 1989, Plant Physiol. 91, 1575-1579; XU et al., 2003, Science in China Series C Vol. 46 No. 6, 561-569). Suitable intron sequences are, for example, the first intron of the sh1 gene from maize, the first intron of the poly-ubiquitin gene 1 from maize, the first intron of the EPSPS gene from rice or one of the first two introns of the PAT1 gene from *Arabidopsis*.

The fact that hyaluronan isolated from the plant cells according to the invention and plants according to the invention has a significantly higher molecular weight than hyaluronan isolated from rooster combs is surprising. A medicament which comprises hyaluronan having a mean molecular weight of $5 \times 10^6$ Da has the highest molecular weight of hyaluronan commercially available to date (Lapcik et al., 1998, Chemical Reviews 98(8), 2663-2684). It is furthermore surprising that hyaluronan isolated from plant cells according to the invention or plants according to the invention has a higher molecular weight than hyaluronan from *E. coli* cells transformed using the same hyaluronan synthase (*Paramecium bursaria Chlorella* virus 1) ($3 \times 10^6$ to $6 \times 10^6$ Da, DeAngelis et al., 1997, Science 278, 1800-1803).

Accordingly, the invention also provides plant cells according to the invention or plants according to the invention which synthesize hyaluronan having a mean molecular weight of at least $7 \times 10^6$ Da.

The molecular weight of hyaluronan can be determined using methods known to the person skilled in the art (see, for example, Hokpusta et al., 2003, Eur Biophys J 31, 450-456). Preferably, the molecular weight is determined by gel permeation chromatography (GPC), particularly preferably using the method described under General Methods item 8b).

The present invention furthermore provides plants comprising plant cells according to the invention. Such plants can be produced by regeneration from plant cells according to the invention.

The present invention also relates to processable or consumable parts of plants according to the invention comprising plant cells according to the invention.

In the context of the present invention, the term "processable parts" is to be understood as meaning plant parts used for preparing food or feed, which are used as raw material source for industrial processes, as raw material source for preparing pharmaceutical products or as raw material source for preparing cosmetic products.

In the context of the present invention, the term "consumable parts" is to be understood as meaning plant parts which serve as food for humans or are used as animal feed.

The plants according to the invention may, in principle, be plants of any plant species, i.e. both monocotyledonous and dicotyledonous plants. They are preferably crop plants, i.e. plants cultivated by man for purposes of nutrition or for technical, in particular industrial, purposes. They are preferably rice, tomato or potato plants.

Preferably the present invention relates to potato plants according to the invention which produce at least 29, more preferably at least 36, particularly preferably at least 46 especially preferably at least 68 µg hyaluronan per gram fresh weight of their tubers. Preferably the determination of the hyaluronan content of potato tubers is determined according to the method described in example 10 b).

In a further preferred embodiment, the present invention relates to tomato plants according to the invention which produce at least 4, more preferably at least 8, particularly preferably at least 14 especially preferably at least 18 µg hyaluronan per gram fresh weight of their fruits. Preferably the determination of the hyaluronan content of tomato fruits is determined according to the method described in example 10e).

The present invention also relates to propagation material of plants according to the invention comprising a plant cell according to the invention.

Here, the term "propagation material" encompasses those components of the plant which are suitable for producing progeny in a vegetative or sexual manner. Suitable for vegetative propagation are, for example, cuttings, callus cultures, rhizomes or tubers. Other propagation material encompasses, for example, fruits, seeds, seedlings, protoplasts, cell cultures, etc. Preferred propagation materials are tubers, fruits or seeds.

In a further embodiment, the present invention relates to harvestable plant parts of plants according to the invention, such as fruits, storage roots, roots, flowers, buds, shoots, leaves or stems, preferably seeds, fruits or tubers, where these harvestable parts comprise plant cells according to the invention.

Preferably, the present invention relates to propagation material or harvestable parts of plants comprising hyaluronan. Particularly preferably, this is propagation material or harvestable parts of plants which synthesize hyaluronan.

A further advantage of the present invention consists in the fact that harvestable parts, propagation material, processable parts or consumable parts of plants according to the invention comprise hyaluronan. Accordingly, these are not only suitable as raw materials from which it is possible to isolate hyaluronan, but they can also be used directly as food/feed or for the preparation of food/feed having a prophylactic or therapeutic character (for example for the prophylaxis of osteoarthritis, U.S. Pat. No. 6,607,745). Thus, for example, it is no longer necessary to add to so-called nutraceuticals hyaluronan prepared by fermentation or isolated from animal tissues when employing plants according to the invention or parts of plants according to the invention for preparing nutraceuticals or using them directly as food/feed. By virtue of the high water-binding capacity of hyaluronan, harvestable parts, propagation material, processable parts or consumable parts of plants according to the invention furthermore have the advantage that fewer thickeners are required when preparing solidified food/feed. Thus, for example, when preparing jelly, it is possible to use less sugar, which has an additional positive effect on health. When preparing food/feed where it is required to remove water from the plant raw material, the advantage of using harvestable parts, propagation material, processable parts or consumable parts of plants according to the invention consists in the fact that less water has to be removed from the plant material in question, resulting in lower production costs, and an increased nutritional value of the food/feed in question is ensured by more gentle preparation processes (for example less or shorter heat input). Thus, for example, when preparing tomato ketchup less energy has to be introduced to achieve the desired consistency.

The present invention furthermore provides a method for preparing a plant which synthesizes hyaluronan, wherein
- a) a nucleic acid molecule coding for a hyaluronan synthase is integrated into the genome of a plant cell
- b) a plant is regenerated from plant cells of step a); and
- c) further plants are, if appropriate, generated with the aid of the plants of step b).

The regeneration of the plants according to step b) can be carried out by methods known to the person skilled in the art (described, for example, in "Plant Cell Culture Protocols", 1999, edt. by R. D. Hall, Humana Press, ISBN 0-89603-549-2).

The generation of further plants according to step c) of the process according to the invention can be carried out, for example, by vegetative propagation (for example via cuttings, tubers or via callous culture and regeneration of entire plants) or by sexual propagation. Here, sexual propagation is preferably in a controlled manner, i.e. selected plants having certain properties are crossbred with one another and propagated. Selection is carried out in a manner such that the further plants generated according to step c) have, integrated into the genome of the plant, the nucleic acid molecule coding for a hyaluronan synthase, and/or they synthesize hyaluronan.

In a preferred embodiment of methods according to the invention for preparing a plant, in an additional process step b)-1, which follows after process step b), the selected plants have, stably integrated into their genome, a nucleic acid molecule coding for a hyaluronan synthase.

In a further preferred embodiment, the methods according to the invention for preparing a plant have a process step, following after process step b) or b)-1, in which hyaluronan-synthesizing plants are identified.

In a further embodiment, methods according to the invention are used for preparing a plant according to the invention.

In a further embodiment, the present invention relates to methods according to the invention for preparing a plant where the nucleic acid molecule coding for a hyaluronan synthase in step a) is selected from the group consisting of:
- a) nucleic acid molecules, characterized in that they code for a hyaluronan synthase Class I,
- b) nucleic acid molecules, characterized in that they code for a human or viral hyaluronan synthase,
- c) nucleic acid molecules, characterized in that they code for a human hyaluronan synthase 3 or a hyaluronan synthase of a virus which infects algae,
- d) nucleic acid molecules, characterized in that they code for a hyaluronan synthase of a *Chlorella*-infecting virus,
- e) nucleic acid molecules, characterized in that they code for a hyaluronan synthase of a *Paramecium bursaria Chlorella* virus 1,
- f) nucleic acid molecules, characterized in that the codons of the nucleic acid molecule coding for a hyaluronan synthase are modified compared to the codons of the nucleic acid molecule coding for the hyaluronan synthase of the parent organism of the hyaluronan synthase,
- g) nucleic acid molecules, characterized in that the codons of the hyaluronan synthase are modified such that they are adapted to the frequency of the use of the codons of the plant cell or the plant into whose genome they are integrated,
- h) nucleic acid molecules, characterized in that they code for a hyaluronan synthase having the amino acid sequence shown in SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 20, SEQ ID NO 22, SEQ ID NO 24, SEQ ID NO 26, SEQ ID NO 28, SEQ ID NO 30, SEQ ID NO 32, SEQ ID NO 34, SEQ ID NO 36, SEQ ID NO 38, SEQ ID NO 40, SEQ ID NO 42, SEQ ID NO 44, SEQ ID NO 46, SEQ ID NO 48, SEQ ID NO 50, SEQ ID NO 52, SEQ ID NO 54, SEQ ID NO 56, SEQ ID NO 58, SEQ ID NO 60 or SEQ ID NO 62,
- i) nucleic acid molecules, characterized in that they code for a protein whose amino acid sequence can be derived from the coding region of the nucleic acid sequence inserted into plasmid DSM16664 or DSM16665,
- j) nucleic acid molecules comprising a nucleic acid sequence shown in SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 19, SEQ ID NO 21, SEQ ID NO 23, SEQ ID NO 25, SEQ ID NO 27, SEQ ID NO 29, SEQ ID NO 31, SEQ ID NO 33, SEQ ID NO 35, SEQ ID NO 37, SEQ ID NO 39, SEQ ID NO 41, SEQ ID NO 43, SEQ ID NO 45, SEQ ID NO 47, SEQ ID NO 49, SEQ ID NO 51, SEQ ID NO 53, SEQ ID NO 55, SEQ ID NO 57, SEQ ID NO 59 or SEQ ID NO 61,
- k) nucleic acid molecules comprising the nucleic acid sequence inserted into plasmid DSM16664 or DSM16665,
- l) nucleic acid molecules, coding for a hyaluronan synthase, where the nucleic acid sequences coding for the hyaluronan synthase are linked to regulatory elements (promoter) which initiate the transcription in plant cells or
- m) nucleic acid molecules according to j), where the promoters are tissue-specific promoters, particularly preferably promoters which initiate the transcription specifically in tuber, fruit or seed cells of plants.

In a further preferred embodiment, methods according to the invention serve for preparing plants synthesizing hyaluronan having a mean molecular weight of at least $7\times10^6$ Da.

The present invention also provides plants obtainable by methods according to the invention for preparing a plant which synthesizes hyaluronan.

Surprisingly, it has been found that hyaluronan isolated from plant cells according to the invention or plants according to the invention have a small molecular weight distribution compared to hyaluronan isolated from rooster combs or prepared by fermentation of *Streptococcus* strains.

Accordingly, the present invention also provides methods for preparing hyaluronan comprising a step where hyaluronan is extracted from plant cells according to the invention, from plants according to the invention, from propagation material according to the invention, from harvestable plant parts according to the invention, from processable plant parts or from plants obtainable by a method according to the invention. Preferably, such a method also comprises the step where the cultivated plant cells according to the invention, the plants according to the invention, the propagation material according to the invention, the harvestable plant parts according o the invention, the processable plant parts according to the invention are harvested prior to extraction of the hyaluronan, and particularly preferably furthermore the step of the cultivation of plant cells according to the invention or plants according to the invention prior to harvesting.

A method according to the invention for preparing hyaluronan preferably relates to a method for preparing hyaluronan having a mean molecular weight of at least $7\times10^6$ Da.

In contrast to bacterial or animal tissues, plant tissues have no hyaluronidases and do not contain any hyaladherins. Accordingly, as already described above, extraction of hyaluronan from plant tissues is possible with the aid of relatively simple methods. If required, the aqueous extracts, described above, of plant cells or tissues containing hyaluronan can be purified further using methods known to the person skilled in the art, such as, for example, repeated precipitation with ethanol. A preferred method for purifying hyaluronan is described under General Methods item 5.

The present invention also provides the use of plant cells according to the invention, plants according to the invention, propagation material according to the invention, harvestable plant parts according to the invention, processable plant parts according to the invention or plants obtainable by a method according to the invention for preparing hyaluronan.

The present invention furthermore provides compositions comprising components of plant cells according to the invention, plants according to the invention, propagation material according to the invention, harvestable plant parts according to the invention, processable plant parts according to the invention, consumable plant parts according to the invention or plants obtainable by a method according to the invention. The compositions are preferably food or feed, pharmaceutical or cosmetic products.

In a preferred embodiment of the present invention, the compositions according to the invention are compositions comprising hyaluronan having a mean molecular weight of at least $7\times10^6$ Da.

In a further preferred embodiment of the present invention the compositions according to the invention comprise plant cells according to the invention. In respect to this, it is meaningless if the plant cells according to the invention are broken or unbroken when present in compositiomns according to the invention.

In a further preferred embodiment of the present invention the compositions according to the invention comprise recombinant nucleic acid molecules characterized in that said recombinant nucleic acid molecules comprise nucleic acid molecules encoding a hyaluronansynthase.

As already mentioned above, it is possible to use plant parts according to the invention, plants according to the invention, propagation material according to the invention, harvestable plant parts according to the invention, processable plant parts according to the invention, consumable plant parts according to the invention or plants obtainable by a method according to the invention to prepare food or feed. However, use as raw materials for industrial applications is also possible, without hyaluronan having to be isolated. Thus, for example, plants according to the invention or parts of plants according to the invention can be applied to areas under agricultural cultivation to achieve increased water binding of the soil. Furthermore, plants according to the invention or plant cells according to the invention can be used for preparing drying agents (for example for use when shipping moisture-sensitive items) or as absorbers of liquids (for example in nappies or for absorbing spilled aqueous liquids). For such applications, it is possible to use entire plants according to the invention, parts of plants according to the invention or comminuted (for example ground) plants according to the invention or plant parts according to the invention, as required. Suitable for applications in which ground plants or plant parts are used are plant parts containing hyaluronan, but only a low proportion of water. These are preferably grains of cereal plants (maize, rice, wheat, rye, oats, barley, sago or sorghum).

The present invention also provides methods for preparing a composition according to the invention, where plant cells according to the invention, plants according to the invention, propagation material according to the invention, harvestable plant parts according to the invention, processable plant parts according to the invention, consumable plant parts according to the invention or plants obtainable by a method according to the invention are used. The methods for preparing a composition according to the invention are preferably methods for preparing food or feed, methods for preparing a pharmaceutical product or methods for preparing a cosmetic product.

In a preferred embodiment of the present invention, methods according to the invention for preparing a composition according to the invention relate to methods for preparing a composition comprising hyaluronan having a mean molecular weight of at least $7\times10^6$ Da.

Methods for preparing food or feed are known to the person skilled in the art. Methods for using plants according to the invention or plant parts according to the invention in industrial areas are also known to the person skilled in the art and include inter alia comminuting or grinding of plants according to the invention or plant parts according to the invention; however, they are not exclusively limited thereto. Some of the advantages resulting from using subject-matters according to the invention for preparing food/feed or for use in industrial areas have already been described above.

The present invention also relates to the use of plant cells according to the invention, plants according to the invention, propagation material according to the invention, harvestable plant parts according to the invention, processable plant parts according to the invention, consumable plant parts according to the invention or plants obtainable by a method according to the invention for preparing a plant according to the invention for preparing a composition according to the invention. Preference is given to the use of plant cells according to the invention, plants according to the invention, propagation material according to the invention, harvestable plant parts according to the invention, processable plant parts according to the invention, consumable plant parts according to the invention or of plants obtainable by a method according to the invention for preparing a plant according to the invention for preparing food or feed, for preparing a pharmaceutic or for preparing a cosmetic product.

Parts of plants are frequently processed into flours. Examples of parts of plants from which flours are produced are, for example, tubers of potato plants and grains of cereal plants. To produce flours from cereal plants, the endosperm-containing grains of these plants are ground and sieved. In the case of other plants which do not comprise an endosperm, but other starch-storing parts such as, for example, tubers or roots, flour is frequently produced by comminuting, drying and subsequently grinding the storage organs in question. Plant cells according to the invention and plants according to the invention synthesize hyaluronan. As hyaluronan has a high water binding capacity, flours produced from plant cells according to the invention, plants according to the invention, propagation material according to the invention, harvestable plant parts according to the invention, processable plant parts according to the invention, consumable plant parts according to the invention or plants obtainable by a method according to the invention for preparing a plant according to the invention have therefore modified properties.

The present invention therefore furthermore relates to flours comprising hyaluronan.

The flours according to the present invention are preferably characterized in that they comprise plant cells according to the invention. In respect to this, it is meaningless if the plant cells according to the invention are broken or unbroken when present in flours according to the invention.

Flours obtainable from plant cells according to the invention, plants according to the invention, propagation material according to the invention, harvestable plant parts according to the invention, processable plant parts according to the invention, consumable plant parts according to the invention or plants obtainable by a method according to the invention for preparing a plant according to the invention are a further embodiment of the present invention.

The present invention furthermore relates to flours which are produced from plant cells according to the invention, plants according to the invention, propagation material according to the invention, harvestable plant parts according to the invention, processable plant parts according to the invention, consumable plant parts according to the invention or plants obtainable by a method according to the invention for preparing a plant according to the invention. Preferred parts of plants according to the invention for the production of flours according to the invention are tubers, storage roots and endosperm-containing grains. Preferably, tubers are tubers of potato plants and grains are grains of plants of the (systematic) family Poaceae; especially preferably, grains are grains of rice, maize or wheat plants.

Preferably the present invention relates to flours according to the invention which contain at least 2, more preferably at least 4, particularly preferably at least 8 especially preferably at least 10 µg hyaluronan per gram flour weight. Preferably the determination of the hyaluronan content flour is determined according to the method described in example 10 g).

In the context of the present invention, the terms "flour" is understood as meaning a powder obtained by grinding plant parts. If appropriate, plant parts are dried before grinding and comminuted and/or sieved after grinding.

As the result of hyaluronan being present in flours according to the invention the respective flours are distinguished in particular by their increased water-binding capacity. This is desired for example for a number of applications when processing flours in the food industry, in particular in the production of baked goods. Thus flours according to the invention can e.g. increase the shelf life of bakery goods. A further advantage of flours according to the present invention is that less flour has to be used in case the flour is used as a thickener in food or feed compositions.

The present invention furthermore relates to a method for the production of flours, comprising the step of grinding plant cells according to the invention, plants according to the invention, propagation material according to the invention, harvestable plant parts according to the invention, processable plant parts according to the invention, consumable plant parts according to the invention or plants obtainable by a method according to the invention for preparing a plant according to the invention.

Flours can be produced by grinding parts of plants according to the invention. The skilled person knows how to produce flours. Preferably, a method for the production of flours also comprises the step of harvesting the cultured plants or plant parts and/or the propagation material or the starch-storing parts of these plants prior to grinding, and especially preferably furthermore the step of culturing plants according to the invention prior to harvesting.

In a further embodiment of the present invention, the method for the production of flours comprises the processing of plant cells according to the invention, plants according to the invention, propagation material according to the invention, harvestable plant parts according to the invention, processable plant parts according to the invention, consumable plant parts according to the invention or plants obtainable by a method according to the invention for preparing a plant according to the invention prior to grinding.

In this context, the processing may be for example a thermal treatment and/or drying. Thermal treatment followed by drying of the material which has been subjected to the thermal treatment is applied for example in the production of flours from storage roots or tubers such as, for example, potato tubers prior to grinding. Plants according to the invention, starch-storing parts of plants according to the invention, propagation material according to the invention or harvestable material according to the invention prior to grinding can likewise constitute the processing for the purposes of the present invention. The removal of plant tissue such as, for example, of husks of the grains, prior to grinding, is also a processing prior to grinding for the purposes of the present invention.

In a further embodiment of the present invention, the method for the production of flours after grinding comprises a processing of the ground material.

For example, the ground material can be sieved after grinding, for example to produce different types of flours.

Flour obtainable by a method fro the production of flours according to the invention is also an embodiment of th present invention.

The flours according to the invention may, in principle, be flours obtained from any plant species, i.e. monocotyledonous and dicotyledonous plants. The flours according to the invention are preferably obtained from crop plants, i.e. plants cultivated by man for purposes of nutrition or for technical, in particular industrial, purposes. They are preferably rice or potato plants.

The present invention furthermore relates to the use of plant cells according to the invention, plants according to the invention, propagation material according to the invention, harvestable plant parts according to the invention, processable plant parts according to the invention, consumable plant parts according to the invention or plants obtainable by a method according to the invention for preparing a plant according to the invention for the production of flours.

It is another object of the present invention to provide means, such as, for example, DNA molecules, for generating plant cells according to the invention and plants according to the invention which synthesize hyaluronan.

Accordingly, the present invention furthermore provides recombinant nucleic acid molecules comprising a nucleic acid sequence coding for a hyaluronan synthase and a nucleic acid sequence which initiates transcription in a plant cell (promoter).

In the context of the present invention, the term "recombinant nucleic acid molecule" is to be understood as meaning a nucleic acid molecule which, in addition to nucleic acid molecules coding for a hyaluronan synthase, contains additional sequences which are not naturally present in a combination as present in the recombinant nucleic acids according to the invention. Here, the additional sequences mentioned may be any sequences; preferably, they are regulatory sequences (promoters, termination signals, enhancers), particularly preferably regulatory sequences active in plant tissue and especially preferably tissue-specific regulatory sequences which are active in plant tissue. Methods for generating recombinant nucleic acid molecules according to the invention are known to the person skilled in the art and include genetic engineering methods, such as, for example, linking of nucleic acid molecules by ligation, genetic recombination or the de novo synthesis of nucleic acid molecules (see, for example, Sambrook et al., Molecular Cloning, A Laboratory Manual, 3rd edition (2001) Cold Spring Harbour Laboratory Press, Cold Spring Harbour, N.Y. ISBN: 0879695773, Ausubel et al., Short Protocols in Molecular Biology, John Wiley & Sons; 5th edition (2002), ISBN: 0471250929).

In a preferred embodiment, the recombinant nucleic acid molecule comprises a tuber-, fruit- or seed-specific promoter.

A further embodiment of inventive recombinant nucleic acid molecules of the present invention are vectors, in particular plasmids, cosmids, virus genomes, bacteriophage genomes and other vectors commonly used in genetic engineering which contain the above-described nucleic acid molecules according to the invention. These are preferably vectors, plasmids, cosmids or virus genomes suitable for transforming plant cells. The transformation of plant cells or plants with the aid of recombinant nucleic acid molecules according to the invention especially preferably results in the stable integration of a hyaluronan synthase-encoding nucleic acid sequence into the genome of the plant cell and the plant, respectively.

In further embodiments, the present invention relates to recombinant nucleic acid molecules according to the invention where the nucleic acid sequence coding for a hyaluronan synthase is selected from the group consisting of:
  a) nucleic acid molecules, characterized in that they code for a hyaluronan synthase Class I,
  b) nucleic acid molecules, characterized in that they code for a human or viral hyaluronan synthase,
  c) nucleic acid molecules, characterized in that they code for a human hyaluronan synthase 3 or a hyaluronan synthase of a virus which infects algae,
  d) nucleic acid molecules, characterized in that they code for a hyaluronan synthase of a *Chlorella*-infecting virus,
  e) nucleic acid molecules, characterized in that they code for a hyaluronan synthase of a *Paramecium bursaria Chlorella* virus 1,
  f) nucleic acid molecules, characterized in that the codons of the nucleic acid molecule coding for a hyaluronan synthase are modified compared to the codons of the nucleic acid molecule coding for the hyaluronan synthase of the parent organism of the hyaluronan synthase,
  g) nucleic acid molecules, characterized in that the codons of the hyaluronan synthase are modified such that they are adapted to the frequency of the use of the codons of the plant cell or the plant into whose genome they are integrated,
  h) nucleic acid molecules, characterized in that they code for a hyaluronan synthase having the amino acid sequence shown in SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 20, SEQ ID NO 22, SEQ ID NO 24, SEQ ID NO 26, SEQ ID NO 28, SEQ ID NO 30, SEQ ID NO 32, SEQ ID NO 34, SEQ ID NO 36, SEQ ID NO 38, SEQ ID NO 40, SEQ ID NO 42, SEQ ID NO 44, SEQ ID NO 46, SEQ ID NO 48, SEQ ID NO 50, SEQ ID NO 52, SEQ ID NO 54, SEQ ID NO 56, SEQ ID NO 58, SEQ ID NO 60 or SEQ ID NO 62,
  i) nucleic acid molecules, characterized in that they code for a protein whose amino acid sequence can be derived from the coding region of the nucleic acid sequence inserted into plasmid DSM16664 or DSM16665,
  j) nucleic acid molecules comprising a nucleic acid sequence shown in SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 19, SEQ ID NO 21, SEQ ID NO 23, SEQ ID NO 25, SEQ ID NO 27, SEQ ID NO 29, SEQ ID NO 31, SEQ ID NO 33, SEQ ID NO 35, SEQ ID NO 37, SEQ ID NO 39, SEQ ID NO 41, SEQ ID NO 43, SEQ ID NO 45, SEQ ID NO 47, SEQ ID NO 49, SEQ ID NO 51, SEQ ID NO 53, SEQ ID NO 55, SEQ ID NO 57, SEQ ID NO 59 or SEQ ID NO 61, or
  k) nucleic acid molecules comprising the nucleic acid sequence inserted into plasmid DSM16664 or DSM16665.

The present invention also provides plant cells or plants containing recombinant nucleic acid molecules according to the invention.

Description of the Sequences

SEQ ID NO 1: Nucleic acid sequence, coding for a hyaluronan synthase of *Paramecium bursaria Chlorella* virus 1.

SEQ ID NO 2: Amino acid sequence of a hyaluronan synthase of *Paramecium bursaria Chlorella* virus 1. The amino acid sequence shown can be derived from SEQ ID NO 1.

SEQ ID NO 3: Synthetic nucleic acid sequence, coding for a hyaluronan synthase of *Paramecium bursaria Chlorella* virus 1. The codons of the sequence shown were synthesized such that it is adapted to the use of codons in plant cells.

SEQ ID NO 4: Amino acid sequence of a hyaluronan synthase of *Paramecium bursaria Chlorella* virus 1. The amino acid sequence shown can be derived from SEQ ID NO 3.

SEQ ID NO 5: Nucleic acid sequence, coding for a hyaluronan synthase 3 from *Homo sapiens*.

SEQ ID NO 6: Amino acid sequence of a hyaluronan synthase 3 from *Homo sapiens*. The amino acid sequence shown can be derived from SEQ ID NO 5.

SEQ ID NO 7: Synthetic nucleic acid sequence, coding for a hyaluronan synthase 3 from *Homo sapiens*. The codons of the sequence shown were synthesized such that it is adapted to the use of codons in plant cells.

SEQ ID NO 8: Amino acid sequence of a hyaluronan synthase 3 from *Homo sapiens*. The amino acid sequence shown can be derived from SEQ ID NO 7.
SEQ ID NO 9: Nucleic acid sequence, coding for a hyaluronan synthase 1 from *Homo sapiens*.
SEQ ID NO 10: Amino acid sequence of a hyaluronan synthase 1 from *Homo sapiens*. The amino acid sequence shown can be derived from SEQ ID NO 9.
SEQ ID NO 11: Nucleic acid sequence, coding for a hyaluronan synthase 2 from *Homo sapiens*.
SEQ ID NO 12: Amino acid sequence of a hyaluronan synthase 2 from *Homo sapiens*. The amino acid sequence shown can be derived from SEQ ID NO 11.
SEQ ID NO 13: Nucleic acid sequence, coding for a hyaluronan synthase 1 from *Papio anubis*.
SEQ ID NO 14: Amino acid sequence of a hyaluronan synthase 1 from *Papio anubis*. The amino acid sequence shown can be derived from SEQ ID NO 13.
SEQ ID NO 15: Nucleic acid sequence, coding for a hyaluronan synthase 1 from *Mus musculus*.
SEQ ID NO 16: Amino acid sequence of a hyaluronan synthase 1 from *Mus musculus*. The amino acid sequence shown can be derived from SEQ ID NO 13.
SEQ ID NO 17: Nucleic acid sequence, coding for a hyaluronan synthase 2 from *Mus musculus*.
SEQ ID NO 18: Amino acid sequence of a hyaluronan synthase 2 from *Mus musculus*. The amino acid sequence shown can be derived from SEQ ID NO 17.
SEQ ID NO 19: Nucleic acid sequence, coding for a hyaluronan synthase 3 from *Mus musculus*.
SEQ ID NO 20: Amino acid sequence of a hyaluronan synthase 3 from *Mus musculus*. The amino acid sequence shown can be derived from SEQ ID NO 19.
SEQ ID NO 21: Nucleic acid sequence, coding for a hyaluronan synthase 1 from *Rattus norvegicus*.
SEQ ID NO 22: Amino acid sequence of a hyaluronan synthase 1 from *Rattus norvegicus*. The amino acid sequence shown can be derived from SEQ ID NO 21.
SEQ ID NO 23: Nucleic acid sequence, coding for a hyaluronan synthase 2 from *Rattus norvegicus*.
SEQ ID NO 24: Amino acid sequence of a hyaluronan synthase 2 from *Rattus norvegicus*. The amino acid sequence shown can be derived from SEQ ID NO 23.
SEQ ID NO 25: Nucleic acid sequence, coding for a hyaluronan synthase 3 from *Rattus norvegicus*.
SEQ ID NO 26: Amino acid sequence of a hyaluronan synthase 3 from *Rattus norvegicus*. The amino acid sequence shown can be derived from SEQ ID NO 25.
SEQ ID NO 27: Nucleic acid sequence, coding for a hyaluronan synthase 2 from *Oryctolagus cuniculus*.
SEQ ID NO 28: Amino acid sequence of a hyaluronan synthase 2 from *Oryctolagus cuniculus*. The amino acid sequence shown can be derived from SEQ ID NO 27.
SEQ ID NO 29: Nucleic acid sequence, coding for a hyaluronan synthase 3 from *Oryctolagus cuniculus*.
SEQ ID NO 30: Amino acid sequence of a hyaluronan synthase 3 from *Oryctolagus cuniculus*. The amino acid sequence shown can be derived from SEQ ID NO 29.
SEQ ID NO 31: Nucleic acid sequence, coding for a hyaluronan synthase 2 from *Equus caballus*.
SEQ ID NO 32: Amino acid sequence of a hyaluronan synthase 2 from *Equus caballus*. The amino acid sequence shown can be derived from SEQ ID NO 31.
SEQ ID NO 33: Nucleic acid sequence, coding for a hyaluronan synthase 2 from *Sus scrofa*.
SEQ ID NO 34: Amino acid sequence of a hyaluronan synthase 2 from *Sus scrofa*. The amino acid sequence shown can be derived from SEQ ID NO 33.
SEQ ID NO 35: Nucleic acid sequence, coding for a hyaluronan synthase 3 from *Sus scrofa*.
SEQ ID NO 36: Amino acid sequence of a hyaluronan synthase 3 from *Sus scrofa*. The amino acid sequence shown can be derived from SEQ ID NO 35.
SEQ ID NO 37: Nucleic acid sequence, coding for a hyaluronan synthase 2 from *Bos taurus*.
SEQ ID NO 38: Amino acid sequence of a hyaluronan synthase 2 from *Bos taurus*. The amino acid sequence shown can be derived from SEQ ID NO 37.
SEQ ID NO 39: Nucleic acid sequence, coding for a hyaluronan synthase 2 from *Gallus gallus*.
SEQ ID NO 40: Amino acid sequence of a hyaluronan synthase 2 from *Gallus gallus*. The amino acid sequence shown can be derived from SEQ ID NO 39.
SEQ ID NO 41: Nucleic acid sequence, coding for a hyaluronan synthase 1 from *Xenopus laevis*.
SEQ ID NO 42: Amino acid sequence of a hyaluronan synthase 1 from *Xenopus laevis*. The amino acid sequence shown can be derived from SEQ ID NO 41.
SEQ ID NO 43: Nucleic acid sequence, coding for a hyaluronan synthase 2 from *Xenopus laevis*.
SEQ ID NO 44: Amino acid sequence of a hyaluronan synthase 2 from *Xenopus laevis*. The amino acid sequence shown can be derived from SEQ ID NO 43.
SEQ ID NO 45: Nucleic acid sequence, coding for a hyaluronan synthase 3 from *Xenopus laevis*.
SEQ ID NO 46: Amino acid sequence of a hyaluronan synthase 3 from *Xenopus laevis*. The amino acid sequence shown can be derived from SEQ ID NO 45.
SEQ ID NO 47: Nucleic acid sequence, coding for a hyaluronan synthase 2 from *Danio rerio*.
SEQ ID NO 48: Amino acid sequence of a hyaluronan synthase 2 from *Danio rerio*. The amino acid sequence shown can be derived from SEQ ID NO 47.
SEQ ID NO 49: Genomic nucleic acid sequence, coding for a hyaluronan synthase 3 from *Danio rerio*.
SEQ ID NO 50: Amino acid sequence of a hyaluronan synthase 3 from *Danio rerio*. The amino acid sequence shown can be derived from SEQ ID NO 49.
SEQ ID NO 51: Nucleic acid sequence, coding for a hyaluronan synthase from *Pasteurella multocida*.
SEQ ID NO 52: Amino acid sequence of a hyaluronan synthase from *Pasteurella multocida*. The amino acid sequence shown can be derived from SEQ ID NO 51.
SEQ ID NO 53: Nucleic acid sequence, coding for a hyaluronan synthase from *Streptococcus pyogenes*.
SEQ ID NO 54: Amino acid sequence of a hyaluronan synthase from *Streptococcus pyogenes*. The amino acid sequence shown can be derived from SEQ ID NO 53.
SEQ ID NO 55: Nucleic acid sequence, coding for a hyaluronan synthase from *Streptococcus equi*.
SEQ ID NO 56: Amino acid sequence of a hyaluronan synthase from *Streptococcus equi*. The amino acid sequence shown can be derived from SEQ ID NO 55.
SEQ ID NO 57: Nucleic acid sequence, coding for a hyaluronan synthase from *Streptococcus uberis*.
SEQ ID NO 58: Amino acid sequence of a hyaluronan synthase from *Streptococcus uberis*. The amino acid sequence shown can be derived from SEQ ID NO 57.
SEQ ID NO 59: Nucleic acid sequence, coding for a hyaluronan synthase from *Streptococcus equisimilis*.

SEQ ID NO 60: Amino acid sequence of a hyaluronan synthase from *Streptococcus equisimilis*. The amino acid sequence shown can be derived from SEQ ID NO 59.

SEQ ID NO 61: Nucleic acid sequence, coding for a hyaluronan synthase from *Sulfolobus tokodaii* strain 7.

SEQ ID NO 62: Amino acid sequence of a hyaluronan synthase from *Sulfolobus tokodaii* strain 7. The amino acid sequence shown can be derived from SEQ ID NO 61.

General Methods

Methods which can be used in connection with the present invention are described below. These methods are specific embodiments; however, the present invention is not limited to these methods. It is known to the person skilled in the art that the invention can be carried out in the same manner by modifying the methods described and/or by replacing individual methods or parts of methods by alternative methods or alternative parts of methods.

1. Transformation of Potato Plants

Potato plants were transformed with the aid of *Agrobacterium*, as described in Rocha-Sosa et al. (EMBO J. 8, (1989), 23-29).

2. Transformation of Tomato Plants

Tomato plants were transformed with the aid of *Agrobacterium* according to the method described in U.S. Pat. No. 5,565,347.

3. Transformation of Rice Plants

Rice plants were transformed by the method described by Hiei et al. (1994, Plant Journal 6(2), 271-282).

4. Isolation of Hyaluronan from Plant Tissue

To detect the presence of hyaluronan and to determine the hyaluronan content in plant tissue, plant material was worked up as follows: 200 µl of water (demineralized, conductivity≥18 MΩ) were added to about 0.3 g of tuber material, and the mixture was comminuted in a laboratory oscillating ball mill (MM200, from Retsch, Germany) (30 sec at 30 Hz). A further 800 µl of water (demineralized, conductivity≥18 MΩ) was then added, and the mixture was mixed well (using, for example, a Vortex mixer). Cell debris and insoluble components were separated from the supernatant by centrifuging at 16 000×g for 5 minutes.

5. Purification of Hyaluronan

About 100 grams of tubers were peeled, cut into pieces of a size of about 1 cm$^3$ and, after addition of 100 ml of water (demineralized, conductivity≥18 MΩ) comminuted in a Warring blender at maximum speed for about 30 seconds. The cell debris was then removed using a tea sieve. The cell debris that had been removed was resuspended in 300 ml of water (demineralized, conductivity≥18 MΩ) and again removed using a tea sieve. The two suspensions obtained (100 ml+300 ml) were combined and centrifuged at 13 000×g for 15 minutes. NaCl was added to the centrifugation supernatant obtained until a final concentration of 1% had been reached. After the NaCl had gone into solution, precipitation was carried out by addition of twice the volume of ethanol followed by thorough mixing and incubation at −20° C. overnight. The mixture was then centrifuged at 13 000×g for 15 minutes. The sedimented precipitate obtained after this centrifugation was dissolved in 100 ml of buffer (50 mM TrisHCl, pH 8, 1 mM CaCl2) and proteinase K was then added to a final concentration of 100 µg/ml and the solution was incubated at 42° C. for 2 hours. This was followed by 10 minutes of incubation at 95° C. Once more, NaCl was added to this solution until a final concentration of 1% had been reached. After the NaCl had gone into solution, another precipitation was carried out by addition of twice the volume of ethanol, thorough mixing and incubation at −20° C. for about 96 hours. This was followed by 15 minutes of centrifugation at 13 000×g. The sedimented precipitate obtained after this centrifugation was dissolved in 30 ml of water (demineralized, conductivity≥18 MΩ), and once more, NaCl was added to a final concentration of 1%. By adding twice the volume of ethanol, thorough mixing and incubation at −20° C. overnight, another precipitation was carried out. The precipitate obtained after subsequent centrifugation at 13 000×g for 15 minutes was dissolved in 20 ml of water (demineralized, conductivity≥18 MΩ).

Further purification was carried out by centrifugal filtration. To this end, in each case 5 ml of the dissolved precipitate were applied to a membrane filter (CentriconAmicon, pore width 10000 NMWL, Prod. No. UCF8 010 96), and the sample was centrifuged at 2200×g until only about 3 ml of the solution above the filter remained. Two more times, in each case 3 ml of water (demineralized, conductivity≥18 MΩ) were then added to the solution above the membrane and in each case re-centrifuged under identical conditions until, at the end, only about 3 ml of the solution above the filter remained. The solutions still present above the membrane after centrifugal filtration were taken off, and the membrane was rinsed repeatedly (three to five times) with about 1.5 ml of water (demineralized, conductivity≥18 MΩ). All solutions which were still present above the membrane and the solutions obtained from rinsing were combined, NaCl was added to a final concentration of 1%, after the NaCl had gone into solution, twice the volume of ethanol was added, the sample was mixed and a precipitate was obtained by storage at −20° C. overnight. The precipitate obtained after subsequent centrifugation at 13 000×g for 15 minutes was dissolved in 4 ml of water (demineralized, conductivity≥18 MΩ) and then freeze-dried (24 hours under a pressure of 0.37 mbar, freeze drying apparatus Christ Alpha 1-4 from Christ, Osterode, Germany).

6. Detection of Hyaluronan and Determination of the Hyaluronan Content

Hyaluronan was detected using a commercial test (hyaluronic acid (HA) test kit from Corgenix, Inc., Colorado, USA, Prod. No. 029-001) according to the instructions of the manufacturer which are herewith incorporated into the description by way of reference. The test principle is based on the availability of a protein which binds specifically to hyaluronan (HABP) and is carried out similarly to an ELISA, where a colour reaction indicates the hyaluronan content in the sample examined. Accordingly, for the quantitative determination of hyaluronan, the samples to be measured should be employed in a concentration such that it is within the stated limits (for example: dilution of the sample in question or use of less water for extracting hyaluronan from plant tissue, depending on whether a limit was exceeded or not reached).

In parallel batches, aliquots of the samples to be determined were initially subjected to hyaluronidase digestion and then measured using the commercial test (hyaluronic acid (HA) test kit from Corgenix, Inc., Colorado, USA, Prod. No. 5 029-001). Hyaluronidase digestion was carried out using 400 µl of potato tuber extract in hyaluronidase buffer (0.1 M potassium phosphate buffer, pH 5.3; 150 mM NaCl) by adding 5 µg (~3 units) of hyaluronidase (hyaluronidase type III from Sigma, Prod. No. H 2251) and incubating at 37° C. for 30 min.

In each case in a dilution of 1:10, all samples were then used for determining the hyaluronan content.

7. Detection of Hyaluronan by NMR Spectroscopy

Analysis by NMR spectroscopy was carried out using a DRX 700 spectrometer at 700 MHz (Bruker Biospin GMBH D-76287 Rheinstetten/Karlsruhe, Germany). The spectrometer was fitted with a TXI sample head and provided with an SGI workstation, and the Bruker Biospin software XWIN-NMR version 3.5 was used for evaluation. About 0.5 mg to 2 mg of the sample were dissolved in 550 ul of $D_2O$. The $^1$H-NMR spectra were measured using 1024 to 12 000 scans, with a relaxation time of 1 s. The $^1$H-NMR spectra were referenced to the water signal at 4.7 ppm.

8. Molecular Weight Analyses of Hyaluronan a) Agarose Gel Electrophoresis

To characterize the size of the hyaluronan isolated from plants, an agarose gel electrophoresis-based system described by Lee and Cowman (1994, Anal. Biochem. 219, 278-287) or Armstrong and Bell (2002, Anal. Biochem. 308, 255-264) was used. To this end, hyaluronan-containing samples were applied to a 0.7% TEA (40 mM Tris, 5 mM sodium acetate, 0.8 mM EDTA, pH 7.9) agarose gel and separated in 1× TEA buffer at 50 V over a period of 3 hours. The agarose gel was then stained overnight using 0.005% Stains-all (3,3'-diethyl-9-methyl4,5,4',5'-dibenzothiacarbocyanine, Fluka, Prod. No. 85663) in 50% ethanol and 50% 1× TEA buffer, and the gel was then decolorized in water and scanned.

b) Gel Permeation Chromatography (GPC)

At a concentration of 1 mg/ml$^{-1}$, the samples were dissolved in GPC mobile phase (0.2 M NaNO$_3$). To this end, the samples were initially stirred on a magnetic stirrer for 1 hour and then allowed to stand at room temperature for 20 hours for equilibration. Prior to the measurement, the samples were filtered through a 5 μm membrane filter. The samples were then analysed by GPC, where the refractive index, light scattering and the viscosity of the eluate were determined. The following instruments and materials were used:

GPC Conditions:

Instruments: Gel Chromatograph PL120 from Polymer Laboratories, Midas Autosampler from Spark, DAWN-EOS light scattering detector from Wyatt Technology Santa Barbara with λ0=690 nm and 16 detectors at an angle range from 14.9° to 162.9°, K5 flow cell, Viscosity/refractive index combination detector η-1002 (WEG Dr. Bures GmbH & Co KG).

Columns: SUPREMA Gel from PSS, Mainz, Germany

Precolumn and three columns with the separation ranges 300 to $10^4$; 5·$10^4$ to 2·$10^6$ and $10^6$ to $10^8$ were series-connected.

Elution: Mobile phase 0.2 M NaNO$_3$, flow rate 0.8 ml/minute, temperature 30° C., injection volume 500 μl.

Evaluation: Using the data obtained, the values given in the examples were calculated. The light scattering data were evaluated using the software ASTRA Software 4.90.08. The viscosity measurements were evaluated using PSS Win GPC 6.

9. Formula for the Calculation of Standard Deviations

Standard Deviations were calculated according to the following formula:

Square root $[n\Sigma x^2 - (\Sigma x)^2/n(n-1)]$

Wherein x is the value of sample and n is the sum of samples used for determination of the Standard Deviation.

EXAMPLES

1. Preparation of the plant expression vector IR 47-71

The plasmid pBinAR is a derivative of the binary vector plasmid pBin19 (Bevan, 1984, Nucl Acids Res 12: 8711-8721) which was constructed as follows:

A fragment of a length of 529 bp which comprised the nucleotides 6909-7437 of the 35S promoter of the cauliflower mosaic virus was isolated as EcoR I/Kpn I fragment from the plasmid pDH51 (Pietrzak et al, 1986 Nucleic Acids Res. 14, 5858) and ligated between the EcoR I and Kpn I restriction sites of the polylinker of pUC18. In this manner, the plasmid pUC18-35S was created. Using the restriction endonucleases Hind III and Pvu II, a fragment of a length of 192 bp which included the polyadenylation signal (3 terminus) of the *Octopin Synthase* gene (gene 3) of the T-DNA of the Ti plasmid pTiACH5 (Gielen et al, 1984, EMBO Journal 3, 835-846) (nucleotides 11 749-11 939) was isolated from the plasmid pAGV40 (Herrera-Estrella et al, 1983 Nature, 303, 209-213). Following addition of Sph I linkers to the Pvu II restriction site, the fragment was ligated between the Sph I and Hind III restriction sites of pUC18-35S. This gave the plasmid pA7. Here, the entire polylinker comprising the 35S promoter and OCS terminator was removed using EcoR I and Hind III and ligated into the appropriately cleaved vector pBin19. This resulted in the plant expression vector pBinAR (Höfgen and Willmitzer, 1990, Plant Science 66, 221-230).

The promoter of the patatin gene B33 from *Solanum tuberosum* (Rocha-Sosa et al., 1989, EMBO J. 8, 23-29) was, as Dra I fragment (nucleotides −1512−+14), ligated into the Sst I-cleaved vector pUC19 whose ends had been blunted using T4-DNA polymerase. This resulted in the plasmid pUC19-B33. From this plasmid, the B33 promoter was removed using EcoR I and Sma I and ligated into the appropriately restricted vector pBinAR. This resulted in the plant expression vector pBinB33.

To facilitate further cloning steps, the MCS (Multiple Cloning Site) was extended. To this end, two complementary oligonucleotides were synthesized, heated at 95° C. for 5 minutes, slowly cooled to room temperature to allow good fixation (annealing) and cloned into the Sal I and Kpn I restriction sites of pBinB33. The oligonucleotides used for this purpose had the following sequence:

5'-TCg ACA ggC CTg gAT CCT TAA TTA AAC TAg TCT CgA ggA gCT Cgg TAC-3'(SEQ ID NO: 63) 5'-CgA gCT CCT CgA gAC TAg TTT AAT TAA ggA TCC Agg CCT g-3'(SEQ ID NO: 64) The plasmid obtained was named IR 47-71.

2. Preparation of the Plant Expression Vector IR 103-123 a) Preparation of the Expression Vector ME5/6 pGSV71 is a derivative of the plasmid pGSV7 which is derived from the intermediate vector pGSV1. pGSV1 is a derivative of pGSC1700 whose construction was described by Cornelissen and Vanderwiele (Nucleic Acid Research 17, (1989), 19-25). pGSV1 was obtained from pGSC1700 by deletion of the carbenicillin resistance gene and deletion of the T-DNA sequences from the TL-DNA region of the plasmid pTiB6S3.

pGSV7 contains the replication origin of the plasmid pBR322 (Bolivar et al., Gene 2, (1977), 95-113) and the replication origin of the *Pseudomonas* plasmid pVS1 (Itoh et al., Plasmid 11, (1984), 206). Moreover, pGSV7 contains the selectable marker gene aadA from the transposon Tn1331 from *Klebsiella pneumoniae* which confers resistance to the antibiotics spectinomycin and streptomycin (Tolmasky, Plasmid 24 (3), (1990), 218-226; Tolmasky and Crosa, Plasmid 29(1), (1993), 31-40).

The plasmid pGSV71 was obtained by cloning a chimeric bar gene between the border regions of pGSV7. The chimeric bar gene contains the promoter sequence of the cauliflower mosaic virus for initiating transcription (Odell et al., Nature 313, (1985), 180), the bar gene from *Streptomyces hygroscopicus* (Thompson et al., Embo J. 6, (1987), 2519-2523) and the 3'-untranslated region of the nopaline synthase gene of the T-DNA from pTiT37 for terminating transcription and polyadenylation. The bar gene bestows tolerance to the herbicide glufosinate-ammonium.

In positions 198-222, the T-DNA contains the right border sequence of the TL-DNA from the plasmid pTiB6S3 (Gielen et al., EMBO J. 3, (1984), 835-846). Between the nucleotides 223-249, there is a polylinker sequence. The nucleotides 250-1634 contain the P35S promoter region of the cauliflower mosaic virus (Odell et al., see above). The coding sequence of the phosphinothricin resistance gene (bar) from *Streptomyces hygroscopicus* (Thompson et al. 1987, see above) is contained between nucleotides 1635-2186. Here, the two terminal codons on the 5'-terminus of the bar wild-type gene were replaced by the codons ATG and GAC. Between nucleotides 2187-2205, there is a polylinker sequence. The TaqI fragment, which has a length of 260 bp, of the non-translated 3'-terminus of the nopaline synthase gene (3'nos) from the T-DNA of the plasmid pTiT37 (Depicker et al., J. Mol. Appl. Genet. 1, (1982), 561-573) is located between nucleotides 2206 and 2465. The nucleotides 2466-2519 contain a polylinker sequence. The left border region of the TL-DNA from pTiB6S3 (Gielen et al., EMBO J. 3, (1984), 835-846) is located between nucleotides 2520-2544.

The vector pGSV71 was then cleaved using the enzyme PstI and blunted. From the vector pB33-Kan, the B33 promoter and the ocs cassette were excised as EcoRI-HindIII fragment, and the fragment was blunted by filling the ends and inserted into the vector pGSV71 which had been cleaved using PstI and blunted. The vector obtained (ME4/6) served as starting vector for constructing ME5/6: with doubling of the PstI restriction site, an oligonucleotide comprising the restriction sites EcoRI, PacI, SpeI, SrfI, SpeI, NotI, PacI and EcoRI was introduced into the PstI restriction site of the vector ME4/6, which restriction site is located between the B33 promoter and the ocs element. The expression vector obtained was called ME5/6.

b) Preparation of the Plasmid pML72-129

In the sequel, a BamHI fragment of ME5/6 was exchanged for a PCR product which had been extended by a number of restriction sites but was otherwise identical, which gave the plasmid pUL1-17. Using the restriction enzymes HindIII and PstI, the B33 promoter present in pUL1-17 was excised and the vector was, after the ends had been blunted, religated, which gave the vector pML18-56. This vector was opened using MunI and PstI, and an MCS (Multiple Cloning Site) having corresponding sticky ends and synthesized using two annealed oligonucleotides (GAG CTC CTA GGC TCG AGT TAA CAC TAG TAA GCT TAA TTA AGA TAT CAT TTA CA (SEQ ID NO: 65) and AAT TGT AAA TGA TAT CTT AAT TAA GCT TAC TAG TGT TAA CTC GAG CCT AGG AGC TCT GCA (SEQ ID NO: 66)) was introduced. The plasmid formed in this manner was named pML72-129.

c) Preparation of the Plasmid pIR96-123

Once more, a modified polylinker was introduced into the plasmid pML72. To this end, the plasmid was cleaved using the restriction enzymes MunI and HpaI and ligated using a DNA fragment consisting of the two hybridized oligonucleotides MCS neuL1 (AAT TGT AAA TGA TAT CTT AAT TAA GCT TAC TAG TGT T(SEQ ID NO: 67)) and MCS neuL2 (AAC ACT AGT AAG CTT AAT TAA GAT ATC ATT TAC (SEQ ID NO: 68)). The resulting vector was named pIR96-123.

d) Preparation of the Plant Expression Vector pIR103-123

Subsequently, an Ecl136II/EcoRV PCR product for the globulin promoter from rice was ligated into the EcoRV restriction site of IR96-123, which gave the basis vector for an endosperm-specific expression of genes of various origins. Hereinbelow, this vector is referred to as IR103-123.

3. Synthesis of the Nucleic Acid Sequences Coding for an HAS Protein of *Paramecium bursaria Chlorella* Virus 1

The nucleic acid sequence coding for an HAS (hyaluronan synthase) protein from *Paramecium bursaria Chlorella* virus 1, was synthesized by Medigenomix GmbH (Munich, Germany) and cloned into the vector pCR2.1 from Invitrogen (Prod. No. K2000-01). The plasmid obtained was named IC 323-215. The synthetic nucleic acid sequence coding for the HAS protein from *Paramecium bursaria Chlorella* virus 1 is shown under SEQ ID NO 3. The corresponding nucleic acid sequence originally isolated from *Paramecium bursaria Chlorella* virus 1 is shown under SEQ ID NO 1.

4. Synthesis of the Nucleic Acid Sequences Coding for an HAS-3 protein from *Homo sapiens*

The nucleic acid sequence coding for an HAS-3 (hyaluronan synthase-3) protein from *Homo sapiens* was synthesized by Entelechon GmbH and cloned into the vector pCR4Topo from Invitrogen (Prod. No. K4510-20). The plasmid obtained was named IC 361-237. The synthetic nucleic acid sequence coding for the HAS-3 protein from *Homo sapiens* is shown in SEQ ID NO 7. The corresponding nucleic acid sequence originally isolated from *Homo sapiens* is shown under SEQ ID NO 5.

5. Preparation of the Plant Expression Vector IC 341-222, which Contains a Coding Nucleic Acid Sequence for an HAS Protein from *Paramecium bursaria Chlorella* Virus 1

By restriction digestion with BamH I and Xho I, the coding sequence of the HAS protein was isolated from the plasmid IC 323-215 and cloned into the BamH I and Xho I restriction sites of the plasmid IR 47-71. The plant expression vector obtained was referred to as IC 341-222.

6. Preparation of the Plant Expression Vector IC 362-237, which Contains a Coding Nucleic Acid Sequence for an HAS-3 Protein from *Homo sapiens*

Using the restriction endonucleases BamH I and Xho I, the coding sequence of the HAS gene was isolated from the plasmid IC 361-237 and cloned into the BamH I and Xho I restriction sites of IR 47-71. The plant expression vector obtained was referred to as IC 362-237.

7. Preparation of the Plant Expression Vector pBA16, which Contains a Coding Nucleic Acid Sequence for an HAS Protein of *Paramecium bursaria Chlorella* Virus 1

Using the restriction endonuclease Asp 7181, the plasmid IC 323-215 was cleaved, the ends were blunted using Klenow polymerase and the resulting fragment was then once more cleaved using the restriction endonuclease Pac I. The fragment obtained in this manner was ligated into the plasmid IR103-123, which had been cleaved using the restriction endonucleases Pac I and Ecl136 II. The plant expression vector obtained was referred to as pBA16.

8. Preparation of the Plant Expression Vector pBA13, which Contains a Coding Nucleic Acid Sequence for an HAS-3 Protein from *Homo sapiens*

Using the restriction endonuclease Xho I and Stu I, the plasmid IC 362-237 was cleaved, and the fragment obtained was ligated into the plasmid IR 103-123, which had been cleaved using the restriction endonucleases Xho I and Ecl136 II. The plant expression vector obtained was referred to as pBA 13.

9. Transformation of Plants with Plant Expression Vectors which Contain Nucleic acid Molecules Coding for HAS Proteins In independent transformations, potato plants were transformed with the plant expression vector IC 341-222, which contains a coding nucleic acid sequence for an HAS protein from *Paramecium bursaria Chlorella* virus 1 under the control of the promoter of the patatin gene B33 from *Solanum tuberosum* (Rocha-Sosa et al., 1989, EMBO J. 8, 23-29), or with the plant expression vector IC 362-237, which contains a coding nucleic acid sequence for an HAS-3 protein from *Homo sapiens* under the control of the promoter of the patatin gene B33 from *Solanum tuberosum* (Rocha-Sosa et al., 1989 EMBO J. 8, 23-29), using the method given under General Methods item 1. The transgenic potato plants obtained which had been transformed with the plasmid IC 341-222 were referred to as 365 ES. The transgenic potato plants obtained which had been transformed with the plasmid IC 362-237 were referred to as 383 ES.

In independent transformations, tomato plants were transformed with the plant expression vector IC 341-222, which contains a coding nucleic acid sequence for an HAS protein from *Paramecium bursaria Chlorella* virus 1 under the control of the promoter of the patatin gene B33 from *Solanum tuberosum* (Rocha-Sosa et al., 1989, EMBO J. 8, 23-29), or with the plant expression vector IC 362-237, which contains a coding nucleic acid sequence for an HAS-3 protein from *Homo sapiens* under the control of the promoter of the patatin gene B33 from *Solanum tuberosum* (Rocha-Sosa et al., 1989 EMBO J. 8, 23-29), using the method given under General Methods item 2. The transgenic tomato plants obtained which had been transformed with the plasmid IC 341-222 were referred to as 367 ES. The transgenic tomato plants obtained which had been transformed with the plasmid IC 362-237 were referred to as 384 ES.

In independent transformations, rice plants were transformed with the plant expression vector pBA16, which contains a coding nucleic acid sequence for an HAS protein from *Paramecium bursaria Chlorella* virus 1 under the control of the promoter of the globulin gene from *Oryza sativa* (Wu et al., 1998, Plant Cell Physiol. 39(8), 885-889), or with the plant expression vector pBA13, which contains a coding nucleic acid sequence for an HAS-3 protein from *Homo sapiens* under the control of the promoter of the globulin gene from *Oryza sativa*, using the method given under General Methods item 3. The transgenic rice plants obtained which had been transformed with the plasmid pBA16 were referred to as Os-pBA16. The transgenic rice plants obtained which had been transformed with the plasmid pBA13 were referred to as Os-pBA13.

10. Analysis of the Transgenic Plants a) Constructing a Calibration Line

A calibration line was constructed using the standard solutions enclosed in the commercial test kit (hyaluronic acid (HA) test kit from Corgenix, Inc., Colorado, USA, Prod. No. 029-001), according to the methods described by the manufacturer. To determine the extinction of 1600 ng/ml of hyaluronan, double the amount, based on the amount of enclosed standard indicated by the manufacturer, comprising 800 ng/ml of hyaluronan was used. In each case, three independent measurement series were carried out, and the corresponding mean was determined. This gave the following calibration line:

TABLE 1

Measure values for constructing a calibration line for the quantitative determination of the hyaluronan content in plant tissue. With the aid of software (Microsoft Office Excel 2002, SP2), the measured values obtained were entered into a diagram and the equation of the function of the trend line was determined (see FIG. 1).

| Hyaluronan concentration | Independent individual measurements | | | Mean | s.d. |
|---|---|---|---|---|---|
| | $E_{450\,nm}$ | $E_{450\,nm}$ | $E_{450\,nm}$ | | |
| 0 ng/ml | 0.100 | 0.096 | 0.096 | 0.097 | 0.002 |
| 50 ng/ml | 0.224 | 0.183 | 0.222 | 0.210 | 0.023 |
| 100 ng/ml | 0.396 | 0.263 | 0.377 | 0.345 | 0.072 |
| 200 ng/ml | 0.554 | 0.443 | 0.653 | 0.550 | 0.105 |
| 500 ng/ml | 1.231 | 0.850 | 1.221 | 1.101 | 0.217 |
| 800 ng/ml | 1.465 | 1.265 | 1.795 | 1.508 | 0.268 |
| 1600 ng/ml | 2.089 | 2.487 | 3.170 | 2.582 | 0.547 |

$E_{450\,nm}$ refers to the extinction at a wavelength of 450 nm,
s.d. is the standard deviation of the calculated mean of the individual values.

b) Potato Tubers of Lines 365 ES

In a greenhouse, individual plants of the line 365 ES were cultivated in soil in 6 cm pots. In each case about 0.3 g of material of potato tubers of the individual plants was processed according to the method described under General Methods item 4. Using the method described under General Methods item 6, the amount of hyaluronan contained in the respective plant extracts was determined, with the aid of the calibration line shown in Example 10a) and FIG. 1. Here, the supernatant obtained after centrifugation was used in a dilution of 1:10 for determining the hyaluronan content. The following results were obtained:

TABLE 2

Amount of hyaluronan (in µg of hyaluronan per g of fresh weight) produced by independent transgenic plants of the line 365 ES. Column 1 refers to the plant from which tuber material was harvested (here, "wild type" refers to untransformed plants which, however, have the genotype used as starting material for the transformation). Column 2 indicates the amount of tuber material of the plant in question used for determining the hyaluronan content. Column 3 contains the measured extinction of a 1:10 dilution of the respective plant extract after the method described in General Methods item 5 had been carried out. Column 4 was calculated with the aid of the regression line equation (see FIG. 1) taking into account the dilution factor, as follows: ((value column 3 − 0.149)/0.00185) × 10. Column 5 indicates the amount of hyaluronan based on the fresh weight used and was calculated as follows: (value column 4/value column 2)/1000.

| Name of the plant | Weight of the plant material employed [g] | Extinction E450 | Amount of hyaluronan [ng/ml] | Hyaluronan based on the fresh weight of the plant material [µg/g] |
|---|---|---|---|---|
| 365 ES 1 | 0.318 | 1.865 | 9276 | 29 |
| 365 ES 2 | 0.303 | 2.216 | 11 173 | 37 |
| 365 ES 3 | 0.305 | 0.112 | — | — |
| 365 ES 4 | 0.310 | 1.812 | 8989 | 29 |
| 365 ES 5 | 0.298 | 1.761 | 8714 | 29 |
| 365 ES 6 | 0.324 | 1.022 | 4719 | 15 |
| 365 ES 7 | | 1.410 | 6816 | |
| 365 ES 8 | 0.323 | 0.101 | — | — |
| 365 ES 9 | 0.305 | 0.902 | 4070 | 13 |
| 365 ES 10 | 0.309 | 2.040 | 10 222 | 33 |
| 365 ES 11 | 0.313 | 2.291 | 11 578 | 37 |
| 365 ES 12 | 0.305 | 1.399 | 6757 | 22 |

TABLE 2-continued

Amount of hyaluronan (in µg of hyaluronan per g of fresh weight) produced by independent transgenic plants of the line 365 ES. Column 1 refers to the plant from which tuber material was harvested (here, "wild type" refers to untransformed plants which, however, have the genotype used as starting material for the transformation). Column 2 indicates the amount of tuber material of the plant in question used for determining the hyaluronan content. Column 3 contains the measured extinction of a 1:10 dilution of the respective plant extract after the method described in General Methods item 5 had been carried out. Column 4 was calculated with the aid of the regression line equation (see FIG. 1) taking into account the dilution factor, as follows: ((value column 3 − 0.149)/0.00185) × 10. Column 5 indicates the amount of hyaluronan based on the fresh weight used and was calculated as follows: (value column 4/value column 2)/1000.

| Name of the plant | Weight of the plant material employed [g] | Extinction E450 | Amount of hyaluronan [ng/ml] | Hyaluronan based on the fresh weight of the plant material [µg/g] |
|---|---|---|---|---|
| 365 ES 13 | 0.297 | 2.746 | 14 038 | 47 |
| 365 ES 14 | 0.297 | 0.105 | — | — |
| 365 ES 15 | 0.302 | 1.952 | 9746 | 32 |
| 365 ES 16 | 0.311 | 1.113 | 5211 | 17 |
| 365 ES 17 | 0.301 | 0.090 | — | — |
| 365 ES 18 | 0.304 | 2.380 | 12 059 | 40 |
| 365 ES 19 | 0.302 | 2.308 | 11 670 | 39 |
| 365 ES 20 | 0.287 | 0.100 | — | — |
| 365 ES 21 | 0.287 | 1.053 | 4886 | 17 |
| 365 ES 22 | 0.286 | 1.527 | 7449 | 26 |
| 365 ES 23 | 0.305 | 2.421 | 12 281 | 40 |
| 365 ES 24 | 0.303 | 0.093 | — | — |
| 365 ES 25 | 0.296 | 1.310 | 6276 | 21 |
| 365 ES 26 | 0.303 | 1.051 | 4876 | 16 |
| 365 ES 27 | 0.306 | 0.118 | — | — |
| 365 ES 28 | 0.301 | 2.123 | 10 670 | 35 |
| 365 ES 29 | 0.294 | 0.113 | — | — |
| 365 ES 30 | 0.287 | 1.965 | 9816 | 34 |
| 365 ES 31 | 0.304 | 0.104 | — | — |
| 365 ES 32 | 0.300 | 1.209 | 5730 | 19 |
| 365 ES 33 | 0.300 | 2.064 | 10 351 | 35 |
| 365 ES 34 | 0.305 | 1.321 | 6335 | 21 |
| 365 ES 35 | 0.303 | 1.826 | 9065 | 30 |
| 365 ES 36 | 0.302 | 1.386 | 6686 | 22 |
| 365 ES 37 | 0.309 | 1.327 | 6368 | 21 |
| 365 ES 38 | 0.290 | 1.631 | 8011 | 28 |
| 365 ES 39 | 0.306 | 1.332 | 6395 | 21 |
| 365 ES 40 | 0.297 | 2.753 | 14 076 | 47 |
| 365 ES 41 | 0.316 | 1.482 | 7205 | 23 |
| 365 ES 42 | 0.316 | 1.820 | 9032 | 29 |
| 365 ES 43 | 0.360 | 1.387 | 6692 | 19 |
| 365 ES 44 | 0.303 | 1.737 | 8584 | 28 |
| 365 ES 45 | 0.313 | 0.100 | — | — |
| 365 ES 47 | 0.301 | 2.164 | 10 892 | 36 |
| 365 ES 48 | 0.302 | 0.093 | — | — |
| 365 ES 49 | 0.300 | 2.160 | 10 870 | 36 |
| 365 ES 50 | 0.316 | 1.014 | 4676 | 15 |
| 365 ES 51 | 0.332 | 1.890 | 9411 | 28 |
| 365 ES 52 | 0.300 | 1.195 | 5654 | 19 |
| 365 ES 53 | 0.309 | 2.078 | 10 427 | 34 |
| 365 ES 55 | 0.290 | 0.102 | — | — |
| 365 ES 56 | 0.307 | 1.854 | 9216 | 30 |
| 365 ES 57 | 0.306 | 1.385 | 6681 | 22 |
| 365 ES 58 | 0.297 | 2.091 | 10 497 | 35 |
| 365 ES 59 | 0.305 | 2.411 | 12 227 | 40 |
| 365 ES 60 | 0.306 | 2.217 | 11 178 | 37 |
| 365 ES 61 | 0.310 | 1.901 | 9470 | 31 |
| 365 ES 62 | 0.310 | 1.276 | 6092 | 20 |
| 365 ES 63 | 0.298 | 1.728 | 8535 | 29 |
| 365 ES 64 | 0.313 | 0.928 | 4211 | 13 |
| 365 ES 65 | 0.320 | 0.159 | 54 | 0 |
| 365 ES 66 | 0.314 | 2.729 | 13 946 | 44 |
| 365 ES 67 | 0.303 | 1.871 | 9308 | 31 |
| 365 ES 68 | 0.293 | 2.078 | 10 427 | 36 |
| 365 ES 69 | 0.304 | 1.950 | 9735 | 32 |
| 365 ES 70 | 0.287 | 1.665 | 8195 | 29 |
| 365 ES 71 | 0.308 | 1.139 | 5351 | 17 |
| 365 ES 72 | 0.211 | 0.122 | — | — |
| 365 ES 73 | 0.190 | 1.754 | 8676 | 46 |
| 365 ES 74 | 0.306 | 4.000 | 20 816 | 68 |
| 365 ES 75 | 0.314 | 0.107 | — | — |
| 365 ES 76 | 0.292 | 2.710 | 13 843 | 47 |
| 365 ES 77 | 0.306 | 2.366 | 11 984 | 39 |
| 365 ES 78 | 0.305 | 0.115 | — | — |
| 365 ES 79 | 0.314 | 2.921 | 14 984 | 48 |
| 365 ES 80 | 0.308 | 2.693 | 13 751 | 45 |
| 365 ES 81 | 0.299 | 1.476 | 7173 | 24 |
| 365 ES 82 | 0.291 | 2.033 | 10 184 | 35 |
| 365 ES 83 | 0.303 | 0.102 | — | — |
| 365 ES 84 | 0.321 | 2.562 | 13 043 | 41 |
| 365 ES 85 | 0.308 | 0.690 | 2924 | 9 |
| 365 ES 86 | 0.313 | 2.102 | 10 557 | 34 |
| 365 ES 87 | 0.306 | 3.381 | 17 470 | 57 |
| 365 ES 88 | 0.305 | 1.896 | 9443 | 31 |
| 365 ES 89 | 0.320 | 2.343 | 11 859 | 37 |
| 365 ES 90 | 0.299 | 0.106 | — | — |
| 365 ES 91 | 0.306 | 0.106 | — | — |
| 365 ES 92 | 0.303 | 3.268 | 16 859 | 56 |
| 365 ES 93 | 0.298 | 2.458 | 12 481 | 42 |
| 365 ES 94 | 0.301 | 1.605 | 7870 | 26 |
| 365 ES 95 | 0.304 | 0.114 | — | — |
| 365 ES 96 | 0.304 | 3.000 | 15 411 | 51 |
| 365 ES 97 | 0.307 | 3.058 | 15 724 | 51 |
| 365 ES 98 | 0.306 | 4.000 | 20 816 | 68 |
| 365 ES 99 | 0.314 | 2.817 | 14 422 | 46 |
| 365 ES 100 | 0.302 | 0.119 | — | — |
| 365 ES 101 | 0.307 | 1.591 | 7795 | 25 |
| 365 ES 102 | 0.302 | 0.114 | — | — |
| Wild type 1 | 0.305 | 0.111 | — | — |
| Wild type 2 | 0.300 | 0.114 | — | — |
| Wild type 3 | 0.308 | 0.123 | — | — | c) Leaves of Potato Plants of Line 365 ES

From various selected potato plants of line 365 ES which had been cultivated in soil in 6 cm pots in a greenhouse, in each case 1 leaf was harvested and frozen in liquid nitrogen. The plant material was then comminuted in a laboratory oscillating bead mill (model MM200, Retsch, Germany), and in each case 200 µl of Tris/HCl buffer, pH 7.5, were then added and the suspension was thoroughly mixed and then centrifuged in an Eppendorf table-top centrifuge at 16 000×g for 5 minutes. The supernatant obtained was used for determining the hyaluronan content, which was carried out as described in Example 10b). However, for carrying out these measurements the leaf extract was not diluted. The following results were obtained:

TABLE 3

Detection of hyaluronan in leaves of selected potato plants of the transgenic line 365 ES. Detection was carried out using the method described under General Methods item 6.

| Plant material | Extinction OD450 |
|---|---|
| Wild type | 0.136 |
| 365 ES 64 | 0.663 |
| 365 ES 52 | 0.591 |
| 365 ES 58 | 0.619 | d) Leaves of Tomato Plants of the Line 367 ES

From various selected tomato plants of line 367 ES which had been cultivated in soil in a greenhouse, in each case 1 leaf was harvested and frozen in liquid nitrogen. Further work-up and the determination of the hyaluronan content were carried out as described in Example 10b) for leaves of potato plants. The following results were obtained:

TABLE 4

Detection of hyaluronan in leaves of selected tomato plants of the transgenic line 367 ES. Detection was carried out using the method described under General Methods item 6.

| Plant material | Extinction OD450 |
|---|---|
| Wild type | 0.106 |
| 367 ES 26 | 3.120 |
| 367 ES 38 | 0.097 |
| 367 ES 16 | 0.474 |

After an extended growth period further leaves from independent transformed plants of the line 367 ES were screened for the presence of hyaluronan. Out of 72 plants originating from independent transformation events screened, more than 88% proved to synthesize a significant amount of hyaluronan (at least 0.1 µg hyaluronan per g fresh weight). For each plant the amount of hyaluronan in 2 to 8 leaves was determined separately for each leaf according to the method described under General Methods, item 6. The mean value of the amount of hyaluronan of independent plants varied between 0.1 and 46.8 µg hyaluronan per g fresh weight in leaves. Results for selected plants are shown in the following table:

TABLE 5

Detection of hyaluronan in leaves of selected tomato plants of the transgenic line 367 ES. Detection was carried out using the method described under General Methods item 6. The amount of hyaluronan is shown as the mean value of the values determined for 2 to 8 leaves harvested from each plant and the standard deviation was calculated according to the formula mentioned in General Methods item 9.

| Plant material | Hyaluronan based on the fresh weight of the plant material [µg/g] | Standard deviation |
|---|---|---|
| 367 ES 18 | 15.78 | 25.4 |
| 367 ES 26 | 38.26 | 11.6 |
| 367 ES 41 | 40.40 | 13.3 |
| 367 ES 42 | 138.58 | 47.6 |
| 367 ES 47 | 80.25 | 30.1 |
| Wild type | −0.02 | 0 | e) Fruits of Tomato Plants of the Line 367 ES

From various tomato plants of line 367 ES red fruits from plants which had been cultivated in soil in a greenhouse were harvested. The fresh weight of each single tomato fruit was determined. Each fruit was then chopped into small pieces and homogenized in a Warning Blendor. The homogenized, liquid material was collected and centrifuged for 5 min. at 2200×g. Solid material accumulating at the top of the tube was removed before the clear liquid solution was concentrated to a volume of about 2 ml by using centrifugal membrane filtration (Amicon, 10000 NMWL, Prod. Nr. UCF8 010 96) at 2200×g. The hyaluronan concentration of the concentrate was determined according to the method described under General Methods, item 6.

From 82 independent plants of line 367 ES more than 80% proved to synthesize a significant amount of hyaluronan (at least 0.1 µg hyaluronan per g fresh weight) in fruits. For each plant the amount of hyaluronan in 8 to 10 red fruits was determined separately for each fruit. The mean value of the amount of hyaluronan of independent plants varied between 0.1 and 8.4 µg hyaluronan per g fresh weight in fruits. Results for selected plants are shown in the following table:

TABLE 6

Detection of hyaluronan in fruits of selected tomato plants of the transgenic line 367 ES. Detection was carried out using the method described under General Methods item 6. The amount of hyaluronan is shown as the mean value of the values determined for 8 to 10 fruits harvested from each plant and the standard deviation was calculated according to the formula mentioned in General Methods item 9.

| Plant material | Hyaluronan based on the fresh weight of the plant material [µg/g] | Standard deviation |
|---|---|---|
| 367 ES 18 | 4.61 | 3.7 |
| 367 ES 26 | 18.97 | 5.3 |
| 367 ES 41 | 14.21 | 9.8 |
| 367 ES 42 | 6.92 | 1.3 |
| 367 ES 44 | 5.58 | 3.5 |
| 367 ES 47 | 6.44 | 1.1 |
| Wild type | −0.02 | 0 |

The promoter of the patatin B33 gene used for expressing hyaluronan synthase in the potato plants of line 365 ES and in tomato plants of line 367 ES is activated not only in potato tubers or in tomato fruits, but, in the presence of high sucrose concentrations, also in other tissues of the plants in question. Accordingly, the good light conditions present in the greenhouse during the cultivation of the potato plants of the line 365 ES and the tomato plants of the line 367 ES evidently resulted in the expression of hyaluronan synthase even in leaf tissue, and it was therefore possible to isolate hyaluronan from these tissues of the plants in question, too. However, the amount of hyaluronan which could be isolated from leaves was significantly lower than that which could be isolated from tubers of the plants in question.

f) Immature Rice Seeds

Immature rice seeds (5 to 10 days after pollination) produced by individual plants of the line OS-pBA16, cultivated in soil in the greenhouse were collected, frozen in liquid nitrogen and stored at −80° C. Three grains frozen grains of each individual plant were selected randomly, the endosperm was squeezed out, pooled weighted, and frozen in liquid nitrogen again. The sample was broken up with a Ball mill (Modell MM200, Firma Retsch, Germany), 100 µl Water was added, the homogenate was mixed, centrifuged (13000×g, 5 min) and the hyaluronan concentration of each sample was determined according to the method described under General Methods, item 6.

Out of 37 seed pools, each comprising 3 immature seeds from independent plants of line OS-pBA16 more than 70% proved to synthesize a significant amount of hyaluronan (at least 0.1 µg hyaluronan per g fresh weight) in seeds. The amount of hyaluronan in seed pools prepared from independent rice plants varied between 0.1 and 15.7 µg hyaluronan per g fresh weight. Results for seed pools each prepared from independent plants are shown in the following table:

TABLE 7

Detection of hyaluronan in seed pools, each prepared from independent plants of the transgenic line OS-pBA16. Detection was carried out using the method described under General Methods item 6.

| Plant material | Hyaluronan based on the fresh weight of the plant material [µg/g] |
| --- | --- |
| OS-pBA16 0612-00102 | 7.30 |
| OS-pBA16 0612-00102 | 0.54 |
| OS-pBA16 0612-00201 | 12.16 |
| OS-pBA16 0612-00401 | 1.12 |
| OS-pBA16 0612-00402 | 7.28 |
| OS-pBA16 0612-00502 | 0.08 |
| OS-pBA16 0612-00601 | 0.37 |
| OS-pBA16 0612-00701 | 0.66 |
| OS-pBA16 0612-00702 | 0.03 |
| OS-pBA16 0612-00801 | 2.48 |
| OS-pBA16 0612-00802 | 3.84 |
| OS-pBA16 0612-00902 | 0.02 |
| OS-pBA16 0612-01001 | 0.02 |
| OS-pBA16 0612-01201 | 1.71 |
| OS-pBA16 0612-01202 | 0.11 |
| OS-pBA16 0612-01301 | 5.84 |
| OS-pBA16 0612-01401 | 0.25 |
| OS-pBA16 0612-01402 | 0.11 |
| OS-pBA16 0612-01501 | 0.16 |
| OS-pBA16 0612-01601 | 1.12 |
| Wild type-1 | 0.01 |
| Wild type-2 | 0.02 |
| Wild type-3 | 0.02 |
| OS-pBA16 0613-00101 | 4.43 |
| OS-pBA16 0613-00102 | 1.95 |
| OS-pBA16 0613-00301 | 0.25 |
| OS-pBA16 0613-00401 | 15.72 |
| OS-pBA16 0613-00402 | 0.38 |
| OS-pBA16 0613-00502 | 0.87 |
| OS-pBA16 0613-00601 | 0.02 |
| OS-pBA16 0613-00602 | 0.01 |
| OS-pBA16 0613-00701 | 0.23 |
| OS-pBA16 0613-00702 | 0.80 |
| OS-pBA16 0613-00801 | 1.72 |
| OS-pBA16 0613-00802 | 0.15 |
| OS-pBA16 0613-00902 | 0.02 |
| OS-pBA16 0613-01001 | 0.02 |
| OS-pBA16 0613-01002 | 0.01 |
| OS-pBA16 0613-01102 | 0.24 |
| OS-pBA16 0613-01202 | 9.48 |
| OS-pBA16 0613-01301 | 13.44 |
| OS-pBA16 0613-01302 | 9.79 |
| OS-pBA16 0613-01501 | 0.63 |
| OS-pBA16 0613-01502 | 6.78 | g) Rice Flour 20-25 mature seeds were harvested from each transformed plant. Husks were removed by a dehusker (Laboratory Paddy sheller, Grainman, Miami, Fla., USA) and brown rice grain was milled with a laboratory mill (Cyclotec, Sample mill, Foss, Denmark). To about 40 mg of the obtained rice flour from the pooled seeds of each independent plant, 1 ml water was added, the sample was mixed, centrifuged (13000×g, 5 min) and the hyaluronan concentration of the supernatant of each sample was determined according to the method described under General Methods, item 6. Results for selected flour samples prepared from independent plants are shown in the following table:

TABLE 8

Detection of hyaluronan in rice flour, sample prepared from 3 seeds of each independent plant of the transgenic line OS-pBA16. Detection was carried out using the method described under General Methods item 6.

| Plant material | Hyaluronan based on the weight of the plant material [µg/g] |
| --- | --- |
| OS-pBA16 0612-00101 | 2.03 |
| OS-pBA16 0612-00102 | 1.19 |
| OS-pBA16 0612-00201 | 1.94 |
| OS-pBA16 0612-00402 | 4.24 |
| OS-pBA16 0612-00502 | 1.19 |
| OS-pBA16 0612-00601 | 1.64 |
| OS-pBA16 0612-00602 | 2.51 |
| OS-pBA16 0612-00701 | 0.87 |
| OS-pBA16 0612-00702 | 1.04 |
| OS-pBA16 0612-00801 | 3.61 |
| OS-pBA16 0612-00802 | 3.88 |
| OS-pBA16 0612-00902 | 1.02 |
| OS-pBA16 0612-01001 | 0.58 |
| OS-pBA16 0612-01201 | 4.86 |
| OS-pBA16 0612-01202 | 2.96 |
| OS-pBA16 0612-01301 | 11.30 |
| OS-pBA16 0612-01401 | 1.64 |
| OS-pBA16 0612-01402 | 1.50 |
| OS-pBA16 0612-01501 | 4.54 |
| OS-pBA16 0612-01601 | 1.90 |
| OS-pBA16 0613-00101 | 3.46 |
| OS-pBA16 0613-00102 | 3.94 |
| OS-pBA16 0613-00301 | 3.32 |
| OS-pBA16 0613-00401 | 5.21 |
| OS-pBA16 0613-00402 | 3.45 |
| OS-pBA16 0613-00502 | 5.20 |
| OS-pBA16 0613-00601 | 0.83 |
| OS-pBA16 0613-00602 | 0.77 |
| OS-pBA16 0613-00701 | 2.63 |
| OS-pBA16 0613-00702 | 3.77 |
| OS-pBA16 0613-00801 | 1.55 |
| OS-pBA16 0613-00802 | 2.81 |
| OS-pBA16 0613-00902 | 2.65 |
| OS-pBA16 0613-01001 | 1.06 |
| OS-pBA16 0613-01002 | 0.59 |
| OS-pBA16 0613-01102 | 1.19 |
| OS-pBA16 0613-01202 | 10.18 |
| OS-pBA16 0613-01301 | 5.02 |
| OS-pBA16 0613-01302 | 3.84 |
| OS-pBA16 0613-01501 | 4.00 |
| OS-pBA16 0613-01502 | 5.63 |
| OS-pBA16 0613-000101 | 0.63 |
| OS-pBA16 0613-000103 | 0.58 |
| OS-pBA16 0613-000104 | 0.87 |

11. Verification of Hyaluronan a) Indirect Detection by Hyaluronidase Digestion

200 µl of hyaluronidase buffer were added to about 0.1 g of tuber material of selected plants of the line 365 ES which had been cultivated as described in Example 10a), and the material was worked up as in General Methods item 4. Half of the supernatant obtained from the centrifugation was then taken off, and hyaluronidase was added. The batch was incubated at 37° C. for 30 minutes, and the reaction mixture was then centrifuged again at 16 000×g for 5 minutes (see General Methods item 4). The supernatant obtained in this manner was used for determining the hyaluronan content. The other half of the solution which had been isolated from plants, but where no hyaluronidase had been added, was treated in the same manner. The following results were obtained:

TABLE 9

Proof of the digestibility of hyaluronan isolated from tubers of selected potato plants of the transgenic line 365 ES. The detection of the presence of hyaluronan was carried out in in each case two aliquots of identical extracts, where hyaluronidase (HAidase) was added to one aliquot of the identical extract but not to the corresponding aliquot, using the method described under General Methods item 6.

|  | Plant material | Extinction OD450 |
|---|---|---|
| without HAidase digestion | Wild type | 0.104 |
|  | 365 ES 87 | 0.910 |
|  | 365 ES 98 | 0.797 |
|  | 365 ES 78 | 0.106 |
| with HAidase digestion | Wild type | 0.095 |
|  | 365 ES 87 | 0.097 |
|  | 365 ES 98 | 0.098 |
|  | 365 ES 78 | 0.104 | b) Detection of the Presence of Hyaluronan by NMR Spectroscopy

Figure 3:
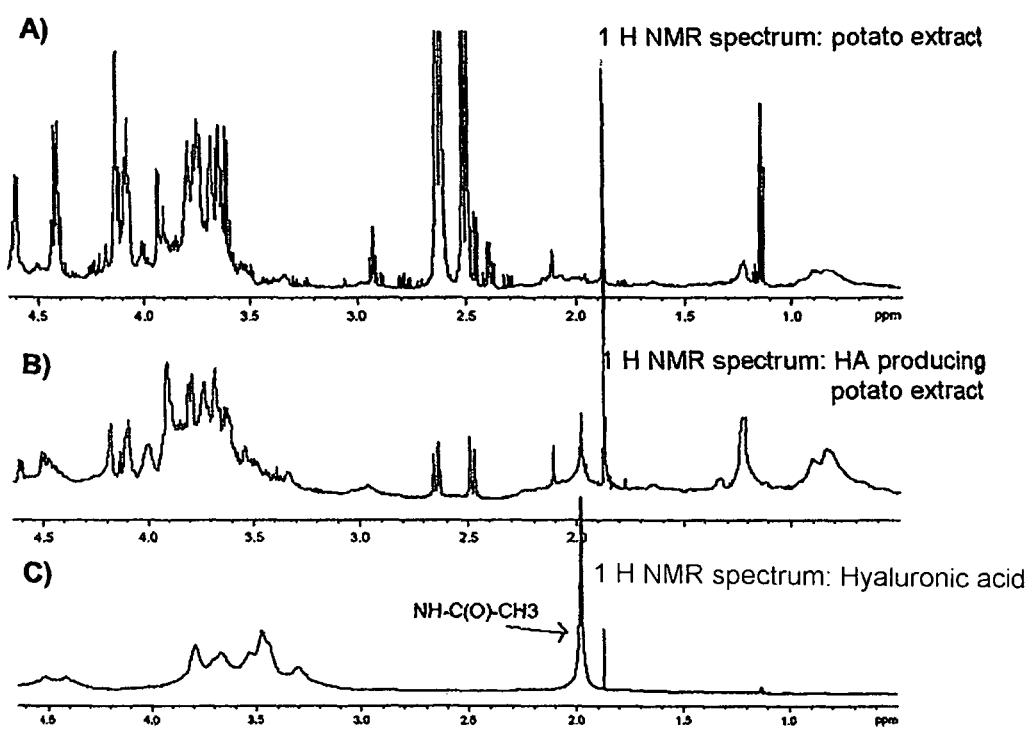
FIG. 3: 1H-NMR spectra of potato extract from tubers of a wild-type plant (A), tubers of a transgenic line which synthesizes hyaluronan (B) and of hyaluronan isolated from rooster comb (Sigma, Prod. No. H5388).
Figure 4:
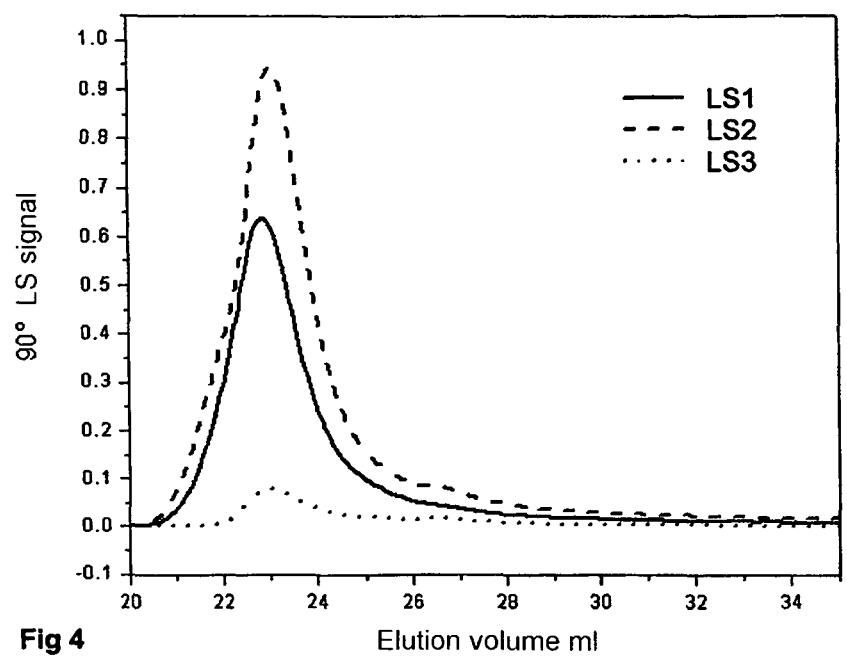
FIG. 4: Chromatogram of potato extract from tubers of a wild-type plant with hyaluronan isolated from rooster comb (Sigma, Prod. No. H5388) mixed in (LS 1), potato extract from tubers of transgenic plants which synthesize hyaluronan (LS 2) and hyaluronidase-digested potato extract from tubers of transgenic plants which synthesize hyaluronan (LS 3). What is shown is the light-scattering signal.
Figure 5:
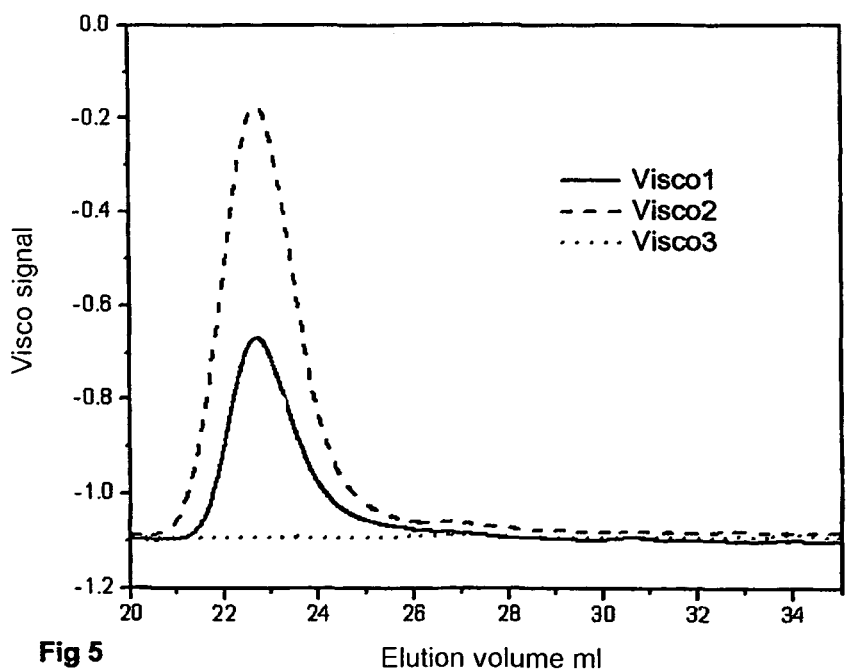
FIG. 5: Chromatogram of potato extract from tubers of a wild-type plant with hyaluronan isolated from rooster comb (Sigma, Prod. No. H5388) mixed in (Visco 1) potato extract from tubers of transgenic plants which synthesize hyaluronan (Visco 2) and hyaluronidase-digested potato extract from tubers of transgenic plants which synthesize hyaluronan (Visco 3). What is shown is the signal of the viscosity detector.

About 20 g of tuber material from hyaluronan-producing plants of the line 365 ES were peeled, cut into pieces of a size of about 1 cm$^3$ and, after addition of 20 ml of water (demineralized, conductivity≥18 MΩ), comminuted in a Warring blender at maximum speed for about 30 seconds. The cell debris was then removed using a tea sieve. The removed cell debris was resuspended in 60 ml of water (demineralized, conductivity≥18 MΩ) and again removed using a tea sieve. The two suspensions obtained (50 ml+60 ml) were combined and centrifuged at 13 000×g for 15 minutes. NaCl was added to the centrifugation supernatant obtained to a final concentration of 1%. After the NaCl had gone into solution, precipitation was caused by adding twice the volume of ethanol followed by thorough mixing and incubation at −20° C. overnight. The mixture was then centrifuged at 13 000×g for 15 minutes. The sedimented precipitate obtained after this centrifugation was dissolved in 10 ml of water (demineralized, conductivity≥18 MΩ), and once more, NaCl was added to a final concentration of 1%. Another precipitation was carried out by adding twice the volume of ethanol, mixing thoroughly and incubating at −20° C. overnight. This was followed by centrifugation, dissolution and re-precipitation under the conditions just described. The precipitate obtained after the final centrifugation was dissolved in about 1 ml of water (demineralized, conductivity≥18 MΩ) and used for the 1H-NMR analysis under the conditions given in General Methods item 7. (See FIG. 3B)).

In parallel, potato tubers of non-transformed wild-type plants were worked up in the same manner as just described and likewise subjected to a 1H-NMR analysis (see FIG. 3A)). Furthermore, as comparative substance, hyaluronan isolated from rooster combs (Sigma, Prod. No. H5388) was subjected to a 1H-NMR analysis (see FIG. 3C)).

Evaluation of the 1H-NMR analysis clearly showed the presence of an NH—C(O)—CH$_3$ group characteristic for N-acetyl-glucosamine in the extracts of the hyaluronan-producing plants and in the comparison sample (hyaluronan isolated from rooster combs), but not in the extracts from wild-type plants.

Figure 2:
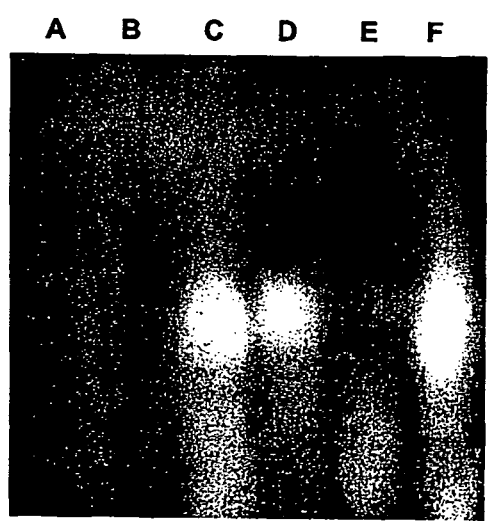
FIG. 2: shows the separation of different hyaluronan-containing samples using an agarose gel. Hyaluronan isolated from rooster comb (Sigma, Prod. No. H5388) was applied in lane A, hyaluronan isolated from the culture supernatant of a fermentation of *Streptococcus* sp. (Calbiochem, Prod. No. 385908) was applied in lane B, extracts of a tuber of a wild-type plant were applied in lane C, extracts of a tuber of the transgenic line 365 ES 66 were applied in lane D, extracts of a tuber of the transgenic line 365 ES 44 were applied in lane E and extracts of a tuber of the transgenic line 365 ES 78, which does not synthesize hyaluronan, were applied in lane F.

12. Molecular Weight Analysis of the Hyaluronan Produced in Plants a) By agarose Gel Electrophoresis Work-up of the plant material was carried out as described under General Methods item 4. To this end, about 0.5 g of tuber material of selected plants of the line 365 ES was worked up in a total of 600 µl of water (demnineralized, conductivity≥18 MΩ). The plant material was then separated by agarose gel electrophoresis and stained according to the method described under General Methods item 8.a). A picture of the agarose gel obtained is shown in FIG. 2. The following samples were applied to the agarose gel:

Lane A: about 3 µg of hyaluronan isolated from rooster combs (Sigma, Prod. No. H5388), Lane B: about 3 µg of hyaluronan isolated from the culture supernatant of a fermentation of *Streptococcus* sp. (Calbiochem, Prod. No. 385908)

Lane C: 20 µl of the extract of a tuber from a wild-type plant

Lane D: 20 µl of the extract of a tuber from the line 365 ES 66

Lane E: 20 µl of the extract of a tuber from the line 365 ES 44

Lane F: 20 µl of the extract of a tuber from the line 365 ES 78

As is evident from Table 2, lines 365 ES 66 and 365 ES 74 are plants which produce hyaluronan, whereas line 365 ES 78 does not produce any hyaluronan. This is confirmed by the agarose gel analysis. Furthermore, on the agarose gel, it can be seen that the hyaluronan isolated from plant material, in contrast to hyaluronan isolated from rooster combs and in contrast to hyaluronan prepared by fermentation of *Streptococcus* species, has a considerably narrower molecular weight distribution.

b) By GPC Analysis

Tuber material of the following plants was used for isolating hyaluronan:

365 ES 2, 365 ES 18, 365 ES 44, 365 ES 58, 365 ES 74, 365 ES 92, 365 ES 4, 365 ES 19, 365 ES 47, 365 ES 59, 365 ES 76, 365 ES 93, 365 ES 5, 365 ES 21, 365 ES 49, 365 ES 60, 365 ES 79, 365 ES 96, 365 ES 6, 365 ES 22, 365 ES 50, 365 ES 61, 365 ES 80, 365 ES 98, 365 ES 23, 365 ES 51, 365 ES 67, 365 ES 81, 365 ES 99, 365 ES 9, 365 ES 33, 365 ES 52, 365 ES 68, 365 ES 84, 365 ES 101, 365 ES 10, 365 ES 41, 365 ES 53, 365 ES 70, 365 ES 85, 365 ES 16, 365 ES 44, 365 ES 57, 365 ES 71, 365 ES 87.

The tuber material originating from these plants was purified as described under General Methods item 5 (sample 2).

In parallel, potato tubers (about 100 gram) of wild-type plants were worked up in the same manner but, prior to comminution using a Warring blender, 5 mg of hyaluronan from rooster scomb (Sigma, Prod. No. H5388) were added to the peeled and diced tubers (sample 1). Furthermore, part of sample 1 was digested with hyaluronidase (see Example 11 a)) prior to GPC analysis (sample 3).

GPC analysis was carried out as described under General Methods item 8 b). The following results were obtained:

TABLE 10

Molecular weight determination (Mw) of hyaluronan isolated from tubers of wild-type potato plants admixed with hyaluronan isolated from rooster combs (sample 1), tubers of transgenic plants of the line 365 ES (sample 2) and tubers of transgenic plants of the line 365 ES, where the isolated hyaluronan had been subjected to hyaluronidase digestion prior to analysis (sample 3).

| Sample | Approximate amount of powder [mg] | Hyaluronan concentration [mg · ml$^{-1}$] | $M_w$ of hyaluronan [·10$^6$ g mol$^{-1}$] |
|---|---|---|---|
| 1 | 10 | 0.145 | 5.84 |
| 2 | 4.5 | 0.181 | 7.30 |
| 3 | 10 | — |  |

The values for the molecular weight obtained for added rooster comb hyaluronan (sample 1) agree with the values published in the literature (Lapcik et al., 1998, Chemical Reviews 98(8), 2663-2684).

Accordingly, the results show unambiguously that the hyaluronan isolated from transgenic plants has a significantly higher molecular weight than the hyaluronan which had been isolated from rooster combs and was treated under identical conditions.

All patents, patent applications, publications and databsase accession numbers referenced throughout this application are hereby incorporated herein by reference in their entireties.

What is claimed is:

1. A plant cell comprising a nucleic acid molecule which is stably integrated into its genome and codes for a hyaluronan synthase, wherein said plant cell produces hyaluronan.

2. The plant cell of claim 1, wherein said nucleic acid is linked to a promoter.

3. The plant cell of claim 2, wherein said promoter is a tissue-specific promoter.

4. The plant cell of claim 1, wherein said nucleic acid is included in a vector.

5. The plant cell of claim 1, wherein said nucleic acid is included in a plasmid.

6. The plant cell of claim 5, wherein said plasmid is DSM16664 or DSM16665.

7. The plant cell of claim 1, wherein said nucleic acid molecule codes for a hyaluronan synthase having the amino acid sequence of SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 20, SEQ ID NO 22, SEQ ID NO 24, SEQ ID NO 26, SEQ ID NO 28, SEQ ID NO 30, SEQ ID NO 32, SEQ ID NO 34, SEQ ID NO 36, SEQ ID NO 38, SEQ ID NO 40, SEQ ID NO 42, SEQ ID NO 44, SEQ ID NO 46, SEQ ID NO 48, SEQ ID NO 50, SEQ ID NO 52, SEQ ID NO 54, SEQ ID NO 56, SEQ ID NO 58, SEQ ID NO 60 or SEQ ID NO 62.

8. The plant cell of claim 1, wherein said nucleic acid molecule codes for a hyaluronan synthase having the amino acid sequence of SEQ ID NO 2, SEQ ID NO 4, SEQ ID NO 6 or SEQ ID NO 8.

9. The plant cell of claim 1, wherein said nucleic acid molecule is SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 19, SEQ ID NO 21, SEQ ID NO 23, SEQ ID NO 25, SEQ ID NO 27, SEQ ID NO 29, SEQ ID NO 31, SEQ ID NO 33, SEQ ID NO 35, SEQ ID NO 37, SEQ ID NO 39, SEQ ID NO 41, SEQ ID NO 43, SEQ ID NO 45, SEQ ID NO 47, SEQ ID NO 49, SEQ ID NO 51, SEQ ID NO 53, SEQ ID NO 55, SEQ ID NO 57, SEQ ID NO 59 or SEQ ID NO 61.

10. The plant cell of claim 1, wherein said nucleic acid molecule is SEQ ID NO 1, SEQ ID NO 3, SEQ ID NO 5 or SEQ ID NO 7.

11. A plant comprising the plant cell according to claim 1.

12. Propagation material comprising the plant cell of claim 1.

13. Harvestable plant parts comprising the plant cell of claim 1.

14. The plant of claim 11, wherein said plant is potato, tomato, rice, maize or wheat.

15. A method for preparing a plant which synthesizes hyaluronan, comprising
   a) integrating a nucleic acid molecule coding for a hyaluronan synthase into the genome of a plant cell;
   b) regenerating a plant from plant cells of step a); and
   c) optionally, generating further plants with the aid of the plants of step b).

16. A method for preparing hyaluronan, comprising extracting hyaluronan from the plant cells according to claim 1.

17. A recombinant nucleic acid molecule comprising a nucleic acid sequence which initiates transcription in a plant cell and a nucleic acid molecule which codes for a hyaluronan synthase.

18. The recombinant nucleic acid molecule of claim 17, wherein said nucleic acid which initiates transcription is a promoter.

19. The recombinant nucleic acid of claim 18, wherein said promoter is a tissue-specific promoter.

20. The recombinant nucleic acid of claim 19, wherein the promoter is a tuber-, fruit- or seed-specific promoter.

21. The plant cell of claim 1, wherein said nucleic acid molecule codes for a hyaluronan synthase Class I.

22. The plant cell of claim 1, wherein said nucleic acid molecule codes for a hyaluronan synthase from vertebrates or a viral hyaluronan synthase.

23. The plant cell of claim 22, wherein said nucleic acid molecule codes for human hyaluronan synthase 3.

24. The plant cell of claim 22, wherein said nucleic acid molecule codes for a hyaluronan synthase of *Paramecium bursaria Chlorella* virus 1.

25. The plant of claim 11, wherein said plant is a potato plant and produces at least 29 µg per grain fresh weight of its tuber.

26. The plant of claim 11, wherein said plant is a tomato plant and produces at least 4 µg hyaluronan per gram fresh weight of its fruit.

* * * * *

```
                        SEQUENCE LISTING

<160> NUMBER OF SEQ ID NOS: 68

<210> SEQ ID NO 1
<211> LENGTH: 1707
<212> TYPE: DNA
<213> ORGANISM: Paramecium bursaria Chlorella Virus 1
<220> FEATURE:
<221> NAME/KEY: CDS
<222> LOCATION: (1)..(1707)
<300> PUBLICATION INFORMATION:
<308> DATABASE ACCESSION NUMBER: PB42580
<309> DATABASE ENTRY DATE: 1995-12-24
<313> RELEVANT RESIDUES IN SEQ ID NO: (50903)..(52609)

<400> SEQUENCE: 1 atg ggt aaa aat ata atc ata atg gtt tcg tgg tac acc atc ata act      48
Met Gly Lys Asn Ile Ile Ile Met Val Ser Trp Tyr Thr Ile Ile Thr
1               5                   10                  15 tca aat cta atc gcg gtt gga gga gcc tct cta atc ttg gct ccg gca      96
Ser Asn Leu Ile Ala Val Gly Gly Ala Ser Leu Ile Leu Ala Pro Ala
                20                  25                  30 att act ggg tat gtt cta cat tgg aat att gct ctc tcg aca atc tgg     144
Ile Thr Gly Tyr Val Leu His Trp Asn Ile Ala Leu Ser Thr Ile Trp
            35                  40                  45 gga gta tca gct tat ggt att ttc gtt ttt ggg ttt ttc ctt gca caa     192
Gly Val Ser Ala Tyr Gly Ile Phe Val Phe Gly Phe Phe Leu Ala Gln
    50                  55                  60 gtt tta ttt tca gaa ctg aac agg aaa cgt ctt cgc aag tgg att tct     240
Val Leu Phe Ser Glu Leu Asn Arg Lys Arg Leu Arg Lys Trp Ile Ser
65                  70                  75                  80 ctc aga cct aag ggt tgg aat gat gtt cgt ttg gct gtg atc att gct     288
Leu Arg Pro Lys Gly Trp Asn Asp Val Arg Leu Ala Val Ile Ile Ala
                85                  90                  95 gga tat cgc gag gat cct tat atg ttc cag aag tgc ctc gag tct gta     336
Gly Tyr Arg Glu Asp Pro Tyr Met Phe Gln Lys Cys Leu Glu Ser Val
            100                 105                 110 cgt gac tct gat tat ggc aac gtt gcc cgt ctg att tgt gtg att gac     384
Arg Asp Ser Asp Tyr Gly Asn Val Ala Arg Leu Ile Cys Val Ile Asp
        115                 120                 125 ggt gat gag gac gat gat atg agg atg gct gcc gtt tac aag gcg atc     432
Gly Asp Glu Asp Asp Asp Met Arg Met Ala Ala Val Tyr Lys Ala Ile
    130                 135                 140 tac aat gat aat atc aag aag ccc gag ttt gtt ctg tgt gag tca gac     480
Tyr Asn Asp Asn Ile Lys Lys Pro Glu Phe Val Leu Cys Glu Ser Asp
145                 150                 155                 160 gac aag gaa ggt gaa cgc atc gac tct gat ttc tct cgc gac att tgt     528
Asp Lys Glu Gly Glu Arg Ile Asp Ser Asp Phe Ser Arg Asp Ile Cys
                165                 170                 175 gtc ctc cag cct cat cgt gga aaa cgg gag tgt ctt tat act ggg ttt     576
Val Leu Gln Pro His Arg Gly Lys Arg Glu Cys Leu Tyr Thr Gly Phe
            180                 185                 190 caa ctt gca aag atg gac ccc agt gtc aat gct gtc gtt ctg att gac     624
Gln Leu Ala Lys Met Asp Pro Ser Val Asn Ala Val Val Leu Ile Asp
        195                 200                 205
```

```
agc gat acc gtt ctc gag aag gat gct att ctg gaa gtt gta tac cca      672
Ser Asp Thr Val Leu Glu Lys Asp Ala Ile Leu Glu Val Val Tyr Pro
    210                 215                 220 ctt gca tgc gat ccc gag atc caa gcc gtt gca ggt gag tgt aag att      720
Leu Ala Cys Asp Pro Glu Ile Gln Ala Val Ala Gly Glu Cys Lys Ile
225                 230                 235                 240 tgg aac aca gac act ctt ttg agt ctt ctc gtc gct tgg cgg tac tat      768
Trp Asn Thr Asp Thr Leu Leu Ser Leu Leu Val Ala Trp Arg Tyr Tyr
                245                 250                 255 tct gcg ttt tgt gtg gag agg agt gcc cag tct ttt ttc agg act gtt      816
Ser Ala Phe Cys Val Glu Arg Ser Ala Gln Ser Phe Phe Arg Thr Val
            260                 265                 270 cag tgc gtt ggg ggg cca ctg ggt gcc tac aag att gat atc att aag      864
Gln Cys Val Gly Gly Pro Leu Gly Ala Tyr Lys Ile Asp Ile Ile Lys
        275                 280                 285 gag att aag gac ccc tgg att tcc cag cgc ttt ctt ggt cag aag tgt      912
Glu Ile Lys Asp Pro Trp Ile Ser Gln Arg Phe Leu Gly Gln Lys Cys
    290                 295                 300 act tac ggt gac gac cgc cgg cta acc aac gag atc ttg atg cgt ggt      960
Thr Tyr Gly Asp Asp Arg Arg Leu Thr Asn Glu Ile Leu Met Arg Gly
305                 310                 315                 320 aaa aag gtt gtg ttc act cca ttt gct gtt ggt tgg tct gac agt ccg     1008
Lys Lys Val Val Phe Thr Pro Phe Ala Val Gly Trp Ser Asp Ser Pro
                325                 330                 335 acc aat gtg ttt cgg tac atc gtt cag cag acc cgc tgg agt aag tcg     1056
Thr Asn Val Phe Arg Tyr Ile Val Gln Gln Thr Arg Trp Ser Lys Ser
            340                 345                 350 tgg tgc cgc gaa att tgg tac acc ctc ttc gcc gcg tgg aag cac ggt     1104
Trp Cys Arg Glu Ile Trp Tyr Thr Leu Phe Ala Ala Trp Lys His Gly
        355                 360                 365 ttg tct gga att tgg ctg gcc ttt gaa tgt ttg tat caa att aca tac     1152
Leu Ser Gly Ile Trp Leu Ala Phe Glu Cys Leu Tyr Gln Ile Thr Tyr
    370                 375                 380 ttc ttc ctc gtg att tac ctc ttt tct cgc cta gcc gtt gag gcc gac     1200
Phe Phe Leu Val Ile Tyr Leu Phe Ser Arg Leu Ala Val Glu Ala Asp
385                 390                 395                 400 cct cgc gcc cag aca gcc acg gtg att gtg agc acc acg gtt gca ttg     1248
Pro Arg Ala Gln Thr Ala Thr Val Ile Val Ser Thr Thr Val Ala Leu
                405                 410                 415 att aag tgt ggg tat ttt tca ttc cga gcc aag gat att cgg gcg ttt     1296
Ile Lys Cys Gly Tyr Phe Ser Phe Arg Ala Lys Asp Ile Arg Ala Phe
            420                 425                 430 tac ttt gtg ctt tat aca ttt gtt tac ttt ttc tgt atg att ccg gcc     1344
Tyr Phe Val Leu Tyr Thr Phe Val Tyr Phe Phe Cys Met Ile Pro Ala
        435                 440                 445 agg att act gca atg atg acg ctt tgg gac att ggc tgg ggt act cgc     1392
Arg Ile Thr Ala Met Met Thr Leu Trp Asp Ile Gly Trp Gly Thr Arg
    450                 455                 460 ggt gga aac gag aag cct tcc gtt ggc acc cgg gtc gct ctg tgg gca     1440
Gly Gly Asn Glu Lys Pro Ser Val Gly Thr Arg Val Ala Leu Trp Ala
465                 470                 475                 480 aag caa tat ctc att gca tat atg tgg tgg gcc gcg gtt gtt ggc gct     1488
Lys Gln Tyr Leu Ile Ala Tyr Met Trp Trp Ala Ala Val Val Gly Ala
                485                 490                 495 gga gtt tac agc atc gtc cat aac tgg atg ttc gat tgg aat tct ctt     1536
Gly Val Tyr Ser Ile Val His Asn Trp Met Phe Asp Trp Asn Ser Leu
            500                 505                 510 tct tat cgt ttt gct ttg gtt ggt att tgt tct tac att gtt ttt att     1584
Ser Tyr Arg Phe Ala Leu Val Gly Ile Cys Ser Tyr Ile Val Phe Ile
        515                 520                 525
```

| | | | | | | | | | | | | | | | | |
|---|---|---|---|---|---|---|---|---|---|---|---|---|---|---|---|---|
| gtt | att | gtg | ctg | gtg | gtt | tat | ttc | acc | ggc | aaa | att | acg | act | tgg | aat | 1632 |
| Val | Ile | Val | Leu | Val | Val | Tyr | Phe | Thr | Gly | Lys | Ile | Thr | Thr | Trp | Asn | |
| | 530 | | | | 535 | | | | | 540 | | | | | | |
| ttc | acg | aag | ctt | cag | aag | gag | cta | atc | gag | gat | cgc | gtt | ctg | tac | gat | 1680 |
| Phe | Thr | Lys | Leu | Gln | Lys | Glu | Leu | Ile | Glu | Asp | Arg | Val | Leu | Tyr | Asp | |
| 545 | | | | 550 | | | | | 555 | | | | | 560 | | |
| gca | act | acc | aat | gct | cag | tct | gtg | tga | | | | | | | | 1707 |
| Ala | Thr | Thr | Asn | Ala | Gln | Ser | Val | | | | | | | | | |
| | | | 565 | | | | | | | | | | | | | |

<210> SEQ ID NO 2
<211> LENGTH: 568
<212> TYPE: PRT
<213> ORGANISM: Paramecium bursaria Chlorella Virus 1

<400> SEQUENCE: 2

Met Gly Lys Asn Ile Ile Met Val Ser Trp Tyr Thr Ile Ile Thr
1               5                   10                  15

Ser Asn Leu Ile Ala Val Gly Gly Ala Ser Leu Ile Leu Ala Pro Ala
            20                  25                  30

Ile Thr Gly Tyr Val Leu His Trp Asn Ile Ala Leu Ser Thr Ile Trp
        35                  40                  45

Gly Val Ser Ala Tyr Gly Ile Phe Val Phe Gly Phe Phe Leu Ala Gln
    50                  55                  60

Val Leu Phe Ser Glu Leu Asn Arg Lys Arg Leu Arg Lys Trp Ile Ser
65                  70                  75                  80

Leu Arg Pro Lys Gly Trp Asn Asp Val Arg Leu Ala Val Ile Ile Ala
                85                  90                  95

Gly Tyr Arg Glu Asp Pro Tyr Met Phe Gln Lys Cys Leu Glu Ser Val
            100                 105                 110

Arg Asp Ser Asp Tyr Gly Asn Val Ala Arg Leu Ile Cys Val Ile Asp
        115                 120                 125

Gly Asp Glu Asp Asp Met Arg Met Ala Ala Val Tyr Lys Ala Ile
    130                 135                 140

Tyr Asn Asp Asn Ile Lys Lys Pro Glu Phe Val Leu Cys Glu Ser Asp
145                 150                 155                 160

Asp Lys Glu Gly Glu Arg Ile Asp Ser Asp Phe Ser Arg Asp Ile Cys
                165                 170                 175

Val Leu Gln Pro His Arg Gly Lys Arg Glu Cys Leu Tyr Thr Gly Phe
            180                 185                 190

Gln Leu Ala Lys Met Asp Pro Ser Val Asn Ala Val Leu Ile Asp
        195                 200                 205

Ser Asp Thr Val Leu Glu Lys Asp Ala Ile Leu Glu Val Val Tyr Pro
    210                 215                 220

Leu Ala Cys Asp Pro Glu Ile Gln Ala Val Ala Gly Glu Cys Lys Ile
225                 230                 235                 240

Trp Asn Thr Asp Thr Leu Leu Ser Leu Leu Val Ala Trp Arg Tyr Tyr
                245                 250                 255

Ser Ala Phe Cys Val Glu Arg Ser Ala Gln Ser Phe Phe Arg Thr Val
            260                 265                 270

Gln Cys Val Gly Gly Pro Leu Gly Ala Tyr Lys Ile Asp Ile Ile Lys
        275                 280                 285

Glu Ile Lys Asp Pro Trp Ile Ser Gln Arg Phe Leu Gly Gln Lys Cys
    290                 295                 300

Thr Tyr Gly Asp Asp Arg Arg Leu Thr Asn Glu Ile Leu Met Arg Gly
305                 310                 315                 320

```
Lys Lys Val Val Phe Thr Pro Phe Ala Val Gly Trp Ser Asp Ser Pro
            325                 330                 335

Thr Asn Val Phe Arg Tyr Ile Val Gln Gln Thr Arg Trp Ser Lys Ser
            340                 345                 350

Trp Cys Arg Glu Ile Trp Tyr Thr Leu Phe Ala Ala Trp Lys His Gly
            355                 360                 365

Leu Ser Gly Ile Trp Leu Ala Phe Glu Cys Leu Tyr Gln Ile Thr Tyr
            370                 375                 380

Phe Phe Leu Val Ile Tyr Leu Phe Ser Arg Leu Ala Val Glu Ala Asp
385                 390                 395                 400

Pro Arg Ala Gln Thr Ala Thr Val Ile Val Ser Thr Val Ala Leu
            405                 410                 415

Ile Lys Cys Gly Tyr Phe Ser Phe Arg Ala Lys Asp Ile Arg Ala Phe
            420                 425                 430

Tyr Phe Val Leu Tyr Thr Phe Val Tyr Phe Cys Met Ile Pro Ala
            435                 440                 445

Arg Ile Thr Ala Met Met Thr Leu Trp Asp Ile Gly Trp Gly Thr Arg
            450                 455                 460

Gly Gly Asn Glu Lys Pro Ser Val Gly Thr Arg Val Ala Leu Trp Ala
465                 470                 475                 480

Lys Gln Tyr Leu Ile Ala Tyr Met Trp Trp Ala Ala Val Val Gly Ala
            485                 490                 495

Gly Val Tyr Ser Ile Val His Asn Trp Met Phe Asp Trp Asn Ser Leu
            500                 505                 510

Ser Tyr Arg Phe Ala Leu Val Gly Ile Cys Ser Tyr Ile Val Phe Ile
            515                 520                 525

Val Ile Val Leu Val Val Tyr Phe Thr Gly Lys Ile Thr Thr Trp Asn
            530                 535                 540

Phe Thr Lys Leu Gln Lys Glu Leu Ile Glu Asp Arg Val Leu Tyr Asp
545                 550                 555                 560

Ala Thr Thr Asn Ala Gln Ser Val
            565

<210> SEQ ID NO 3
<211> LENGTH: 1707
<212> TYPE: DNA
<213> ORGANISM: Artificial sequence
<220> FEATURE:
<223> OTHER INFORMATION: Synthetic sequence coding for a Paramecium
      bursaria Chlorella Virus 1 Hyaluronansynthase protein
<220> FEATURE:
<221> NAME/KEY: CDS
<222> LOCATION: (1)..(1707)

<400

```
                65                  70                  75                  80
ctt aga cca aag ggg tgg aat gac gtt cgt ctc gct gtc att atc gct          288
Leu Arg Pro Lys Gly Trp Asn Asp Val Arg Leu Ala Val Ile Ile Ala
                    85                  90                  95 ggc tac cgt gaa gat cct tac atg ttt caa aag tgc ttg gaa tca gtt          336
Gly Tyr Arg Glu Asp Pro Tyr Met Phe Gln Lys Cys Leu Glu Ser Val
                100                 105                 110 agg gat agt gat tat ggc aac gtc gct aga ctg atc tgt gtg att gat          384
Arg Asp Ser Asp Tyr Gly Asn Val Ala Arg Leu Ile Cys Val Ile Asp
                    115                 120                 125 gga gat gag gac gac gat atg agg atg gca gct gtt tat aag gct atc          432
Gly Asp Glu Asp Asp Asp Met Arg Met Ala Ala Val Tyr Lys Ala Ile
            130                 135                 140 tat aat gat aac att aag aag cct gaa ttt gtt ctt tgc gag tct gat          480
Tyr Asn Asp Asn Ile Lys Lys Pro Glu Phe Val Leu Cys Glu Ser Asp
145                 150                 155                 160 gac aag gaa gga gaa cgg att gat tca gat ttc tca cgt gat atc tgc          528
Asp Lys Glu Gly Glu Arg Ile Asp Ser Asp Phe Ser Arg Asp Ile Cys
                    165                 170                 175 gtt ctc caa cct cat cgt ggg aag cgt gaa tgt ctt tat aca ggt ttc          576
Val Leu Gln Pro His Arg Gly Lys Arg Glu Cys Leu Tyr Thr Gly Phe
                180                 185                 190 caa ctc gcc aaa atg gac cca tca gtg aac gct gtg gtt ctt atc gat          624
Gln Leu Ala Lys Met Asp Pro Ser Val Asn Ala Val Val Leu Ile Asp
            195                 200                 205 agt gat act gtg ctg gag aaa gat gct atc ttg gag gtt gtt tac cct          672
Ser Asp Thr Val Leu Glu Lys Asp Ala Ile Leu Glu Val Val Tyr Pro
        210                 215                 220 ctt gcc tgt gat cct gaa att caa gct gtg gct gga gag tgc aag atc          720
Leu Ala Cys Asp Pro Glu Ile Gln Ala Val Ala Gly Glu Cys Lys Ile
225                 230                 235                 240 tgg aac aca gat act ctt ctt tct ctg ctt gtc gca tgg aga tat tac          768
Trp Asn Thr Asp Thr Leu Leu Ser Leu Leu Val Ala Trp Arg Tyr Tyr
                    245                 250                 255 tcc gca ttc tgt gtg gag agg agc gct caa tcc ttt ttc cgt acc gtt          816
Ser Ala Phe Cys Val Glu Arg Ser Ala Gln Ser Phe Phe Arg Thr Val
                260                 265                 270 caa tgc gtt ggt ggt cct ttg gga gct tac aaa att gat atc atc aag          864
Gln Cys Val Gly Gly Pro Leu Gly Ala Tyr Lys Ile Asp Ile Ile Lys
            275                 280                 285 gag att aag gac cca tgg att agt caa agg ttt ctt ggt cag aag tgc          912
Glu Ile Lys Asp Pro Trp Ile Ser Gln Arg Phe Leu Gly Gln Lys Cys
        290                 295                 300 act tat ggc gat gat cgt aga ttg act aac gaa atc ctt atg agg ggc          960
Thr Tyr Gly Asp Asp Arg Arg Leu Thr Asn Glu Ile Leu Met Arg Gly
305                 310                 315                 320 aag aaa gtc gtt ttt act cca ttt gct gtc gga tgg tct gat tca cct         1008
Lys Lys Val Val Phe Thr Pro Phe Ala Val Gly Trp Ser Asp Ser Pro
                    325                 330                 335 aca aat gtt ttc cgt tat att gtg caa caa aca cgt tgg agt aag agc         1056
Thr Asn Val Phe Arg Tyr Ile Val Gln Gln Thr Arg Trp Ser Lys Ser
                340                 345                 350 tgg tgt agg gag atc tgg tac act ttg ttc gct gct tgg aag cac ggg         1104
Trp Cys Arg Glu Ile Trp Tyr Thr Leu Phe Ala Ala Trp Lys His Gly
            355                 360                 365 ctt agc gga att tgg ctt gct ttt gaa tgc ctt tac cag att aca tac         1152
Leu Ser Gly Ile Trp Leu Ala Phe Glu Cys Leu Tyr Gln Ile Thr Tyr
        370                 375                 380 ttt ttc ttg gtg atc tat ttg ttt tca cgt ctt gcc gtc gag gct gac         1200
Phe Phe Leu Val Ile Tyr Leu Phe Ser Arg Leu Ala Val Glu Ala Asp
```

```
                385                 390                 395                 400
cct aga gca cag act gca act gtg att gtt tct act aca gtc gca ctt       1248
Pro Arg Ala Gln Thr Ala Thr Val Ile Val Ser Thr Thr Val Ala Leu
            405                 410                 415 att aag tgt ggc tat ttc agt ttt aga gca aaa gat att aga gcc ttc       1296
Ile Lys Cys Gly Tyr Phe Ser Phe Arg Ala Lys Asp Ile Arg Ala Phe
        420                 425                 430 tat ttt gtt ttg tac aca ttt gtt tat ttc ttt tgc atg att cca gct       1344
Tyr Phe Val Leu Tyr Thr Phe Val Tyr Phe Phe Cys Met Ile Pro Ala
    435                 440                 445 cgt att acc gct atg atg acc ttg tgg gac atc gga tgg gga act aga       1392
Arg Ile Thr Ala Met Met Thr Leu Trp Asp Ile Gly Trp Gly Thr Arg
450                 455                 460 ggt ggt aac gaa aag cct tct gtg gga aca agg gtg gcc ctt tgg gca       1440
Gly Gly Asn Glu Lys Pro Ser Val Gly Thr Arg Val Ala Leu Trp Ala
465                 470                 475                 480 aaa caa tat ctc atc gcc tac atg tgg tgg gcc gct gtc gtt ggt gcc       1488
Lys Gln Tyr Leu Ile Ala Tyr Met Trp Trp Ala Ala Val Val Gly Ala
            485                 490                 495 gga gtg tac tca atc gtt cat aac tgg atg ttt gac tgg aac tct ttg       1536
Gly Val Tyr Ser Ile Val His Asn Trp Met Phe Asp Trp Asn Ser Leu
        500                 505                 510 agc tat cgt ttc gct ctt gtg ggt att tgt tct tac att gtt ttc atc       1584
Ser Tyr Arg Phe Ala Leu Val Gly Ile Cys Ser Tyr Ile Val Phe Ile
    515                 520                 525 gtg att gtg ctc gtt gtg tat ttc act ggt aaa atc aca acc tgg aat       1632
Val Ile Val Leu Val Val Tyr Phe Thr Gly Lys Ile Thr Thr Trp Asn
530                 535                 540 ttc act aaa ctt caa aag gaa ttg att gaa gac agg gtt ctg tat gat       1680
Phe Thr Lys Leu Gln Lys Glu Leu Ile Glu Asp Arg Val Leu Tyr Asp
545                 550                 555                 560 gct act acc aac gcc cag tca gtt taa                                    1707
Ala Thr Thr Asn Ala Gln Ser Val
                565

<210> SEQ ID NO 4
<211> LENGTH: 568
<212> TYPE: PRT
<213> ORGANISM: Artificial sequence
<220> FEATURE:
<223> OTHER INFORMATION: Synthetic Construct

<400> SEQUENCE: 4

Met Gly Lys Asn Ile Ile Ile Met Val Ser Trp Tyr Thr Ile Ile Thr
1               5                   10                  15

Ser Asn Leu Ile Ala Val Gly Gly Ala Ser Leu Ile Leu Ala Pro Ala
            20                  25                  30

Ile Thr Gly Tyr Val Leu His Trp Asn Ile Ala Leu Ser Thr Ile Trp
        35                  40                  45

Gly Val Ser Ala Tyr Gly Ile Phe Val Phe Gly Phe Leu Ala Gln
    50                  55                  60

Val Leu Phe Ser Glu Leu Asn Arg Lys Arg Leu Arg Lys Trp Ile Ser
65                  70                  75                  80

Leu Arg Pro Lys Gly Trp Asn Asp Val Arg Leu Ala Val Ile Ala
            85                  90                  95

Gly Tyr Arg Glu Asp Pro Tyr Met Phe Gln Lys Cys Leu Glu Ser Val
        100                 105                 110

Arg Asp Ser Asp Tyr Gly Asn Val Ala Arg Leu Ile Cys Val Ile Asp
    115                 120                 125
```

```
Gly Asp Glu Asp Asp Met Arg Met Ala Ala Val Tyr Lys Ala Ile
130                 135                 140

Tyr Asn Asp Asn Ile Lys Lys Pro Glu Phe Val Leu Cys Glu Ser Asp
145                 150                 155                 160

Asp Lys Glu Gly Glu Arg Ile Asp Ser Asp Phe Ser Arg Asp Ile Cys
                165                 170                 175

Val Leu Gln Pro His Arg Gly Lys Arg Glu Cys Leu Tyr Thr Gly Phe
            180                 185                 190

Gln Leu Ala Lys Met Asp Pro Ser Val Asn Ala Val Val Leu Ile Asp
        195                 200                 205

Ser Asp Thr Val Leu Glu Lys Asp Ala Ile Leu Glu Val Tyr Pro
210                 215                 220

Leu Ala Cys Asp Pro Glu Ile Gln Ala Val Ala Gly Glu Cys Lys Ile
225                 230                 235                 240

Trp Asn Thr Asp Thr Leu Leu Ser Leu Leu Val Ala Trp Arg Tyr Tyr
                245                 250                 255

Ser Ala Phe Cys Val Glu Arg Ser Ala Gln Ser Phe Phe Arg Thr Val
            260                 265                 270

Gln Cys Val Gly Gly Pro Leu Gly Ala Tyr Lys Ile Asp Ile Ile Lys
        275                 280                 285

Glu Ile Lys Asp Pro Trp Ile Ser Gln Arg Phe Leu Gly Gln Lys Cys
290                 295                 300

Thr Tyr Gly Asp Asp Arg Arg Leu Thr Asn Glu Ile Leu Met Arg Gly
305                 310                 315                 320

Lys Lys Val Val Phe Thr Pro Phe Ala Val Gly Trp Ser Asp Ser Pro
                325                 330                 335

Thr Asn Val Phe Arg Tyr Ile Val Gln Gln Thr Arg Trp Ser Lys Ser
            340                 345                 350

Trp Cys Arg Glu Ile Trp Tyr Thr Leu Phe Ala Ala Trp Lys His Gly
        355                 360                 365

Leu Ser Gly Ile Trp Leu Ala Phe Glu Cys Leu Tyr Gln Ile Thr Tyr
370                 375                 380

Phe Phe Leu Val Ile Tyr Leu Phe Ser Arg Leu Ala Val Glu Ala Asp
385                 390                 395                 400

Pro Arg Ala Gln Thr Ala Thr Val Ile Val Ser Thr Thr Val Ala Leu
                405                 410                 415

Ile Lys Cys Gly Tyr Phe Ser Phe Arg Ala Lys Asp Ile Arg Ala Phe
            420                 425                 430

Tyr Phe Val Leu Tyr Thr Phe Val Tyr Phe Phe Cys Met Ile Pro Ala
        435                 440                 445

Arg Ile Thr Ala Met Met Thr Leu Trp Asp Ile Gly Trp Gly Thr Arg
450                 455                 460

Gly Gly Asn Glu Lys Pro Ser Val Gly Thr Arg Val Ala Leu Trp Ala
465                 470                 475                 480

Lys Gln Tyr Leu Ile Ala Tyr Met Trp Trp Ala Val Val Gly Ala
                485                 490                 495

Gly Val Tyr Ser Ile Val His Asn Trp Met Phe Asp Trp Asn Ser Leu
            500                 505                 510

Ser Tyr Arg Phe Ala Leu Val Gly Ile Cys Ser Tyr Ile Val Phe Ile
        515                 520                 525

Val Ile Val Leu Val Tyr Phe Thr Gly Lys Ile Thr Thr Trp Asn
530                 535                 540

Phe Thr Lys Leu Gln Lys Glu Leu Ile Glu Asp Arg Val Leu Tyr Asp
545                 550                 555                 560
```

Ala Thr Thr Asn Ala Gln Ser Val
                565

<210> SEQ ID NO 5
<211> LENGTH: 1662
<212> TYPE: DNA
<213> ORGANISM: Homo sapiens
<220> FEATURE:
<221> NAME/KEY: CDS
<222> LOCATION: (1)..(1662)

<400> SEQUENCE: 5

| | | | | | | | | | | | | | | | | |
|---|---|---|---|---|---|---|---|---|---|---|---|---|---|---|---|---|
| atg | ccg | gtc | cag | ctg | acg | aca | gcc | ctg | cgt | gtg | gtg | ggc | acc | agc | ctg | 48 |
| Met | Pro | Val | Gln | Leu | Thr | Thr | Ala | Leu | Arg | Val | Val | Gly | Thr | Ser | Leu | |
| 1 | | | | 5 | | | | | 10 | | | | | 15 | | |
| ttt | gcc | ctg | gca | gtg | ctg | ggt | ggc | atc | ctg | gca | gcc | tat | gtg | acg | ggc | 96 |
| Phe | Ala | Leu | Ala | Val | Leu | Gly | Gly | Ile | Leu | Ala | Ala | Tyr | Val | Thr | Gly | |
| | | | 20 | | | | | 25 | | | | | 30 | | | |
| tac | cag | ttc | atc | cac | acg | gaa | aag | cac | tac | ctg | tcc | ttc | ggc | ctg | tac | 144 |
| Tyr | Gln | Phe | Ile | His | Thr | Glu | Lys | His | Tyr | Leu | Ser | Phe | Gly | Leu | Tyr | |
| | | 35 | | | | | 40 | | | | | 45 | | | | |
| ggc | gcc | atc | ctg | ggc | ctg | cac | ctg | ctc | att | cag | agc | ctt | ttt | gcc | ttc | 192 |
| Gly | Ala | Ile | Leu | Gly | Leu | His | Leu | Leu | Ile | Gln | Ser | Leu | Phe | Ala | Phe | |
| | 50 | | | | | 55 | | | | | 60 | | | | | |
| ctg | gag | cac | cgg | cgc | atg | caa | cgt | gcc | ggc | cag | gcc | ctg | aag | ctg | ccc | 240 |
| Leu | Glu | His | Arg | Arg | Met | Gln | Arg | Ala | Gly | Gln | Ala | Leu | Lys | Leu | Pro | |
| 65 | | | | | 70 | | | | | 75 | | | | | 80 | |
| tcc | ccg | cgg | cgg | ggc | tcg | gtg | gca | ctg | tgc | att | gcc | gca | tac | cag | gag | 288 |
| Ser | Pro | Arg | Arg | Gly | Ser | Val | Ala | Leu | Cys | Ile | Ala | Ala | Tyr | Gln | Glu | |
| | | | | 85 | | | | | 90 | | | | | 95 | | |
| gac | cct | gac | tac | ttg | cgc | aag | tgc | ctg | cgc | tcg | gcc | cag | cgc | atc | tcc | 336 |
| Asp | Pro | Asp | Tyr | Leu | Arg | Lys | Cys | Leu | Arg | Ser | Ala | Gln | Arg | Ile | Ser | |
| | | | 100 | | | | | 105 | | | | | 110 | | | |
| ttc | cct | gac | ctc | aag | gtg | gtc | atg | gtg | gtg | gat | ggc | aac | cgc | cag | gag | 384 |
| Phe | Pro | Asp | Leu | Lys | Val | Val | Met | Val | Val | Asp | Gly | Asn | Arg | Gln | Glu | |
| | | 115 | | | | | 120 | | | | | 125 | | | | |
| gac | gcc | tac | atg | ctg | gac | atc | ttc | cac | gag | gtg | ctg | ggc | ggc | acc | gag | 432 |
| Asp | Ala | Tyr | Met | Leu | Asp | Ile | Phe | His | Glu | Val | Leu | Gly | Gly | Thr | Glu | |
| | 130 | | | | | 135 | | | | | 140 | | | | | |
| cag | gcc | ggc | ttc | ttt | gtg | tgg | cgc | agc | aac | ttc | cat | gag | gca | ggc | gag | 480 |
| Gln | Ala | Gly | Phe | Phe | Val | Trp | Arg | Ser | Asn | Phe | His | Glu | Ala | Gly | Glu | |
| 145 | | | | | 150 | | | | | 155 | | | | | 160 | |
| ggt | gag | acg | gag | gcc | agc | ctg | cag | gag | ggc | atg | gac | cgt | gtg | cgg | gat | 528 |
| Gly | Glu | Thr | Glu | Ala | Ser | Leu | Gln | Glu | Gly | Met | Asp | Arg | Val | Arg | Asp | |
| | | | | 165 | | | | | 170 | | | | | 175 | | |
| gtg | gtg | cgg | gcc | agc | acc | ttc | tcg | tgc | atc | atg | cag | aag | tgg | gga | ggc | 576 |
| Val | Val | Arg | Ala | Ser | Thr | Phe | Ser | Cys | Ile | Met | Gln | Lys | Trp | Gly | Gly | |
| | | | 180 | | | | | 185 | | | | | 190 | | | |
| aag | cgc | gag | gtc | atg | tac | acg | gcc | ttc | aag | gcc | ctc | ggc | gat | tcg | gtg | 624 |
| Lys | Arg | Glu | Val | Met | Tyr | Thr | Ala | Phe | Lys | Ala | Leu | Gly | Asp | Ser | Val | |
| | | 195 | | | | | 200 | | | | | 205 | | | | |
| gac | tac | atc | cag | gtg | tgc | gac | tct | gac | act | gtg | ctg | gat | cca | gcc | tgc | 672 |
| Asp | Tyr | Ile | Gln | Val | Cys | Asp | Ser | Asp | Thr | Val | Leu | Asp | Pro | Ala | Cys | |
| | 210 | | | | | 215 | | | | | 220 | | | | | |
| acc | atc | gag | atg | ctt | cga | gtc | ctg | gag | gag | gat | ccc | caa | gta | ggg | gga | 720 |
| Thr | Ile | Glu | Met | Leu | Arg | Val | Leu | Glu | Glu | Asp | Pro | Gln | Val | Gly | Gly | |
| 225 | | | | | 230 | | | | | 235 | | | | | 240 | |
| gtc | ggg | gga | gat | gtc | cag | atc | ctc | aac | aag | tac | gac | tca | tgg | att | tcc | 768 |
| Val | Gly | Gly | Asp | Val | Gln | Ile | Leu | Asn | Lys | Tyr | Asp | Ser | Trp | Ile | Ser | |
| | | | | 245 | | | | | 250 | | | | | 255 | | |
| ttc | ctg | agc | agc | gtg | cgg | tac | tgg | atg | gcc | ttc | aac | gtg | gag | cgg | gcc | 816 |

```
Phe Leu Ser Ser Val Arg Tyr Trp Met Ala Phe Asn Val Glu Arg Ala
            260                 265                 270 tgc cag tcc tac ttt ggc tgt gtg cag tgt att agt ggg ccc ttg ggc     864
Cys Gln Ser Tyr Phe Gly Cys Val Gln Cys Ile Ser Gly Pro Leu Gly
            275                 280                 285 atg tac cgc aac agc ctc ctc cag cag ttc ctg gag gac tgg tac cat     912
Met Tyr Arg Asn Ser Leu Leu Gln Gln Phe Leu Glu Asp Trp Tyr His
        290                 295                 300 cag aag ttc cta ggc agc aag tgc agc ttc ggg gat gac cgg cac ctc     960
Gln Lys Phe Leu Gly Ser Lys Cys Ser Phe Gly Asp Asp Arg His Leu
305                 310                 315                 320 acc aac cga gtc ctg agc ctt ggc tac cga act aag tat acc gcg cgc    1008
Thr Asn Arg Val Leu Ser Leu Gly Tyr Arg Thr Lys Tyr Thr Ala Arg
                325                 330                 335 tcc aag tgc ctc aca gag acc ccc act aag tac ctc cgg tgg ctc aac    1056
Ser Lys Cys Leu Thr Glu Thr Pro Thr Lys Tyr Leu Arg Trp Leu Asn
            340                 345                 350 cag caa acc cgc tgg agc aag tct tac ttc cgg gag tgg ctc tac aac    1104
Gln Gln Thr Arg Trp Ser Lys Ser Tyr Phe Arg Glu Trp Leu Tyr Asn
            355                 360                 365 tct ctg tgg ttc cat aag cac cac ctc tgg atg acc tac gag tca gtg    1152
Ser Leu Trp Phe His Lys His His Leu Trp Met Thr Tyr Glu Ser Val
370                 375                 380 gtc acg ggt ttc ttc ccc ttc ttc ctc att gcc acg gtt ata cag ctt    1200
Val Thr Gly Phe Phe Pro Phe Phe Leu Ile Ala Thr Val Ile Gln Leu
385                 390                 395                 400 ttc tac cgg ggc cgc atc tgg aac att ctc ctc ttc ctg ctg acg gtg    1248
Phe Tyr Arg Gly Arg Ile Trp Asn Ile Leu Leu Phe Leu Leu Thr Val
                405                 410                 415 cag ctg gtg ggc att atc aag gcc acc tac gcc tgc ttc ctt cgg ggc    1296
Gln Leu Val Gly Ile Ile Lys Ala Thr Tyr Ala Cys Phe Leu Arg Gly
            420                 425                 430 aat gca gag atg atc ttc atg tcc ctc tac tcc ctc ctc tat atg tcc    1344
Asn Ala Glu Met Ile Phe Met Ser Leu Tyr Ser Leu Leu Tyr Met Ser
            435                 440                 445 agc ctt ctg ccg gcc aag atc ttt gcc att gct acc atc aac aaa tct    1392
Ser Leu Leu Pro Ala Lys Ile Phe Ala Ile Ala Thr Ile Asn Lys Ser
450                 455                 460 ggc tgg ggc acc tct ggc cga aaa acc att gtg gtg aac ttc att ggc    1440
Gly Trp Gly Thr Ser Gly Arg Lys Thr Ile Val Val Asn Phe Ile Gly
465                 470                 475                 480 ctc att cct gtg tcc atc tgg gtg gca gtt ctc ctg gga ggg ctg gcc    1488
Leu Ile Pro Val Ser Ile Trp Val Ala Val Leu Leu Gly Gly Leu Ala
                485                 490                 495 tac aca gct tat tgc cag gac ctg ttc agt gag aca gag cta gcc ttc    1536
Tyr Thr Ala Tyr Cys Gln Asp Leu Phe Ser Glu Thr Glu Leu Ala Phe
            500                 505                 510 ctt gtc tct ggg gct ata ctg tat ggc tgc tac tgg gtg gcc ctc ctc    1584
Leu Val Ser Gly Ala Ile Leu Tyr Gly Cys Tyr Trp Val Ala Leu Leu
            515                 520                 525 atg cta tat ctg gcc atc atc gcc cgg cga tgt ggg aag aag ccg gag    1632
Met Leu Tyr Leu Ala Ile Ile Ala Arg Arg Cys Gly Lys Lys Pro Glu
530                 535                 540 cag tca agc ttg gct ttt gct gag gtg tga                             1662
Gln Ser Ser Leu Ala Phe Ala Glu Val
545                 550

<210> SEQ ID NO 6
<211> LENGTH: 553
<212> TYPE: PRT
<213> ORGANISM: Homo sapiens
```

<400> SEQUENCE: 6

```
Met Pro Val Gln Leu Thr Thr Ala Leu Arg Val Val Gly Thr Ser Leu
1               5                   10                  15

Phe Ala Leu Ala Val Leu Gly Gly Ile Leu Ala Ala Tyr Val Thr Gly
            20                  25                  30

Tyr Gln Phe Ile His Thr Glu Lys His Tyr Leu Ser Phe Gly Leu Tyr
        35                  40                  45

Gly Ala Ile Leu Gly Leu His Leu Leu Ile Gln Ser Leu Phe Ala Phe
    50                  55                  60

Leu Glu His Arg Arg Met Gln Arg Ala Gly Ala Leu Lys Leu Pro
65                  70                  75                  80

Ser Pro Arg Arg Gly Ser Val Ala Leu Cys Ile Ala Ala Tyr Gln Glu
                85                  90                  95

Asp Pro Asp Tyr Leu Arg Lys Cys Leu Arg Ser Ala Gln Arg Ile Ser
            100                 105                 110

Phe Pro Asp Leu Lys Val Val Met Val Val Asp Gly Asn Arg Gln Glu
        115                 120                 125

Asp Ala Tyr Met Leu Asp Ile Phe His Glu Val Leu Gly Gly Thr Glu
    130                 135                 140

Gln Ala Gly Phe Phe Val Trp Arg Ser Asn Phe His Glu Ala Gly Glu
145                 150                 155                 160

Gly Glu Thr Glu Ala Ser Leu Gln Glu Gly Met Asp Arg Val Arg Asp
                165                 170                 175

Val Val Arg Ala Ser Thr Phe Ser Cys Ile Met Gln Lys Trp Gly Gly
            180                 185                 190

Lys Arg Glu Val Met Tyr Thr Ala Phe Lys Ala Leu Gly Asp Ser Val
        195                 200                 205

Asp Tyr Ile Gln Val Cys Asp Ser Asp Thr Val Leu Asp Pro Ala Cys
    210                 215                 220

Thr Ile Glu Met Leu Arg Val Leu Glu Glu Asp Pro Gln Val Gly Gly
225                 230                 235                 240

Val Gly Gly Asp Val Gln Ile Leu Asn Lys Tyr Asp Ser Trp Ile Ser
                245                 250                 255

Phe Leu Ser Ser Val Arg Tyr Trp Met Ala Phe Asn Val Glu Arg Ala
            260                 265                 270

Cys Gln Ser Tyr Phe Gly Cys Val Gln Cys Ile Ser Gly Pro Leu Gly
        275                 280                 285

Met Tyr Arg Asn Ser Leu Leu Gln Gln Phe Leu Glu Asp Trp Tyr His
    290                 295                 300

Gln Lys Phe Leu Gly Ser Lys Cys Ser Phe Gly Asp Asp Arg His Leu
305                 310                 315                 320

Thr Asn Arg Val Leu Ser Leu Gly Tyr Arg Thr Lys Tyr Thr Ala Arg
                325                 330                 335

Ser Lys Cys Leu Thr Glu Thr Pro Thr Lys Tyr Leu Arg Trp Leu Asn
            340                 345                 350

Gln Gln Thr Arg Trp Ser Lys Ser Tyr Phe Arg Glu Trp Leu Tyr Asn
        355                 360                 365

Ser Leu Trp Phe His Lys His His Leu Trp Met Thr Tyr Glu Ser Val
    370                 375                 380

Val Thr Gly Phe Phe Pro Phe Leu Ile Ala Thr Val Ile Gln Leu
385                 390                 395                 400

Phe Tyr Arg Gly Arg Ile Trp Asn Ile Leu Leu Phe Leu Leu Thr Val
                405                 410                 415
```

```
Gln Leu Val Gly Ile Ile Lys Ala Thr Tyr Ala Cys Phe Leu Arg Gly
                420                 425                 430

Asn Ala Glu Met Ile Phe Met Ser Leu Tyr Ser Leu Leu Tyr Met Ser
            435                 440                 445

Ser Leu Leu Pro Ala Lys Ile Phe Ala Ile Ala Thr Ile Asn Lys Ser
        450                 455                 460

Gly Trp Gly Thr Ser Gly Arg Lys Thr Ile Val Val Asn Phe Ile Gly
465                 470                 475                 480

Leu Ile Pro Val Ser Ile Trp Val Ala Val Leu Leu Gly Gly Leu Ala
                485                 490                 495

Tyr Thr Ala Tyr Cys Gln Asp Leu Phe Ser Glu Thr Glu Leu Ala Phe
            500                 505                 510

Leu Val Ser Gly Ala Ile Leu Tyr Gly Cys Tyr Trp Val Ala Leu Leu
        515                 520                 525

Met Leu Tyr Leu Ala Ile Ile Ala Arg Arg Cys Gly Lys Lys Pro Glu
530                 535                 540

Gln Ser Ser Leu Ala Phe Ala Glu Val
545                 550

<210> SEQ ID NO 7
<211> LENGTH: 1662
<212> TYPE: DNA
<213> ORGANISM: Artificial sequence
<220> FEATURE:
<223> OTHER INFORMATION: Synthetic sequence coding for a Homo sapiens
      Hyaluronansynthase-3 protein
<220> FEATURE:
<221> NAME/KEY: CDS
<222> LOCATION: (1)..(1662)

<400> SEQUENCE: 7 atg cct gtt cag ctg act aca gca ctt aga gtc gta ggt aca agc ttg      48
Met Pro Val Gln Leu Thr Thr Ala Leu Arg Val Val Gly Thr Ser Leu
1               5                   10                  15 ttc gct ctg gca gtg ttg ggc ggt att cta gct gca tat gta act gga      96
Phe Ala Leu Ala Val Leu Gly Gly Ile Leu Ala Ala Tyr Val Thr Gly
                20                  25                  30 tat cag ttc att cat act gag aag cac tac cta tca ttc gga tta tac     144
Tyr Gln Phe Ile His Thr Glu Lys His Tyr Leu Ser Phe Gly Leu Tyr
            35                  40                  45 ggt gca att ttg ggt ttg cac ttg cta att caa tct ttg ttt gct ttt     192
Gly Ala Ile Leu Gly Leu His Leu Leu Ile Gln Ser Leu Phe Ala Phe
        50                  55                  60 ctt gag cat cgt aga atg caa aga gcc gga caa gct ttg aaa ctt cca     240
Leu Glu His Arg Arg Met Gln Arg Ala Gly Gln Ala Leu Lys Leu Pro
65                  70                  75                  80 tct cca agg aga ggg agt gtg gca tta tgc atc gct gcc tac caa gaa     288
Ser Pro Arg Arg Gly Ser Val Ala Leu Cys Ile Ala Ala Tyr Gln Glu
                85                  90                  95 gat cca gat tat ctt cgt aag tgt tta aga tca gca caa agg ata tct     336
Asp Pro Asp Tyr Leu Arg Lys Cys Leu Arg Ser Ala Gln Arg Ile Ser
            100                 105                 110 ttc cct gat cta aaa gtc gtt atg gtt gtg gat ggg aat aga caa gag     384
Phe Pro Asp Leu Lys Val Val Met Val Val Asp Gly Asn Arg Gln Glu
        115                 120                 125 gat gct tat atg ttg gat ata ttc cat gaa gtt tta ggt gga aca gaa     432
Asp Ala Tyr Met Leu Asp Ile Phe His Glu Val Leu Gly Gly Thr Glu
130                 135                 140 cag gct ggt ttc ttt gtt tgg agg tct aac ttc cac gag gct ggc gag     480
Gln Ala Gly Phe Phe Val Trp Arg Ser Asn Phe His Glu Ala Gly Glu
```

-continued

```
             145                 150                 155                 160
gga aac act gag gct tct ttg cag gag ggg atg gat aga gtc agg gat          528
Gly Glu Thr Glu Ala Ser Leu Gln Glu Gly Met Asp Arg Val Arg Asp
                165                 170                 175 gtg gtt cga gcc agt acc ttt tca tgc att atg caa aaa tgg ggt gga          576
Val Val Arg Ala Ser Thr Phe Ser Cys Ile Met Gln Lys Trp Gly Gly
            180                 185                 190 aaa agg gaa gtg atg tac act gct ttt aag gct ttg ggt gac tcc gtt          624
Lys Arg Glu Val Met Tyr Thr Ala Phe Lys Ala Leu Gly Asp Ser Val
        195                 200                 205 gat tat atc cag gta tgc gac tca gac act gtt ttg gac cca gca tgt          672
Asp Tyr Ile Gln Val Cys Asp Ser Asp Thr Val Leu Asp Pro Ala Cys
    210                 215                 220 acc att gaa atg ctc cgt gtt ctt gag gaa gat cca cag gtg ggg ggt          720
Thr Ile Glu Met Leu Arg Val Leu Glu Glu Asp Pro Gln Val Gly Gly
225                 230                 235                 240 gta gga ggt gat gta cag ata ctc aac aaa tat gac agt tgg atc tca          768
Val Gly Gly Asp Val Gln Ile Leu Asn Lys Tyr Asp Ser Trp Ile Ser
                245                 250                 255 ttc ctt tcc tct gtc agg tac tgg atg gca ttt aat gtt gaa aga gcc          816
Phe Leu Ser Ser Val Arg Tyr Trp Met Ala Phe Asn Val Glu Arg Ala
            260                 265                 270 tgc caa tct tat ttt ggc tgt gtt caa tgt att tct gga cct ttg ggt          864
Cys Gln Ser Tyr Phe Gly Cys Val Gln Cys Ile Ser Gly Pro Leu Gly
        275                 280                 285 atg tac aga aat agt tta ctt caa cag ttc ctg gaa gat tgg tat cac          912
Met Tyr Arg Asn Ser Leu Leu Gln Gln Phe Leu Glu Asp Trp Tyr His
    290                 295                 300 caa aaa ttt cta ggg agt aag tgt tct ttt gga gac gat aga cat cta          960
Gln Lys Phe Leu Gly Ser Lys Cys Ser Phe Gly Asp Asp Arg His Leu
305                 310                 315                 320 aca aat cgt gtc ctc agt ctt ggc tac agg act aag tat acc gct aga         1008
Thr Asn Arg Val Leu Ser Leu Gly Tyr Arg Thr Lys Tyr Thr Ala Arg
                325                 330                 335 agt aaa tgc ctg act gaa act cct aca aag tat ctg aga tgg tta aat         1056
Ser Lys Cys Leu Thr Glu Thr Pro Thr Lys Tyr Leu Arg Trp Leu Asn
            340                 345                 350 cag caa act aga tgg tca aag tct tac ttc agg gaa tgg ttg tac aat         1104
Gln Gln Thr Arg Trp Ser Lys Ser Tyr Phe Arg Glu Trp Leu Tyr Asn
        355                 360                 365 tca tta tgg ttt cat aaa cat cat ctg tgg atg aca tac gaa tcc gtt         1152
Ser Leu Trp Phe His Lys His His Leu Trp Met Thr Tyr Glu Ser Val
    370                 375                 380 gtc aca ggt ttt ttc cca ttt ttc tta att gca aca gtt att cag ctt         1200
Val Thr Gly Phe Phe Pro Phe Phe Leu Ile Ala Thr Val Ile Gln Leu
385                 390                 395                 400 ttt tat aga gga agg atc tgg aac att ctt ttg ttt ctc ctt aca gtt         1248
Phe Tyr Arg Gly Arg Ile Trp Asn Ile Leu Leu Phe Leu Leu Thr Val
                405                 410                 415 caa ttg gtg ggc att ata aag gct aca tat gca tgt ttt ctc agg gga         1296
Gln Leu Val Gly Ile Ile Lys Ala Thr Tyr Ala Cys Phe Leu Arg Gly
            420                 425                 430 aac gca gaa atg att ttc atg tca ctt tac agc ctg tta tat atg tcc         1344
Asn Ala Glu Met Ile Phe Met Ser Leu Tyr Ser Leu Leu Tyr Met Ser
        435                 440                 445 tca ctt tta ccc gca aag atc ttt gct att gct acc ata aat aag tct         1392
Ser Leu Leu Pro Ala Lys Ile Phe Ala Ile Ala Thr Ile Asn Lys Ser
    450                 455                 460 ggg tgg gga act tct gga cga aag aca atc gtt gtg aat ttt att ggc         1440
Gly Trp Gly Thr Ser Gly Arg Lys Thr Ile Val Val Asn Phe Ile Gly
```

```
                 465                  470                  475                  480
ttg  ata  ccc  gtt  tca  att  tgg  gta  gct  gtt  ctt  ctc  ggt  gga  ctt  gca      1488
Leu  Ile  Pro  Val  Ser  Ile  Trp  Val  Ala  Val  Leu  Leu  Gly  Gly  Leu  Ala
                         485                  490                  495 tat  act  gct  tac  tgt  caa  gat  ctt  ttt  tca  gag  act  gaa  ctt  gcc  ttt      1536
Tyr  Thr  Ala  Tyr  Cys  Gln  Asp  Leu  Phe  Ser  Glu  Thr  Glu  Leu  Ala  Phe
                    500                  505                  510 ctc  gtt  agt  gga  gct  att  ttg  tat  gga  tgt  tat  tgg  gtg  gct  ctt  cta      1584
Leu  Val  Ser  Gly  Ala  Ile  Leu  Tyr  Gly  Cys  Tyr  Trp  Val  Ala  Leu  Leu
                515                  520                  525 atg  ctt  tat  ctt  gca  atc  ata  gcc  cgt  cga  tgt  ggt  aaa  aaa  cct  gaa      1632
Met  Leu  Tyr  Leu  Ala  Ile  Ile  Ala  Arg  Arg  Cys  Gly  Lys  Lys  Pro  Glu
           530                  535                  540 caa  agc  tcc  ctc  gct  ttt  gct  gag  gtg  taa                                     1662
Gln  Ser  Ser  Leu  Ala  Phe  Ala  Glu  Val
545                  550

<210> SEQ ID NO 8
<211> LENGTH: 553
<212> TYPE: PRT
<213> ORGANISM: Artificial sequence
<220> FEATURE:
<223> OTHER INFORMATION: Synthetic Construct

<400> SEQUENCE: 8

Met  Pro  Val  Gln  Leu  Thr  Thr  Ala  Leu  Arg  Val  Val  Gly  Thr  Ser  Leu
1                  5                    10                   15

Phe  Ala  Leu  Ala  Val  Leu  Gly  Gly  Ile  Leu  Ala  Ala  Tyr  Val  Thr  Gly
                20                   25                   30

Tyr  Gln  Phe  Ile  His  Thr  Glu  Lys  His  Tyr  Leu  Ser  Phe  Gly  Leu  Tyr
           35                   40                   45

Gly  Ala  Ile  Leu  Gly  Leu  His  Leu  Leu  Ile  Gln  Ser  Leu  Phe  Ala  Phe
      50                   55                   60

Leu  Glu  His  Arg  Arg  Met  Gln  Arg  Ala  Gly  Gln  Ala  Leu  Lys  Leu  Pro
65                   70                   75                   80

Ser  Pro  Arg  Arg  Gly  Ser  Val  Ala  Leu  Cys  Ile  Ala  Ala  Tyr  Gln  Glu
                85                   90                   95

Asp  Pro  Asp  Tyr  Leu  Arg  Lys  Cys  Leu  Arg  Ser  Ala  Gln  Arg  Ile  Ser
           100                  105                  110

Phe  Pro  Asp  Leu  Lys  Val  Val  Met  Val  Val  Asp  Gly  Asn  Arg  Gln  Glu
      115                  120                  125

Asp  Ala  Tyr  Met  Leu  Asp  Ile  Phe  His  Glu  Val  Leu  Gly  Gly  Thr  Glu
130                  135                  140

Gln  Ala  Gly  Phe  Phe  Val  Trp  Arg  Ser  Asn  Phe  His  Glu  Ala  Gly  Glu
145                  150                  155                  160

Gly  Glu  Thr  Glu  Ala  Ser  Leu  Gln  Glu  Gly  Met  Asp  Arg  Val  Arg  Asp
                165                  170                  175

Val  Val  Arg  Ala  Ser  Thr  Phe  Ser  Cys  Ile  Met  Gln  Lys  Trp  Gly  Gly
           180                  185                  190

Lys  Arg  Glu  Val  Met  Tyr  Thr  Ala  Phe  Lys  Ala  Leu  Gly  Asp  Ser  Val
      195                  200                  205

Asp  Tyr  Ile  Gln  Val  Cys  Asp  Ser  Asp  Thr  Val  Leu  Asp  Pro  Ala  Cys
210                  215                  220

Thr  Ile  Glu  Met  Leu  Arg  Val  Leu  Glu  Glu  Asp  Pro  Gln  Val  Gly  Gly
225                  230                  235                  240

Val  Gly  Gly  Asp  Val  Gln  Ile  Leu  Asn  Lys  Tyr  Asp  Ser  Trp  Ile  Ser
                245                  250                  255
```

-continued

```
Phe Leu Ser Ser Val Arg Tyr Trp Met Ala Phe Asn Val Glu Arg Ala
            260                 265                 270
Cys Gln Ser Tyr Phe Gly Cys Val Gln Cys Ile Ser Gly Pro Leu Gly
        275                 280                 285
Met Tyr Arg Asn Ser Leu Leu Gln Gln Phe Leu Glu Asp Trp Tyr His
290                 295                 300
Gln Lys Phe Leu Gly Ser Lys Cys Ser Phe Gly Asp Asp Arg His Leu
305                 310                 315                 320
Thr Asn Arg Val Leu Ser Leu Gly Tyr Arg Thr Lys Tyr Thr Ala Arg
                325                 330                 335
Ser Lys Cys Leu Thr Glu Thr Pro Thr Lys Tyr Leu Arg Trp Leu Asn
            340                 345                 350
Gln Gln Thr Arg Trp Ser Lys Ser Tyr Phe Arg Glu Trp Leu Tyr Asn
        355                 360                 365
Ser Leu Trp Phe His Lys His His Leu Trp Met Thr Tyr Glu Ser Val
370                 375                 380
Val Thr Gly Phe Phe Pro Phe Leu Ile Ala Thr Val Ile Gln Leu
385                 390                 395                 400
Phe Tyr Arg Gly Arg Ile Trp Asn Ile Leu Leu Phe Leu Leu Thr Val
                405                 410                 415
Gln Leu Val Gly Ile Ile Lys Ala Thr Tyr Ala Cys Phe Leu Arg Gly
            420                 425                 430
Asn Ala Glu Met Ile Phe Met Ser Leu Tyr Ser Leu Leu Tyr Met Ser
        435                 440                 445
Ser Leu Leu Pro Ala Lys Ile Phe Ala Ile Ala Thr Ile Asn Lys Ser
450                 455                 460
Gly Trp Gly Thr Ser Gly Arg Lys Thr Ile Val Val Asn Phe Ile Gly
465                 470                 475                 480
Leu Ile Pro Val Ser Ile Trp Val Ala Val Leu Leu Gly Gly Leu Ala
                485                 490                 495
Tyr Thr Ala Tyr Cys Gln Asp Leu Phe Ser Glu Thr Glu Leu Ala Phe
            500                 505                 510
Leu Val Ser Gly Ala Ile Leu Tyr Gly Cys Tyr Trp Val Ala Leu Leu
        515                 520                 525
Met Leu Tyr Leu Ala Ile Ile Ala Arg Arg Cys Gly Lys Lys Pro Glu
530                 535                 540
Gln Ser Ser Leu Ala Phe Ala Glu Val
545                 550
```

```
<210> SEQ ID NO 9
<211> LENGTH: 1632
<212> TYPE: DNA
<213> ORGANISM: Homo sapiens
<220> FEATURE:
<221> NAME/KEY: CDS
<222> LOCATION: (1)..(1632)
<300> PUBLICATION INFORMATION:
<308> DATABASE ACCESSION NUMBER: D84424.1
<309> DATABASE ENTRY DATE: 1996-07-02
<313> RELEVANT RESIDUES IN SEQ ID NO: (149)..(1780)

<400> SEQUENCE: 9
```

```
atg acc tgg gcc tac gcc gcc ggg gtg ccg ctg gcc tcc gat cgc tac      48
Met Thr Trp Ala Tyr Ala Ala Gly Val Pro Leu Ala Ser Asp Arg Tyr
1               5                   10                  15 ggc ctc ctg gcc ttc ggc ctc tac ggg gcc ttc ctt tca gcg cac ctg      96
Gly Leu Leu Ala Phe Gly Leu Tyr Gly Ala Phe Leu Ser Ala His Leu
                20                  25                  30
```

```
gtg gcg cag agc ctc ttc gcg tac ctg gag cac cgg cgg gtg gcg gcg      144
Val Ala Gln Ser Leu Phe Ala Tyr Leu Glu His Arg Arg Val Ala Ala
         35                  40                  45 gcg gcg cgg ggg ccg ctg gat gca gcc acc gcg cgt agt gtg gcg ctg      192
Ala Ala Arg Gly Pro Leu Asp Ala Ala Thr Ala Arg Ser Val Ala Leu
 50                  55                  60 acc atc tcc gcc tac cag gag gac ccc gcg tac ctg cgc cag tgc ctg      240
Thr Ile Ser Ala Tyr Gln Glu Asp Pro Ala Tyr Leu Arg Gln Cys Leu
 65                  70                  75                  80 gcg tcc gcc cgc gcc ctg ctg tac ccg cgc gcg cgt gtg cgc gtc ctc      288
Ala Ser Ala Arg Ala Leu Leu Tyr Pro Arg Ala Arg Val Arg Val Leu
                 85                  90                  95 atg gtg gtg gat ggc aac cgc gcc gag gac ctc tac atg gtc gac atg      336
Met Val Val Asp Gly Asn Arg Ala Glu Asp Leu Tyr Met Val Asp Met
            100                 105                 110 ttc cgc gag gtc ttc gct gac gag gac ccc gcc acg tac gtg tgg gac      384
Phe Arg Glu Val Phe Ala Asp Glu Asp Pro Ala Thr Tyr Val Trp Asp
        115                 120                 125 ggc aac tac cac cag ccc tgg gaa ccc gcg gcg gcg ggc gcg gtg ggc      432
Gly Asn Tyr His Gln Pro Trp Glu Pro Ala Ala Ala Gly Ala Val Gly
    130                 135                 140 gcc gga gcc tat cgg gag gtg gag gcg gag gat cct ggg cgg ctg gca      480
Ala Gly Ala Tyr Arg Glu Val Glu Ala Glu Asp Pro Gly Arg Leu Ala
145                 150                 155                 160 gtg gag gcg ctg gtg agg act cgc agg tgc gtg tgc gtg gcg cag cgc      528
Val Glu Ala Leu Val Arg Thr Arg Arg Cys Val Cys Val Ala Gln Arg
                165                 170                 175 tgg ggc ggc aag cgc gag gtc atg tac aca gcc ttc aag gcg ctc gga      576
Trp Gly Gly Lys Arg Glu Val Met Tyr Thr Ala Phe Lys Ala Leu Gly
            180                 185                 190 gat tcg gtg gac tac gtg cag gtc tgt gac tcg gac aca agg ttg gac      624
Asp Ser Val Asp Tyr Val Gln Val Cys Asp Ser Asp Thr Arg Leu Asp
        195                 200                 205 ccc atg gca ctg ctg gag ctc gtg cgg gta ctg gac gag gac ccc cgg      672
Pro Met Ala Leu Leu Glu Leu Val Arg Val Leu Asp Glu Asp Pro Arg
210                 215                 220 gta ggg gct gtt ggt ggg gat gtg cgg atc ctt aac cct ctg gac tcc      720
Val Gly Ala Val Gly Gly Asp Val Arg Ile Leu Asn Pro Leu Asp Ser
225                 230                 235                 240 tgg gtc agc ttc cta agc agc ctg cga tac tgg gta gcc ttc aat gtg      768
Trp Val Ser Phe Leu Ser Ser Leu Arg Tyr Trp Val Ala Phe Asn Val
                245                 250                 255 gag cgg gct tgt cag agc tac ttc cac tgt gta tcc tgc atc agc ggt      816
Glu Arg Ala Cys Gln Ser Tyr Phe His Cys Val Ser Cys Ile Ser Gly
            260                 265                 270 cct cta ggc cta tat agg aat aac ctc ttg cag cag ttt ctt gag gcc      864
Pro Leu Gly Leu Tyr Arg Asn Asn Leu Leu Gln Gln Phe Leu Glu Ala
        275                 280                 285 tgg tac aac cag aag ttc ctg ggt acc cac tgt act ttt ggg gat gac      912
Trp Tyr Asn Gln Lys Phe Leu Gly Thr His Cys Thr Phe Gly Asp Asp
    290                 295                 300 cgg cac ctc acc aac cgc atg ctc agc atg ggt tat gct acc aag tac      960
Arg His Leu Thr Asn Arg Met Leu Ser Met Gly Tyr Ala Thr Lys Tyr
305                 310                 315                 320 acc tcc agg tcc cgc tgc tac tca gag acg ccc tcg tcc ttc ctg cgg     1008
Thr Ser Arg Ser Arg Cys Tyr Ser Glu Thr Pro Ser Ser Phe Leu Arg
                325                 330                 335 tgg ctg agc cag cag aca cgc tgg tcc aag tcg tac ttc cgt gag tgg     1056
Trp Leu Ser Gln Gln Thr Arg Trp Ser Lys Ser Tyr Phe Arg Glu Trp
            340                 345                 350
```

```
ctg tac aac gcg ctc tgg tgg cac cgg cac cat gcg tgg atg acc tac    1104
Leu Tyr Asn Ala Leu Trp Trp His Arg His His Ala Trp Met Thr Tyr
        355                 360                 365 gag gcg gtg gtc tcc ggc ctg ttc ccc ttc ttc gtg gcg gcc act gtg    1152
Glu Ala Val Val Ser Gly Leu Phe Pro Phe Phe Val Ala Ala Thr Val
370                 375                 380 ctg cgt ctg ttc tac gcg ggc cgc cct tgg gcg ctg ctg tgg gtg ctg    1200
Leu Arg Leu Phe Tyr Ala Gly Arg Pro Trp Ala Leu Leu Trp Val Leu
385                 390                 395                 400 ctg tgc gtg cag ggc gtg gca ctg gcc aag gcg gcc ttc gcg gcc tgg    1248
Leu Cys Val Gln Gly Val Ala Leu Ala Lys Ala Ala Phe Ala Ala Trp
                405                 410                 415 ctg cgg ggc tgc ctg cgc atg gtg ctt ctg tcg ctc tac gcg ccc ctc    1296
Leu Arg Gly Cys Leu Arg Met Val Leu Leu Ser Leu Tyr Ala Pro Leu
            420                 425                 430 tac atg tgt ggc ctc ctg cct gcc aag ttc ctg gcg cta gtc acc atg    1344
Tyr Met Cys Gly Leu Leu Pro Ala Lys Phe Leu Ala Leu Val Thr Met
        435                 440                 445 aac cag agt ggc tgg ggc acc tcg ggc cgg cgg aag ctg gcc gct aac    1392
Asn Gln Ser Gly Trp Gly Thr Ser Gly Arg Arg Lys Leu Ala Ala Asn
    450                 455                 460 tac gtc cct ctg ctg ccc ctg gcg ctc tgg gcg ctg ctg ctt ggg    1440
Tyr Val Pro Leu Leu Pro Leu Ala Leu Trp Ala Leu Leu Leu Gly
465                 470                 475                 480 ggc ctg gtc cgc agc gta gca cac gag gcc agg gcc gac tgg agc ggc    1488
Gly Leu Val Arg Ser Val Ala His Glu Ala Arg Ala Asp Trp Ser Gly
                485                 490                 495 cct tcc cgc gca gcc gag gcc tac cac ttg gcc gcg ggg gcc ggc gcc    1536
Pro Ser Arg Ala Ala Glu Ala Tyr His Leu Ala Ala Gly Ala Gly Ala
            500                 505                 510 tac gtg ggc tac tgg gtg gcc atg ttg acg ctg tac tgg gtg ggc gtg    1584
Tyr Val Gly Tyr Trp Val Ala Met Leu Thr Leu Tyr Trp Val Gly Val
        515                 520                 525 cgg agg ctt tgc cgg cgg cgg acc ggg ggc tac cgc gtc cag gtg tga    1632
Arg Arg Leu Cys Arg Arg Arg Thr Gly Gly Tyr Arg Val Gln Val
    530                 535                 540

<210> SEQ ID NO 10
<211> LENGTH: 543
<212> TYPE: PRT
<213> ORGANISM: Homo sapiens

<400> SEQUENCE: 10

Met Thr Trp Ala Tyr Ala Ala Gly Val Pro Leu Ala Ser Asp Arg Tyr
1               5                   10                  15

Gly Leu Leu Ala Phe Gly Leu Tyr Gly Ala Phe Leu Ser Ala His Leu
            20                  25                  30

Val Ala Gln Ser Leu Phe Ala Tyr Leu Glu His Arg Val Ala Ala
        35                  40                  45

Ala Ala Arg Gly Pro Leu Asp Ala Thr Ala Arg Ser Val Ala Leu
    50                  55                  60

Thr Ile Ser Ala Tyr Gln Glu Asp Pro Ala Tyr Leu Arg Gln Cys Leu
65                  70                  75                  80

Ala Ser Ala Arg Ala Leu Leu Tyr Pro Arg Ala Arg Val Arg Val Leu
                85                  90                  95

Met Val Val Asp Gly Asn Arg Ala Glu Asp Leu Tyr Met Val Asp Met
            100                 105                 110

Phe Arg Glu Val Phe Ala Asp Glu Asp Pro Ala Thr Tyr Val Trp Asp
        115                 120                 125
```

```
Gly Asn Tyr His Gln Pro Trp Glu Pro Ala Ala Gly Ala Val Gly
            130                 135                 140

Ala Gly Ala Tyr Arg Glu Val Glu Ala Asp Pro Gly Arg Leu Ala
145                 150                 155                 160

Val Glu Ala Leu Val Arg Thr Arg Arg Cys Val Cys Val Ala Gln Arg
                165                 170                 175

Trp Gly Gly Lys Arg Glu Val Met Tyr Thr Ala Phe Lys Ala Leu Gly
            180                 185                 190

Asp Ser Val Asp Tyr Val Gln Val Cys Asp Ser Asp Thr Arg Leu Asp
            195                 200                 205

Pro Met Ala Leu Leu Glu Leu Val Arg Val Leu Asp Glu Asp Pro Arg
210                 215                 220

Val Gly Ala Val Gly Gly Asp Val Arg Ile Leu Asn Pro Leu Asp Ser
225                 230                 235                 240

Trp Val Ser Phe Leu Ser Ser Leu Arg Tyr Trp Val Ala Phe Asn Val
                245                 250                 255

Glu Arg Ala Cys Gln Ser Tyr Phe His Cys Val Ser Cys Ile Ser Gly
                260                 265                 270

Pro Leu Gly Leu Tyr Arg Asn Asn Leu Leu Gln Gln Phe Leu Glu Ala
            275                 280                 285

Trp Tyr Asn Gln Lys Phe Leu Gly Thr His Cys Thr Phe Gly Asp Asp
290                 295                 300

Arg His Leu Thr Asn Arg Met Leu Ser Met Gly Tyr Ala Thr Lys Tyr
305                 310                 315                 320

Thr Ser Arg Ser Arg Cys Tyr Ser Glu Thr Pro Ser Ser Phe Leu Arg
                325                 330                 335

Trp Leu Ser Gln Gln Thr Arg Trp Ser Lys Ser Tyr Phe Arg Glu Trp
            340                 345                 350

Leu Tyr Asn Ala Leu Trp Trp His Arg His His Ala Trp Met Thr Tyr
            355                 360                 365

Glu Ala Val Val Ser Gly Leu Phe Pro Phe Phe Val Ala Ala Thr Val
370                 375                 380

Leu Arg Leu Phe Tyr Ala Gly Arg Pro Trp Ala Leu Leu Trp Val Leu
385                 390                 395                 400

Leu Cys Val Gln Gly Val Ala Leu Ala Lys Ala Ala Phe Ala Ala Trp
                405                 410                 415

Leu Arg Gly Cys Leu Arg Met Val Leu Leu Ser Leu Tyr Ala Pro Leu
            420                 425                 430

Tyr Met Cys Gly Leu Leu Pro Ala Lys Phe Leu Ala Leu Val Thr Met
            435                 440                 445

Asn Gln Ser Gly Trp Gly Thr Ser Gly Arg Arg Lys Leu Ala Ala Asn
450                 455                 460

Tyr Val Pro Leu Leu Pro Leu Ala Leu Trp Ala Leu Leu Leu Gly
465                 470                 475                 480

Gly Leu Val Arg Ser Val Ala His Glu Ala Arg Ala Asp Trp Ser Gly
                485                 490                 495

Pro Ser Arg Ala Ala Glu Ala Tyr His Leu Ala Ala Gly Ala Gly Ala
            500                 505                 510

Tyr Val Gly Tyr Trp Val Ala Met Leu Thr Leu Tyr Trp Val Gly Val
            515                 520                 525

Arg Arg Leu Cys Arg Arg Thr Gly Gly Tyr Arg Val Gln Val
530                 535                 540
```

<210> SEQ ID NO 11

-continued

```
<211> LENGTH: 1659
<212> TYPE: DNA
<213> ORGANISM: Homo sapiens
<220> FEATURE:
<221> NAME/KEY: CDS
<222> LOCATION: (1)..(1659)
<300> PUBLICATION INFORMATION:
<308> DATABASE ACCESSION NUMBER: U54804.1
<309> DATABASE ENTRY DATE: 1996-08-10
<313> RELEVANT RESIDUES IN SEQ ID NO: (536)..(2194)

<400> SEQUENCE: 11 atg cat tgt gag agg ttt cta tgt atc ctg aga ata att gga acc aca      48
Met His Cys Glu Arg Phe Leu Cys Ile Leu Arg Ile Ile Gly Thr Thr
1               5                   10                  15 ctc ttt gga gtc tct ctc ctc ctt gga atc aca gct gct tat att gtt      96
Leu Phe Gly Val Ser Leu Leu Leu Gly Ile Thr Ala Ala Tyr Ile Val
            20                  25                  30 ggc tac cag ttt atc caa acg gat aat tac tat ttc tct ttt gga ctg     144
Gly Tyr Gln Phe Ile Gln Thr Asp Asn Tyr Tyr Phe Ser Phe Gly Leu
        35                  40                  45 tat ggt gcc ttt ttg gca tca cac ctc atc atc caa agc ctg ttt gcc     192
Tyr Gly Ala Phe Leu Ala Ser His Leu Ile Ile Gln Ser Leu Phe Ala
    50                  55                  60 ttt ttg gag cac cga aaa atg aaa aaa tcc cta gaa acc ccc ata aag     240
Phe Leu Glu His Arg Lys Met Lys Lys Ser Leu Glu Thr Pro Ile Lys
65                  70                  75                  80 ttg aac aaa aca gtt gcc ctt tgc atc gct gcc tat caa gaa gat cca     288
Leu Asn Lys Thr Val Ala Leu Cys Ile Ala Ala Tyr Gln Glu Asp Pro
                85                  90                  95 gac tac tta agg aaa tgt ttg caa tct gtg aaa agg cta acc tac cct     336
Asp Tyr Leu Arg Lys Cys Leu Gln Ser Val Lys Arg Leu Thr Tyr Pro
            100                 105                 110 ggg att aaa gtt gtc atg gtc ata gat ggg aac tca gaa gat gac ctt     384
Gly Ile Lys Val Val Met Val Ile Asp Gly Asn Ser Glu Asp Asp Leu
        115                 120                 125 tac atg atg gac atc ttc agt gaa gtc atg ggc aga gac aaa tca gcc     432
Tyr Met Met Asp Ile Phe Ser Glu Val Met Gly Arg Asp Lys Ser Ala
    130                 135                 140 act tat atc tgg aag aac aac ttc cac gaa aag ggt ccc ggt gag aca     480
Thr Tyr Ile Trp Lys Asn Asn Phe His Glu Lys Gly Pro Gly Glu Thr
145                 150                 155                 160 gat gag tca cat aaa gaa agc tcg caa cac gta acg caa ttg gtc ttg     528
Asp Glu Ser His Lys Glu Ser Ser Gln His Val Thr Gln Leu Val Leu
                165                 170                 175 tcc aac aaa agt atc tgc atc atg caa aaa tgg ggt gga aaa aga gaa     576
Ser Asn Lys Ser Ile Cys Ile Met Gln Lys Trp Gly Gly Lys Arg Glu
            180                 185                 190 gtc atg tac aca gcc ttc aga gca ctg gga cga agt gtg gat tat gta     624
Val Met Tyr Thr Ala Phe Arg Ala Leu Gly Arg Ser Val Asp Tyr Val
        195                 200                 205 cag gtt tgt gat tca gac act atg ctt gac cca gcc tca tct gtg gag     672
Gln Val Cys Asp Ser Asp Thr Met Leu Asp Pro Ala Ser Ser Val Glu
    210                 215                 220 atg gta aaa gtt tta gaa gaa gat ccc atg gtt gga ggt gtt ggg gga     720
Met Val Lys Val Leu Glu Glu Asp Pro Met Val Gly Gly Val Gly Gly
225                 230                 235                 240 gat gtc cag att tta aac aag tac gat tcc tgg atc tca ttc ctc agc     768
Asp Val Gln Ile Leu Asn Lys Tyr Asp Ser Trp Ile Ser Phe Leu Ser
                245                 250                 255 agt gta aga tat tgg atg gct ttt aat ata gaa agg gcc tgt cag tct     816
Ser Val Arg Tyr Trp Met Ala Phe Asn Ile Glu Arg Ala Cys Gln Ser
            260                 265                 270
```

```
tat ttt ggg tgt gtt cag tgc att agt gga cct ctg gga atg tac aga       864
Tyr Phe Gly Cys Val Gln Cys Ile Ser Gly Pro Leu Gly Met Tyr Arg
            275                 280                 285 aac tcc ttg ttg cat gag ttt gtg gaa gat tgg tac aat caa gaa ttt       912
Asn Ser Leu Leu His Glu Phe Val Glu Asp Trp Tyr Asn Gln Glu Phe
        290                 295                 300 atg ggc aac caa tgt agc ttt ggt gat gac agg cat ctc acg aac cgg       960
Met Gly Asn Gln Cys Ser Phe Gly Asp Asp Arg His Leu Thr Asn Arg
305                 310                 315                 320 gtg ctg agc ctg ggc tat gca aca aaa tac aca gct cga tct aag tgc      1008
Val Leu Ser Leu Gly Tyr Ala Thr Lys Tyr Thr Ala Arg Ser Lys Cys
                325                 330                 335 ctt act gaa aca cct ata gag tat ctc aga tgg cta aac cag cag acc      1056
Leu Thr Glu Thr Pro Ile Glu Tyr Leu Arg Trp Leu Asn Gln Gln Thr
            340                 345                 350 cgt tgg agc aag tcc tac ttc cga gaa tgg ctg tac aat gca atg tgg      1104
Arg Trp Ser Lys Ser Tyr Phe Arg Glu Trp Leu Tyr Asn Ala Met Trp
        355                 360                 365 ttt cac aaa cat cac ttg tgg atg acc tac gaa gcg att atc act gga      1152
Phe His Lys His His Leu Trp Met Thr Tyr Glu Ala Ile Ile Thr Gly
370                 375                 380 ttc ttt cct ttc ttt ctc att gcc aca gta atc cag ctc ttc tac cgg      1200
Phe Phe Pro Phe Phe Leu Ile Ala Thr Val Ile Gln Leu Phe Tyr Arg
385                 390                 395                 400 ggt aaa att tgg aac att ctc ctc ttc ttg tta act gtc cag cta gta      1248
Gly Lys Ile Trp Asn Ile Leu Leu Phe Leu Leu Thr Val Gln Leu Val
            405                 410                 415 ggt ctc ata aaa tca tct ttt gcc agc tgc ctt aga gga aat atc gtc      1296
Gly Leu Ile Lys Ser Ser Phe Ala Ser Cys Leu Arg Gly Asn Ile Val
        420                 425                 430 atg gtc ttc atg tct ctc tac tca gtg tta tac atg tcg agt tta ctt      1344
Met Val Phe Met Ser Leu Tyr Ser Val Leu Tyr Met Ser Ser Leu Leu
435                 440                 445 ccc gcc aag atg ttt gca att gca aca ata aac aaa gct ggg tgg ggc      1392
Pro Ala Lys Met Phe Ala Ile Ala Thr Ile Asn Lys Ala Gly Trp Gly
            450                 455                 460 aca tca gga agg aaa acc att gtt gtt aat ttc ata gga ctc att cca      1440
Thr Ser Gly Arg Lys Thr Ile Val Val Asn Phe Ile Gly Leu Ile Pro
465                 470                 475                 480 gta tca gtt tgg ttt aca atc ctc ctg ggt ggt gtg att ttc acc att      1488
Val Ser Val Trp Phe Thr Ile Leu Leu Gly Gly Val Ile Phe Thr Ile
            485                 490                 495 tat aag gag tct aaa agg cca ttt tca gaa tcc aaa cag aca gtt cta      1536
Tyr Lys Glu Ser Lys Arg Pro Phe Ser Glu Ser Lys Gln Thr Val Leu
        500                 505                 510 att gtt gga acg ttg ctc tat gca tgc tat tgg gtc atg ctt ttg acg      1584
Ile Val Gly Thr Leu Leu Tyr Ala Cys Tyr Trp Val Met Leu Leu Thr
515                 520                 525 ctg tat gta gtt ctc atc aat aag tgt ggc agg cgg aag aag gga caa      1632
Leu Tyr Val Val Leu Ile Asn Lys Cys Gly Arg Arg Lys Lys Gly Gln
            530                 535                 540 caa tat gac atg gtg ctt gat gta tga                                  1659
Gln Tyr Asp Met Val Leu Asp Val
545                 550
```

<210> SEQ ID NO 12
<211> LENGTH: 552
<212> TYPE: PRT
<213> ORGANISM: Homo sapiens

<400> SEQUENCE: 12

-continued

```
Met His Cys Glu Arg Phe Leu Cys Ile Leu Arg Ile Ile Gly Thr Thr
1               5                   10                  15

Leu Phe Gly Val Ser Leu Leu Leu Gly Ile Thr Ala Ala Tyr Ile Val
            20                  25                  30

Gly Tyr Gln Phe Ile Gln Thr Asp Asn Tyr Tyr Phe Ser Phe Gly Leu
                35                  40                  45

Tyr Gly Ala Phe Leu Ala Ser His Leu Ile Ile Gln Ser Leu Phe Ala
        50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Gln Ser Val Lys Arg Leu Thr Tyr Pro
            100                 105                 110

Gly Ile Lys Val Val Met Val Ile Asp Gly Asn Ser Glu Asp Asp Leu
        115                 120                 125

Tyr Met Met Asp Ile Phe Ser Glu Val Met Gly Arg Asp Lys Ser Ala
    130                 135                 140

Thr Tyr Ile Trp Lys Asn Asn Phe His Glu Lys Gly Pro Gly Glu Thr
145                 150                 155                 160

Asp Glu Ser His Lys Glu Ser Ser Gln His Val Thr Gln Leu Val Leu
                165                 170                 175

Ser Asn Lys Ser Ile Cys Ile Met Gln Lys Trp Gly Gly Lys Arg Glu
            180                 185                 190

Val Met Tyr Thr Ala Phe Arg Ala Leu Gly Arg Ser Val Asp Tyr Val
        195                 200                 205

Gln Val Cys Asp Ser Asp Thr Met Leu Asp Pro Ala Ser Ser Val Glu
    210                 215                 220

Met Val Lys Val Leu Glu Glu Asp Pro Met Val Gly Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
            260                 265                 270

Tyr Phe Gly Cys Val Gln Cys Ile Ser Gly Pro Leu Gly Met Tyr Arg
        275                 280                 285

Asn Ser Leu Leu His Glu Phe Val Glu Asp Trp Tyr Asn Gln Glu Phe
    290                 295                 300

Met Gly Asn Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
            340                 345                 350

Arg Trp Ser Lys Ser Tyr Phe Arg Glu Trp Leu Tyr Asn Ala Met Trp
        355                 360                 365

Phe His Lys His His Leu Trp Met Thr Tyr Glu Ala Ile Ile Thr Gly
    370                 375                 380

Phe Phe Pro Phe Leu Ile Ala Thr Val Ile Gln Leu Phe Tyr Arg
385                 390                 395                 400

Gly Lys Ile Trp Asn Ile Leu Phe Leu Leu Thr Val Gln Leu Val
                405                 410                 415

Gly Leu Ile Lys Ser Ser Phe Ala Ser Cys Leu Arg Gly Asn Ile Val
```

```
                        420                 425                 430
    Met Val Phe Met Ser Leu Tyr Ser Val Leu Tyr Met Ser Ser Leu Leu
                    435                 440                 445

Pro Ala Lys Met Phe Ala Ile Ala Thr Ile Asn Lys Ala Gly Trp Gly
                450                 455                 460

Thr Ser Gly Arg Lys Thr Ile Val Val Asn Phe Ile Gly Leu Ile Pro
    465                 470                 475                 480

Val Ser Val Trp Phe Thr Ile Leu Leu Gly Gly Val Ile Phe Thr Ile
                    485                 490                 495

Tyr Lys Glu Ser Lys Arg Pro Phe Ser Glu Ser Lys Gln Thr Val Leu
                500                 505                 510

Ile Val Gly Thr Leu Leu Tyr Ala Cys Tyr Trp Val Met Leu Leu Thr
                515                 520                 525

Leu Tyr Val Val Leu Ile Asn Lys Cys Gly Arg Arg Lys Lys Gly Gln
                530                 535                 540

Gln Tyr Asp Met Val Leu Asp Val
    545                 550

<210> SEQ ID NO 13
<211> LENGTH: 1752
<212> TYPE: DNA
<213> ORGANISM: Papio anubis
<220> FEATURE:
<221> NAME/KEY: CDS
<222> LOCATION: (1)..(1752)
<300> PUBLICATION INFORMATION:
<308> DATABASE ACCESSION NUMBER: AY463695
<309> DATABASE ENTRY DATE: 2003-12-08
<313> RELEVANT RESIDUES IN SEQ ID NO: (36)..(1787)

<400> SEQUENCE: 13 atg aca cag cgg gac acg ccc aag ccc act cct gca gcc cgc cgc tgc      48
Met Thr Gln Arg Asp Thr Pro Lys Pro Thr Pro Ala Ala Arg Arg Cys
1               5                   10                  15 tcc ggc ctg gcc cgg agg gtg ctg acc atc gcc ttc gcc ctg ctc atc      96
Ser Gly Leu Ala Arg Arg Val Leu Thr Ile Ala Phe Ala Leu Leu Ile
            20                  25                  30 ctg ggc ctc atg acc tgg gcc tac gcc gcc ggg gtg ccg ctg gcc tcc     144
Leu Gly Leu Met Thr Trp Ala Tyr Ala Ala Gly Val Pro Leu Ala Ser
        35                  40                  45 gat cgc tac ggc ctc ctg gcc ttc ggc ctc tac ggg gcc ttc ctc tcg     192
Asp Arg Tyr Gly Leu Leu Ala Phe Gly Leu Tyr Gly Ala Phe Leu Ser
    50                  55                  60 gcg cac ctg ttg gcg cag agc ctc ttc gcg tac ctg gag cat cgg cgg     240
Ala His Leu Leu Ala Gln Ser Leu Phe Ala Tyr Leu Glu His Arg Arg
65                  70                  75                  80 gtg gcg gcg gcg cgg cgc gcg gcg gca cgg ggg cgc ctg gat gca          288
Val Ala Ala Ala Arg Arg Ala Ala Ala Arg Gly Arg Leu Asp Ala
                85                  90                  95 gcc acg gcg cgc agc gtg gcg ctg acc att tcc gcc tac cag gag gac     336
Ala Thr Ala Arg Ser Val Ala Leu Thr Ile Ser Ala Tyr Gln Glu Asp
                100                 105                 110 ccc gcg tac ctg cgc cag tgc ctg gtg tcc gcc cgc gcc ctg ctg tac     384
Pro Ala Tyr Leu Arg Gln Cys Leu Val Ser Ala Arg Ala Leu Leu Tyr
            115                 120                 125 ccg cgc gcg cgg ctg cgc gtc ctc atg gtg gtg gac ggc aac cgc ccc     432
Pro Arg Ala Arg Leu Arg Val Leu Met Val Val Asp Gly Asn Arg Pro
        130                 135                 140 gag gac ctc tac atg gta gac atg ttc cgc gag gtc ttc gcc gac gag     480
Glu Asp Leu Tyr Met Val Asp Met Phe Arg Glu Val Phe Ala Asp Glu
145                 150                 155                 160
```

```
gac ccc gcc acg tac gtg tgg gac ggc aac tac cac cag ccc tgg gaa      528
Asp Pro Ala Thr Tyr Val Trp Asp Gly Asn Tyr His Gln Pro Trp Glu
                165                 170                 175 ccc gcg gcg gtg ggc gcg gtg ggc gtc gga gcc tac cgg gag gtg gag      576
Pro Ala Ala Val Gly Ala Val Gly Val Gly Ala Tyr Arg Glu Val Glu
            180                 185                 190 gcg gag gat ccc ggg cgg ttg gcg gtg gag gcg ctg gtg agg act cgc      624
Ala Glu Asp Pro Gly Arg Leu Ala Val Glu Ala Leu Val Arg Thr Arg
        195                 200                 205 agg tgc gtg tgc gtg gcg cag cgc tgg ggc ggc aag cgc gag gtc atg      672
Arg Cys Val Cys Val Ala Gln Arg Trp Gly Gly Lys Arg Glu Val Met
    210                 215                 220 tac acc gcc ttc aag gcg ctc gga gac tcg gtg gac tac gtg cag gtc      720
Tyr Thr Ala Phe Lys Ala Leu Gly Asp Ser Val Asp Tyr Val Gln Val
225                 230                 235                 240 tgt gac tcg gac aca agg ttg gac ccc atg gca ctg ctg gag ctc gtg      768
Cys Asp Ser Asp Thr Arg Leu Asp Pro Met Ala Leu Leu Glu Leu Val
                245                 250                 255 cag gtc ctg gat gag gac ccc cgg gta ggg gct gtt ggt ggg gac gtg      816
Gln Val Leu Asp Glu Asp Pro Arg Val Gly Ala Val Gly Gly Asp Val
            260                 265                 270 cgg atc ctt aac cct ctg gac tcc tgg gtc agc ttc cta agc agc ctg      864
Arg Ile Leu Asn Pro Leu Asp Ser Trp Val Ser Phe Leu Ser Ser Leu
        275                 280                 285 cga tac tgg gta gcc ttc aat gtg gag cgg gct tgt cag agc tac ttc      912
Arg Tyr Trp Val Ala Phe Asn Val Glu Arg Ala Cys Gln Ser Tyr Phe
    290                 295                 300 cac tgt gtg tcc tgc atc agt ggt cct cta ggc cta tat agg aac aac      960
His Cys Val Ser Cys Ile Ser Gly Pro Leu Gly Leu Tyr Arg Asn Asn
305                 310                 315                 320 ctc ttg cag cag ttt ctt gag gcc tgg tac aac cag aag ttc ctg gga     1008
Leu Leu Gln Gln Phe Leu Glu Ala Trp Tyr Asn Gln Lys Phe Leu Gly
                325                 330                 335 acc cac tgt act ttt ggg gac gac cgg cac ctc acc aac cgc atg ctc     1056
Thr His Cys Thr Phe Gly Asp Asp Arg His Leu Thr Asn Arg Met Leu
            340                 345                 350 agc atg ggt tat gct acc aag tac acc tcc agg tct cgt tgc tac tca     1104
Ser Met Gly Tyr Ala Thr Lys Tyr Thr Ser Arg Ser Arg Cys Tyr Ser
        355                 360                 365 gag aca ccc tcg tcc ttc ctg cgc tgg ctg agt cag cag act cgc tgg     1152
Glu Thr Pro Ser Ser Phe Leu Arg Trp Leu Ser Gln Gln Thr Arg Trp
    370                 375                 380 tcc aag tcg tac ttc cgt gaa tgg ctg tac aac gcg ctc tgg tgg cac     1200
Ser Lys Ser Tyr Phe Arg Glu Trp Leu Tyr Asn Ala Leu Trp Trp His
385                 390                 395                 400 cgg cat cac gcc tgg atg acc tac gag gcg gtg gtc tcg ggc ctg ttc     1248
Arg His His Ala Trp Met Thr Tyr Glu Ala Val Val Ser Gly Leu Phe
                405                 410                 415 ccc ttc ttc gtg gcg gcc acg gtg ctg cgt ctg ttc tat gcg ggc cgc     1296
Pro Phe Phe Val Ala Ala Thr Val Leu Arg Leu Phe Tyr Ala Gly Arg
            420                 425                 430 ccg tgg gcg ctg ctg tgg gtg ctg cta tgc gtg cag ggc gtg gca ctg     1344
Pro Trp Ala Leu Leu Trp Val Leu Leu Cys Val Gln Gly Val Ala Leu
        435                 440                 445 gcc aag gcg gcc ttt gcg gcc tgg ctg cgg ggc tgc ctg cgt atg gtg     1392
Ala Lys Ala Ala Phe Ala Ala Trp Leu Arg Gly Cys Leu Arg Met Val
    450                 455                 460 ctg ctg tcg ctc tac gcg ccc ctc tac atg tgt ggc ctc ctg ccc gcc     1440
Leu Leu Ser Leu Tyr Ala Pro Leu Tyr Met Cys Gly Leu Leu Pro Ala
465                 470                 475                 480
```

| | | | | | | | | | | | | | | | | |
|---|---|---|---|---|---|---|---|---|---|---|---|---|---|---|---|---|
| aag | ttc | ctg | gcg | ctg | gtc | acc | atg | aac | cag | agt | ggc | tgg | ggc | acc | tcg | 1488 |
| Lys | Phe | Leu | Ala | Leu | Val | Thr | Met | Asn | Gln | Ser | Gly | Trp | Gly | Thr | Ser | |
| | | | 485 | | | | | | 490 | | | | | | 495 | |
| ggc | cgg | cgg | aag | ctg | gcc | gct | aat | tac | gtc | cct | ctg | ctg | ccc | ctg | gcg | 1536 |
| Gly | Arg | Arg | Lys | Leu | Ala | Ala | Asn | Tyr | Val | Pro | Leu | Leu | Pro | Leu | Ala | |
| | | 500 | | | | | 505 | | | | | 510 | | | | |
| ctc | tgg | gcg | ctg | ctg | ctt | ggg | ggc | ctg | gtc | cgc | agt | gtg | gca | cac | | 1584 |
| Leu | Trp | Ala | Leu | Leu | Leu | Gly | Gly | Leu | Val | Arg | Ser | Val | Ala | His | | |
| | 515 | | | | | 520 | | | | | 525 | | | | | |
| gag | gcc | agg | gcc | gac | tgg | agc | ggc | cct | tcc | cgc | gca | gcg | gag | gcc | tac | 1632 |
| Glu | Ala | Arg | Ala | Asp | Trp | Ser | Gly | Pro | Ser | Arg | Ala | Ala | Glu | Ala | Tyr | |
| | 530 | | | | | 535 | | | | | 540 | | | | | |
| cac | tta | gcc | gcg | ggg | gcc | ggc | gcc | tac | gtg | ggc | tac | tgg | gtg | gtc | atg | 1680 |
| His | Leu | Ala | Ala | Gly | Ala | Gly | Ala | Tyr | Val | Gly | Tyr | Trp | Val | Val | Met | |
| 545 | | | | 550 | | | | 555 | | | | | 560 | | | |
| ttg | acg | ctg | tac | tgg | gtg | ggc | gtg | cgg | agg | ctt | tgc | cgg | cgg | cgg | acc | 1728 |
| Leu | Thr | Leu | Tyr | Trp | Val | Gly | Val | Arg | Arg | Leu | Cys | Arg | Arg | Arg | Thr | |
| | | | | 565 | | | | | 570 | | | | | 575 | | |
| ggg | ggc | tac | cgt | gtc | cag | gtg | tga | | | | | | | | | 1752 |
| Gly | Gly | Tyr | Arg | Val | Gln | Val | | | | | | | | | | |
| | | | 580 | | | | | | | | | | | | | |

<210> SEQ ID NO 14
<211> LENGTH: 583
<212> TYPE: PRT
<213> ORGANISM: Papio anubis

<400> SEQUENCE: 14

Met Thr Gln Arg Asp Thr Pro Lys Pro Thr Pro Ala Ala Arg Arg Cys
1               5                   10                  15

Ser Gly Leu Ala Arg Arg Val Leu Thr Ile Ala Phe Ala Leu Leu Ile
            20                  25                  30

Leu Gly Leu Met Thr Trp Ala Tyr Ala Ala Gly Val Pro Leu Ala Ser
        35                  40                  45

Asp Arg Tyr Gly Leu Leu Ala Phe Gly Leu Tyr Gly Ala Phe Leu Ser
    50                  55                  60

Ala His Leu Leu Ala Gln Ser Leu Phe Ala Tyr Leu Glu His Arg Arg
65                  70                  75                  80

Val Ala Ala Ala Arg Arg Ala Ala Ala Arg Gly Arg Leu Asp Ala
                85                  90                  95

Ala Thr Ala Arg Ser Val Ala Leu Thr Ile Ser Ala Tyr Gln Glu Asp
            100                 105                 110

Pro Ala Tyr Leu Arg Gln Cys Leu Val Ser Ala Arg Ala Leu Leu Tyr
        115                 120                 125

Pro Arg Ala Arg Leu Arg Val Leu Met Val Val Asp Gly Asn Arg Pro
    130                 135                 140

Glu Asp Leu Tyr Met Val Asp Met Phe Arg Glu Val Phe Ala Asp Glu
145                 150                 155                 160

Asp Pro Ala Thr Tyr Val Trp Asp Gly Asn Tyr His Gln Pro Trp Glu
                165                 170                 175

Pro Ala Ala Val Gly Ala Val Gly Ala Tyr Arg Glu Val Glu
            180                 185                 190

Ala Glu Asp Pro Gly Arg Leu Ala Val Glu Ala Leu Val Arg Thr Arg
        195                 200                 205

Arg Cys Val Cys Val Ala Gln Arg Trp Gly Gly Lys Arg Glu Val Met
    210                 215                 220

Tyr Thr Ala Phe Lys Ala Leu Gly Asp Ser Val Asp Tyr Val Gln Val

```
                225                 230                 235                 240

Cys Asp Ser Asp Thr Arg Leu Asp Pro Met Ala Leu Leu Glu Leu Val
                245                 250                 255

Gln Val Leu Asp Glu Asp Pro Arg Val Gly Ala Val Gly Gly Asp Val
                260                 265                 270

Arg Ile Leu Asn Pro Leu Asp Ser Trp Val Ser Phe Leu Ser Ser Leu
                275                 280                 285

Arg Tyr Trp Val Ala Phe Asn Val Glu Arg Ala Cys Gln Ser Tyr Phe
            290                 295                 300

His Cys Val Ser Cys Ile Ser Gly Pro Leu Gly Leu Tyr Arg Asn Asn
305                 310                 315                 320

Leu Leu Gln Gln Phe Leu Glu Ala Trp Tyr Asn Gln Lys Phe Leu Gly
                325                 330                 335

Thr His Cys Thr Phe Gly Asp Asp Arg His Leu Thr Asn Arg Met Leu
                340                 345                 350

Ser Met Gly Tyr Ala Thr Lys Tyr Thr Ser Arg Ser Arg Cys Tyr Ser
            355                 360                 365

Glu Thr Pro Ser Ser Phe Leu Arg Trp Leu Ser Gln Gln Thr Arg Trp
        370                 375                 380

Ser Lys Ser Tyr Phe Arg Glu Trp Leu Tyr Asn Ala Leu Trp Trp His
385                 390                 395                 400

Arg His His Ala Trp Met Thr Tyr Glu Ala Val Val Ser Gly Leu Phe
                405                 410                 415

Pro Phe Phe Val Ala Ala Thr Val Leu Arg Leu Phe Tyr Ala Gly Arg
                420                 425                 430

Pro Trp Ala Leu Leu Trp Val Leu Cys Val Gln Gly Val Ala Leu
                435                 440                 445

Ala Lys Ala Ala Phe Ala Ala Trp Leu Arg Gly Cys Leu Arg Met Val
        450                 455                 460

Leu Leu Ser Leu Tyr Ala Pro Leu Tyr Met Cys Gly Leu Leu Pro Ala
465                 470                 475                 480

Lys Phe Leu Ala Leu Val Thr Met Asn Gln Ser Gly Trp Gly Thr Ser
                485                 490                 495

Gly Arg Arg Lys Leu Ala Ala Asn Tyr Val Pro Leu Leu Pro Leu Ala
            500                 505                 510

Leu Trp Ala Leu Leu Leu Leu Gly Gly Leu Val Arg Ser Val Ala His
        515                 520                 525

Glu Ala Arg Ala Asp Trp Ser Gly Pro Ser Arg Ala Ala Glu Ala Tyr
        530                 535                 540

His Leu Ala Ala Gly Ala Gly Ala Tyr Val Gly Tyr Trp Val Val Met
545                 550                 555                 560

Leu Thr Leu Tyr Trp Val Gly Val Arg Arg Leu Cys Arg Arg Arg Thr
                565                 570                 575

Gly Gly Tyr Arg Val Gln Val
            580

<210> SEQ ID NO 15
<211> LENGTH: 1752
<212> TYPE: DNA
<213> ORGANISM: Mus musculus
<220> FEATURE:
<221> NAME/KEY: CDS
<222> LOCATION: (1)..(1752)
<300> PUBLICATION INFORMATION:
<308> DATABASE ACCESSION NUMBER: D82964.1
<309> DATABASE ENTRY DATE: 1996-05-31
<313> RELEVANT RESIDUES IN SEQ ID NO: (49)..(1800)
```

<400> SEQUENCE: 15

```
atg aga cag gac atg cca aag ccc tca gag gca gcg cgt tgc tgc tct      48
Met Arg Gln Asp Met Pro Lys Pro Ser Glu Ala Ala Arg Cys Cys Ser
1               5                   10                  15 ggc ctg gcc agg cga gca ctc acg atc atc ttt gcc ctg ctc atc ctg      96
Gly Leu Ala Arg Arg Ala Leu Thr Ile Ile Phe Ala Leu Leu Ile Leu
            20                  25                  30 ggc ctc atg acc tgg gcc tac gcc gca ggc gtt cct ctg gct tca gat     144
Gly Leu Met Thr Trp Ala Tyr Ala Ala Gly Val Pro Leu Ala Ser Asp
        35                  40                  45 cgc tat gga ctc ctg gcc ttt ggc ctc tat ggg gca ttc ctc agc gca     192
Arg Tyr Gly Leu Leu Ala Phe Gly Leu Tyr Gly Ala Phe Leu Ser Ala
    50                  55                  60 cac cta gtg gca cag agc ctc ttc gct tac ctg gag cac cga agg gtg     240
His Leu Val Ala Gln Ser Leu Phe Ala Tyr Leu Glu His Arg Arg Val
65                  70                  75                  80 gca gcg gct gcg cgg cgc tcc ttg gcg aag ggg ccc ctg gat gcg gcc     288
Ala Ala Ala Ala Arg Arg Ser Leu Ala Lys Gly Pro Leu Asp Ala Ala
                85                  90                  95 act gca cgc agc gtg gca ctc acc atc tca gcc tac caa gag gat ccc     336
Thr Ala Arg Ser Val Ala Leu Thr Ile Ser Ala Tyr Gln Glu Asp Pro
            100                 105                 110 gct tac ctg cgc cag tgc ttg acc tcc gcg cgc gcc ttg ctg tac ccg     384
Ala Tyr Leu Arg Gln Cys Leu Thr Ser Ala Arg Ala Leu Leu Tyr Pro
        115                 120                 125 cac acg agg tta cgc gtg ctc atg gtg gtg gac ggc aac cgc gct gag     432
His Thr Arg Leu Arg Val Leu Met Val Val Asp Gly Asn Arg Ala Glu
    130                 135                 140 gat ctg tac atg gtg gac atg ttc cga gaa gtc ttc gcc gat gag gac     480
Asp Leu Tyr Met Val Asp Met Phe Arg Glu Val Phe Ala Asp Glu Asp
145                 150                 155                 160 ccc gcc act tat gtg tgg gat ggc aac tac cat cag ccc tgg gaa cca     528
Pro Ala Thr Tyr Val Trp Asp Gly Asn Tyr His Gln Pro Trp Glu Pro
                165                 170                 175 gcg gag gct acg ggc gct gtc ggt gaa ggt gcc tac cgg gag gtg gag     576
Ala Glu Ala Thr Gly Ala Val Gly Glu Gly Ala Tyr Arg Glu Val Glu
            180                 185                 190 gcg gag gac ccc ggg cgg ttg gcg gtg gag gcg ctg gtg aga aca cgc     624
Ala Glu Asp Pro Gly Arg Leu Ala Val Glu Ala Leu Val Arg Thr Arg
        195                 200                 205 agg tgc gtg tgc gtg gct cag cgt tgg ggc ggc aaa cgt gag gtc atg     672
Arg Cys Val Cys Val Ala Gln Arg Trp Gly Gly Lys Arg Glu Val Met
    210                 215                 220 tac aca gct ttc aag gca ctg ggc gac tcc gtg gac tac gtg cag gtc     720
Tyr Thr Ala Phe Lys Ala Leu Gly Asp Ser Val Asp Tyr Val Gln Val
225                 230                 235                 240 tgt gac tca gac aca aga cta gac ccc atg gca ctg ctg gag ctt gtg     768
Cys Asp Ser Asp Thr Arg Leu Asp Pro Met Ala Leu Leu Glu Leu Val
                245                 250                 255 cga gtg ttg gat gaa gac ccc cgg gta ggg gct gtt gga ggg gat gtg     816
Arg Val Leu Asp Glu Asp Pro Arg Val Gly Ala Val Gly Gly Asp Val
            260                 265                 270 agg atc ctt aac cct ctg gac tcc tgg gtc agc ttc ttg agc agt ctt     864
Arg Ile Leu Asn Pro Leu Asp Ser Trp Val Ser Phe Leu Ser Ser Leu
        275                 280                 285 cga tac tgg gta gcc ttc aat gtg gaa cga gct tgt cag agc tac ttc     912
Arg Tyr Trp Val Ala Phe Asn Val Glu Arg Ala Cys Gln Ser Tyr Phe
    290                 295                 300 cac tgt gtg tcc tgc atc agt ggt cct ctg ggt cta tac aga aac aat     960
```

```
                His Cys Val Ser Cys Ile Ser Gly Pro Leu Gly Leu Tyr Arg Asn Asn
                305                 310                 315                 320 ctc ctg cag cag ttc ttg gag gcc tgg tac aac caa aag ttc ctg ggc         1008
Leu Leu Gln Gln Phe Leu Glu Ala Trp Tyr Asn Gln Lys Phe Leu Gly
                325                 330                 335 acc cac tgc aca ttt ggg gat gac agg cac ctc acc aac cga atg ctt         1056
Thr His Cys Thr Phe Gly Asp Asp Arg His Leu Thr Asn Arg Met Leu
            340                 345                 350 agc atg ggc tat gct acc aag tat acc tcg cgc tcc aga tgc tac tcg         1104
Ser Met Gly Tyr Ala Thr Lys Tyr Thr Ser Arg Ser Arg Cys Tyr Ser
        355                 360                 365 gag acg ccc tcc tcc ttc ctt cgt tgg ttg agc caa cag acc cgc tgg         1152
Glu Thr Pro Ser Ser Phe Leu Arg Trp Leu Ser Gln Gln Thr Arg Trp
    370                 375                 380 tcc aaa tct tac ttc cga gag tgg cta tac aat gct ctg tgg tgg cat         1200
Ser Lys Ser Tyr Phe Arg Glu Trp Leu Tyr Asn Ala Leu Trp Trp His
385                 390                 395                 400 cgc cac cac gca tgg atg acc tat gaa gcg gtg gtc tcg ggc ctc ttc         1248
Arg His His Ala Trp Met Thr Tyr Glu Ala Val Val Ser Gly Leu Phe
                405                 410                 415 cct ttc ttc gtg gct gcc acg gtg ttg agg ctc ttc tat gca ggg cgc         1296
Pro Phe Phe Val Ala Ala Thr Val Leu Arg Leu Phe Tyr Ala Gly Arg
            420                 425                 430 ccg tgg gct ctg ctc tgg gtg ctg ctc tgt gtg cag ggc gta gca ctg         1344
Pro Trp Ala Leu Leu Trp Val Leu Leu Cys Val Gln Gly Val Ala Leu
        435                 440                 445 gca aag gca gcc ttt gca gcc tgg ctg cgt ggc tgc gtg cgc atg gtg         1392
Ala Lys Ala Ala Phe Ala Ala Trp Leu Arg Gly Cys Val Arg Met Val
    450                 455                 460 ctg ctg tca ctc tat gca cca ctc tac atg tgc ggc ctc ctg cct gcc         1440
Leu Leu Ser Leu Tyr Ala Pro Leu Tyr Met Cys Gly Leu Leu Pro Ala
465                 470                 475                 480 aaa ttc cta gcg ttg gtt acc atg aat caa agt ggt tgg ggt acc tcg         1488
Lys Phe Leu Ala Leu Val Thr Met Asn Gln Ser Gly Trp Gly Thr Ser
                485                 490                 495 ggc cgg aag aaa ctg gct gct aac tat gtc ccc gtg ttg ccc ctg gca         1536
Gly Arg Lys Lys Leu Ala Ala Asn Tyr Val Pro Val Leu Pro Leu Ala
            500                 505                 510 ctc tgg gct cta ctg ctg ctt gga ggc ctg gcc cgc agt gtg gcc cag         1584
Leu Trp Ala Leu Leu Leu Gly Gly Leu Ala Arg Ser Val Ala Gln
        515                 520                 525 gag gcc aga gct gac tgg agt ggc cca tcc cga gca gct gaa gcc tac         1632
Glu Ala Arg Ala Asp Trp Ser Gly Pro Ser Arg Ala Ala Glu Ala Tyr
    530                 535                 540 cac ctt gct gct ggg gct ggt gcc tat gtg gcc tac tgg gtg gta atg         1680
His Leu Ala Ala Gly Ala Gly Ala Tyr Val Ala Tyr Trp Val Val Met
545                 550                 555                 560 tta act atc tac tgg gta ggt gtg agg agg ctg tgc aga cgt cgg agc         1728
Leu Thr Ile Tyr Trp Val Gly Val Arg Arg Leu Cys Arg Arg Arg Ser
                565                 570                 575 ggt ggt tac cgt gtc caa gta tga                                         1752
Gly Gly Tyr Arg Val Gln Val
                580

<210> SEQ ID NO 16
<211> LENGTH: 583
<212> TYPE: PRT
<213> ORGANISM: Mus musculus

<400> SEQUENCE: 16

Met Arg Gln Asp Met Pro Lys Pro Ser Glu Ala Ala Arg Cys Cys Ser
```

-continued

```
1               5                   10                  15
Gly Leu Ala Arg Arg Ala Leu Thr Ile Ile Phe Ala Leu Leu Ile Leu
                20                  25                  30

Gly Leu Met Thr Trp Ala Tyr Ala Ala Gly Val Pro Leu Ala Ser Asp
            35                  40                  45

Arg Tyr Gly Leu Leu Ala Phe Gly Leu Tyr Gly Ala Phe Leu Ser Ala
        50                  55                  60

His Leu Val Ala Gln Ser Leu Phe Ala Tyr Leu Glu His Arg Arg Val
65                  70                  75                  80

Ala Ala Ala Ala Arg Arg Ser Leu Ala Lys Gly Pro Leu Asp Ala Ala
                85                  90                  95

Thr Ala Arg Ser Val Ala Leu Thr Ile Ser Ala Tyr Gln Glu Asp Pro
            100                 105                 110

Ala Tyr Leu Arg Gln Cys Leu Thr Ser Ala Arg Ala Leu Leu Tyr Pro
        115                 120                 125

His Thr Arg Leu Arg Val Leu Met Val Val Asp Gly Asn Arg Ala Glu
    130                 135                 140

Asp Leu Tyr Met Val Asp Met Phe Arg Glu Val Phe Ala Asp Glu Asp
145                 150                 155                 160

Pro Ala Thr Tyr Val Trp Asp Gly Asn Tyr His Gln Pro Trp Glu Pro
                165                 170                 175

Ala Glu Ala Thr Gly Ala Val Gly Glu Gly Ala Tyr Arg Glu Val Glu
            180                 185                 190

Ala Glu Asp Pro Gly Arg Leu Ala Val Glu Ala Leu Val Arg Thr Arg
        195                 200                 205

Arg Cys Val Cys Val Ala Gln Arg Trp Gly Gly Lys Arg Glu Val Met
    210                 215                 220

Tyr Thr Ala Phe Lys Ala Leu Gly Asp Ser Val Asp Tyr Val Gln Val
225                 230                 235                 240

Cys Asp Ser Asp Thr Arg Leu Asp Pro Met Ala Leu Leu Glu Leu Val
                245                 250                 255

Arg Val Leu Asp Glu Asp Pro Arg Val Gly Ala Val Gly Gly Asp Val
            260                 265                 270

Arg Ile Leu Asn Pro Leu Asp Ser Trp Val Ser Phe Leu Ser Ser Leu
        275                 280                 285

Arg Tyr Trp Val Ala Phe Asn Val Glu Arg Ala Cys Gln Ser Tyr Phe
    290                 295                 300

His Cys Val Ser Cys Ile Ser Gly Pro Leu Gly Leu Tyr Arg Asn Asn
305                 310                 315                 320

Leu Leu Gln Gln Phe Leu Glu Ala Trp Tyr Asn Gln Lys Phe Leu Gly
                325                 330                 335

Thr His Cys Thr Phe Gly Asp Asp Arg His Leu Thr Asn Arg Met Leu
            340                 345                 350

Ser Met Gly Tyr Ala Thr Lys Tyr Thr Ser Arg Ser Arg Cys Tyr Ser
        355                 360                 365

Glu Thr Pro Ser Ser Phe Leu Arg Trp Leu Ser Gln Gln Thr Arg Trp
    370                 375                 380

Ser Lys Ser Tyr Phe Arg Glu Trp Leu Tyr Asn Ala Leu Trp His His
385                 390                 395                 400

Arg His His Ala Trp Met Thr Tyr Glu Ala Val Val Ser Gly Leu Phe
                405                 410                 415

Pro Phe Phe Val Ala Ala Thr Val Leu Arg Leu Phe Tyr Ala Gly Arg
            420                 425                 430
```

```
Pro Trp Ala Leu Leu Trp Val Leu Leu Cys Val Gln Gly Val Ala Leu
        435                 440                 445

Ala Lys Ala Ala Phe Ala Ala Trp Leu Arg Gly Cys Val Arg Met Val
    450                 455                 460

Leu Leu Ser Leu Tyr Ala Pro Leu Tyr Met Cys Gly Leu Leu Pro Ala
465                 470                 475                 480

Lys Phe Leu Ala Leu Val Thr Met Asn Gln Ser Gly Trp Gly Thr Ser
                485                 490                 495

Gly Arg Lys Lys Leu Ala Ala Asn Tyr Val Pro Val Leu Pro Leu Ala
            500                 505                 510

Leu Trp Ala Leu Leu Leu Gly Gly Leu Ala Arg Ser Val Ala Gln
            515                 520                 525

Glu Ala Arg Ala Asp Trp Ser Gly Pro Ser Arg Ala Ala Glu Ala Tyr
    530                 535                 540

His Leu Ala Ala Gly Ala Gly Ala Tyr Val Ala Tyr Trp Val Val Met
545                 550                 555                 560

Leu Thr Ile Tyr Trp Val Gly Val Arg Arg Leu Cys Arg Arg Arg Ser
                565                 570                 575

Gly Gly Tyr Arg Val Gln Val
            580
```

<210> SEQ ID NO 17
<211> LENGTH: 1659
<212> TYPE: DNA
<213> ORGANISM: Mus musculus
<220> FEATURE:
<221> NAME/KEY: CDS
<222> LOCATION: (1)..(1659)
<300> PUBLICATION INFORMATION:
<308> DATABASE ACCESSION NUMBER: U52524.2
<309> DATABASE ENTRY DATE: 1996-10-15
<313> RELEVANT RESIDUES IN SEQ ID NO: (508)..(2166)

<400> SEQUENCE: 17

```
atg cat tgt gag agg ttt cta tgt gtc ctg aga ata att gga act aca      48
Met His Cys Glu Arg Phe Leu Cys Val Leu Arg Ile Ile Gly Thr Thr
1               5                   10                  15 ctt ttt gga gtg tct ctc ctc ctc gga atc aca gct gct tat att gtt      96
Leu Phe Gly Val Ser Leu Leu Leu Gly Ile Thr Ala Ala Tyr Ile Val
                20                  25                  30 ggc tac cag ttt atc caa aca gat aat tac tac ttc tca ttt gga ctg     144
Gly Tyr Gln Phe Ile Gln Thr Asp Asn Tyr Tyr Phe Ser Phe Gly Leu
            35                  40                  45 tac ggt gcc ttt tta gcc tcg cat ctc atc atc caa agc ctc ttt gcc     192
Tyr Gly Ala Phe Leu Ala Ser His Leu Ile Ile Gln Ser Leu Phe Ala
        50                  55                  60 ttt ttg gaa cac cgg aaa atg aag aag tcc ctt gaa acc ccg att aaa     240
Phe Leu Glu His Arg Lys Met Lys Lys Ser Leu Glu Thr Pro Ile Lys
65                  70                  75                  80 ttg aac aaa acg gta gca ctc tgc atc gct gcg tac caa gag gac cct     288
Leu Asn Lys Thr Val Ala Leu Cys Ile Ala Ala Tyr Gln Glu Asp Pro
                85                  90                  95 gac tac tta cgg aaa tgt ttg caa tct gtg aaa agg ctg acc tac cct     336
Asp Tyr Leu Arg Lys Cys Leu Gln Ser Val Lys Arg Leu Thr Tyr Pro
            100                 105                 110 ggg att aaa gtc gtg atg gtc atc gat ggg aac tca gac gac gac ctt     384
Gly Ile Lys Val Val Met Val Ile Asp Gly Asn Ser Asp Asp Asp Leu
        115                 120                 125 tac atg atg gac ata ttc agc gaa gtt att ggc agg gac aaa tcg gcc     432
Tyr Met Met Asp Ile Phe Ser Glu Val Ile Gly Arg Asp Lys Ser Ala
130                 135                 140
```

```
acg tac atc tgg aag aac aac ttt cat gaa aag gga cct ggt gag aca         480
Thr Tyr Ile Trp Lys Asn Asn Phe His Glu Lys Gly Pro Gly Glu Thr
145                 150                 155                 160 gaa gag tcc cat aaa gaa agt tca caa cat gtc acc caa ttg gtc ttg         528
Glu Glu Ser His Lys Glu Ser Ser Gln His Val Thr Gln Leu Val Leu
                165                 170                 175 tct aac aaa agt att tgc atc atg caa aaa tgg ggt gga aag aga gaa         576
Ser Asn Lys Ser Ile Cys Ile Met Gln Lys Trp Gly Gly Lys Arg Glu
            180                 185                 190 gtc atg tac aca gcc ttc aga gca ctg ggg cga agc gtg gat tat gta         624
Val Met Tyr Thr Ala Phe Arg Ala Leu Gly Arg Ser Val Asp Tyr Val
        195                 200                 205 cag gtg tgt gac tca gat act atg ctt gac cct gcc tca tct gtg gag         672
Gln Val Cys Asp Ser Asp Thr Met Leu Asp Pro Ala Ser Ser Val Glu
    210                 215                 220 atg gtg aag gtc tta gag gaa gac cct atg gtt gga ggt gtt gga gga         720
Met Val Lys Val Leu Glu Glu Asp Pro Met Val Gly Gly Val Gly Gly
225                 230                 235                 240 gat gtc cag att tta aac aag tat gat tcc tgg atc tcc ttc ctc agc         768
Asp Val Gln Ile Leu Asn Lys Tyr Asp Ser Trp Ile Ser Phe Leu Ser
                245                 250                 255 agc gtg aga tac tgg atg gct ttt aat ata gaa agg gcc tgc cag tct         816
Ser Val Arg Tyr Trp Met Ala Phe Asn Ile Glu Arg Ala Cys Gln Ser
            260                 265                 270 tat ttt ggc tgt gtc cag tgc ata agc ggt cct ctg gga atg tac aga         864
Tyr Phe Gly Cys Val Gln Cys Ile Ser Gly Pro Leu Gly Met Tyr Arg
        275                 280                 285 aac tcc ttg ctg cat gaa ttt gtg gaa gac tgg tac aat cag gaa ttc         912
Asn Ser Leu Leu His Glu Phe Val Glu Asp Trp Tyr Asn Gln Glu Phe
    290                 295                 300 atg ggt aac caa tgc agt ttt ggt gac gac agg cac ctt acc aac agg         960
Met Gly Asn Gln Cys Ser Phe Gly Asp Asp Arg His Leu Thr Asn Arg
305                 310                 315                 320 gtg ttg agt ctg ggc tat gca act aaa tac acg gct cgg tcc aag tgc        1008
Val Leu Ser Leu Gly Tyr Ala Thr Lys Tyr Thr Ala Arg Ser Lys Cys
                325                 330                 335 ctt act gaa act ccc ata gaa tat ctg aga tgg ctg aac cag cag acc        1056
Leu Thr Glu Thr Pro Ile Glu Tyr Leu Arg Trp Leu Asn Gln Gln Thr
            340                 345                 350 cga tgg agc aag tcc tac ttc cga gag tgg ctg tac aat gcc atg tgg        1104
Arg Trp Ser Lys Ser Tyr Phe Arg Glu Trp Leu Tyr Asn Ala Met Trp
        355                 360                 365 ttt cac aag cat cac ctg tgg atg acc tat gaa gct gtt atc act gga        1152
Phe His Lys His His Leu Trp Met Thr Tyr Glu Ala Val Ile Thr Gly
    370                 375                 380 ttc ttt cct ttc ttt ctc att gcc aca gtc atc cag ctc ttc tac agg        1200
Phe Phe Pro Phe Phe Leu Ile Ala Thr Val Ile Gln Leu Phe Tyr Arg
385                 390                 395                 400 ggt aaa atc tgg aac atc ctc ctc ttc ctg tta act gtc cag cta gtg        1248
Gly Lys Ile Trp Asn Ile Leu Leu Phe Leu Leu Thr Val Gln Leu Val
                405                 410                 415 ggt ctc atc aag tca tct ttt gcc agc tgc ctt aga gga aat atc gtc        1296
Gly Leu Ile Lys Ser Ser Phe Ala Ser Cys Leu Arg Gly Asn Ile Val
            420                 425                 430 atg gta ttc atg tct ctg tat tca gtg tta tac atg tca agt cta ctt        1344
Met Val Phe Met Ser Leu Tyr Ser Val Leu Tyr Met Ser Ser Leu Leu
        435                 440                 445 cct gcc aag atg ttt gca att gca acc ata aac aaa gct ggg tgg ggc        1392
Pro Ala Lys Met Phe Ala Ile Ala Thr Ile Asn Lys Ala Gly Trp Gly
    450                 455                 460
```

```
aca tct gga agg aag acc att gtt gtt aat ttc ata gga ctt att cca     1440
Thr Ser Gly Arg Lys Thr Ile Val Val Asn Phe Ile Gly Leu Ile Pro
465                 470                 475                 480 gtg tcc gtg tgg ttt aca atc ctt cta ggt ggt gta att ttc acc att     1488
Val Ser Val Trp Phe Thr Ile Leu Leu Gly Gly Val Ile Phe Thr Ile
            485                 490                 495 tat aag gaa tct aaa aag cca ttt tcc gaa tcc aaa cag act gtt ctc     1536
Tyr Lys Glu Ser Lys Lys Pro Phe Ser Glu Ser Lys Gln Thr Val Leu
        500                 505                 510 atc gtg gga act ttg atc tat gca tgc tac tgg gtc atg ctt ttg act     1584
Ile Val Gly Thr Leu Ile Tyr Ala Cys Tyr Trp Val Met Leu Leu Thr
    515                 520                 525 ctc tat gtg gtt ctc atc aat aag tgt ggc agg cgg aag aag gga caa     1632
Leu Tyr Val Val Leu Ile Asn Lys Cys Gly Arg Arg Lys Lys Gly Gln
530                 535                 540 cag tat gac atg gtg ctt gat gta tga                                 1659
Gln Tyr Asp Met Val Leu Asp Val
545                 550

<210> SEQ ID NO 18
<211> LENGTH: 552
<212> TYPE: PRT
<213> ORGANISM: Mus musculus

<400> SEQUENCE: 18

Met His Cys Glu Arg Phe Leu Cys Val Leu Arg Ile Ile Gly Thr Thr
1               5                   10                  15

Leu Phe Gly Val Ser Leu Leu Leu Gly Ile Thr Ala Ala Tyr Ile Val
            20                  25                  30

Gly Tyr Gln Phe Ile Gln Thr Asp Asn Tyr Tyr Phe Ser Phe Gly Leu
        35                  40                  45

Tyr Gly Ala Phe Leu Ala Ser His Leu Ile Ile Gln Ser Leu Phe Ala
    50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Gln Ser Val Lys Arg Leu Thr Tyr Pro
            100                 105                 110

Gly Ile Lys Val Val Met Val Ile Asp Gly Asn Ser Asp Asp Asp Leu
        115                 120                 125

Tyr Met Met Asp Ile Phe Ser Glu Val Ile Gly Arg Asp Lys Ser Ala
    130                 135                 140

Thr Tyr Ile Trp Lys Asn Asn Phe His Glu Lys Gly Pro Gly Glu Thr
145                 150                 155                 160

Glu Glu Ser His Lys Glu Ser Ser Gln His Val Thr Gln Leu Val Leu
                165                 170                 175

Ser Asn Lys Ser Ile Cys Ile Met Gln Lys Trp Gly Lys Arg Glu
            180                 185                 190

Val Met Tyr Thr Ala Phe Arg Ala Leu Gly Arg Ser Val Asp Tyr Val
        195                 200                 205

Gln Val Cys Asp Ser Asp Thr Met Leu Asp Pro Ala Ser Ser Val Glu
    210                 215                 220

Met Val Lys Val Leu Glu Glu Asp Pro Met Val Gly Gly Val Gly Gly
225                 230                 235                 240

Asp Val Gln Ile Leu Asn Lys Tyr Asp Ser Trp Ile Ser Phe Leu Ser
                245                 250                 255
```

```
Ser Val Arg Tyr Trp Met Ala Phe Asn Ile Glu Arg Ala Cys Gln Ser
        260                 265                 270

Tyr Phe Gly Cys Val Gln Cys Ile Ser Gly Pro Leu Gly Met Tyr Arg
    275                 280                 285

Asn Ser Leu Leu His Glu Phe Val Glu Asp Trp Tyr Asn Gln Glu Phe
    290                 295                 300

Met Gly Asn Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
            340                 345                 350

Arg Trp Ser Lys Ser Tyr Phe Arg Glu Trp Leu Tyr Asn Ala Met Trp
        355                 360                 365

Phe His Lys His His Leu Trp Met Thr Tyr Glu Ala Val Ile Thr Gly
    370                 375                 380

Phe Phe Pro Phe Phe Leu Ile Ala Thr Val Ile Gln Leu Phe Tyr Arg
385                 390                 395                 400

Gly Lys Ile Trp Asn Ile Leu Leu Phe Leu Leu Thr Val Gln Leu Val
                405                 410                 415

Gly Leu Ile Lys Ser Ser Phe Ala Ser Cys Leu Arg Gly Asn Ile Val
            420                 425                 430

Met Val Phe Met Ser Leu Tyr Ser Val Leu Tyr Met Ser Ser Leu Leu
        435                 440                 445

Pro Ala Lys Met Phe Ala Ile Ala Thr Ile Asn Lys Ala Gly Trp Gly
    450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                485                 490                 495

Tyr Lys Glu Ser Lys Lys Pro Phe Ser Glu Ser Lys Gln Thr Val Leu
            500                 505                 510

Ile Val Gly Thr Leu Ile Tyr Ala Cys Tyr Trp Val Met Leu Leu Thr
        515                 520                 525

Leu Tyr Val Val Leu Ile Asn Lys Cys Gly Arg Arg Lys Lys Gly Gln
    530                 535                 540

Gln Tyr Asp Met Val Leu Asp Val
545                 550

<210> SEQ ID NO 19
<211> LENGTH: 1665
<212> TYPE: DNA
<213> ORGANISM: Mus musculus
<220> FEATURE:
<221> NAME/KEY: CDS
<222> LOCATION: (1)..(1665)
<300> PUBLICATION INFORMATION:
<308> DATABASE ACCESSION NUMBER: U86408.2
<309> DATABASE ENTRY DATE: 1997-04-16
<313> RELEVANT RESIDUES IN SEQ ID NO: (175)..(1839)

<400> SEQUENCE: 19 atg ccg gtc cag ctg act aca gcc ctg cgt gtg gtg ggc acc agt ctg      48
Met Pro Val Gln Leu Thr Thr Ala Leu Arg Val Val Gly Thr Ser Leu
1               5                   10                  15 ttt gcc ctg gta gtg ctg gga ggc atc ctg gcg gcc tat gtg aca ggc      96
Phe Ala Leu Val Val Leu Gly Gly Ile Leu Ala Ala Tyr Val Thr Gly
                20                  25                  30
```

-continued

| | | |
|---|---|---|
| tac cag ttt atc cac aca gaa aag cac tac ctg tcc ttt ggc ctc tac<br>Tyr Gln Phe Ile His Thr Glu Lys His Tyr Leu Ser Phe Gly Leu Tyr<br>       35                 40                    45 | | 144 |
| ggt gcc atc ctg ggt cta cat ctg ctc atc cag agc ctg ttt gcc ttc<br>Gly Ala Ile Leu Gly Leu His Leu Leu Ile Gln Ser Leu Phe Ala Phe<br>    50                    55                    60 | | 192 |
| ctg gag cac cgt cga atg cgc agg gca ggg cgc ccc ctc aag ctg cac<br>Leu Glu His Arg Arg Met Arg Arg Ala Gly Arg Pro Leu Lys Leu His<br>65                    70                    75                    80 | | 240 |
| tgc tcc cag agg tcg cgt tca gtg gca ctc tgc att gct gcc tac caa<br>Cys Ser Gln Arg Ser Arg Ser Val Ala Leu Cys Ile Ala Ala Tyr Gln<br>                   85                    90                    95 | | 288 |
| gag gac ccc gaa tac ctg cgc aag tgc ctt cgc tca gct cag cgc att<br>Glu Asp Pro Glu Tyr Leu Arg Lys Cys Leu Arg Ser Ala Gln Arg Ile<br>            100                  105                110 | | 336 |
| gcc ttt cca aac ctc aag gtg gtc atg gta gtg gat ggc aat cgc cag<br>Ala Phe Pro Asn Leu Lys Val Val Met Val Val Asp Gly Asn Arg Gln<br>        115                 120                125 | | 384 |
| gaa gat acc tac atg ttg gac atc ttc cat gag gtg ctg ggt ggc act<br>Glu Asp Thr Tyr Met Leu Asp Ile Phe His Glu Val Leu Gly Gly Thr<br>130                    135                    140 | | 432 |
| gag caa gct ggc ttc ttt gtg tgg cgt agc aat ttc cat gag gcg ggt<br>Glu Gln Ala Gly Phe Phe Val Trp Arg Ser Asn Phe His Glu Ala Gly<br>145                    150                    155                160 | | 480 |
| gaa gga gag aca gag gcc agc ctg cag gaa ggc atg gag cgt gtg cga<br>Glu Gly Glu Thr Glu Ala Ser Leu Gln Glu Gly Met Glu Arg Val Arg<br>                   165                    170                175 | | 528 |
| gct gtg gtg tgg gcc agc acc ttc tca tgc atc atg cag aag tgg ggg<br>Ala Val Val Trp Ala Ser Thr Phe Ser Cys Ile Met Gln Lys Trp Gly<br>        180                 185                190 | | 576 |
| ggc aag cgt gag gtc atg tac act gcc ttc aag gcc ctt ggc aac tca<br>Gly Lys Arg Glu Val Met Tyr Thr Ala Phe Lys Ala Leu Gly Asn Ser<br>            195                  200                205 | | 624 |
| gtg gac tac atc cag gtg tgt gac tct gac act gtg ctg gac cca gcc<br>Val Asp Tyr Ile Gln Val Cys Asp Ser Asp Thr Val Leu Asp Pro Ala<br>210                    215                    220 | | 672 |
| tgc acc att gag atg ctt cga gtc ttg gaa gaa gat ccc caa gta gga<br>Cys Thr Ile Glu Met Leu Arg Val Leu Glu Glu Asp Pro Gln Val Gly<br>225                    230                    235                240 | | 720 |
| ggt gtt gga gga gat gtc caa atc ctc aac aag tat gat tca tgg atc<br>Gly Val Gly Gly Asp Val Gln Ile Leu Asn Lys Tyr Asp Ser Trp Ile<br>            245                  250                255 | | 768 |
| tcc ttc ctg agc agt gtg agg tac tgg atg gct ttc aac gtg gag cgg<br>Ser Phe Leu Ser Ser Val Arg Tyr Trp Met Ala Phe Asn Val Glu Arg<br>               260                    265                270 | | 816 |
| gcc tgc cag tcc tac ttt ggc tgt gtg caa tgt att agt ggg cct ttg<br>Ala Cys Gln Ser Tyr Phe Gly Cys Val Gln Cys Ile Ser Gly Pro Leu<br>        275                 280                285 | | 864 |
| ggc atg tac cgc aac agc ctc ctt cag cag ttc ctg gag gat tgg tac<br>Gly Met Tyr Arg Asn Ser Leu Leu Gln Gln Phe Leu Glu Asp Trp Tyr<br>290                    295                    300 | | 912 |
| cat cag aag ttc cta ggc agc aag tgc agc ttt ggg gat gat cgg cac<br>His Gln Lys Phe Leu Gly Ser Lys Cys Ser Phe Gly Asp Asp Arg His<br>305                    310                    315                320 | | 960 |
| ctt acc aac cga gtc ctg agt ctt ggc tac cgg act aag tat aca gca<br>Leu Thr Asn Arg Val Leu Ser Leu Gly Tyr Arg Thr Lys Tyr Thr Ala<br>            325                  330                335 | | 1008 |
| cgc tct aag tgc ctc aca gag acc ccc act agg tac ctt cga tgg ctc<br>Arg Ser Lys Cys Leu Thr Glu Thr Pro Thr Arg Tyr Leu Arg Trp Leu<br>               340                    345                350 | | 1056 |

```
aat cag caa acc cgc tgg agc aag tct tac ttt cgg gaa tgg ctc tac    1104
Asn Gln Gln Thr Arg Trp Ser Lys Ser Tyr Phe Arg Glu Trp Leu Tyr
        355                 360                 365 aat tct ctg tgg ttc cat aag cac cac ctc tgg atg acc tat gaa tca    1152
Asn Ser Leu Trp Phe His Lys His His Leu Trp Met Thr Tyr Glu Ser
370                 375                 380 gtg gtc aca ggt ttc ttc cca ttc ttc ctc att gct aca gtc ata caa    1200
Val Val Thr Gly Phe Phe Pro Phe Phe Leu Ile Ala Thr Val Ile Gln
385                 390                 395                 400 ctt ttc tac cgt ggc cgc atc tgg aac att ctc ctc ttc ctg cta aca    1248
Leu Phe Tyr Arg Gly Arg Ile Trp Asn Ile Leu Leu Phe Leu Leu Thr
                405                 410                 415 gtg cag ctg gtg ggc att atc aag gct acc tat gcc tgc ttc ctt cga    1296
Val Gln Leu Val Gly Ile Ile Lys Ala Thr Tyr Ala Cys Phe Leu Arg
            420                 425                 430 ggc aat gca gag atg atc ttc atg tcc ctc tac tcc ctt ctc tat atg    1344
Gly Asn Ala Glu Met Ile Phe Met Ser Leu Tyr Ser Leu Leu Tyr Met
        435                 440                 445 tcc agc ctc ttg cca gcc aag atc ttt gct att gct acc atc aac aag    1392
Ser Ser Leu Leu Pro Ala Lys Ile Phe Ala Ile Ala Thr Ile Asn Lys
    450                 455                 460 tct ggc tgg ggc act tct ggc agg aaa acc att gtc gtg aac ttc att    1440
Ser Gly Trp Gly Thr Ser Gly Arg Lys Thr Ile Val Val Asn Phe Ile
465                 470                 475                 480 ggc cta atc ccc gtg tcc atc tgg gtg gca gtt ctt cta ggg ggg tta    1488
Gly Leu Ile Pro Val Ser Ile Trp Val Ala Val Leu Leu Gly Gly Leu
                485                 490                 495 gcc tac aca gct tat tgc cag gac ctg ttc agt gag acc gag cta gcc    1536
Ala Tyr Thr Ala Tyr Cys Gln Asp Leu Phe Ser Glu Thr Glu Leu Ala
            500                 505                 510 ttc cta gtc tct ggg gcc atc ctg tat ggc tgc tac tgg gtg gcc ctc    1584
Phe Leu Val Ser Gly Ala Ile Leu Tyr Gly Cys Tyr Trp Val Ala Leu
        515                 520                 525 ctc atg ctg tat ctg gcc att att gcc cgg agg tgt ggg aag aag cca    1632
Leu Met Leu Tyr Leu Ala Ile Ile Ala Arg Arg Cys Gly Lys Lys Pro
    530                 535                 540 gaa cag tat agc ctg gct ttt gcg gag gtg tga                        1665
Glu Gln Tyr Ser Leu Ala Phe Ala Glu Val
545                 550

<210> SEQ ID NO 20
<211> LENGTH: 554
<212> TYPE: PRT
<213> ORGANISM: Mus musculus

<400> SEQUENCE: 20

Met Pro Val Gln Leu Thr Thr Ala Leu Arg Val Gly Thr Ser Leu
1               5                   10                  15

Phe Ala Leu Val Val Leu Gly Gly Ile Leu Ala Ala Tyr Val Thr Gly
            20                  25                  30

Tyr Gln Phe Ile His Thr Glu Lys His Tyr Leu Ser Phe Gly Leu Tyr
        35                  40                  45

Gly Ala Ile Leu Gly Leu His Leu Leu Ile Gln Ser Leu Phe Ala Phe
    50                  55                  60

Leu Glu His Arg Arg Met Arg Arg Ala Gly Arg Pro Leu Lys Leu His
65                  70                  75                  80

Cys Ser Gln Arg Ser Arg Ser Val Ala Leu Cys Ile Ala Ala Tyr Gln
                85                  90                  95

Glu Asp Pro Glu Tyr Leu Arg Lys Cys Leu Arg Ser Ala Gln Arg Ile
```

```
                100                 105                 110
Ala Phe Pro Asn Leu Lys Val Met Val Val Asp Gly Asn Arg Gln
            115                 120                 125

Glu Asp Thr Tyr Met Leu Asp Ile Phe His Glu Val Leu Gly Gly Thr
130                 135                 140

Glu Gln Ala Gly Phe Phe Val Trp Arg Ser Asn Phe His Glu Ala Gly
145                 150                 155                 160

Glu Gly Glu Thr Glu Ala Ser Leu Gln Glu Gly Met Glu Arg Val Arg
                165                 170                 175

Ala Val Val Trp Ala Ser Thr Phe Ser Cys Ile Met Gln Lys Trp Gly
            180                 185                 190

Gly Lys Arg Glu Val Met Tyr Thr Ala Phe Lys Ala Leu Gly Asn Ser
        195                 200                 205

Val Asp Tyr Ile Gln Val Cys Asp Ser Asp Thr Val Leu Asp Pro Ala
        210                 215                 220

Cys Thr Ile Glu Met Leu Arg Val Leu Glu Glu Asp Pro Gln Val Gly
225                 230                 235                 240

Gly Val Gly Gly Asp Val Gln Ile Leu Asn Lys Tyr Asp Ser Trp Ile
            245                 250                 255

Ser Phe Leu Ser Ser Val Arg Tyr Trp Met Ala Phe Asn Val Glu Arg
            260                 265                 270

Ala Cys Gln Ser Tyr Phe Gly Cys Val Gln Cys Ile Ser Gly Pro Leu
            275                 280                 285

Gly Met Tyr Arg Asn Ser Leu Leu Gln Gln Phe Leu Glu Asp Trp Tyr
        290                 295                 300

His Gln Lys Phe Leu Gly Ser Lys Cys Ser Phe Gly Asp Asp Arg His
305                 310                 315                 320

Leu Thr Asn Arg Val Leu Ser Leu Gly Tyr Arg Thr Lys Tyr Thr Ala
            325                 330                 335

Arg Ser Lys Cys Leu Thr Glu Thr Pro Thr Arg Tyr Leu Arg Trp Leu
            340                 345                 350

Asn Gln Gln Thr Arg Trp Ser Lys Ser Tyr Phe Arg Glu Trp Leu Tyr
        355                 360                 365

Asn Ser Leu Trp Phe His Lys His Leu Trp Met Thr Tyr Glu Ser
370                 375                 380

Val Val Thr Gly Phe Phe Pro Phe Phe Leu Ile Ala Thr Val Ile Gln
385                 390                 395                 400

Leu Phe Tyr Arg Gly Arg Ile Trp Asn Ile Leu Leu Phe Leu Leu Thr
            405                 410                 415

Val Gln Leu Val Gly Ile Ile Lys Ala Thr Tyr Ala Cys Phe Leu Arg
            420                 425                 430

Gly Asn Ala Glu Met Ile Phe Met Ser Leu Tyr Ser Leu Leu Tyr Met
        435                 440                 445

Ser Ser Leu Leu Pro Ala Lys Ile Phe Ala Ile Ala Thr Ile Asn Lys
        450                 455                 460

Ser Gly Trp Gly Thr Ser Gly Arg Lys Thr Ile Val Val Asn Phe Ile
465                 470                 475                 480

Gly Leu Ile Pro Val Ser Ile Trp Val Ala Val Leu Leu Gly Gly Leu
            485                 490                 495

Ala Tyr Thr Ala Tyr Cys Gln Asp Leu Phe Ser Glu Thr Glu Leu Ala
        500                 505                 510

Phe Leu Val Ser Gly Ala Ile Leu Tyr Gly Cys Tyr Trp Val Ala Leu
        515                 520                 525
```

```
Leu Met Leu Tyr Leu Ala Ile Ile Ala Arg Arg Cys Gly Lys Lys Pro
            530                 535                 540

Glu Gln Tyr Ser Leu Ala Phe Ala Glu Val
545                 550

<210> SEQ ID NO 21
<211> LENGTH: 1752
<212> TYPE: DNA
<213> ORGANISM: Rattus norvegicus
<220> FEATURE:
<221> NAME/KEY: CDS
<222> LOCATION: (1)..(1752)
<300> PUBLICATION INFORMATION:
<308> DATABASE ACCESSION NUMBER: AB097568
<309> DATABASE ENTRY DATE: 2004-04-28

<400> SEQUENCE: 21 atg aga cag gac atg cca aag ccc tca gag gca gca cgt tgc tgc tcc      48
Met Arg Gln Asp Met Pro Lys Pro Ser Glu Ala Ala Arg Cys Cys Ser
1               5                   10                  15 ggt ctg gcc agg cgg gtg ctc acg atc acc ttc gcc ctg ctc atc ctg      96
Gly Leu Ala Arg Arg Val Leu Thr Ile Thr Phe Ala Leu Leu Ile Leu
            20                  25                  30 ggc ctc atg acc tgg gcc tac gca gca gga gta cct ctg gct tct gat     144
Gly Leu Met Thr Trp Ala Tyr Ala Ala Gly Val Pro Leu Ala Ser Asp
        35                  40                  45 ccc tat ggc ctc ctg gcc ttt ggg ctc tat ggg gcg ttc ctc agt gcg     192
Pro Tyr Gly Leu Leu Ala Phe Gly Leu Tyr Gly Ala Phe Leu Ser Ala
    50                  55                  60 cac cta gtg gca cag agc ctc ttc gct tac ctg gag cac cga agg gtg     240
His Leu Val Ala Gln Ser Leu Phe Ala Tyr Leu Glu His Arg Arg Val
65                  70                  75                  80 acc gtg gct gcg cgg cgc gct ttt gcg aag gga ccc ctg gat gcg gcc     288
Thr Val Ala Ala Arg Arg Ala Phe Ala Lys Gly Pro Leu Asp Ala Ala
                85                  90                  95 act gcg cgc agc gtg gca ctc acc atc tca gcc tac cag gag gac ccc     336
Thr Ala Arg Ser Val Ala Leu Thr Ile Ser Ala Tyr Gln Glu Asp Pro
            100                 105                 110 act tac ctg cgc cag tgc ttg acc tcc gcg cgc gcc ttg ctg tac ccg     384
Thr Tyr Leu Arg Gln Cys Leu Thr Ser Ala Arg Ala Leu Leu Tyr Pro
        115                 120                 125 cgc acg cgg ctg cgc gtg ctt atg gtt gta gac ggc aat cgc gcg gag     432
Arg Thr Arg Leu Arg Val Leu Met Val Val Asp Gly Asn Arg Ala Glu
    130                 135                 140 gat ctg tac atg gtg gac atg ttc cga gaa gtc ttc gca gat gag gac     480
Asp Leu Tyr Met Val Asp Met Phe Arg Glu Val Phe Ala Asp Glu Asp
145                 150                 155                 160 cct gcc act tat gtg tgg gat ggc aac tac cat cag cct tgg gag cca     528
Pro Ala Thr Tyr Val Trp Asp Gly Asn Tyr His Gln Pro Trp Glu Pro
                165                 170                 175 gct gag gcg gcg ggt gct gtg ggt gaa ggt gcc tac cgc gag gtg gag     576
Ala Glu Ala Ala Gly Ala Val Gly Glu Gly Ala Tyr Arg Glu Val Glu
            180                 185                 190 gct gag gac cct ggg cgg ctg gcg gta gag gcg ctg gtg agg acc cgc     624
Ala Glu Asp Pro Gly Arg Leu Ala Val Glu Ala Leu Val Arg Thr Arg
        195                 200                 205 agg tgc gtg tgc gtg gct cag cgc tgg ggt ggc aag cgc gaa gtc atg     672
Arg Cys Val Cys Val Ala Gln Arg Trp Gly Gly Lys Arg Glu Val Met
    210                 215                 220 tac acg gct ttc aag gca ctg ggt gac tcc gtg gac tac gtg cag gtc     720
Tyr Thr Ala Phe Lys Ala Leu Gly Asp Ser Val Asp Tyr Val Gln Val
225                 230                 235                 240
```

```
tgt gac tca gac aca agg tta gac ccc atg gca ctg ctg gag ctt gtg      768
Cys Asp Ser Asp Thr Arg Leu Asp Pro Met Ala Leu Leu Glu Leu Val
            245                 250                 255 cga gtg ctg gat gaa gac ccc cgg gta ggt gct gtt gga gga gat gtg      816
Arg Val Leu Asp Glu Asp Pro Arg Val Gly Ala Val Gly Gly Asp Val
        260                 265                 270 aga atc ctt aac cct ctg gac tct tgg gtc agc ttc ttg agc agc ctt      864
Arg Ile Leu Asn Pro Leu Asp Ser Trp Val Ser Phe Leu Ser Ser Leu
    275                 280                 285 cga tac tgg gta gcc ttc aat gtg gag cga gct tgt cag agc tac ttt      912
Arg Tyr Trp Val Ala Phe Asn Val Glu Arg Ala Cys Gln Ser Tyr Phe
290                 295                 300 cac tgt gtg tcc tgc atc agt ggt cct ctg ggt cta tac aga aac aat      960
His Cys Val Ser Cys Ile Ser Gly Pro Leu Gly Leu Tyr Arg Asn Asn
305                 310                 315                 320 ctc ctg cag cag ttc ctg gag gcc tgg tac aac cag aag ttc ctg ggc     1008
Leu Leu Gln Gln Phe Leu Glu Ala Trp Tyr Asn Gln Lys Phe Leu Gly
                325                 330                 335 acc cac tgc aca ttt ggg gat gac agg cac ctc acc aac cgc atg ctt     1056
Thr His Cys Thr Phe Gly Asp Asp Arg His Leu Thr Asn Arg Met Leu
            340                 345                 350 agc atg ggc tac gct acc aag tat acc tcg cgc tcc aga tgc tat tca     1104
Ser Met Gly Tyr Ala Thr Lys Tyr Thr Ser Arg Ser Arg Cys Tyr Ser
        355                 360                 365 gag acg ccc tcc tct ttc ctt cgt tgg ctg agc cag cag acc cgc tgg     1152
Glu Thr Pro Ser Ser Phe Leu Arg Trp Leu Ser Gln Gln Thr Arg Trp
    370                 375                 380 tcc aaa tct tat ttc cga gag tgg cta tac aac gcc ctg tgg tgg cac     1200
Ser Lys Ser Tyr Phe Arg Glu Trp Leu Tyr Asn Ala Leu Trp Trp His
385                 390                 395                 400 cgc cac cac gcg tgg atg acc tat gaa gcg gtg gtt tct ggc ctc ttc     1248
Arg His His Ala Trp Met Thr Tyr Glu Ala Val Val Ser Gly Leu Phe
                405                 410                 415 cct ttc ttt gtg gct gcc acg gtg ctg agg ctc ttc tat gca ggg cgc     1296
Pro Phe Phe Val Ala Ala Thr Val Leu Arg Leu Phe Tyr Ala Gly Arg
            420                 425                 430 cca tgg gct ctg ctc tgg gtg ctg ctc tgc gtg cag ggc gtg gca ctg     1344
Pro Trp Ala Leu Leu Trp Val Leu Leu Cys Val Gln Gly Val Ala Leu
        435                 440                 445 gca aag gca gcc ttt gca gcc tgg ctg cgt ggc tgc ctg cgc atg gtg     1392
Ala Lys Ala Ala Phe Ala Ala Trp Leu Arg Gly Cys Leu Arg Met Val
    450                 455                 460 ctg ctg tca ctc tat gca cca ctc tac atg tgc ggc ctg ctg cct gcc     1440
Leu Leu Ser Leu Tyr Ala Pro Leu Tyr Met Cys Gly Leu Leu Pro Ala
465                 470                 475                 480 aag ttc ctg gcg ttg gtt acc atg aat caa agt ggt tgg ggc acc tcg     1488
Lys Phe Leu Ala Leu Val Thr Met Asn Gln Ser Gly Trp Gly Thr Ser
                485                 490                 495 ggc cgg aag aaa ctg gct gct aac tat gta ccc gtg ttg ccc ctg gca     1536
Gly Arg Lys Lys Leu Ala Ala Asn Tyr Val Pro Val Leu Pro Leu Ala
            500                 505                 510 ctc tgg gct cta ctg ctg ctt gga ggc ctg atc cgc agt gtg gcc cag     1584
Leu Trp Ala Leu Leu Leu Leu Gly Gly Leu Ile Arg Ser Val Ala Gln
        515                 520                 525 gag gtc aga gct gac tgg agt ggc cca tca cga gca gct gaa gcc tac     1632
Glu Val Arg Ala Asp Trp Ser Gly Pro Ser Arg Ala Ala Glu Ala Tyr
    530                 535                 540 cac ctt gct gct ggg gcc agt gcc tat gtg gcc tac tgg gtg ata atg     1680
His Leu Ala Ala Gly Ala Ser Ala Tyr Val Ala Tyr Trp Val Ile Met
545                 550                 555                 560
```

```
ttg act atc tat tgg gta ggt gta agg aga ctg tgc aga cgt cgg agc    1728
Leu Thr Ile Tyr Trp Val Gly Val Arg Arg Leu Cys Arg Arg Arg Ser
                565                 570                 575 ggt ggc tac cgt gtc caa gta tga                                    1752
Gly Gly Tyr Arg Val Gln Val
                580
```

<210> SEQ ID NO 22
<211> LENGTH: 583
<212> TYPE: PRT
<213> ORGANISM: Rattus norvegicus

<400> SEQUENCE: 22

```
Met Arg Gln Asp Met Pro Lys Pro Ser Glu Ala Ala Arg Cys Cys Ser
1               5                   10                  15

Gly Leu Ala Arg Arg Val Leu Thr Ile Thr Phe Ala Leu Leu Ile Leu
                20                  25                  30

Gly Leu Met Thr Trp Ala Tyr Ala Ala Gly Val Pro Leu Ala Ser Asp
            35                  40                  45

Pro Tyr Gly Leu Leu Ala Phe Gly Leu Tyr Gly Ala Phe Leu Ser Ala
    50                  55                  60

His Leu Val Ala Gln Ser Leu Phe Ala Tyr Leu Glu His Arg Arg Val
65                  70                  75                  80

Thr Val Ala Ala Arg Arg Ala Phe Ala Lys Gly Pro Leu Asp Ala Ala
                85                  90                  95

Thr Ala Arg Ser Val Ala Leu Thr Ile Ser Ala Tyr Gln Glu Asp Pro
            100                 105                 110

Thr Tyr Leu Arg Gln Cys Leu Thr Ser Ala Arg Ala Leu Leu Tyr Pro
    115                 120                 125

Arg Thr Arg Leu Arg Val Leu Met Val Val Asp Gly Asn Arg Ala Glu
130                 135                 140

Asp Leu Tyr Met Val Asp Met Phe Arg Glu Val Phe Ala Asp Glu Asp
145                 150                 155                 160

Pro Ala Thr Tyr Val Trp Asp Gly Asn Tyr His Gln Pro Trp Glu Pro
                165                 170                 175

Ala Glu Ala Ala Gly Ala Val Gly Glu Gly Ala Tyr Arg Glu Val Glu
            180                 185                 190

Ala Glu Asp Pro Gly Arg Leu Ala Val Glu Ala Leu Val Arg Thr Arg
    195                 200                 205

Arg Cys Val Cys Val Ala Gln Arg Trp Gly Gly Lys Arg Glu Val Met
210                 215                 220

Tyr Thr Ala Phe Lys Ala Leu Gly Asp Ser Val Asp Tyr Val Gln Val
225                 230                 235                 240

Cys Asp Ser Asp Thr Arg Leu Asp Pro Met Ala Leu Leu Glu Leu Val
                245                 250                 255

Arg Val Leu Asp Glu Asp Pro Arg Val Gly Ala Val Gly Gly Asp Val
            260                 265                 270

Arg Ile Leu Asn Pro Leu Asp Ser Trp Val Ser Phe Leu Ser Ser Leu
    275                 280                 285

Arg Tyr Trp Val Ala Phe Asn Val Glu Arg Ala Cys Gln Ser Tyr Phe
290                 295                 300

His Cys Val Ser Cys Ile Ser Gly Pro Leu Gly Leu Tyr Arg Asn Asn
305                 310                 315                 320

Leu Leu Gln Gln Phe Leu Glu Ala Trp Tyr Asn Gln Lys Phe Leu Gly
                325                 330                 335

Thr His Cys Thr Phe Gly Asp Asp Arg His Leu Thr Asn Arg Met Leu
```

-continued

```
                       340                 345                 350
Ser Met Gly Tyr Ala Thr Lys Tyr Thr Ser Arg Ser Arg Cys Tyr Ser
            355                 360                 365

Glu Thr Pro Ser Ser Phe Leu Arg Trp Leu Ser Gln Gln Thr Arg Trp
        370                 375                 380

Ser Lys Ser Tyr Phe Arg Glu Trp Leu Tyr Asn Ala Leu Trp Trp His
385                 390                 395                 400

Arg His His Ala Trp Met Thr Tyr Glu Ala Val Val Ser Gly Leu Phe
                405                 410                 415

Pro Phe Phe Val Ala Ala Thr Val Leu Arg Leu Phe Tyr Ala Gly Arg
            420                 425                 430

Pro Trp Ala Leu Leu Trp Val Leu Cys Val Gln Gly Val Ala Leu
            435                 440                 445

Ala Lys Ala Ala Phe Ala Ala Trp Leu Arg Gly Cys Leu Arg Met Val
        450                 455                 460

Leu Leu Ser Leu Tyr Ala Pro Leu Tyr Met Cys Gly Leu Leu Pro Ala
465                 470                 475                 480

Lys Phe Leu Ala Leu Val Thr Met Asn Gln Ser Gly Trp Gly Thr Ser
                485                 490                 495

Gly Arg Lys Lys Leu Ala Ala Asn Tyr Val Pro Val Leu Pro Leu Ala
            500                 505                 510

Leu Trp Ala Leu Leu Leu Gly Gly Leu Ile Arg Ser Val Ala Gln
            515                 520                 525

Glu Val Arg Ala Asp Trp Ser Gly Pro Ser Arg Ala Ala Glu Ala Tyr
        530                 535                 540

His Leu Ala Ala Gly Ala Ser Ala Tyr Val Ala Tyr Trp Val Ile Met
545                 550                 555                 560

Leu Thr Ile Tyr Trp Val Gly Val Arg Arg Leu Cys Arg Arg Arg Ser
                565                 570                 575

Gly Gly Tyr Arg Val Gln Val
            580

<210> SEQ ID NO 23
<211> LENGTH: 1659
<212> TYPE: DNA
<213> ORGANISM: Rattus norvegicus
<220> FEATURE:
<221> NAME/KEY: CDS
<222> LOCATION: (1)..(1659)
<300> PUBLICATION INFORMATION:
<308> DATABASE ACCESSION NUMBER: AF008201.1
<309> DATABASE ENTRY DATE: 1997-07-16
<313> RELEVANT RESIDUES IN SEQ ID NO: (507)..(2165)

<400> SEQUENCE: 23 atg cat tgt gag agg ttt cta tgt gtc ctg aga ata atc gga acc aca      48
Met His Cys Glu Arg Phe Leu Cys Val Leu Arg Ile Ile Gly Thr Thr
1               5                   10                  15 ctg ttt gga gtg tct ctc ctc ctc gga atc aca gct gct tat att gtt      96
Leu Phe Gly Val Ser Leu Leu Leu Gly Ile Thr Ala Ala Tyr Ile Val
            20                  25                  30 ggc tac cag ttt atc caa aca gat aat tac tat ttc tcc ttt ggg ctg     144
Gly Tyr Gln Phe Ile Gln Thr Asp Asn Tyr Tyr Phe Ser Phe Gly Leu
        35                  40                  45 tat ggt gcc ttt tta gcc tca cac ctc atc atc caa agc ctc ttt gcc     192
Tyr Gly Ala Phe Leu Ala Ser His Leu Ile Ile Gln Ser Leu Phe Ala
    50                  55                  60 ttt ttg gaa cac cgg aaa atg aaa aag tcc ctt gaa acc ccc att aaa     240
Phe Leu Glu His Arg Lys Met Lys Lys Ser Leu Glu Thr Pro Ile Lys
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 65  |     |     |     | 70  |     |     |     | 75  |     |     |     | 80  |     |     |      |
| ttg | aac | aaa | act | gta | gct | ctc | tgc | att | gct | gcg | tat | caa | gaa | gac | cct | 288  |
| Leu | Asn | Lys | Thr | Val | Ala | Leu | Cys | Ile | Ala | Ala | Tyr | Gln | Glu | Asp | Pro |      |
|     |     |     |     |     | 85  |     |     |     |     | 90  |     |     |     |     | 95  |      |
| gac | tac | tta | cgg | aaa | tgt | ttg | caa | tct | gtg | aaa | agg | ctg | acc | tac | cct | 336  |
| Asp | Tyr | Leu | Arg | Lys | Cys | Leu | Gln | Ser | Val | Lys | Arg | Leu | Thr | Tyr | Pro |      |
|     |     |     |     | 100 |     |     |     |     | 105 |     |     |     |     | 110 |     |      |
| ggg | atc | aaa | gtc | gtg | atg | gtc | ata | gat | gga | aat | tca | gat | gac | gac | ctt | 384  |
| Gly | Ile | Lys | Val | Val | Met | Val | Ile | Asp | Gly | Asn | Ser | Asp | Asp | Asp | Leu |      |
|     |     |     | 115 |     |     |     |     | 120 |     |     |     |     | 125 |     |     |      |
| tac | atg | atg | gac | atc | ttc | agt | gaa | gtc | atg | ggc | agg | gac | aaa | tca | gtc | 432  |
| Tyr | Met | Met | Asp | Ile | Phe | Ser | Glu | Val | Met | Gly | Arg | Asp | Lys | Ser | Val |      |
|     | 130 |     |     |     |     | 135 |     |     |     |     | 140 |     |     |     |     |      |
| act | tac | atc | tgg | aag | aac | aac | ttc | cat | gaa | agg | gga | cct | ggt | gag | aca | 480  |
| Thr | Tyr | Ile | Trp | Lys | Asn | Asn | Phe | His | Glu | Arg | Gly | Pro | Gly | Glu | Thr |      |
| 145 |     |     |     |     | 150 |     |     |     |     | 155 |     |     |     |     | 160 |      |
| gaa | gag | tcc | cat | aaa | gaa | agt | tcg | caa | cat | gta | acc | caa | ttg | gtc | ttg | 528  |
| Glu | Glu | Ser | His | Lys | Glu | Ser | Ser | Gln | His | Val | Thr | Gln | Leu | Val | Leu |      |
|     |     |     |     | 165 |     |     |     |     | 170 |     |     |     |     | 175 |     |      |
| tct | aac | aag | agt | att | tgc | atc | atg | caa | aaa | tgg | ggt | gga | aag | aga | gaa | 576  |
| Ser | Asn | Lys | Ser | Ile | Cys | Ile | Met | Gln | Lys | Trp | Gly | Gly | Lys | Arg | Glu |      |
|     |     |     | 180 |     |     |     |     | 185 |     |     |     |     | 190 |     |     |      |
| gtc | atg | tac | acc | gcc | ttc | aga | gca | ctg | ggc | aga | agc | gtg | gat | tat | gta | 624  |
| Val | Met | Tyr | Thr | Ala | Phe | Arg | Ala | Leu | Gly | Arg | Ser | Val | Asp | Tyr | Val |      |
|     | 195 |     |     |     |     | 200 |     |     |     |     | 205 |     |     |     |     |      |
| cag | gtg | tgt | gac | tca | gac | acc | atg | ctt | gac | cct | gcc | tcg | tct | gtg | gag | 672  |
| Gln | Val | Cys | Asp | Ser | Asp | Thr | Met | Leu | Asp | Pro | Ala | Ser | Ser | Val | Glu |      |
| 210 |     |     |     |     | 215 |     |     |     |     | 220 |     |     |     |     |     |      |
| atg | gtg | aag | gtc | tta | gaa | gaa | gac | ccg | atg | gtt | gga | ggt | gtt | ggg | gga | 720  |
| Met | Val | Lys | Val | Leu | Glu | Glu | Asp | Pro | Met | Val | Gly | Gly | Val | Gly | Gly |      |
| 225 |     |     |     |     | 230 |     |     |     |     | 235 |     |     |     |     | 240 |      |
| gat | gtt | cag | att | tta | aac | aag | tat | gat | tct | tgg | atc | tcc | ttc | ctc | agc | 768  |
| Asp | Val | Gln | Ile | Leu | Asn | Lys | Tyr | Asp | Ser | Trp | Ile | Ser | Phe | Leu | Ser |      |
|     |     |     | 245 |     |     |     |     | 250 |     |     |     |     | 255 |     |     |      |
| agt | gtg | aga | tac | tgg | atg | gct | ttt | aat | ata | gaa | agg | gcc | tgc | cag | tct | 816  |
| Ser | Val | Arg | Tyr | Trp | Met | Ala | Phe | Asn | Ile | Glu | Arg | Ala | Cys | Gln | Ser |      |
|     |     | 260 |     |     |     |     | 265 |     |     |     |     | 270 |     |     |     |      |
| tat | ttt | ggc | tgt | gtc | cag | tgc | ata | agc | ggt | cct | ctg | gga | atg | tac | aga | 864  |
| Tyr | Phe | Gly | Cys | Val | Gln | Cys | Ile | Ser | Gly | Pro | Leu | Gly | Met | Tyr | Arg |      |
|     | 275 |     |     |     |     | 280 |     |     |     |     | 285 |     |     |     |     |      |
| aac | tcc | ttg | ttg | cat | gag | ttt | gtg | gaa | gac | tgg | tac | aat | cag | gaa | ttc | 912  |
| Asn | Ser | Leu | Leu | His | Glu | Phe | Val | Glu | Asp | Trp | Tyr | Asn | Gln | Glu | Phe |      |
| 290 |     |     |     |     | 295 |     |     |     |     | 300 |     |     |     |     |     |      |
| atg | ggt | aac | caa | tgc | agt | ttc | ggt | gat | gat | agg | cac | ctt | acc | aac | agg | 960  |
| Met | Gly | Asn | Gln | Cys | Ser | Phe | Gly | Asp | Asp | Arg | His | Leu | Thr | Asn | Arg |      |
| 305 |     |     |     |     | 310 |     |     |     |     | 315 |     |     |     |     | 320 |      |
| gta | ctg | agt | ctg | ggc | tat | gca | act | aaa | tac | acg | gct | cgg | tcc | aag | tgc | 1008 |
| Val | Leu | Ser | Leu | Gly | Tyr | Ala | Thr | Lys | Tyr | Thr | Ala | Arg | Ser | Lys | Cys |      |
|     |     |     |     | 325 |     |     |     |     | 330 |     |     |     |     | 335 |     |      |
| ctt | act | gaa | aca | ccc | ata | gaa | tat | ctg | aga | tgg | ctg | aac | cag | cag | acc | 1056 |
| Leu | Thr | Glu | Thr | Pro | Ile | Glu | Tyr | Leu | Arg | Trp | Leu | Asn | Gln | Gln | Thr |      |
|     |     |     | 340 |     |     |     |     | 345 |     |     |     |     | 350 |     |     |      |
| cgt | tgg | agc | aag | tcc | tac | ttc | cga | gag | tgg | cta | tac | aat | gcc | atg | tgg | 1104 |
| Arg | Trp | Ser | Lys | Ser | Tyr | Phe | Arg | Glu | Trp | Leu | Tyr | Asn | Ala | Met | Trp |      |
|     |     | 355 |     |     |     |     | 360 |     |     |     |     | 365 |     |     |     |      |
| ttt | cac | aag | cat | cac | ttg | tgg | atg | acc | tac | gaa | gct | gtt | atc | act | gga | 1152 |
| Phe | His | Lys | His | His | Leu | Trp | Met | Thr | Tyr | Glu | Ala | Val | Ile | Thr | Gly |      |
|     | 370 |     |     |     |     | 375 |     |     |     |     | 380 |     |     |     |     |      |
| ttc | ttt | cct | ttc | ttt | ctc | att | gcc | aca | gtc | atc | cag | ctc | ttc | tac | agg | 1200 |
| Phe | Phe | Pro | Phe | Phe | Leu | Ile | Ala | Thr | Val | Ile | Gln | Leu | Phe | Tyr | Arg |      |

```
                385                 390                 395                 400
ggt aaa atc tgg aac atc ctc ttc ctg tta act gtc cag cta gtg         1248
Gly Lys Ile Trp Asn Ile Leu Leu Phe Leu Leu Thr Val Gln Leu Val
                405                 410                 415 ggt ctc atc aag tcg tct ttc gcc agc tgc ctt aga gga aat atc gtc     1296
Gly Leu Ile Lys Ser Ser Phe Ala Ser Cys Leu Arg Gly Asn Ile Val
                420                 425                 430 atg gtc ttc atg tct ctc tac tca gtg ttg tac atg tca agt cta ctt     1344
Met Val Phe Met Ser Leu Tyr Ser Val Leu Tyr Met Ser Ser Leu Leu
                435                 440                 445 cct gcc aag atg ttt gca att gca acc ata aac aaa gct ggg tgg ggc     1392
Pro Ala Lys Met Phe Ala Ile Ala Thr Ile Asn Lys Ala Gly Trp Gly
                450                 455                 460 aca tct gga agg aaa acc att gtc gtt aat ttc ata gga ctt att cca     1440
Thr Ser Gly Arg Lys Thr Ile Val Val Asn Phe Ile Gly Leu Ile Pro
465                 470                 475                 480 gtg tcc gtg tgg ttt aca atc ctt cta ggt ggt gtg att ttc acc att     1488
Val Ser Val Trp Phe Thr Ile Leu Leu Gly Gly Val Ile Phe Thr Ile
                485                 490                 495 tat aag gaa tct aaa aag cca ttt tcc gaa tcc aaa cag act gtt ctc     1536
Tyr Lys Glu Ser Lys Lys Pro Phe Ser Glu Ser Lys Gln Thr Val Leu
                500                 505                 510 att gtg gga acc ttg atc tat gcg tgc tac tgg gtc gtg ctt ttg act     1584
Ile Val Gly Thr Leu Ile Tyr Ala Cys Tyr Trp Val Val Leu Leu Thr
                515                 520                 525 ctg tat gtg gtt ctc atc aat aag tgt ggc agg cgg aag aag gga caa     1632
Leu Tyr Val Val Leu Ile Asn Lys Cys Gly Arg Arg Lys Lys Gly Gln
                530                 535                 540 cag tac gac atg gtg ctt gat gta tga                                 1659
Gln Tyr Asp Met Val Leu Asp Val
545                 550

<210> SEQ ID NO 24
<211> LENGTH: 552
<212> TYPE: PRT
<213> ORGANISM: Rattus norvegicus

<400> SEQUENCE: 24

Met His Cys Glu Arg Phe Leu Cys Val Leu Arg Ile Ile Gly Thr Thr
1               5                   10                  15

Leu Phe Gly Val Ser Leu Leu Leu Gly Ile Thr Ala Ala Tyr Ile Val
                20                  25                  30

Gly Tyr Gln Phe Ile Gln Thr Asp Asn Tyr Tyr Phe Ser Phe Gly Leu
            35                  40                  45

Tyr Gly Ala Phe Leu Ala Ser His Leu Ile Ile Gln Ser Leu Phe Ala
        50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Gln Ser Val Lys Arg Leu Thr Tyr Pro
            100                 105                 110

Gly Ile Lys Val Val Met Val Ile Asp Gly Asn Ser Asp Asp Asp Leu
        115                 120                 125

Tyr Met Met Asp Ile Phe Ser Glu Val Met Gly Arg Asp Lys Ser Val
    130                 135                 140

Thr Tyr Ile Trp Lys Asn Asn Phe His Glu Arg Gly Pro Gly Glu Thr
145                 150                 155                 160
```

```
Glu Glu Ser His Lys Glu Ser Gln His Val Thr Gln Leu Val Leu
                165                 170                 175

Ser Asn Lys Ser Ile Cys Ile Met Gln Lys Trp Gly Gly Lys Arg Glu
            180                 185                 190

Val Met Tyr Thr Ala Phe Arg Ala Leu Gly Arg Ser Val Asp Tyr Val
        195                 200                 205

Gln Val Cys Asp Ser Asp Thr Met Leu Asp Pro Ala Ser Ser Val Glu
    210                 215                 220

Met Val Lys Val Leu Glu Glu Asp Pro Met Val Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
            260                 265                 270

Tyr Phe Gly Cys Val Gln Cys Ile Ser Gly Pro Leu Gly Met Tyr Arg
        275                 280                 285

Asn Ser Leu Leu His Glu Phe Val Glu Asp Trp Tyr Asn Gln Glu Phe
    290                 295                 300

Met Gly Asn Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
            340                 345                 350

Arg Trp Ser Lys Ser Tyr Phe Arg Glu Trp Leu Tyr Asn Ala Met Trp
        355                 360                 365

Phe His Lys His His Leu Trp Met Thr Tyr Glu Ala Val Ile Thr Gly
    370                 375                 380

Phe Phe Pro Phe Phe Leu Ile Ala Thr Val Ile Gln Leu Phe Tyr Arg
385                 390                 395                 400

Gly Lys Ile Trp Asn Ile Leu Leu Phe Leu Leu Thr Val Gln Leu Val
                405                 410                 415

Gly Leu Ile Lys Ser Ser Phe Ala Ser Cys Leu Arg Gly Asn Ile Val
            420                 425                 430

Met Val Phe Met Ser Leu Tyr Ser Val Leu Tyr Met Ser Ser Leu Leu
        435                 440                 445

Pro Ala Lys Met Phe Ala Ile Ala Thr Ile Asn Lys Ala Gly Trp Gly
    450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                485                 490                 495

Tyr Lys Glu Ser Lys Lys Pro Phe Ser Glu Ser Lys Gln Thr Val Leu
            500                 505                 510

Ile Val Gly Thr Leu Ile Leu Tyr Ala Cys Tyr Trp Val Leu Leu Thr
        515                 520                 525

Leu Tyr Val Val Leu Ile Asn Lys Cys Gly Arg Arg Lys Lys Gly Gln
    530                 535                 540

Gln Tyr Asp Met Val Leu Asp Val
545                 550

<210> SEQ ID NO 25
<211> LENGTH: 1665
<212> TYPE: DNA
<213> ORGANISM: Rattus norvegicus
```

```
<220> FEATURE:
<221> NAME/KEY: CDS
<222> LOCATION: (1)..(1665)
<300> PUBLICATION INFORMATION:
<308> DATABASE ACCESSION NUMBER: NM 172319
<309> DATABASE ENTRY DATE: 2004-08-21

<400> SEQUENCE: 25 atg ccg gtg cag ctg act aca gcc ctt cgt gtg gtg ggc acc agt ctg      48
Met Pro Val Gln Leu Thr Thr Ala Leu Arg Val Val Gly Thr Ser Leu
1               5                  10                  15 ttt gcc ctg gta gtg ctg ggg ggc atc ctg gca gcc tat gtc aca ggc      96
Phe Ala Leu Val Val Leu Gly Gly Ile Leu Ala Ala Tyr Val Thr Gly
            20                  25                  30 tac cag ttt atc cac acg gaa aag cac tat ctg tcc ttc ggc ctc tac     144
Tyr Gln Phe Ile His Thr Glu Lys His Tyr Leu Ser Phe Gly Leu Tyr
        35                  40                  45 ggt gcc atc ctg ggt ctg cat ctg ctc atc cag agc ctg ttt gcc ttc     192
Gly Ala Ile Leu Gly Leu His Leu Leu Ile Gln Ser Leu Phe Ala Phe
    50                  55                  60 ctg gag cac cgt cgc atg cgc agg gca ggg cgc cca ctg aag ctg cac     240
Leu Glu His Arg Arg Met Arg Arg Ala Gly Arg Pro Leu Lys Leu His
65                  70                  75                  80 tgc tct cag aga cgg cgt tcg gtg gca ctc tgc atc gct gcc tac caa     288
Cys Ser Gln Arg Arg Arg Ser Val Ala Leu Cys Ile Ala Ala Tyr Gln
                85                  90                  95 gag gac cct gag tac ttg cgc aag tgc ctt cgc tca gct cag cgc att     336
Glu Asp Pro Glu Tyr Leu Arg Lys Cys Leu Arg Ser Ala Gln Arg Ile
            100                 105                 110 gcc ttc cca aac ctc aag gtg gtc atg gta gtg gat ggc aat cgc cag     384
Ala Phe Pro Asn Leu Lys Val Val Met Val Val Asp Gly Asn Arg Gln
        115                 120                 125 gaa gat gcc tac atg ctg gac atc ttc cat gag gtc ctg ggt ggc act     432
Glu Asp Ala Tyr Met Leu Asp Ile Phe His Glu Val Leu Gly Gly Thr
    130                 135                 140 gag caa gct ggc ttc ttt gtg tgg cgt agc aat ttc cat gag gcg ggt     480
Glu Gln Ala Gly Phe Phe Val Trp Arg Ser Asn Phe His Glu Ala Gly
145                 150                 155                 160 gaa gga gag aca gag gcc agc ttg cag gaa ggc atg gag cgt gtt cga     528
Glu Gly Glu Thr Glu Ala Ser Leu Gln Glu Gly Met Glu Arg Val Arg
                165                 170                 175 gct gtg gtg tgg gcc agc acc ttc tca tgc atc atg cag aag tgg ggg     576
Ala Val Val Trp Ala Ser Thr Phe Ser Cys Ile Met Gln Lys Trp Gly
            180                 185                 190 ggc aag cgt gaa gtc atg tac aca gct ttc aag gcc ctt ggc aac tca     624
Gly Lys Arg Glu Val Met Tyr Thr Ala Phe Lys Ala Leu Gly Asn Ser
        195                 200                 205 gtg gac tac atc cag gtg tgt gac tct gac act gtg ctg gac cca gcc     672
Val Asp Tyr Ile Gln Val Cys Asp Ser Asp Thr Val Leu Asp Pro Ala
    210                 215                 220 tgc acc att gag atg ctt cgg gtc ttg gag gaa gat ccc caa gta gga     720
Cys Thr Ile Glu Met Leu Arg Val Leu Glu Glu Asp Pro Gln Val Gly
225                 230                 235                 240 ggt gtt gga gga gat gtc caa atc ctc aac aaa tac gat tca tgg atc     768
Gly Val Gly Gly Asp Val Gln Ile Leu Asn Lys Tyr Asp Ser Trp Ile
                245                 250                 255 tcc ttc ctg agc agc gtg agg tac tgg atg gcc ttc aac gtg gag cgg     816
Ser Phe Leu Ser Ser Val Arg Tyr Trp Met Ala Phe Asn Val Glu Arg
            260                 265                 270 gcc tgc cag tcc tac ttt ggc tgt gtg cag tgt att agt ggg cct ctg     864
Ala Cys Gln Ser Tyr Phe Gly Cys Val Gln Cys Ile Ser Gly Pro Leu
        275                 280                 285
```

```
ggc atg tac cgc aac agc ctc ctt cag cag ttc ctg gag gac tgg tac      912
Gly Met Tyr Arg Asn Ser Leu Leu Gln Gln Phe Leu Glu Asp Trp Tyr
        290                 295                 300 cat cag aag ttc cta ggc agc aag tgc agc ttt ggg gat gat cgg cac      960
His Gln Lys Phe Leu Gly Ser Lys Cys Ser Phe Gly Asp Asp Arg His
305                 310                 315                 320 ctt acc aac cga gtc ctg agt ctt ggc tac cgg act aag tat aca gca     1008
Leu Thr Asn Arg Val Leu Ser Leu Gly Tyr Arg Thr Lys Tyr Thr Ala
                325                 330                 335 cgc tcc aag tgc ctc aca gag acc ccc act aag tat ctc cga tgg ctc     1056
Arg Ser Lys Cys Leu Thr Glu Thr Pro Thr Lys Tyr Leu Arg Trp Leu
        340                 345                 350 aac cag cag acc cgc tgg agc aag tct tac ttt cgg gag tgg ctc tac     1104
Asn Gln Gln Thr Arg Trp Ser Lys Ser Tyr Phe Arg Glu Trp Leu Tyr
355                 360                 365 aac tct ctg tgg ttc cat aag cac cac ctg tgg atg acc tat gag tca     1152
Asn Ser Leu Trp Phe His Lys His His Leu Trp Met Thr Tyr Glu Ser
                370                 375                 380 gtg gtc aca ggc ttc ttc ccc ttc ttc ctc atc gcc aca gtc ata caa     1200
Val Val Thr Gly Phe Phe Pro Phe Phe Leu Ile Ala Thr Val Ile Gln
385                 390                 395                 400 ctt ttc tac cgt ggc cgc atc tgg aac att ctc ctc ttc cta cta acg     1248
Leu Phe Tyr Arg Gly Arg Ile Trp Asn Ile Leu Leu Phe Leu Leu Thr
                405                 410                 415 gtg cag ctg gtg ggc att atc aag gct acc tat gcc tgc ttc ctc cga     1296
Val Gln Leu Val Gly Ile Ile Lys Ala Thr Tyr Ala Cys Phe Leu Arg
        420                 425                 430 ggc aat gca gag atg atc ttc atg tcc ctc tac tcc ctt ctc tat atg     1344
Gly Asn Ala Glu Met Ile Phe Met Ser Leu Tyr Ser Leu Leu Tyr Met
            435                 440                 445 tcc agc ctg ctg cca gcc aag atc ttt gct att gct acc atc aac aag     1392
Ser Ser Leu Leu Pro Ala Lys Ile Phe Ala Ile Ala Thr Ile Asn Lys
450                 455                 460 tct ggc tgg ggc act tct ggc agg aaa acc att gta gtg aac ttc att     1440
Ser Gly Trp Gly Thr Ser Gly Arg Lys Thr Ile Val Val Asn Phe Ile
465                 470                 475                 480 ggc cta atc cct gtg tcc atc tgg gtg gca gtt ctt cta ggg ggg tta     1488
Gly Leu Ile Pro Val Ser Ile Trp Val Ala Val Leu Leu Gly Gly Leu
                485                 490                 495 gcc tac aca gct tat tgt cag gac ctg ttc agt gag act gag cta gcc     1536
Ala Tyr Thr Ala Tyr Cys Gln Asp Leu Phe Ser Glu Thr Glu Leu Ala
        500                 505                 510 ttc ctg gtc tct ggg gcc atc ttg tat ggc tgc tac tgg gtg gcc ctc     1584
Phe Leu Val Ser Gly Ala Ile Leu Tyr Gly Cys Tyr Trp Val Ala Leu
            515                 520                 525 ctc atg ctg tat ttg gcc att att gcc cgg agg tgt ggg aaa aag cca     1632
Leu Met Leu Tyr Leu Ala Ile Ile Ala Arg Arg Cys Gly Lys Lys Pro
530                 535                 540 gaa cag tat agc ctg gct ttt gct gag gtg tga                         1665
Glu Gln Tyr Ser Leu Ala Phe Ala Glu Val
545                 550

<210> SEQ ID NO 26
<211> LENGTH: 554
<212> TYPE: PRT
<213> ORGANISM: Rattus norvegicus

<400> SEQUENCE: 26

Met Pro Val Gln Leu Thr Thr Ala Leu Arg Val Val Gly Thr Ser Leu
1               5                   10                  15
```

-continued

```
Phe Ala Leu Val Val Leu Gly Ile Leu Ala Ala Tyr Val Thr Gly
                20                  25                  30

Tyr Gln Phe Ile His Thr Glu Lys His Tyr Leu Ser Phe Gly Leu Tyr
                35                  40                  45

Gly Ala Ile Leu Gly Leu His Leu Leu Ile Gln Ser Leu Phe Ala Phe
 50                  55                  60

Leu Glu His Arg Arg Met Arg Arg Ala Gly Arg Pro Leu Lys Leu His
 65                  70                  75                  80

Cys Ser Gln Arg Arg Ser Val Ala Leu Cys Ile Ala Ala Tyr Gln
                85                  90                  95

Glu Asp Pro Glu Tyr Leu Arg Lys Cys Leu Arg Ser Ala Gln Arg Ile
                100                 105                 110

Ala Phe Pro Asn Leu Lys Val Val Met Val Val Asp Gly Asn Arg Gln
                115                 120                 125

Glu Asp Ala Tyr Met Leu Asp Ile Phe His Glu Val Leu Gly Gly Thr
                130                 135                 140

Glu Gln Ala Gly Phe Phe Val Trp Arg Ser Asn Phe His Glu Ala Gly
145                 150                 155                 160

Glu Gly Glu Thr Glu Ala Ser Leu Gln Glu Gly Met Glu Arg Val Arg
                165                 170                 175

Ala Val Val Trp Ala Ser Thr Phe Ser Cys Ile Met Gln Lys Trp Gly
                180                 185                 190

Gly Lys Arg Glu Val Met Tyr Thr Ala Phe Lys Ala Leu Gly Asn Ser
                195                 200                 205

Val Asp Tyr Ile Gln Val Cys Asp Ser Asp Thr Val Leu Asp Pro Ala
                210                 215                 220

Cys Thr Ile Glu Met Leu Arg Val Leu Glu Glu Asp Pro Gln Val Gly
225                 230                 235                 240

Gly Val Gly Gly Asp Val Gln Ile Leu Asn Lys Tyr Asp Ser Trp Ile
                245                 250                 255

Ser Phe Leu Ser Ser Val Arg Tyr Trp Met Ala Phe Asn Val Glu Arg
                260                 265                 270

Ala Cys Gln Ser Tyr Phe Gly Cys Val Gln Cys Ile Ser Gly Pro Leu
                275                 280                 285

Gly Met Tyr Arg Asn Ser Leu Leu Gln Gln Phe Leu Glu Asp Trp Tyr
                290                 295                 300

His Gln Lys Phe Leu Gly Ser Lys Cys Ser Phe Gly Asp Asp Arg His
305                 310                 315                 320

Leu Thr Asn Arg Val Leu Ser Leu Gly Tyr Arg Thr Lys Tyr Thr Ala
                325                 330                 335

Arg Ser Lys Cys Leu Thr Glu Thr Pro Thr Lys Tyr Leu Arg Trp Leu
                340                 345                 350

Asn Gln Gln Thr Arg Trp Ser Lys Ser Tyr Phe Arg Glu Trp Leu Tyr
                355                 360                 365

Asn Ser Leu Trp Phe His Lys His Leu Trp Met Thr Tyr Glu Ser
                370                 375                 380

Val Val Thr Gly Phe Phe Pro Phe Phe Leu Ile Ala Thr Val Ile Gln
385                 390                 395                 400

Leu Phe Tyr Arg Gly Arg Ile Trp Asn Ile Leu Leu Phe Leu Leu Thr
                405                 410                 415

Val Gln Leu Val Gly Ile Ile Lys Ala Thr Tyr Ala Cys Phe Leu Arg
                420                 425                 430

Gly Asn Ala Glu Met Ile Phe Met Ser Leu Tyr Ser Leu Leu Tyr Met
                435                 440                 445
```

```
Ser Ser Leu Leu Pro Ala Lys Ile Phe Ala Ile Ala Thr Ile Asn Lys
    450                 455                 460
Ser Gly Trp Gly Thr Ser Gly Arg Lys Thr Ile Val Val Asn Phe Ile
465                 470                 475                 480
Gly Leu Ile Pro Val Ser Ile Trp Val Ala Val Leu Leu Gly Gly Leu
                485                 490                 495
Ala Tyr Thr Ala Tyr Cys Gln Asp Leu Phe Ser Glu Thr Glu Leu Ala
            500                 505                 510
Phe Leu Val Ser Gly Ala Ile Leu Tyr Gly Cys Tyr Trp Val Ala Leu
        515                 520                 525
Leu Met Leu Tyr Leu Ala Ile Ile Ala Arg Arg Cys Gly Lys Lys Pro
    530                 535                 540
Glu Gln Tyr Ser Leu Ala Phe Ala Glu Val
545                 550
```

```
<210> SEQ ID NO 27
<211> LENGTH: 1659
<212> TYPE: DNA
<213> ORGANISM: Oryctolagus cuniculus
<220> FEATURE:
<221> NAME/KEY: CDS
<222> LOCATION: (1)..(1659)
<300> PUBLICATION INFORMATION:
<308> DATABASE ACCESSION NUMBER: AB055978
<309> DATABASE ENTRY DATE: 2001-08-21
<313> RELEVANT RESIDUES IN SEQ ID NO: (1)..(1659)

<400> SEQUENCE: 27
```

| | | | | | | | | | | | | | | | | |
|---|---|---|---|---|---|---|---|---|---|---|---|---|---|---|---|---|
| atg | cat | tgt | gag | agg | ttt | ata | tgt | atc | ctg | aga | ata | att | gga | acc | aca | 48 |
| Met | His | Cys | Glu | Arg | Phe | Ile | Cys | Ile | Leu | Arg | Ile | Ile | Gly | Thr | Thr | |
| 1 | | | | 5 | | | | | 10 | | | | | 15 | | |
| ctg | ttt | gga | gtc | tct | ctc | ctt | ctg | gga | atc | aca | gct | gct | tat | att | gtt | 96 |
| Leu | Phe | Gly | Val | Ser | Leu | Leu | Leu | Gly | Ile | Thr | Ala | Ala | Tyr | Ile | Val | |
| | | | 20 | | | | | 25 | | | | | 30 | | | |
| gga | tac | cag | ttt | atc | caa | acg | gat | aat | tac | tat | ttc | tct | ttt | gga | ctg | 144 |
| Gly | Tyr | Gln | Phe | Ile | Gln | Thr | Asp | Asn | Tyr | Tyr | Phe | Ser | Phe | Gly | Leu | |
| | | 35 | | | | | 40 | | | | | 45 | | | | |
| tat | ggt | gcc | ttt | tta | gca | tca | cac | ctc | atc | atc | caa | agc | ctg | ttt | gcc | 192 |
| Tyr | Gly | Ala | Phe | Leu | Ala | Ser | His | Leu | Ile | Ile | Gln | Ser | Leu | Phe | Ala | |
| | 50 | | | | | 55 | | | | | 60 | | | | | |
| ttt | ttg | gag | cac | cga | aaa | atg | aaa | aaa | tcc | cta | gaa | acc | ccc | att | aag | 240 |
| Phe | Leu | Glu | His | Arg | Lys | Met | Lys | Lys | Ser | Leu | Glu | Thr | Pro | Ile | Lys | |
| 65 | | | | | 70 | | | | | 75 | | | | | 80 | |
| ttg | aac | aaa | aca | gtt | gct | ctt | tgc | atc | gct | gcc | tat | caa | gaa | gac | cca | 288 |
| Leu | Asn | Lys | Thr | Val | Ala | Leu | Cys | Ile | Ala | Ala | Tyr | Gln | Glu | Asp | Pro | |
| | | | | 85 | | | | | 90 | | | | | 95 | | |
| gac | tac | tta | agg | aaa | tgt | tta | caa | tct | gtg | aaa | agg | ctg | acc | tac | cct | 336 |
| Asp | Tyr | Leu | Arg | Lys | Cys | Leu | Gln | Ser | Val | Lys | Arg | Leu | Thr | Tyr | Pro | |
| | | | 100 | | | | | 105 | | | | | 110 | | | |
| ggg | att | aaa | gtt | gtc | atg | gtc | att | gat | ggg | aac | tca | gaa | gat | gat | gtt | 384 |
| Gly | Ile | Lys | Val | Val | Met | Val | Ile | Asp | Gly | Asn | Ser | Glu | Asp | Asp | Val | |
| | | 115 | | | | | 120 | | | | | 125 | | | | |
| tac | atg | atg | gac | atc | ttc | agt | gaa | gtc | atg | ggc | agg | gaa | aca | tca | gcc | 432 |
| Tyr | Met | Met | Asp | Ile | Phe | Ser | Glu | Val | Met | Gly | Arg | Glu | Thr | Ser | Ala | |
| | 130 | | | | | 135 | | | | | 140 | | | | | |
| act | tac | atc | tgg | aag | aac | aac | ttt | cat | gaa | aag | ggg | cct | ggg | gag | act | 480 |
| Thr | Tyr | Ile | Trp | Lys | Asn | Asn | Phe | His | Glu | Lys | Gly | Pro | Gly | Glu | Thr | |
| 145 | | | | | 150 | | | | | 155 | | | | | 160 | |
| gat | gag | tca | cat | aaa | gaa | agc | tca | caa | cat | gta | acc | caa | ctg | gtc | ttg | 528 |
| Asp | Glu | Ser | His | Lys | Glu | Ser | Ser | Gln | His | Val | Thr | Gln | Leu | Val | Leu | |
| | | | | 165 | | | | | 170 | | | | | 175 | | |

| | | |
|---|---|---|
| tcg aac aaa agt gtt tgc atc atg cag aaa tgg ggt gga aag aga gaa<br>Ser Asn Lys Ser Val Cys Ile Met Gln Lys Trp Gly Gly Lys Arg Glu<br>180 185 190 | | 576 |
| gtc atg tac aca gcc ttc aga gca ctg gga cga agc gtg gat tat gta<br>Val Met Tyr Thr Ala Phe Arg Ala Leu Gly Arg Ser Val Asp Tyr Val<br>195 200 205 | | 624 |
| cag gtt tgt gat tca gat acc atg ctt gat cct gct tca tct gtg gag<br>Gln Val Cys Asp Ser Asp Thr Met Leu Asp Pro Ala Ser Ser Val Glu<br>210 215 220 | | 672 |
| atg gtg aaa gtt tta gaa gaa gat ccc atg gtg gga ggt gtg ggg gga<br>Met Val Lys Val Leu Glu Glu Asp Pro Met Val Gly Gly Val Gly Gly<br>225 230 235 240 | | 720 |
| gat gtc cag att tta aac aag tac gac tcc tgg atc tcc ttc ctc agc<br>Asp Val Gln Ile Leu Asn Lys Tyr Asp Ser Trp Ile Ser Phe Leu Ser<br>245 250 255 | | 768 |
| agt gtg aga tac tgg atg gct ttt aat ata gaa agg gcc tgc cag tct<br>Ser Val Arg Tyr Trp Met Ala Phe Asn Ile Glu Arg Ala Cys Gln Ser<br>260 265 270 | | 816 |
| tat ttt ggg tgt gtc cag tgc att agt gga cct ctt gga atg tac agg<br>Tyr Phe Gly Cys Val Gln Cys Ile Ser Gly Pro Leu Gly Met Tyr Arg<br>275 280 285 | | 864 |
| aac tcc ttg ctg cat gag ttt gtg gaa gac tgg tac aat cag gaa ttt<br>Asn Ser Leu Leu His Glu Phe Val Glu Asp Trp Tyr Asn Gln Glu Phe<br>290 295 300 | | 912 |
| atg ggc aac cag tgt agt ttt ggt gat gat agg cat ctg aca aac cga<br>Met Gly Asn Gln Cys Ser Phe Gly Asp Asp Arg His Leu Thr Asn Arg<br>305 310 315 320 | | 960 |
| gtg ctg agt ctg ggc tac gca aca aaa tac aca gct cga tcc aag tgc<br>Val Leu Ser Leu Gly Tyr Ala Thr Lys Tyr Thr Ala Arg Ser Lys Cys<br>325 330 335 | | 1008 |
| ctt act gaa acc cct ata gaa tat ctc cgg tgg tta aac cag cag acc<br>Leu Thr Glu Thr Pro Ile Glu Tyr Leu Arg Trp Leu Asn Gln Gln Thr<br>340 345 350 | | 1056 |
| cgt tgg agc aag tcc tac ttc cga gag tgg ctg tac aat gca atg tgg<br>Arg Trp Ser Lys Ser Tyr Phe Arg Glu Trp Leu Tyr Asn Ala Met Trp<br>355 360 365 | | 1104 |
| ttt cat aaa cat cac ttg tgg atg acc tat gaa gcg gtt atc act gga<br>Phe His Lys His His Leu Trp Met Thr Tyr Glu Ala Val Ile Thr Gly<br>370 375 380 | | 1152 |
| ttc ttc ccc ttc ttt ctc att gcc aca gta atc cag ctc ttc tac cgg<br>Phe Phe Pro Phe Phe Leu Ile Ala Thr Val Ile Gln Leu Phe Tyr Arg<br>385 390 395 400 | | 1200 |
| ggt aaa atc tgg aac atc ctc ctc ttc ttg tta act gtc cag cta gta<br>Gly Lys Ile Trp Asn Ile Leu Leu Phe Leu Leu Thr Val Gln Leu Val<br>405 410 415 | | 1248 |
| ggt ctc ata aaa tca tct ttt gcc agt tgc ctt aga gga aat atc gtc<br>Gly Leu Ile Lys Ser Ser Phe Ala Ser Cys Leu Arg Gly Asn Ile Val<br>420 425 430 | | 1296 |
| atg gtc ttt atg tct ctc tac tca gtg ctg tac atg tca agt tta ctt<br>Met Val Phe Met Ser Leu Tyr Ser Val Leu Tyr Met Ser Ser Leu Leu<br>435 440 445 | | 1344 |
| ccg gcc aag atg ttt gca att gca aca ata aac aaa gct ggg tgg ggc<br>Pro Ala Lys Met Phe Ala Ile Ala Thr Ile Asn Lys Ala Gly Trp Gly<br>450 455 460 | | 1392 |
| act tct gga agg aaa acc att gtt gtt aat ttc ata gga ctc att cca<br>Thr Ser Gly Arg Lys Thr Ile Val Val Asn Phe Ile Gly Leu Ile Pro<br>465 470 475 480 | | 1440 |
| gta tca gtt tgg ttt aca att ctg ctg ggt ggt gtc att ttc acc att<br>Val Ser Val Trp Phe Thr Ile Leu Leu Gly Gly Val Ile Phe Thr Ile<br>485 490 495 | | 1488 |

```
tat aag gaa tct aaa aag cca ttt tca gaa tcc aaa cag aca gtt cta    1536
Tyr Lys Glu Ser Lys Lys Pro Phe Ser Glu Ser Lys Gln Thr Val Leu
            500                 505                 510 att gtt gga acg ttg ctc tat gca tgc tac tgg gtc atg ctt ttg acg    1584
Ile Val Gly Thr Leu Leu Tyr Ala Cys Tyr Trp Val Met Leu Leu Thr
        515                 520                 525 ctg tat gtg gtc ctc atc aat aag tgt ggc cgg cgg aag aag gga caa    1632
Leu Tyr Val Val Leu Ile Asn Lys Cys Gly Arg Arg Lys Lys Gly Gln
    530                 535                 540 cag tat gac atg gtg ctt gat gta tga                                 1659
Gln Tyr Asp Met Val Leu Asp Val
545                 550
```

<210> SEQ ID NO 28
<211> LENGTH: 552
<212> TYPE: PRT
<213> ORGANISM: Oryctolagus cuniculus

<400> SEQUENCE: 28

```
Met His Cys Glu Arg Phe Ile Cys Ile Leu Arg Ile Ile Gly Thr Thr
1               5                   10                  15

Leu Phe Gly Val Ser Leu Leu Leu Gly Ile Thr Ala Ala Tyr Ile Val
            20                  25                  30

Gly Tyr Gln Phe Ile Gln Thr Asp Asn Tyr Tyr Phe Ser Phe Gly Leu
        35                  40                  45

Tyr Gly Ala Phe Leu Ala Ser His Leu Ile Ile Gln Ser Leu Phe Ala
    50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Gln Ser Val Lys Arg Leu Thr Tyr Pro
            100                 105                 110

Gly Ile Lys Val Val Met Val Ile Asp Gly Asn Ser Glu Asp Asp Val
        115                 120                 125

Tyr Met Met Asp Ile Phe Ser Glu Val Met Gly Arg Glu Thr Ser Ala
    130                 135                 140

Thr Tyr Ile Trp Lys Asn Asn Phe His Glu Lys Gly Pro Gly Glu Thr
145                 150                 155                 160

Asp Glu Ser His Lys Glu Ser Ser Gln His Val Thr Gln Leu Val Leu
                165                 170                 175

Ser Asn Lys Ser Val Cys Ile Met Gln Lys Trp Gly Lys Arg Glu
            180                 185                 190

Val Met Tyr Thr Ala Phe Arg Ala Leu Gly Arg Ser Val Asp Tyr Val
        195                 200                 205

Gln Val Cys Asp Ser Asp Thr Met Leu Asp Pro Ala Ser Ser Val Glu
    210                 215                 220

Met Val Lys Val Leu Glu Glu Asp Pro Met Val Gly Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
            260                 265                 270

Tyr Phe Gly Cys Val Gln Cys Ile Ser Gly Pro Leu Gly Met Tyr Arg
        275                 280                 285

Asn Ser Leu Leu His Glu Phe Val Glu Asp Trp Tyr Asn Gln Glu Phe
```

```
                     290                 295                 300
Met Gly Asn Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
            340                 345                 350

Arg Trp Ser Lys Ser Tyr Phe Arg Glu Trp Leu Tyr Asn Ala Met Trp
        355                 360                 365

Phe His Lys His His Leu Trp Met Thr Tyr Glu Ala Val Ile Thr Gly
370                 375                 380

Phe Phe Pro Phe Phe Leu Ile Ala Thr Val Ile Gln Leu Phe Tyr Arg
385                 390                 395                 400

Gly Lys Ile Trp Asn Ile Leu Leu Phe Leu Leu Thr Val Gln Leu Val
                405                 410                 415

Gly Leu Ile Lys Ser Ser Phe Ala Ser Cys Leu Arg Gly Asn Ile Val
            420                 425                 430

Met Val Phe Met Ser Leu Tyr Ser Val Leu Tyr Met Ser Ser Leu Leu
        435                 440                 445

Pro Ala Lys Met Phe Ala Ile Ala Thr Ile Asn Lys Ala Gly Trp Gly
450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                485                 490                 495

Tyr Lys Glu Ser Lys Lys Pro Phe Ser Glu Ser Lys Gln Thr Val Leu
            500                 505                 510

Ile Val Gly Thr Leu Leu Tyr Ala Cys Tyr Trp Val Met Leu Leu Thr
        515                 520                 525

Leu Tyr Val Val Leu Ile Asn Lys Cys Gly Arg Arg Lys Lys Gly Gln
        530                 535                 540

Gln Tyr Asp Met Val Leu Asp Val
545                 550

<210> SEQ ID NO 29
<211> LENGTH: 1659
<212> TYPE: DNA
<213> ORGANISM: Oryctolagus cuniculus
<220> FEATURE:
<221> NAME/KEY: CDS
<222> LOCATION: (1)..(1659)
<300> PUBLICATION INFORMATION:
<308> DATABASE ACCESSION NUMBER: AB055979.1
<309> DATABASE ENTRY DATE: 2001-08-21
<313> RELEVANT RESIDUES IN SEQ ID NO: (1)..(1659)

<400> SEQUENCE: 29 atg cca gtg caa ctg aca aca gcc ttg cgt gtg gtg ggc acc agc ctg      48
Met Pro Val Gln Leu Thr Thr Ala Leu Arg Val Val Gly Thr Ser Leu
1               5                   10                  15 ttt gcc ttg gcg gtg ctg ggt ggc atc ctg gca gcc tat gtg aca ggc      96
Phe Ala Leu Ala Val Leu Gly Gly Ile Leu Ala Ala Tyr Val Thr Gly
            20                  25                  30 tac cag ttc atc cac aca gag aag cac tac ctg tcc ttc ggc ctg tac     144
Tyr Gln Phe Ile His Thr Glu Lys His Tyr Leu Ser Phe Gly Leu Tyr
        35                  40                  45 ggc gct atc ctg ggc ctg cac ctg ctc atc cag agc ctg ttt gcc ttc     192
Gly Ala Ile Leu Gly Leu His Leu Leu Ile Gln Ser Leu Phe Ala Phe
    50                  55                  60
```

```
ctg gag cac cgg cgc atg cgg cgg gcc agg cgg ccg ctg aag ctg ccc      240
Leu Glu His Arg Arg Met Arg Arg Ala Arg Arg Pro Leu Lys Leu Pro
 65                  70                  75                  80 tca cgg cgg cgc tct gtg gcg ctc tgc atc gcc gcc tac cag gag gac      288
Ser Arg Arg Arg Ser Val Ala Leu Cys Ile Ala Ala Tyr Gln Glu Asp
                 85                  90                  95 ccc gac tac ttg cgc aag tgc ctg cgc tca gcc cag cgc atc gcc ttc      336
Pro Asp Tyr Leu Arg Lys Cys Leu Arg Ser Ala Gln Arg Ile Ala Phe
            100                 105                 110 cct gac ctc aag gtg gtt atg gtg gtc gat ggc aac cgc cag gaa gac      384
Pro Asp Leu Lys Val Val Met Val Val Asp Gly Asn Arg Gln Glu Asp
        115                 120                 125 gcc tac atg ctg gac atc ttc cat gag gtg ctg ggt ggc act gag cag      432
Ala Tyr Met Leu Asp Ile Phe His Glu Val Leu Gly Gly Thr Glu Gln
    130                 135                 140 gcc ggc ttc ttt gtg tgg cgc agc aac ttc cac gag gca ggc gag ggc      480
Ala Gly Phe Phe Val Trp Arg Ser Asn Phe His Glu Ala Gly Glu Gly
145                 150                 155                 160 gag acc gag gcc agc ctg cag gaa ggc atg gag cgc gtg cgg gct gtg      528
Glu Thr Glu Ala Ser Leu Gln Glu Gly Met Glu Arg Val Arg Ala Val
                165                 170                 175 gtg cgg acc agc acc ttc tcg tgc atc atg cag aag tgg gga ggc aag      576
Val Arg Thr Ser Thr Phe Ser Cys Ile Met Gln Lys Trp Gly Gly Lys
            180                 185                 190 cgt gag gtc atg tac aca gcc ttc aag gcc ctc ggc gat tca gtg gac      624
Arg Glu Val Met Tyr Thr Ala Phe Lys Ala Leu Gly Asp Ser Val Asp
        195                 200                 205 tac atc cag gta tgt gac tcg gac acg gtg ctg gac cca gcc tgt acc      672
Tyr Ile Gln Val Cys Asp Ser Asp Thr Val Leu Asp Pro Ala Cys Thr
    210                 215                 220 atc gag atg ctt cgc gtc ctg gaa gag gat ccc caa gta ggg gga gtc      720
Ile Glu Met Leu Arg Val Leu Glu Glu Asp Pro Gln Val Gly Gly Val
225                 230                 235                 240 ggg gga gat gtc caa atc ctc aac aag tat gac tca tgg atc tcg ttc      768
Gly Gly Asp Val Gln Ile Leu Asn Lys Tyr Asp Ser Trp Ile Ser Phe
                245                 250                 255 ctg agc agt gtg cgg tac tgg atg gcc ttc aac gtg gag cgg gcg tgc      816
Leu Ser Ser Val Arg Tyr Trp Met Ala Phe Asn Val Glu Arg Ala Cys
            260                 265                 270 cag tcc tac ttt ggc tgt gtg cag tgt atc agt ggg ccc ttg ggc atg      864
Gln Ser Tyr Phe Gly Cys Val Gln Cys Ile Ser Gly Pro Leu Gly Met
        275                 280                 285 tac cgc aac agt ctc ctc cag caa ttc ctg gag gac tgg tac cat cag      912
Tyr Arg Asn Ser Leu Leu Gln Gln Phe Leu Glu Asp Trp Tyr His Gln
    290                 295                 300 aag ttc cta ggc agc aag tgc agc ttt ggg gat gac agg cac ctc acc      960
Lys Phe Leu Gly Ser Lys Cys Ser Phe Gly Asp Asp Arg His Leu Thr
305                 310                 315                 320 aac cga gtc ctg agt ctt ggc tac cga act aag tat aca gca cgc tcc     1008
Asn Arg Val Leu Ser Leu Gly Tyr Arg Thr Lys Tyr Thr Ala Arg Ser
                325                 330                 335 aag tgc ctc act gag acc cct acc aag tac cta cgg tgg ctc aac caa     1056
Lys Cys Leu Thr Glu Thr Pro Thr Lys Tyr Leu Arg Trp Leu Asn Gln
            340                 345                 350 cag acg cgc tgg agc aag tct tac ttc cgg gag tgg ctc tac aac tct     1104
Gln Thr Arg Trp Ser Lys Ser Tyr Phe Arg Glu Trp Leu Tyr Asn Ser
        355                 360                 365 ctg tgg ttc cat aag cac cat ctc tgg atg acc tac gag tcg gtg gtc     1152
Leu Trp Phe His Lys His His Leu Trp Met Thr Tyr Glu Ser Val Val
    370                 375                 380
```

```
aca ggt ttc ttc ccc ttc ttc ctc atc gcc aca gtc ata cag ctt ttc      1200
Thr Gly Phe Phe Pro Phe Phe Leu Ile Ala Thr Val Ile Gln Leu Phe
385                 390                 395                 400 tac cgt ggc cgc atc tgg aac atc ctc ctc ttc ctg ctg acc gtg cag      1248
Tyr Arg Gly Arg Ile Trp Asn Ile Leu Leu Phe Leu Leu Thr Val Gln
            405                 410                 415 ctg gtg ggc atc atc aaa gct acc tat gcc tgc ttc ctt cgg ggc aat      1296
Leu Val Gly Ile Ile Lys Ala Thr Tyr Ala Cys Phe Leu Arg Gly Asn
        420                 425                 430 gca gag atg atc ttc atg tcc ctc tac tcc ctt ctc tac atg tct agc      1344
Ala Glu Met Ile Phe Met Ser Leu Tyr Ser Leu Leu Tyr Met Ser Ser
    435                 440                 445 ctc ctg ccc gcc aag atc ttt gcc att gct acc atc aac aag tct ggc      1392
Leu Leu Pro Ala Lys Ile Phe Ala Ile Ala Thr Ile Asn Lys Ser Gly
450                 455                 460 tgg ggc act tct ggc cga aaa aca att gtg gtg aac ttc att ggc ctc      1440
Trp Gly Thr Ser Gly Arg Lys Thr Ile Val Val Asn Phe Ile Gly Leu
465                 470                 475                 480 atc cct gtg tcc atc tgg gtg gca gtt ctt ttg ggg ggt ctg gcc tac      1488
Ile Pro Val Ser Ile Trp Val Ala Val Leu Leu Gly Gly Leu Ala Tyr
                485                 490                 495 acg gct tat tgc cag gac ctg ttc agt gag aca gag tta gcc ttc ctt      1536
Thr Ala Tyr Cys Gln Asp Leu Phe Ser Glu Thr Glu Leu Ala Phe Leu
            500                 505                 510 gtt tca ggg gcc att ctg tat ggc tgc tac tgg gtg gcc ctc ctc atg      1584
Val Ser Gly Ala Ile Leu Tyr Gly Cys Tyr Trp Val Ala Leu Leu Met
        515                 520                 525 ctg tat ctg gcc atc ata gcc cgg aga tgt ggg aag aag cca gaa caa      1632
Leu Tyr Leu Ala Ile Ile Ala Arg Arg Cys Gly Lys Lys Pro Glu Gln
    530                 535                 540 tat agc ttg gcc ttt gct gag gtg tga                                  1659
Tyr Ser Leu Ala Phe Ala Glu Val
545                 550

<210> SEQ ID NO 30
<211> LENGTH: 552
<212> TYPE: PRT
<213> ORGANISM: Oryctolagus cuniculus

<400> SEQUENCE: 30

Met Pro Val Gln Leu Thr Thr Ala Leu Arg Val Val Gly Thr Ser Leu
1               5                   10                  15

Phe Ala Leu Ala Val Leu Gly Gly Ile Leu Ala Ala Tyr Val Thr Gly
            20                  25                  30

Tyr Gln Phe Ile His Thr Glu Lys His Tyr Leu Ser Phe Gly Leu Tyr
        35                  40                  45

Gly Ala Ile Leu Gly Leu His Leu Leu Ile Gln Ser Leu Phe Ala Phe
    50                  55                  60

Leu Glu His Arg Arg Met Arg Arg Ala Arg Arg Pro Leu Lys Leu Pro
65                  70                  75                  80

Ser Arg Arg Arg Ser Val Ala Leu Cys Ile Ala Ala Tyr Gln Glu Asp
                85                  90                  95

Pro Asp Tyr Leu Arg Lys Cys Leu Arg Ser Ala Gln Arg Ile Ala Phe
            100                 105                 110

Pro Asp Leu Lys Val Val Met Val Val Asp Gly Asn Arg Gln Glu Asp
        115                 120                 125

Ala Tyr Met Leu Asp Ile Phe His Glu Val Leu Gly Gly Thr Glu Gln
    130                 135                 140
```

```
Ala Gly Phe Phe Val Trp Arg Ser Asn Phe His Glu Ala Gly Glu Gly
145                 150                 155                 160

Glu Thr Glu Ala Ser Leu Gln Glu Gly Met Glu Arg Val Arg Ala Val
            165                 170                 175

Val Arg Thr Ser Thr Phe Ser Cys Ile Met Gln Lys Trp Gly Gly Lys
            180                 185                 190

Arg Glu Val Met Tyr Thr Ala Phe Lys Ala Leu Gly Asp Ser Val Asp
            195                 200                 205

Tyr Ile Gln Val Cys Asp Ser Asp Thr Val Leu Asp Pro Ala Cys Thr
210                 215                 220

Ile Glu Met Leu Arg Val Leu Glu Glu Asp Pro Gln Val Gly Gly Val
225                 230                 235                 240

Gly Gly Asp Val Gln Ile Leu Asn Lys Tyr Asp Ser Trp Ile Ser Phe
                245                 250                 255

Leu Ser Ser Val Arg Tyr Trp Met Ala Phe Asn Val Glu Arg Ala Cys
            260                 265                 270

Gln Ser Tyr Phe Gly Cys Val Gln Cys Ile Ser Gly Pro Leu Gly Met
        275                 280                 285

Tyr Arg Asn Ser Leu Leu Gln Gln Phe Leu Asp Trp Tyr His Gln
290                 295                 300

Lys Phe Leu Gly Ser Lys Cys Ser Phe Gly Asp Asp Arg His Leu Thr
305                 310                 315                 320

Asn Arg Val Leu Ser Leu Gly Tyr Arg Thr Lys Tyr Thr Ala Arg Ser
                325                 330                 335

Lys Cys Leu Thr Glu Thr Pro Thr Lys Tyr Leu Arg Trp Leu Asn Gln
            340                 345                 350

Gln Thr Arg Trp Ser Lys Ser Tyr Phe Arg Glu Trp Leu Tyr Asn Ser
        355                 360                 365

Leu Trp Phe His Lys His His Leu Trp Met Thr Tyr Glu Ser Val Val
370                 375                 380

Thr Gly Phe Phe Pro Phe Leu Ile Ala Thr Val Ile Gln Leu Phe
385                 390                 395                 400

Tyr Arg Gly Arg Ile Trp Asn Ile Leu Leu Phe Leu Leu Thr Val Gln
                405                 410                 415

Leu Val Gly Ile Ile Lys Ala Thr Tyr Ala Cys Phe Leu Arg Gly Asn
            420                 425                 430

Ala Glu Met Ile Phe Met Ser Leu Tyr Ser Leu Leu Tyr Met Ser Ser
        435                 440                 445

Leu Leu Pro Ala Lys Ile Phe Ala Ile Ala Thr Ile Asn Lys Ser Gly
    450                 455                 460

Trp Gly Thr Ser Gly Arg Lys Thr Ile Val Asn Phe Ile Gly Leu
465                 470                 475                 480

Ile Pro Val Ser Ile Trp Val Ala Val Leu Leu Gly Leu Ala Tyr
                485                 490                 495

Thr Ala Tyr Cys Gln Asp Leu Phe Ser Glu Thr Glu Leu Ala Phe Leu
            500                 505                 510

Val Ser Gly Ala Ile Leu Tyr Gly Cys Tyr Trp Val Ala Leu Leu Met
        515                 520                 525

Leu Tyr Leu Ala Ile Ile Ala Arg Arg Cys Gly Lys Lys Pro Glu Gln
    530                 535                 540

Tyr Ser Leu Ala Phe Ala Glu Val
545                 550
```

<210> SEQ ID NO 31

```
<211> LENGTH: 1659
<212> TYPE: DNA
<213> ORGANISM: Equus caballus
<220> FEATURE:
<221> NAME/KEY: CDS
<222> LOCATION: (1)..(1659)
<300> PUBLICATION INFORMATION:
<308> DATABASE ACCESSION NUMBER: AY056582.1
<309> DATABASE ENTRY DATE: 2002-11-05
<313> RELEVANT RESIDUES IN SEQ ID NO: (437)..(2095)

<400> SEQUENCE: 31 atg cat tgt gag agg ttt ata tgt atc ctg aga ata att gga acc aca        48
Met His Cys Glu Arg Phe Ile Cys Ile Leu Arg Ile Ile Gly Thr Thr
1               5                   10                  15 ctt ttt gga gtc tct ctc cta ctt gga atc aca gct gct tat att gtt        96
Leu Phe Gly Val Ser Leu Leu Leu Gly Ile Thr Ala Ala Tyr Ile Val
            20                  25                  30 ggc tac caa ttt atc caa aca gat aat tac tat ttc tct ttt gga cta       144
Gly Tyr Gln Phe Ile Gln Thr Asp Asn Tyr Tyr Phe Ser Phe Gly Leu
        35                  40                  45 tat ggt gcc ttt tta gca tca cac ctc atc atc caa agc ctg ttt gcc       192
Tyr Gly Ala Phe Leu Ala Ser His Leu Ile Ile Gln Ser Leu Phe Ala
    50                  55                  60 ttt ttg gag cat cga aaa atg aaa aaa tcc cta gaa acc ccc att aag       240
Phe Leu Glu His Arg Lys Met Lys Lys Ser Leu Glu Thr Pro Ile Lys
65                  70                  75                  80 ttg aac aaa act gtt gct ctt tgc atc gct gcg tat caa gaa gat cca       288
Leu Asn Lys Thr Val Ala Leu Cys Ile Ala Ala Tyr Gln Glu Asp Pro
                85                  90                  95 gac tac tta cgg aaa tgc ttg caa tct gtg aaa agg cta acc tac cct       336
Asp Tyr Leu Arg Lys Cys Leu Gln Ser Val Lys Arg Leu Thr Tyr Pro
            100                 105                 110 ggg att aaa gtt gtc atg gtc ata gat ggg aac tca gaa gat gat ctt       384
Gly Ile Lys Val Val Met Val Ile Asp Gly Asn Ser Glu Asp Asp Leu
        115                 120                 125 tac atg atg gac atc ttc agt gaa gtc atg ggc agg gac aaa tca gcc       432
Tyr Met Met Asp Ile Phe Ser Glu Val Met Gly Arg Asp Lys Ser Ala
    130                 135                 140 act tac atc tgg aag aac aac ttc cac gag aag ggt cct ggt gag acg       480
Thr Tyr Ile Trp Lys Asn Asn Phe His Glu Lys Gly Pro Gly Glu Thr
145                 150                 155                 160 gat gag tca cat aaa gaa agc tct caa cat gtt acc caa ttg gtc ttg       528
Asp Glu Ser His Lys Glu Ser Ser Gln His Val Thr Gln Leu Val Leu
                165                 170                 175 tcc aac aaa agt att tgc atc atg caa aaa tgg ggt gga aaa aga gaa       576
Ser Asn Lys Ser Ile Cys Ile Met Gln Lys Trp Gly Gly Lys Arg Glu
            180                 185                 190 gtc atg tac acg gcc ttc aga gca ctg gga cga agt gtg gat tat gtg       624
Val Met Tyr Thr Ala Phe Arg Ala Leu Gly Arg Ser Val Asp Tyr Val
        195                 200                 205 cag gtt tgt gat tca gat acc atg ctt gac cct gcc tcg tct gtg gag       672
Gln Val Cys Asp Ser Asp Thr Met Leu Asp Pro Ala Ser Ser Val Glu
    210                 215                 220 atg gta aaa gtt tta gaa gaa gac ccc atg gtt gga ggt gtc gga gga       720
Met Val Lys Val Leu Glu Glu Asp Pro Met Val Gly Gly Val Gly Gly
225                 230                 235                 240 gat gtc cag att tta aac aag tac gat tcc tgg atc tcc ttc ctc agc       768
Asp Val Gln Ile Leu Asn Lys Tyr Asp Ser Trp Ile Ser Phe Leu Ser
                245                 250                 255 agt gtg aga tac tgg atg gct ttt aac ata gaa aga gcc tgt cag tct       816
Ser Val Arg Tyr Trp Met Ala Phe Asn Ile Glu Arg Ala Cys Gln Ser
            260                 265                 270
```

```
tat ttt ggg tgc gtc cag tgc att agt gga ccc ctg gga atg tac aga     864
Tyr Phe Gly Cys Val Gln Cys Ile Ser Gly Pro Leu Gly Met Tyr Arg
        275                 280                 285 aac tcc ttg ctg cat gaa ttc gta gaa gac tgg tac aat cag gaa ttt     912
Asn Ser Leu Leu His Glu Phe Val Glu Asp Trp Tyr Asn Gln Glu Phe
    290                 295                 300 atg ggc agc caa tgt agt ttt ggc gat gac cgg cat cta acg aac cga     960
Met Gly Ser Gln Cys Ser Phe Gly Asp Asp Arg His Leu Thr Asn Arg
305                 310                 315                 320 gtg ctg agt ctg ggt tat gca aca aaa tac aca gct cga tcc aag tgc    1008
Val Leu Ser Leu Gly Tyr Ala Thr Lys Tyr Thr Ala Arg Ser Lys Cys
                325                 330                 335 ctt act gaa aca cct ata gaa tat ctc aga tgg tta aac cag cag acc    1056
Leu Thr Glu Thr Pro Ile Glu Tyr Leu Arg Trp Leu Asn Gln Gln Thr
            340                 345                 350 cgt tgg agc aag tcc tac ttc cga gag tgg ctg tac aat gcg atg tgg    1104
Arg Trp Ser Lys Ser Tyr Phe Arg Glu Trp Leu Tyr Asn Ala Met Trp
        355                 360                 365 ttt cat aaa cat cac ttg tgg atg acc tac gaa gcg gtt atc act gga    1152
Phe His Lys His His Leu Trp Met Thr Tyr Glu Ala Val Ile Thr Gly
370                 375                 380 ttc ttc cct ttc ttt ctc att gcc aca gta atc cag ctc ttc tac cgg    1200
Phe Phe Pro Phe Phe Leu Ile Ala Thr Val Ile Gln Leu Phe Tyr Arg
385                 390                 395                 400 ggt aaa att tgg aat atc ctc ctc ttc ttg tta aca gtc cag tta gta    1248
Gly Lys Ile Trp Asn Ile Leu Leu Phe Leu Leu Thr Val Gln Leu Val
                405                 410                 415 ggt ctc ata aag tct tcc ttt gcc agc tgc ctt aga gga aac atc gtc    1296
Gly Leu Ile Lys Ser Ser Phe Ala Ser Cys Leu Arg Gly Asn Ile Val
            420                 425                 430 atg gtc ttc atg tcc ctc tac tca gtg tta tac atg tca agt tta ctg    1344
Met Val Phe Met Ser Leu Tyr Ser Val Leu Tyr Met Ser Ser Leu Leu
        435                 440                 445 ccc gcc aaa atg ttt gct att gcc acg ata aac aaa gct ggg tgg ggc    1392
Pro Ala Lys Met Phe Ala Ile Ala Thr Ile Asn Lys Ala Gly Trp Gly
450                 455                 460 aca tct gga agg aaa acc att gtt gtt aat ttc ata gga ctc att cca    1440
Thr Ser Gly Arg Lys Thr Ile Val Val Asn Phe Ile Gly Leu Ile Pro
465                 470                 475                 480 gta tca gtg tgg ttt aca atc ctc ctg ggt gga gtc att ttc acc att    1488
Val Ser Val Trp Phe Thr Ile Leu Leu Gly Gly Val Ile Phe Thr Ile
                485                 490                 495 tat atg gaa tct aaa aag cca ttc tca gaa tcc aaa cag aca gtt cta    1536
Tyr Met Glu Ser Lys Lys Pro Phe Ser Glu Ser Lys Gln Thr Val Leu
            500                 505                 510 atc gtt gga acg ttg ctc tat gca tgc tat tgg gtc atg ctt ttg acg    1584
Ile Val Gly Thr Leu Leu Tyr Ala Cys Tyr Trp Val Met Leu Leu Thr
        515                 520                 525 ctg tac gtg gtt ctc atc aac aaa tgt ggc agg cgg aag aag gga caa    1632
Leu Tyr Val Val Leu Ile Asn Lys Cys Gly Arg Arg Lys Lys Gly Gln
530                 535                 540 cag tat gac atg gtg ctt gat gta tga                                1659
Gln Tyr Asp Met Val Leu Asp Val
545                 550

<210> SEQ ID NO 32
<211> LENGTH: 552
<212> TYPE: PRT
<213> ORGANISM: Equus caballus

<400> SEQUENCE: 32
```

```
Met His Cys Glu Arg Phe Ile Cys Ile Leu Arg Ile Ile Gly Thr Thr
1               5                   10                  15

Leu Phe Gly Val Ser Leu Leu Leu Gly Ile Thr Ala Ala Tyr Ile Val
                20                  25                  30

Gly Tyr Gln Phe Ile Gln Thr Asp Asn Tyr Tyr Phe Ser Phe Gly Leu
                35                  40                  45

Tyr Gly Ala Phe Leu Ala Ser His Leu Ile Ile Gln Ser Leu Phe Ala
        50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Gln Ser Val Lys Arg Leu Thr Tyr Pro
                100                 105                 110

Gly Ile Lys Val Val Met Val Ile Asp Gly Asn Ser Glu Asp Asp Leu
            115                 120                 125

Tyr Met Met Asp Ile Phe Ser Glu Val Met Gly Arg Asp Lys Ser Ala
        130                 135                 140

Thr Tyr Ile Trp Lys Asn Asn Phe His Glu Lys Gly Pro Gly Glu Thr
145                 150                 155                 160

Asp Glu Ser His Lys Glu Ser Ser Gln His Val Thr Gln Leu Val Leu
                165                 170                 175

Ser Asn Lys Ser Ile Cys Ile Met Gln Lys Trp Gly Gly Lys Arg Glu
                180                 185                 190

Val Met Tyr Thr Ala Phe Arg Ala Leu Gly Arg Ser Val Asp Tyr Val
            195                 200                 205

Gln Val Cys Asp Ser Asp Thr Met Leu Asp Pro Ala Ser Ser Val Glu
        210                 215                 220

Met Val Lys Val Leu Glu Glu Asp Pro Met Val Gly Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
                260                 265                 270

Tyr Phe Gly Cys Val Gln Cys Ile Ser Gly Pro Leu Gly Met Tyr Arg
            275                 280                 285

Asn Ser Leu Leu His Glu Phe Val Glu Asp Trp Tyr Asn Gln Glu Phe
        290                 295                 300

Met Gly Ser Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
                340                 345                 350

Arg Trp Ser Lys Ser Tyr Phe Arg Glu Trp Leu Tyr Asn Ala Met Trp
            355                 360                 365

Phe His Lys His His Leu Trp Met Thr Tyr Glu Ala Val Ile Thr Gly
        370                 375                 380

Phe Phe Pro Phe Leu Ile Ala Thr Val Ile Gln Leu Phe Tyr Arg
385                 390                 395                 400

Gly Lys Ile Trp Asn Ile Leu Leu Phe Leu Leu Thr Val Gln Leu Val
                405                 410                 415

Gly Leu Ile Lys Ser Ser Phe Ala Ser Cys Leu Arg Gly Asn Ile Val
```

```
                420           425           430
Met Val Phe Met Ser Leu Tyr Ser Val Leu Tyr Met Ser Ser Leu Leu
            435                   440                   445

Pro Ala Lys Met Phe Ala Ile Ala Thr Ile Asn Lys Ala Gly Trp Gly
    450                   455                   460

Thr Ser Gly Arg Lys Thr Ile Val Val Asn Phe Ile Gly Leu Ile Pro
465                   470                   475                   480

Val Ser Val Trp Phe Thr Ile Leu Leu Gly Gly Val Ile Phe Thr Ile
                485                   490                   495

Tyr Met Glu Ser Lys Lys Pro Phe Ser Glu Ser Lys Gln Thr Val Leu
                500                   505                   510

Ile Val Gly Thr Leu Leu Tyr Ala Cys Tyr Trp Val Met Leu Leu Thr
            515                   520                   525

Leu Tyr Val Val Leu Ile Asn Lys Cys Gly Arg Arg Lys Lys Gly Gln
    530                   535                   540

Gln Tyr Asp Met Val Leu Asp Val
545                   550

<210> SEQ ID NO 33
<211> LENGTH: 1659
<212> TYPE: DNA
<213> ORGANISM: Sus scrofa
<220> FEATURE:
<221> NAME/KEY: CDS
<222> LOCATION: (1)..(1659)
<300> PUBLICATION INFORMATION:
<308> DATABASE ACCESSION NUMBER: NM_214053.1
<309> DATABASE ENTRY DATE: 2004-08-23
<313> RELEVANT RESIDUES IN SEQ ID NO: (568)..(2226)

<400> SEQUENCE: 33 atg cat tgt gag agg ttt cta tgt atc ctg aga ata att gga acc aca      48
Met His Cys Glu Arg Phe Leu Cys Ile Leu Arg Ile Ile Gly Thr Thr
1               5                   10                  15 ctt ttt gga gtt tct ctc ctc ctt gga att acc gct gct tat atc gtt      96
Leu Phe Gly Val Ser Leu Leu Leu Gly Ile Thr Ala Ala Tyr Ile Val
                20                  25                  30 ggc tac caa ttt atc caa aca gat aat tac tat ttc ttt ttt ggg cta     144
Gly Tyr Gln Phe Ile Gln Thr Asp Asn Tyr Tyr Phe Phe Phe Gly Leu
            35                  40                  45 tat ggt gcc ttt tta gca tca cac ctt atc atc caa agc ttg ttt gcc     192
Tyr Gly Ala Phe Leu Ala Ser His Leu Ile Ile Gln Ser Leu Phe Ala
        50                  55                  60 ttt ttg gag cac cgg aaa atg aaa aaa tct cta gaa acc ccc att aaa     240
Phe Leu Glu His Arg Lys Met Lys Lys Ser Leu Glu Thr Pro Ile Lys
65                  70                  75                  80 ttg aac aaa act gtc gct ctt tgc atc gcg gcc tat caa gaa gat cca     288
Leu Asn Lys Thr Val Ala Leu Cys Ile Ala Ala Tyr Gln Glu Asp Pro
                85                  90                  95 gac tac ttg cga aag tgt ttg caa tct gtg aaa agg cta acc tac cct     336
Asp Tyr Leu Arg Lys Cys Leu Gln Ser Val Lys Arg Leu Thr Tyr Pro
            100                 105                 110 gga att aaa gtg gtc atg gtc ata gat ggg aac tcg gaa gat gac ctt     384
Gly Ile Lys Val Val Met Val Ile Asp Gly Asn Ser Glu Asp Asp Leu
        115                 120                 125 tac atg atg gac atc ttc agt gaa gtc atg ggc agg gac aat tca gcc     432
Tyr Met Met Asp Ile Phe Ser Glu Val Met Gly Arg Asp Asn Ser Ala
    130                 135                 140 act tat atc tgg aag aac aac ttc cac gaa aag ggc cct ggt gag acg     480
Thr Tyr Ile Trp Lys Asn Asn Phe His Glu Lys Gly Pro Gly Glu Thr
145                 150                 155                 160
```

-continued

| | |
|---|---|
| gat gag tca cat aaa gaa agc tcc caa cat gtc acc caa ctg gtc ttg<br>Asp Glu Ser His Lys Glu Ser Ser Gln His Val Thr Gln Leu Val Leu<br>              165                        170                      175 | 528 |
| tcc aac aaa agt att tgc atc atg caa aaa tgg ggt gga aaa aga gaa<br>Ser Asn Lys Ser Ile Cys Ile Met Gln Lys Trp Gly Gly Lys Arg Glu<br>              180                        185                      190 | 576 |
| gtc atg tac acg gcc ttc aga gct ctg gga cga agt gtg gat tat gta<br>Val Met Tyr Thr Ala Phe Arg Ala Leu Gly Arg Ser Val Asp Tyr Val<br>        195                        200                      205 | 624 |
| cag gtt tgt gat tca gac acc atg ctt gac cct gcc tca tct gtg gag<br>Gln Val Cys Asp Ser Asp Thr Met Leu Asp Pro Ala Ser Ser Val Glu<br>210                        215                      220 | 672 |
| atg gtg aaa gtt tta gaa gaa gac ccc atg gtt gga ggt gtc gga gga<br>Met Val Lys Val Leu Glu Glu Asp Pro Met Val Gly Gly Val Gly Gly<br>225                        230                      235                      240 | 720 |
| gat gtc cag att tta aac aag tat gat tcc tgg atc tcc ttc ctc agc<br>Asp Val Gln Ile Leu Asn Lys Tyr Asp Ser Trp Ile Ser Phe Leu Ser<br>              245                        250                      255 | 768 |
| agt gtg aga tac tgg atg gct ttt aac ata gaa agg gcc tgc cag tct<br>Ser Val Arg Tyr Trp Met Ala Phe Asn Ile Glu Arg Ala Cys Gln Ser<br>        260                        265                      270 | 816 |
| tat ttt gga tgt gtc cag tgc att agt gga cct ctg ggg atg tac aga<br>Tyr Phe Gly Cys Val Gln Cys Ile Ser Gly Pro Leu Gly Met Tyr Arg<br>        275                        280                      285 | 864 |
| aac tcc tta ctg cat gaa ttt gtg gaa gac tgg tac aat caa gag ttt<br>Asn Ser Leu Leu His Glu Phe Val Glu Asp Trp Tyr Asn Gln Glu Phe<br>290                        295                      300 | 912 |
| atg ggc agc caa tgt agt ttt gga gat gac agg cat cta acg aac cga<br>Met Gly Ser Gln Cys Ser Phe Gly Asp Asp Arg His Leu Thr Asn Arg<br>305                        310                      315                      320 | 960 |
| gtg ctg agt ctg ggc tat gca aca aaa tac aca gct cgg tcc aag tgc<br>Val Leu Ser Leu Gly Tyr Ala Thr Lys Tyr Thr Ala Arg Ser Lys Cys<br>              325                        330                      335 | 1008 |
| ctt act gag acg cct ata gaa tat ctc aga tgg tta aac cag cag acc<br>Leu Thr Glu Thr Pro Ile Glu Tyr Leu Arg Trp Leu Asn Gln Gln Thr<br>              340                        345                      350 | 1056 |
| cgt tgg agc aag tcc tac ttc cga gag tgg ctg tac aat gcg atg tgg<br>Arg Trp Ser Lys Ser Tyr Phe Arg Glu Trp Leu Tyr Asn Ala Met Trp<br>        355                        360                      365 | 1104 |
| ttt cat aag cat cat ttg tgg atg acc tat gag gca gtt atc acc ggg<br>Phe His Lys His His Leu Trp Met Thr Tyr Glu Ala Val Ile Thr Gly<br>370                        375                      380 | 1152 |
| ttc ttc cct ttc ttt ctc att gcc aca gta atc cag ctc ttc tac agg<br>Phe Phe Pro Phe Phe Leu Ile Ala Thr Val Ile Gln Leu Phe Tyr Arg<br>385                        390                      395                      400 | 1200 |
| ggt aaa att tgg aac atc ctc ctc ttc ttg tta act gtc cag tta gta<br>Gly Lys Ile Trp Asn Ile Leu Leu Phe Leu Leu Thr Val Gln Leu Val<br>              405                        410                      415 | 1248 |
| ggt ctc ata aaa tca tcc ttt gcc agc tgc ctt aga gga aat atc gtc<br>Gly Leu Ile Lys Ser Ser Phe Ala Ser Cys Leu Arg Gly Asn Ile Val<br>              420                        425                      430 | 1296 |
| atg gtc ttc atg tcc ctc tac tcg gtg ttg tac atg tca agt tta ctt<br>Met Val Phe Met Ser Leu Tyr Ser Val Leu Tyr Met Ser Ser Leu Leu<br>        435                        440                      445 | 1344 |
| ccc gcc aag atg ttt gcc att gca acg ata aac aaa gct ggc tgg ggc<br>Pro Ala Lys Met Phe Ala Ile Ala Thr Ile Asn Lys Ala Gly Trp Gly<br>450                        455                      460 | 1392 |
| aca tct gga agg aaa acc atc gtt gtg aat ttc ata gga ctc att cca<br>Thr Ser Gly Arg Lys Thr Ile Val Val Asn Phe Ile Gly Leu Ile Pro<br>465                        470                      475                      480 | 1440 |

```
gtg tca gtt tgg ttt aca atc ctc ctg ggt ggt gtg att ttc acc att     1488
Val Ser Val Trp Phe Thr Ile Leu Leu Gly Gly Val Ile Phe Thr Ile
            485                 490                 495 tat aag gaa tct aaa aag cca ttc tca gaa tcc aaa cag aca gtt tta     1536
Tyr Lys Glu Ser Lys Lys Pro Phe Ser Glu Ser Lys Gln Thr Val Leu
        500                 505                 510 att gtt gga acg ttg ctc tat gca tgc tat tgg gtc atg ctt ttg aca     1584
Ile Val Gly Thr Leu Leu Tyr Ala Cys Tyr Trp Val Met Leu Leu Thr
            515                 520                 525 ctg tat gtg gtt ctc atc aat aaa tgt ggc cgg cgg aag aag gga caa     1632
Leu Tyr Val Val Leu Ile Asn Lys Cys Gly Arg Arg Lys Lys Gly Gln
        530                 535                 540 cag tac gac atg gtg ctt gat gta tga                                 1659
Gln Tyr Asp Met Val Leu Asp Val
545                 550

<210> SEQ ID NO 34
<211> LENGTH: 552
<212> TYPE: PRT
<213> ORGANISM: Sus scrofa

<400> SEQUENCE: 34

Met His Cys Glu Arg Phe Leu Cys Ile Leu Arg Ile Ile Gly Thr Thr
1               5                   10                  15

Leu Phe Gly Val Ser Leu Leu Leu Gly Ile Thr Ala Ala Tyr Ile Val
            20                  25                  30

Gly Tyr Gln Phe Ile Gln Thr Asp Asn Tyr Tyr Phe Phe Gly Leu
        35                  40                  45

Tyr Gly Ala Phe Leu Ala Ser His Leu Ile Ile Gln Ser Leu Phe Ala
50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
            85                  90                  95

Asp Tyr Leu Arg Lys Cys Leu Gln Ser Val Lys Arg Leu Thr Tyr Pro
        100                 105                 110

Gly Ile Lys Val Val Met Val Ile Asp Gly Asn Ser Glu Asp Asp Leu
    115                 120                 125

Tyr Met Met Asp Ile Phe Ser Glu Val Met Gly Arg Asp Asn Ser Ala
130                 135                 140

Thr Tyr Ile Trp Lys Asn Asn Phe His Glu Lys Gly Pro Gly Glu Thr
145                 150                 155                 160

Asp Glu Ser His Lys Glu Ser Ser Gln His Val Thr Gln Leu Val Leu
            165                 170                 175

Ser Asn Lys Ser Ile Cys Ile Met Gln Lys Trp Gly Gly Lys Arg Glu
        180                 185                 190

Val Met Tyr Thr Ala Phe Arg Ala Leu Gly Arg Ser Val Asp Tyr Val
    195                 200                 205

Gln Val Cys Asp Ser Asp Thr Met Leu Asp Pro Ala Ser Ser Val Glu
210                 215                 220

Met Val Lys Val Leu Glu Glu Asp Pro Met Val Gly Val Gly Gly
225                 230                 235                 240

Asp Val Gln Ile Leu Asn Lys Tyr Asp Ser Trp Ile Ser Phe Leu Ser
            245                 250                 255

Ser Val Arg Tyr Trp Met Ala Phe Asn Ile Glu Arg Ala Cys Gln Ser
        260                 265                 270
```

```
Tyr Phe Gly Cys Val Gln Cys Ile Ser Gly Pro Leu Gly Met Tyr Arg
        275                 280                 285

Asn Ser Leu Leu His Glu Phe Val Glu Asp Trp Tyr Asn Gln Glu Phe
290                 295                 300

Met Gly Ser Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
            340                 345                 350

Arg Trp Ser Lys Ser Tyr Phe Arg Glu Trp Leu Tyr Asn Ala Met Trp
        355                 360                 365

Phe His Lys His His Leu Trp Met Thr Tyr Glu Ala Val Ile Thr Gly
    370                 375                 380

Phe Phe Pro Phe Phe Leu Ile Ala Thr Val Ile Gln Leu Phe Tyr Arg
385                 390                 395                 400

Gly Lys Ile Trp Asn Ile Leu Phe Leu Leu Thr Val Gln Leu Val
                405                 410                 415

Gly Leu Ile Lys Ser Ser Phe Ala Ser Cys Leu Arg Gly Asn Ile Val
            420                 425                 430

Met Val Phe Met Ser Leu Tyr Ser Val Leu Tyr Met Ser Ser Leu Leu
        435                 440                 445

Pro Ala Lys Met Phe Ala Ile Ala Thr Ile Asn Lys Ala Gly Trp Gly
    450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                485                 490                 495

Tyr Lys Glu Ser Lys Lys Pro Phe Ser Glu Ser Lys Gln Thr Val Leu
            500                 505                 510

Ile Val Gly Thr Leu Leu Tyr Ala Cys Tyr Trp Val Met Leu Leu Thr
        515                 520                 525

Leu Tyr Val Val Leu Ile Asn Lys Cys Gly Arg Arg Lys Lys Gly Gln
    530                 535                 540

Gln Tyr Asp Met Val Leu Asp Val
545                 550

<210> SEQ ID NO 35
<211> LENGTH: 1662
<212> TYPE: DNA
<213> ORGANISM: Sus scrofa
<220> FEATURE:
<221> NAME/KEY: CDS
<222> LOCATION: (1)..(1662)
<300> PUBLICATION INFORMATION:
<308> DATABASE ACCESSION NUMBER: AB159675
<309> DATABASE ENTRY DATE: 2004-05-08
<313> RELEVANT RESIDUES IN SEQ ID NO: (1)..(1662)

<400> SEQUENCE: 35 atg ccg gtt cag ctg acg aca gcc ctg cgt gtg gtg ggc acc agc ctg      48
Met Pro Val Gln Leu Thr Thr Ala Leu Arg Val Val Gly Thr Ser Leu
1               5                   10                  15 ttt gcc ctg gca gtg ctg ggc ggc att ctg gca gca tat gtg aca ggc      96
Phe Ala Leu Ala Val Leu Gly Gly Ile Leu Ala Ala Tyr Val Thr Gly
            20                  25                  30 tac cag ttc atc cac aca gaa aag cac tac ctg tcc ttt ggg ctg tat     144
Tyr Gln Phe Ile His Thr Glu Lys His Tyr Leu Ser Phe Gly Leu Tyr
        35                  40                  45
```

```
ggt gcc atc ctg ggc ctg cac ctg ctc atc cag agc ctg ttt gcc ttc      192
Gly Ala Ile Leu Gly Leu His Leu Leu Ile Gln Ser Leu Phe Ala Phe
         50                  55                  60 ctg gag cac cgg cgc atg cgg cgg gca ggc cgg cca ctg aag ctg ccc      240
Leu Glu His Arg Arg Met Arg Arg Ala Gly Arg Pro Leu Lys Leu Pro
 65                  70                  75                  80 tcc ccg ctg cag cgc tca gtg gcg ctc tgc atc gcc gcg tac cag gag      288
Ser Pro Leu Gln Arg Ser Val Ala Leu Cys Ile Ala Ala Tyr Gln Glu
                 85                  90                  95 gac ccc gac tac ttg cgc aag tgc ctg cgc tcg gcc cag cgc atc gcc      336
Asp Pro Asp Tyr Leu Arg Lys Cys Leu Arg Ser Ala Gln Arg Ile Ala
            100                 105                 110 ttc ccc gat ctc aag gtg gtc atg gtg gtg gac ggc aat cgc cag gag      384
Phe Pro Asp Leu Lys Val Val Met Val Val Asp Gly Asn Arg Gln Glu
        115                 120                 125 gat gcc tac atg ttg gac atc ttc cac gag gtg cta ggt ggc aac gag      432
Asp Ala Tyr Met Leu Asp Ile Phe His Glu Val Leu Gly Gly Asn Glu
130                 135                 140 caa gcc ggc ttc ttt gtg tgg cgc agc aac ttc cat gag gcg ggt gag      480
Gln Ala Gly Phe Phe Val Trp Arg Ser Asn Phe His Glu Ala Gly Glu
145                 150                 155                 160 ggc gag acg gag gcc agc ctg cag gag ggc atg gac cgt gtg cgg aat      528
Gly Glu Thr Glu Ala Ser Leu Gln Glu Gly Met Asp Arg Val Arg Asn
                165                 170                 175 gtg gtg cgg gcc agc acc ttc tcc tgc atc atg cag aag tgg gga gga      576
Val Val Arg Ala Ser Thr Phe Ser Cys Ile Met Gln Lys Trp Gly Gly
            180                 185                 190 aag cga gag gtc atg tac acg gcc ttc aag gcc ctt ggt gac tcc gtg      624
Lys Arg Glu Val Met Tyr Thr Ala Phe Lys Ala Leu Gly Asp Ser Val
        195                 200                 205 gac tac att cag gtg tgt gac tct gac act gta ctg gat cca gcc tgt      672
Asp Tyr Ile Gln Val Cys Asp Ser Asp Thr Val Leu Asp Pro Ala Cys
    210                 215                 220 acc ttc gag atg ctt cga gtc ttg gag gag gac ccc caa gta ggg gga      720
Thr Phe Glu Met Leu Arg Val Leu Glu Glu Asp Pro Gln Val Gly Gly
225                 230                 235                 240 gtt ggg gga gat gtc caa atc ctc aat aag tat gac tcc tgg atc tcc      768
Val Gly Gly Asp Val Gln Ile Leu Asn Lys Tyr Asp Ser Trp Ile Ser
                245                 250                 255 ttc ctg agc agt gtg cgg tac tgg atg gcc ttc aac gtg gaa cgg gct      816
Phe Leu Ser Ser Val Arg Tyr Trp Met Ala Phe Asn Val Glu Arg Ala
            260                 265                 270 tgc cag tcc tac ttc ggc tgt gtg cag tgt atc agt ggg ccc ctg ggc      864
Cys Gln Ser Tyr Phe Gly Cys Val Gln Cys Ile Ser Gly Pro Leu Gly
        275                 280                 285 atg tac cgg aac agc ctg ctt cag cag ttc ttg gag gac tgg tac cat      912
Met Tyr Arg Asn Ser Leu Leu Gln Gln Phe Leu Glu Asp Trp Tyr His
    290                 295                 300 cag aag ttc cta ggt agc aag tgc agt ttt ggg gat gac cgg cac ctc      960
Gln Lys Phe Leu Gly Ser Lys Cys Ser Phe Gly Asp Asp Arg His Leu
305                 310                 315                 320 acc aac cga gtc ctg agt ctc ggc tac agg act aag tac aca gca cgc      1008
Thr Asn Arg Val Leu Ser Leu Gly Tyr Arg Thr Lys Tyr Thr Ala Arg
                325                 330                 335 tct aaa tgc ctc aca gag acc ccc acc aag tac ctc cgg tgg ctc aac      1056
Ser Lys Cys Leu Thr Glu Thr Pro Thr Lys Tyr Leu Arg Trp Leu Asn
            340                 345                 350 caa cag acc cgc tgg agc aag tct tac ttc cgg gag tgg ctc tac aac      1104
Gln Gln Thr Arg Trp Ser Lys Ser Tyr Phe Arg Glu Trp Leu Tyr Asn
        355                 360                 365
```

| | | | | | | | | | | | | | | | | |
|---|---|---|---|---|---|---|---|---|---|---|---|---|---|---|---|---|
| tct | ctg | tgg | ttc | cac | aag | cac | cac | ctc | tgg | atg | acc | tac | gag | tca | gtg | 1152 |
| Ser | Leu | Trp | Phe | His | Lys | His | His | Leu | Trp | Met | Thr | Tyr | Glu | Ser | Val | |
| | 370 | | | | | 375 | | | | | 380 | | | | | |
| gtc | aca | ggt | ttt | ttc | ccc | ttc | ttc | ctt | att | gcc | aca | gtc | ata | cag | ctt | 1200 |
| Val | Thr | Gly | Phe | Phe | Pro | Phe | Phe | Leu | Ile | Ala | Thr | Val | Ile | Gln | Leu | |
| 385 | | | | | 390 | | | | | 395 | | | | | 400 | |
| ttc | tac | cgt | ggc | cgc | atc | tgg | aac | att | ctc | ctc | ttc | ctg | ctg | aca | gtg | 1248 |
| Phe | Tyr | Arg | Gly | Arg | Ile | Trp | Asn | Ile | Leu | Leu | Phe | Leu | Leu | Thr | Val | |
| | | | | 405 | | | | | 410 | | | | | 415 | | |
| cag | ttg | gta | ggc | atc | atc | aag | gct | acc | tat | gcc | tgc | ttt | ctt | cgg | ggc | 1296 |
| Gln | Leu | Val | Gly | Ile | Ile | Lys | Ala | Thr | Tyr | Ala | Cys | Phe | Leu | Arg | Gly | |
| | | | 420 | | | | | 425 | | | | | 430 | | | |
| aat | gca | gag | atg | atc | ttc | atg | tct | ctc | tac | tcc | ctt | ctc | tac | atg | tcc | 1344 |
| Asn | Ala | Glu | Met | Ile | Phe | Met | Ser | Leu | Tyr | Ser | Leu | Leu | Tyr | Met | Ser | |
| | | 435 | | | | | 440 | | | | | 445 | | | | |
| agc | ctc | ctg | cca | gcc | aag | atc | ttc | gcc | att | gct | acc | atc | aac | aaa | tct | 1392 |
| Ser | Leu | Leu | Pro | Ala | Lys | Ile | Phe | Ala | Ile | Ala | Thr | Ile | Asn | Lys | Ser | |
| 450 | | | | | 455 | | | | | 460 | | | | | | |
| ggc | tgg | ggc | act | tct | ggc | cga | aaa | acc | att | gtg | gtg | aac | ttc | att | ggc | 1440 |
| Gly | Trp | Gly | Thr | Ser | Gly | Arg | Lys | Thr | Ile | Val | Val | Asn | Phe | Ile | Gly | |
| 465 | | | | 470 | | | | | 475 | | | | | 480 | | |
| ctc | atc | cct | gtg | tcc | atc | tgg | gtg | gca | gtc | ctt | ctg | ggg | gga | ctg | gcc | 1488 |
| Leu | Ile | Pro | Val | Ser | Ile | Trp | Val | Ala | Val | Leu | Leu | Gly | Gly | Leu | Ala | |
| | | | | 485 | | | | | 490 | | | | | 495 | | |
| tat | aca | gct | tac | tgt | cag | gac | ctg | ttc | agt | gag | acg | gag | cta | gcc | ttc | 1536 |
| Tyr | Thr | Ala | Tyr | Cys | Gln | Asp | Leu | Phe | Ser | Glu | Thr | Glu | Leu | Ala | Phe | |
| | | | 500 | | | | | 505 | | | | | 510 | | | |
| ctg | gtc | tca | ggg | gcc | atc | ctt | tat | ggc | tgc | tac | tgg | gtg | gcc | ctc | ctt | 1584 |
| Leu | Val | Ser | Gly | Ala | Ile | Leu | Tyr | Gly | Cys | Tyr | Trp | Val | Ala | Leu | Leu | |
| | | 515 | | | | | 520 | | | | | 525 | | | | |
| atg | ctg | tat | ctg | gcc | atc | atc | gcc | cgg | cgg | tgc | ggg | aag | aag | ccg | gag | 1632 |
| Met | Leu | Tyr | Leu | Ala | Ile | Ile | Ala | Arg | Arg | Cys | Gly | Lys | Lys | Pro | Glu | |
| | 530 | | | | | 535 | | | | | 540 | | | | | |
| cag | tat | agc | tta | gct | ttt | gct | gag | gtg | tga | | | | | | | 1662 |
| Gln | Tyr | Ser | Leu | Ala | Phe | Ala | Glu | Val | | | | | | | | |
| 545 | | | | 550 | | | | | | | | | | | | |

<210> SEQ ID NO 36
<211> LENGTH: 553
<212> TYPE: PRT
<213> ORGANISM: Sus scrofa

<400> SEQUENCE: 36

Met Pro Val Gln Leu Thr Thr Ala Leu Arg Val Val Gly Thr Ser Leu
1               5                   10                  15

Phe Ala Leu Ala Val Leu Gly Gly Ile Leu Ala Ala Tyr Val Thr Gly
            20                  25                  30

Tyr Gln Phe Ile His Thr Glu Lys His Tyr Leu Ser Phe Gly Leu Tyr
        35                  40                  45

Gly Ala Ile Leu Gly Leu His Leu Leu Ile Gln Ser Leu Phe Ala Phe
    50                  55                  60

Leu Glu His Arg Arg Met Arg Arg Ala Gly Arg Pro Leu Lys Leu Pro
65                  70                  75                  80

Ser Pro Leu Gln Arg Ser Val Ala Leu Cys Ile Ala Ala Tyr Gln Glu
                85                  90                  95

Asp Pro Asp Tyr Leu Arg Lys Cys Leu Arg Ser Ala Gln Arg Ile Ala
            100                 105                 110

Phe Pro Asp Leu Lys Val Val Met Val Val Asp Gly Asn Arg Gln Glu
        115                 120                 125

```
Asp Ala Tyr Met Leu Asp Ile Phe His Glu Val Leu Gly Gly Asn Glu
    130                 135                 140
Gln Ala Gly Phe Phe Val Trp Arg Ser Asn Phe His Glu Ala Gly Glu
145                 150                 155                 160
Gly Glu Thr Glu Ala Ser Leu Gln Glu Gly Met Asp Arg Val Arg Asn
                165                 170                 175
Val Val Arg Ala Ser Thr Phe Ser Cys Ile Met Gln Lys Trp Gly Gly
            180                 185                 190
Lys Arg Glu Val Met Tyr Thr Ala Phe Lys Ala Leu Gly Asp Ser Val
        195                 200                 205
Asp Tyr Ile Gln Val Cys Asp Ser Asp Thr Val Leu Asp Pro Ala Cys
    210                 215                 220
Thr Phe Glu Met Leu Arg Val Leu Glu Glu Asp Pro Gln Val Gly Gly
225                 230                 235                 240
Val Gly Gly Asp Val Gln Ile Leu Asn Lys Tyr Asp Ser Trp Ile Ser
                245                 250                 255
Phe Leu Ser Ser Val Arg Tyr Trp Met Ala Phe Asn Val Glu Arg Ala
            260                 265                 270
Cys Gln Ser Tyr Phe Gly Cys Val Gln Cys Ile Ser Gly Pro Leu Gly
        275                 280                 285
Met Tyr Arg Asn Ser Leu Leu Gln Gln Phe Leu Glu Asp Trp Tyr His
    290                 295                 300
Gln Lys Phe Leu Gly Ser Lys Cys Ser Phe Gly Asp Asp Arg His Leu
305                 310                 315                 320
Thr Asn Arg Val Leu Ser Leu Gly Tyr Arg Thr Lys Tyr Thr Ala Arg
                325                 330                 335
Ser Lys Cys Leu Thr Glu Thr Pro Thr Lys Tyr Leu Arg Trp Leu Asn
            340                 345                 350
Gln Gln Thr Arg Trp Ser Lys Ser Tyr Phe Arg Glu Trp Leu Tyr Asn
        355                 360                 365
Ser Leu Trp Phe His Lys His His Leu Trp Met Thr Tyr Glu Ser Val
    370                 375                 380
Val Thr Gly Phe Phe Pro Phe Leu Ile Ala Thr Val Ile Gln Leu
385                 390                 395                 400
Phe Tyr Arg Gly Arg Ile Trp Asn Ile Leu Leu Phe Leu Leu Thr Val
                405                 410                 415
Gln Leu Val Gly Ile Ile Lys Ala Thr Tyr Ala Cys Phe Leu Arg Gly
            420                 425                 430
Asn Ala Glu Met Ile Phe Met Ser Leu Tyr Ser Leu Leu Tyr Met Ser
        435                 440                 445
Ser Leu Leu Pro Ala Lys Ile Phe Ala Ile Ala Thr Ile Asn Lys Ser
    450                 455                 460
Gly Trp Gly Thr Ser Gly Arg Lys Thr Ile Val Val Asn Phe Ile Gly
465                 470                 475                 480
Leu Ile Pro Val Ser Ile Trp Val Ala Val Leu Leu Gly Gly Leu Ala
                485                 490                 495
Tyr Thr Ala Tyr Cys Gln Asp Leu Phe Ser Glu Thr Glu Leu Ala Phe
            500                 505                 510
Leu Val Ser Gly Ala Ile Leu Tyr Gly Cys Tyr Trp Val Ala Leu Leu
        515                 520                 525
Met Leu Tyr Leu Ala Ile Ile Ala Arg Arg Cys Gly Lys Lys Pro Glu
    530                 535                 540
Gln Tyr Ser Leu Ala Phe Ala Glu Val
```

<210> SEQ ID NO 37
<211> LENGTH: 1659
<212> TYPE: DNA
<213> ORGANISM: Bos taurus
<220> FEATURE:
<221> NAME/KEY: CDS
<222> LOCATION: (1)..(1659)
<300> PUBLICATION INFORMATION:
<308> DATABASE ACCESSION NUMBER: AJ004951.1
<309> DATABASE ENTRY DATE: 1998-11-24
<313> RELEVANT RESIDUES IN SEQ ID NO: (545)..(2203)

<400> SEQUENCE: 37

| | | | | | | | | | | | | | | | | |
|---|---|---|---|---|---|---|---|---|---|---|---|---|---|---|---|---|
| atg | cat | tgt | gag | aga | ttt | cta | tgt | atc | ctg | aga | ata | att | gga | acc | aca | 48 |
| Met | His | Cys | Glu | Arg | Phe | Leu | Cys | Ile | Leu | Arg | Ile | Ile | Gly | Thr | Thr | |
| 1 | | | | 5 | | | | | 10 | | | | | 15 | | |
| ctt | ttt | gga | gtc | tct | ctc | ctc | ctt | gga | atc | aca | gct | gct | tat | att | gtt | 96 |
| Leu | Phe | Gly | Val | Ser | Leu | Leu | Leu | Gly | Ile | Thr | Ala | Ala | Tyr | Ile | Val | |
| | | | 20 | | | | | 25 | | | | | 30 | | | |
| ggc | tat | caa | ttt | atc | caa | aca | gat | aat | tac | tat | ttc | tct | ttt | gga | ctg | 144 |
| Gly | Tyr | Gln | Phe | Ile | Gln | Thr | Asp | Asn | Tyr | Tyr | Phe | Ser | Phe | Gly | Leu | |
| | 35 | | | | | 40 | | | | | 45 | | | | | |
| tat | ggt | gcc | ttt | tta | gca | tca | cac | ctc | atc | atc | caa | agc | ctg | ttt | gcc | 192 |
| Tyr | Gly | Ala | Phe | Leu | Ala | Ser | His | Leu | Ile | Ile | Gln | Ser | Leu | Phe | Ala | |
| 50 | | | | | 55 | | | | | 60 | | | | | | |
| ttt | ttg | gag | cac | cgg | aaa | atg | aaa | aaa | tct | cta | gaa | acc | ccc | att | aag | 240 |
| Phe | Leu | Glu | His | Arg | Lys | Met | Lys | Lys | Ser | Leu | Glu | Thr | Pro | Ile | Lys | |
| 65 | | | | | 70 | | | | | 75 | | | | | 80 | |
| ttg | aac | aaa | act | gtt | gct | ctt | tgc | att | gct | gca | tat | caa | gaa | gat | cca | 288 |
| Leu | Asn | Lys | Thr | Val | Ala | Leu | Cys | Ile | Ala | Ala | Tyr | Gln | Glu | Asp | Pro | |
| | | | | 85 | | | | | 90 | | | | | 95 | | |
| gac | tat | ttg | cgg | aaa | tgt | ttg | caa | tct | gtg | aaa | agg | cta | acc | tac | ccc | 336 |
| Asp | Tyr | Leu | Arg | Lys | Cys | Leu | Gln | Ser | Val | Lys | Arg | Leu | Thr | Tyr | Pro | |
| | | | 100 | | | | | 105 | | | | | 110 | | | |
| gga | att | aaa | gtt | gtc | atg | gtc | ata | gat | gga | aac | tcg | gaa | gat | gac | ctt | 384 |
| Gly | Ile | Lys | Val | Val | Met | Val | Ile | Asp | Gly | Asn | Ser | Glu | Asp | Asp | Leu | |
| | | 115 | | | | | 120 | | | | | 125 | | | | |
| tac | atg | atg | gac | atc | ttc | agt | gaa | gtc | atg | ggc | agg | gac | aag | tca | gcc | 432 |
| Tyr | Met | Met | Asp | Ile | Phe | Ser | Glu | Val | Met | Gly | Arg | Asp | Lys | Ser | Ala | |
| | 130 | | | | | 135 | | | | | 140 | | | | | |
| act | tat | atc | tgg | aag | aac | aac | tac | cat | gtg | aag | ggt | cct | gga | gag | acg | 480 |
| Thr | Tyr | Ile | Trp | Lys | Asn | Asn | Tyr | His | Val | Lys | Gly | Pro | Gly | Glu | Thr | |
| 145 | | | | | 150 | | | | | 155 | | | | | 160 | |
| gat | gag | tcg | cac | aaa | gaa | agc | tca | cag | cat | gtc | acc | cag | ttg | gtc | ttg | 528 |
| Asp | Glu | Ser | His | Lys | Glu | Ser | Ser | Gln | His | Val | Thr | Gln | Leu | Val | Leu | |
| | | | | 165 | | | | | 170 | | | | | 175 | | |
| tcc | aac | aag | agt | att | tgc | acc | atg | caa | aaa | tgg | ggt | gga | aaa | aga | gaa | 576 |
| Ser | Asn | Lys | Ser | Ile | Cys | Thr | Met | Gln | Lys | Trp | Gly | Gly | Lys | Arg | Glu | |
| | | | 180 | | | | | 185 | | | | | 190 | | | |
| gtc | atg | tac | aca | gcc | ttc | aga | gca | ctg | ggg | cga | agt | gtg | gat | tat | gta | 624 |
| Val | Met | Tyr | Thr | Ala | Phe | Arg | Ala | Leu | Gly | Arg | Ser | Val | Asp | Tyr | Val | |
| | | 195 | | | | | 200 | | | | | 205 | | | | |
| cag | gtt | tgt | gat | tca | gac | acc | atg | ctt | gac | cca | gca | tca | tct | gtg | gag | 672 |
| Gln | Val | Cys | Asp | Ser | Asp | Thr | Met | Leu | Asp | Pro | Ala | Ser | Ser | Val | Glu | |
| | 210 | | | | | 215 | | | | | 220 | | | | | |
| atg | gta | aaa | gtt | tta | gaa | gaa | gat | ccc | atg | gtt | gga | ggt | gtc | ggg | gga | 720 |
| Met | Val | Lys | Val | Leu | Glu | Glu | Asp | Pro | Met | Val | Gly | Gly | Val | Gly | Gly | |
| 225 | | | | | 230 | | | | | 235 | | | | | 240 | |
| gat | gtc | cag | att | tta | aac | aag | tat | gat | tcc | tgg | atc | tcc | ttc | ctc | agc | 768 |
| Asp | Val | Gln | Ile | Leu | Asn | Lys | Tyr | Asp | Ser | Trp | Ile | Ser | Phe | Leu | Ser | |
| | | | | 245 | | | | | 250 | | | | | 255 | | |

```
agt gtg aga tac tgg atg gct ttt aac ata gaa agg gcc tgt cag tct      816
Ser Val Arg Tyr Trp Met Ala Phe Asn Ile Glu Arg Ala Cys Gln Ser
        260                 265                 270 tat ttc gga tgt gtc cag tgc att agc gga cct ctg gga atg tac aga      864
Tyr Phe Gly Cys Val Gln Cys Ile Ser Gly Pro Leu Gly Met Tyr Arg
            275                 280                 285 aac tcc tta ctg cat gaa ttt gtg gaa gac tgg tac aat caa gaa ttt      912
Asn Ser Leu Leu His Glu Phe Val Glu Asp Trp Tyr Asn Gln Glu Phe
        290                 295                 300 atg ggc agc caa tgt agt ttt gga gat gac agg cat cta acg aac cga      960
Met Gly Ser Gln Cys Ser Phe Gly Asp Asp Arg His Leu Thr Asn Arg
305                 310                 315                 320 gtg ctg agt ctg ggc tat gca acg aaa tac aca gct cga tcc aag tgc     1008
Val Leu Ser Leu Gly Tyr Ala Thr Lys Tyr Thr Ala Arg Ser Lys Cys
                325                 330                 335 ctt act gaa aca cct ata gaa tat ctc aga tgg tta aac cag cag acc     1056
Leu Thr Glu Thr Pro Ile Glu Tyr Leu Arg Trp Leu Asn Gln Gln Thr
            340                 345                 350 cgc tgg agc aag tcg tac ttc cga gag tgg ctg tac aac gct atg tgg     1104
Arg Trp Ser Lys Ser Tyr Phe Arg Glu Trp Leu Tyr Asn Ala Met Trp
        355                 360                 365 ttt cat aaa cat cac ttg tgg atg acc tat gaa gcc gtc atc act ggg     1152
Phe His Lys His His Leu Trp Met Thr Tyr Glu Ala Val Ile Thr Gly
    370                 375                 380 ttc ttc cct ttc ttt ctc att gcc acg gta atc cag ctc ttc tac agg     1200
Phe Phe Pro Phe Phe Leu Ile Ala Thr Val Ile Gln Leu Phe Tyr Arg
385                 390                 395                 400 ggt aaa att tgg aac acc ctc ctc ttc ttg tta act gtc cag tta gtg     1248
Gly Lys Ile Trp Asn Thr Leu Leu Phe Leu Leu Thr Val Gln Leu Val
                405                 410                 415 ggt ctc ata aaa tca tct ttt gcc agc tgc ctt aga gga aac att gtc     1296
Gly Leu Ile Lys Ser Ser Phe Ala Ser Cys Leu Arg Gly Asn Ile Val
            420                 425                 430 atg gtc ttc atg tcc ctc tac tca gtg tta tac atg tca agt tta ctt     1344
Met Val Phe Met Ser Leu Tyr Ser Val Leu Tyr Met Ser Ser Leu Leu
        435                 440                 445 ccg gcc aag atg ttt gca att gca aca ata aac aaa gct ggg tgg ggc     1392
Pro Ala Lys Met Phe Ala Ile Ala Thr Ile Asn Lys Ala Gly Trp Gly
    450                 455                 460 aca tct gga agg aaa acc att gtc gtt aat ttc ata gga ctc att ccc     1440
Thr Ser Gly Arg Lys Thr Ile Val Val Asn Phe Ile Gly Leu Ile Pro
465                 470                 475                 480 gta tcg gtt tgg ttt aca ata ctc ctg ggt ggt gtg att ttc acc att     1488
Val Ser Val Trp Phe Thr Ile Leu Leu Gly Gly Val Ile Phe Thr Ile
                485                 490                 495 tat aag gaa tct aaa aag cca ttc tca gaa tcc aaa cag aca gtt tta     1536
Tyr Lys Glu Ser Lys Lys Pro Phe Ser Glu Ser Lys Gln Thr Val Leu
            500                 505                 510 att gtt gga acg ttg cta tat gca tgc tat tgg gtc atg ctt ttg aca     1584
Ile Val Gly Thr Leu Leu Tyr Ala Cys Tyr Trp Val Met Leu Leu Thr
        515                 520                 525 ctg tac gtg gtt ctc atc aat aaa tgt ggc agg cgg aag aag gga caa     1632
Leu Tyr Val Val Leu Ile Asn Lys Cys Gly Arg Arg Lys Lys Gly Gln
    530                 535                 540 cag tac gac atg gtg ctt gat gta tga                                 1659
Gln Tyr Asp Met Val Leu Asp Val
545                 550

<210> SEQ ID NO 38
<211> LENGTH: 552
```

<212> TYPE: PRT
<213> ORGANISM: Bos taurus

<400> SEQUENCE: 38

Met His Cys Glu Arg Phe Leu Cys Ile Leu Arg Ile Ile Gly Thr Thr
1               5                   10                  15

Leu Phe Gly Val Ser Leu Leu Gly Ile Thr Ala Ala Tyr Ile Val
            20                  25                  30

Gly Tyr Gln Phe Ile Gln Thr Asp Asn Tyr Tyr Phe Ser Phe Gly Leu
            35                  40                  45

Tyr Gly Ala Phe Leu Ala Ser His Leu Ile Ile Gln Ser Leu Phe Ala
        50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Gln Ser Val Lys Arg Leu Thr Tyr Pro
            100                 105                 110

Gly Ile Lys Val Val Met Val Ile Asp Gly Asn Ser Glu Asp Asp Leu
        115                 120                 125

Tyr Met Met Asp Ile Phe Ser Glu Val Met Gly Arg Asp Lys Ser Ala
130                 135                 140

Thr Tyr Ile Trp Lys Asn Asn Tyr His Val Lys Gly Pro Gly Glu Thr
145                 150                 155                 160

Asp Glu Ser His Lys Glu Ser Ser Gln His Val Thr Gln Leu Val Leu
                165                 170                 175

Ser Asn Lys Ser Ile Cys Thr Met Gln Lys Trp Gly Gly Lys Arg Glu
            180                 185                 190

Val Met Tyr Thr Ala Phe Arg Ala Leu Gly Arg Ser Val Asp Tyr Val
        195                 200                 205

Gln Val Cys Asp Ser Asp Thr Met Leu Asp Pro Ala Ser Ser Val Glu
210                 215                 220

Met Val Lys Val Leu Glu Glu Asp Pro Met Val Gly Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
            260                 265                 270

Tyr Phe Gly Cys Val Gln Cys Ile Ser Gly Pro Leu Gly Met Tyr Arg
        275                 280                 285

Asn Ser Leu Leu His Glu Phe Val Glu Asp Trp Tyr Asn Gln Glu Phe
290                 295                 300

Met Gly Ser Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
            340                 345                 350

Arg Trp Ser Lys Ser Tyr Phe Arg Glu Trp Leu Tyr Asn Ala Met Trp
        355                 360                 365

Phe His Lys His His Leu Trp Met Thr Tyr Glu Ala Val Ile Thr Gly
370                 375                 380

Phe Phe Pro Phe Phe Leu Ile Ala Thr Val Ile Gln Leu Phe Tyr Arg
385                 390                 395                 400

```
Gly Lys Ile Trp Asn Thr Leu Leu Phe Leu Leu Thr Val Gln Leu Val
                405                 410                 415

Gly Leu Ile Lys Ser Ser Phe Ala Ser Cys Leu Arg Gly Asn Ile Val
            420                 425                 430

Met Val Phe Met Ser Leu Tyr Ser Val Leu Tyr Met Ser Ser Leu Leu
        435                 440                 445

Pro Ala Lys Met Phe Ala Ile Ala Thr Ile Asn Lys Ala Gly Trp Gly
    450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                485                 490                 495

Tyr Lys Glu Ser Lys Lys Pro Phe Ser Glu Ser Lys Gln Thr Val Leu
                500                 505                 510

Ile Val Gly Thr Leu Leu Tyr Ala Cys Tyr Trp Val Met Leu Leu Thr
            515                 520                 525

Leu Tyr Val Val Leu Ile Asn Lys Cys Gly Arg Arg Lys Lys Gly Gln
    530                 535                 540

Gln Tyr Asp Met Val Leu Asp Val
545                 550
```

<210> SEQ ID NO 39
<211> LENGTH: 1659
<212> TYPE: DNA
<213> ORGANISM: Gallus gallus
<220> FEATURE:
<221> NAME/KEY: CDS
<222> LOCATION: (1)..(1659)
<300> PUBLICATION INFORMATION:
<308> DATABASE ACCESSION NUMBER: AF106940.1
<309> DATABASE ENTRY DATE: 1999-12-10
<313> RELEVANT RESIDUES IN SEQ ID NO: (563)..(2221)

<400> SEQUENCE: 39

```
atg tat tgt gag agg ttt ata tgt atc ctg aga ata ctt gga acc aca      48
Met Tyr Cys Glu Arg Phe Ile Cys Ile Leu Arg Ile Leu Gly Thr Thr
1               5                   10                  15 ctc ttt gga gtg tcc ctc ctg ctg gga atc acc gct gct tac att gtg      96
Leu Phe Gly Val Ser Leu Leu Leu Gly Ile Thr Ala Ala Tyr Ile Val
            20                  25                  30 ggc tac cag ttt atc caa aca gac aat tac tac ttc tcc ttt gga ctc     144
Gly Tyr Gln Phe Ile Gln Thr Asp Asn Tyr Tyr Phe Ser Phe Gly Leu
        35                  40                  45 tat ggt gct atc ctg gca tca cat ctc atc atc caa agc ctg ttt gcc     192
Tyr Gly Ala Ile Leu Ala Ser His Leu Ile Ile Gln Ser Leu Phe Ala
50                  55                  60 tac cta gag cac agg aaa atg aag cgg tcg cta gag act cca atc aag     240
Tyr Leu Glu His Arg Lys Met Lys Arg Ser Leu Glu Thr Pro Ile Lys
65                  70                  75                  80 ctg aac aaa act gtt gcc ctt tgt att gct gcc tat caa gag gat cct     288
Leu Asn Lys Thr Val Ala Leu Cys Ile Ala Ala Tyr Gln Glu Asp Pro
                85                  90                  95 gac tac tta aga aaa tgt tta ctt tct gtg aaa aga ttg acc tac cct     336
Asp Tyr Leu Arg Lys Cys Leu Leu Ser Val Lys Arg Leu Thr Tyr Pro
            100                 105                 110 gga att aaa gtt gtt atg gtc att gat ggg aac tca gaa gat gac gtt     384
Gly Ile Lys Val Val Met Val Ile Asp Gly Asn Ser Glu Asp Asp Val
        115                 120                 125 tac atg atg gac att ttt act gaa atc atg ggg agg gac aaa tct gcc     432
Tyr Met Met Asp Ile Phe Thr Glu Ile Met Gly Arg Asp Lys Ser Ala
130                 135                 140
```

-continued

| | | |
|---|---|---|
| act tat atc tgg agt aac aac ttc cat gac aaa ggt cca ggt gag acg<br>Thr Tyr Ile Trp Ser Asn Asn Phe His Asp Lys Gly Pro Gly Glu Thr<br>145                       150                   155               160 | 480 |
| gag gag tct cac aga gag agc atg cag cac gta tct cag ctg gtc ctg<br>Glu Glu Ser His Arg Glu Ser Met Gln His Val Ser Gln Leu Val Leu<br>                   165                   170                   175 | 528 |
| tcc aac aaa agt gtt tgc atc atg cag aaa tgg ggt gga aaa aga gaa<br>Ser Asn Lys Ser Val Cys Ile Met Gln Lys Trp Gly Gly Lys Arg Glu<br>        180                   185                   190 | 576 |
| gta atg tac aca gca ttc aaa gca ctg gga gaa gcg tgg aat tat gta<br>Val Met Tyr Thr Ala Phe Lys Ala Leu Gly Glu Ala Trp Asn Tyr Val<br>             195                   200                  205 | 624 |
| cag gtc tgt gat tca gac aca atg ctc gat cca gct tca tca gtg gaa<br>Gln Val Cys Asp Ser Asp Thr Met Leu Asp Pro Ala Ser Ser Val Glu<br>210                       215                   220 | 672 |
| atg gta aag gtc tta gaa gaa gat cca atg gtt gga gga gtt gga ggc<br>Met Val Lys Val Leu Glu Glu Asp Pro Met Val Gly Gly Val Gly Gly<br>225                       230                   235               240 | 720 |
| gat gtg cag att ttg aac aag tat gat tcc tgg atc tcc ttt ctg agc<br>Asp Val Gln Ile Leu Asn Lys Tyr Asp Ser Trp Ile Ser Phe Leu Ser<br>                   245                   250                   255 | 768 |
| agt gtg aga tac tgg atg gca ttt aac ata gaa aga gcc tgc cag tcc<br>Ser Val Arg Tyr Trp Met Ala Phe Asn Ile Glu Arg Ala Cys Gln Ser<br>        260                   265                   270 | 816 |
| tat ttt ggc tgc gta cag tgc atc agt gga cct ctg gga atg tac aga<br>Tyr Phe Gly Cys Val Gln Cys Ile Ser Gly Pro Leu Gly Met Tyr Arg<br>             275                   280                  285 | 864 |
| aac tct tta ctc cat gaa ttt gtg gaa gat tgg tac aat caa gaa ttt<br>Asn Ser Leu Leu His Glu Phe Val Glu Asp Trp Tyr Asn Gln Glu Phe<br>290                       295                   300 | 912 |
| atg ggc tcc cag tgc agc ttt gga gac gac agg cat cta act aac cga<br>Met Gly Ser Gln Cys Ser Phe Gly Asp Asp Arg His Leu Thr Asn Arg<br>305                       310                   315               320 | 960 |
| gtg cta agt ctg ggc tat gca aca aaa tac aca gct aga tcc aag tgc<br>Val Leu Ser Leu Gly Tyr Ala Thr Lys Tyr Thr Ala Arg Ser Lys Cys<br>                   325                   330                  335 | 1008 |
| ctt act gaa aca cca ata gag tat ctc agg tgg ctg aat cag cag acc<br>Leu Thr Glu Thr Pro Ile Glu Tyr Leu Arg Trp Leu Asn Gln Gln Thr<br>        340                   345                   350 | 1056 |
| cgc tgg agt aaa tcg tat ttt aga gag tgg ctt tat aat gca atg tgg<br>Arg Trp Ser Lys Ser Tyr Phe Arg Glu Trp Leu Tyr Asn Ala Met Trp<br>             355                   360                  365 | 1104 |
| ttc cac aag cac cat ttg tgg atg acc tat gaa gct gta atc act gga<br>Phe His Lys His His Leu Trp Met Thr Tyr Glu Ala Val Ile Thr Gly<br>370                       375                   380 | 1152 |
| ttc ttt cct ttc ttc ctt atc gct aca gtc att cag ctc ttc tac agg<br>Phe Phe Pro Phe Phe Leu Ile Ala Thr Val Ile Gln Leu Phe Tyr Arg<br>385                       390                   395               400 | 1200 |
| gga aaa atc tgg aac atc ctc ctt ttc ttg ttg aca gtt cag tta gtg<br>Gly Lys Ile Trp Asn Ile Leu Leu Phe Leu Leu Thr Val Gln Leu Val<br>                   405                   410                   415 | 1248 |
| ggc ctg ata aag tct tcc ttt gcc agt ttc ctt agg ggc aac att gtc<br>Gly Leu Ile Lys Ser Ser Phe Ala Ser Phe Leu Arg Gly Asn Ile Val<br>                   420                   425                  430 | 1296 |
| atg gtt ttc atg tca ctc tac tca gtg ttg tat atg tcg agt tta ctg<br>Met Val Phe Met Ser Leu Tyr Ser Val Leu Tyr Met Ser Ser Leu Leu<br>             435                   440                  445 | 1344 |
| cca gca aag atg ttt gca atc gcc acg ata aac aaa gca ggg tgg ggc<br>Pro Ala Lys Met Phe Ala Ile Ala Thr Ile Asn Lys Ala Gly Trp Gly<br>450                       455                   460 | 1392 |

| | | | | | | | | | | | | | | | | |
|---|---|---|---|---|---|---|---|---|---|---|---|---|---|---|---|---|
|aca|tca|gga|aga|aaa|acc|att|gta|gtt|aat|ttt|ata|gga|ctc|att|cca|1440|
|Thr|Ser|Gly|Arg|Lys|Thr|Ile|Val|Val|Asn|Phe|Ile|Gly|Leu|Ile|Pro| |
|465| | | |470| | | |475| | | |480| | | | |

|gtc|tcc|att|tgg|ttt|aca|atc|ctc|cta|ggt|cgc|gta|att|ttc|act|atc|1488|
|Val|Ser|Ile|Trp|Phe|Thr|Ile|Leu|Leu|Gly|Arg|Val|Ile|Phe|Thr|Ile| |
| | | | |485| | | |490| | | |495| | | | |

|tac|aag|gaa|tca|aaa|aag|cca|ttc|tct|gag|tca|aaa|aca|aca|gtt|ctc|1536|
|Tyr|Lys|Glu|Ser|Lys|Lys|Pro|Phe|Ser|Glu|Ser|Lys|Thr|Thr|Val|Leu| |
|500| | | | |505| | | | |510| | | | | | |

|gtc|att|ggt|aca|atc|ctc|tat|gca|tgt|tac|tgg|gtt|ctt|cta|ttg|act|1584|
|Val|Ile|Gly|Thr|Ile|Leu|Tyr|Ala|Cys|Tyr|Trp|Val|Leu|Leu|Leu|Thr| |
| |515| | | | |520| | | | |525| | | | | |

|ttg|tac|ttg|gtt|ctc|atc|acc|aaa|tgt|ggc|agg|cgg|aag|aaa|gag|caa|1632|
|Leu|Tyr|Leu|Val|Leu|Ile|Thr|Lys|Cys|Gly|Arg|Arg|Lys|Lys|Glu|Gln| |
|530| | | | |535| | | | |540| | | | | | |

|cac|tat|gac|atg|gtg|cta|gat|gta|tga| | | | | | | |1659|
|His|Tyr|Asp|Met|Val|Leu|Asp|Val| | | | | | | | | |
|545| | | |550| | | | | | | | | | | | |

<210> SEQ ID NO 40
<211> LENGTH: 552
<212> TYPE: PRT
<213> ORGANISM: Gallus gallus

<400> SEQUENCE: 40

Met Tyr Cys Glu Arg Phe Ile Cys Ile Leu Arg Ile Leu Gly Thr Thr
1               5                   10                  15

Leu Phe Gly Val Ser Leu Leu Leu Gly Ile Thr Ala Ala Tyr Ile Val
            20                  25                  30

Gly Tyr Gln Phe Ile Gln Thr Asp Asn Tyr Tyr Phe Ser Phe Gly Leu
        35                  40                  45

Tyr Gly Ala Ile Leu Ala Ser His Leu Ile Ile Gln Ser Leu Phe Ala
    50                  55                  60

Tyr Leu Glu His Arg Lys Met Lys Arg Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Leu Ser Val Lys Arg Leu Thr Tyr Pro
            100                 105                 110

Gly Ile Lys Val Val Met Val Ile Asp Gly Asn Ser Glu Asp Asp Val
        115                 120                 125

Tyr Met Met Asp Ile Phe Thr Glu Ile Met Gly Arg Asp Lys Ser Ala
    130                 135                 140

Thr Tyr Ile Trp Ser Asn Asn Phe His Asp Lys Gly Pro Gly Glu Thr
145                 150                 155                 160

Glu Glu Ser His Arg Glu Ser Met Gln His Val Ser Gln Leu Val Leu
                165                 170                 175

Ser Asn Lys Ser Val Cys Ile Met Gln Lys Trp Gly Lys Arg Glu
            180                 185                 190

Val Met Tyr Thr Ala Phe Lys Ala Leu Gly Glu Ala Trp Asn Tyr Val
        195                 200                 205

Gln Val Cys Asp Ser Asp Thr Met Leu Asp Pro Ala Ser Ser Val Glu
    210                 215                 220

Met Val Lys Val Leu Glu Glu Asp Pro Met Val Gly Gly Val Gly Gly
225                 230                 235                 240

Asp Val Gln Ile Leu Asn Lys Tyr Asp Ser Trp Ile Ser Phe Leu Ser
                245                 250                 255

-continued

```
Ser Val Arg Tyr Trp Met Ala Phe Asn Ile Glu Arg Ala Cys Gln Ser
        260                 265                 270
Tyr Phe Gly Cys Val Gln Cys Ile Ser Gly Pro Leu Gly Met Tyr Arg
    275                 280                 285
Asn Ser Leu Leu His Glu Phe Val Glu Asp Trp Tyr Asn Gln Glu Phe
290                 295                 300
Met Gly Ser Gln Cys Ser Phe Gly Asp Asp Arg His Leu Thr Asn Arg
305                 310                 315                 320
Val Leu Ser Leu Gly Tyr Ala Thr Lys Tyr Thr Ala Arg Ser Lys Cys
                325                 330                 335
Leu Thr Glu Thr Pro Ile Glu Tyr Leu Arg Trp Leu Asn Gln Gln Thr
            340                 345                 350
Arg Trp Ser Lys Ser Tyr Phe Arg Glu Trp Leu Tyr Asn Ala Met Trp
        355                 360                 365
Phe His Lys His His Leu Trp Met Thr Tyr Glu Ala Val Ile Thr Gly
    370                 375                 380
Phe Phe Pro Phe Phe Leu Ile Ala Thr Val Ile Gln Leu Phe Tyr Arg
385                 390                 395                 400
Gly Lys Ile Trp Asn Ile Leu Leu Phe Leu Leu Thr Val Gln Leu Val
                405                 410                 415
Gly Leu Ile Lys Ser Ser Phe Ala Ser Phe Leu Arg Gly Asn Ile Val
            420                 425                 430
Met Val Phe Met Ser Leu Tyr Ser Val Leu Tyr Met Ser Ser Leu Leu
        435                 440                 445
Pro Ala Lys Met Phe Ala Ile Ala Thr Ile Asn Lys Ala Gly Trp Gly
    450                 455                 460
Thr Ser Gly Arg Lys Thr Ile Val Val Asn Phe Ile Gly Leu Ile Pro
465                 470                 475                 480
Val Ser Ile Trp Phe Thr Ile Leu Leu Gly Arg Val Ile Phe Thr Ile
                485                 490                 495
Tyr Lys Glu Ser Lys Lys Pro Phe Ser Glu Ser Lys Thr Thr Val Leu
            500                 505                 510
Val Ile Gly Thr Ile Leu Tyr Ala Cys Tyr Trp Val Leu Leu Leu Thr
        515                 520                 525
Leu Tyr Leu Val Leu Ile Thr Lys Cys Gly Arg Arg Lys Lys Glu Gln
    530                 535                 540
His Tyr Asp Met Val Leu Asp Val
545                 550
```

<210> SEQ ID NO 41
<211> LENGTH: 1767
<212> TYPE: DNA
<213> ORGANISM: Xenopus laevis
<220> FEATURE:
<221> NAME/KEY: CDS
<222> LOCATION: (1)..(1767)
<300> PUBLICATION INFORMATION:
<308> DATABASE ACCESSION NUMBER: M22249.1
<309> DATABASE ENTRY DATE: 1989-04-22
<313> RELEVANT RESIDUES IN SEQ ID NO: (527)..(2293)

<400> SEQUENCE: 41

```
atg aag gaa aaa gct gca gaa aca atg gag att cct gaa ggg atc ccc     48
Met Lys Glu Lys Ala Ala Glu Thr Met Glu Ile Pro Glu Gly Ile Pro
1               5                   10                  15 aaa gat cta gag cca aaa cac ccc acc ctt tgg agg ata att tat tat     96
Lys Asp Leu Glu Pro Lys His Pro Thr Leu Trp Arg Ile Ile Tyr Tyr
            20                  25                  30
```

| | | |
|---|---|---|
| tct ttt ggt gtg gtg cta tta gct acc att aca gca gcc tat gtg gca<br>Ser Phe Gly Val Val Leu Leu Ala Thr Ile Thr Ala Ala Tyr Val Ala<br>35 40 45 | | 144 |
| gag ttc cag gtc ctc aaa cat gaa gcc att ctc ttc tcc ctt ggg ctt<br>Glu Phe Gln Val Leu Lys His Glu Ala Ile Leu Phe Ser Leu Gly Leu<br>50 55 60 | | 192 |
| tat ggt ctt gca atg ctt ctc cac ctg atg atg cag agc ctc ttt gcc<br>Tyr Gly Leu Ala Met Leu Leu His Leu Met Met Gln Ser Leu Phe Ala<br>65 70 75 80 | | 240 |
| ttc ctg gag ata cgc agg gta aat aag agt gag ctt cct tgc agc ttt<br>Phe Leu Glu Ile Arg Arg Val Asn Lys Ser Glu Leu Pro Cys Ser Phe<br>85 90 95 | | 288 |
| aag aag aca gtg gct ctg acc att gct ggg tat cag gag aac cct gag<br>Lys Lys Thr Val Ala Leu Thr Ile Ala Gly Tyr Gln Glu Asn Pro Glu<br>100 105 110 | | 336 |
| tac ctg ata aag tgc ttg gaa tcc tgc aag tat gtg aaa tac ccc aaa<br>Tyr Leu Ile Lys Cys Leu Glu Ser Cys Lys Tyr Val Lys Tyr Pro Lys<br>115 120 125 | | 384 |
| gat aaa ctc aag atc att ttg gtc atc gat ggg aac aca gag gat gat<br>Asp Lys Leu Lys Ile Ile Leu Val Ile Asp Gly Asn Thr Glu Asp Asp<br>130 135 140 | | 432 |
| gcc tac atg atg gag atg ttc aaa gac gtg ttc cac ggt gaa gat gta<br>Ala Tyr Met Met Glu Met Phe Lys Asp Val Phe His Gly Glu Asp Val<br>145 150 155 160 | | 480 |
| ggc acc tac gta tgg aag gga aat tac cac act gtt aaa aag cct gag<br>Gly Thr Tyr Val Trp Lys Gly Asn Tyr His Thr Val Lys Lys Pro Glu<br>165 170 175 | | 528 |
| gag acc aat aag gga tcc tgt cct gag gtt tct aag ccc ttg aat gaa<br>Glu Thr Asn Lys Gly Ser Cys Pro Glu Val Ser Lys Pro Leu Asn Glu<br>180 185 190 | | 576 |
| gat gaa ggt atc aat atg gtg gaa gaa ctt gtt aga aac aag aga tgt<br>Asp Glu Gly Ile Asn Met Val Glu Glu Leu Val Arg Asn Lys Arg Cys<br>195 200 205 | | 624 |
| gtg tgc atc atg caa cag tgg ggc gga aaa aga gag gtc atg tac aca<br>Val Cys Ile Met Gln Gln Trp Gly Gly Lys Arg Glu Val Met Tyr Thr<br>210 215 220 | | 672 |
| gca ttc cag gcc att ggg act tct gtg gac tat gta cag gtc tgt gac<br>Ala Phe Gln Ala Ile Gly Thr Ser Val Asp Tyr Val Gln Val Cys Asp<br>225 230 235 240 | | 720 |
| tcg gac acc aaa ctg gat gaa ctg gca aca gtg gaa atg gtg aag gtt<br>Ser Asp Thr Lys Leu Asp Glu Leu Ala Thr Val Glu Met Val Lys Val<br>245 250 255 | | 768 |
| ctg gaa tcc aat gac atg tac ggc gca gtg gga gga gac gtt cgc att<br>Leu Glu Ser Asn Asp Met Tyr Gly Ala Val Gly Gly Asp Val Arg Ile<br>260 265 270 | | 816 |
| ctg aac cct tat gat tcc ttc att agt ttc atg agc agc ctg cgt tac<br>Leu Asn Pro Tyr Asp Ser Phe Ile Ser Phe Met Ser Ser Leu Arg Tyr<br>275 280 285 | | 864 |
| tgg atg gcg ttt aac gtg gag agg gcc tgc cag tct tac ttc gac tgc<br>Trp Met Ala Phe Asn Val Glu Arg Ala Cys Gln Ser Tyr Phe Asp Cys<br>290 295 300 | | 912 |
| gtg tcc tgt ata agt gga cct ctg gga atg tac cgg aac aac att ctc<br>Val Ser Cys Ile Ser Gly Pro Leu Gly Met Tyr Arg Asn Asn Ile Leu<br>305 310 315 320 | | 960 |
| cag gtg ttt ttg gaa gcc tgg tac aga cag aaa ttt ttg gga acc tat<br>Gln Val Phe Leu Glu Ala Trp Tyr Arg Gln Lys Phe Leu Gly Thr Tyr<br>325 330 335 | | 1008 |
| tgt act ttg gga gat gat aga cat ctg aca aac cga gtg ctc agc atg<br>Cys Thr Leu Gly Asp Asp Arg His Leu Thr Asn Arg Val Leu Ser Met<br>340 345 350 | | 1056 |

```
gga tat cgc acc aaa tac acc cac aaa tcc aga gca ttc tcc gaa act      1104
Gly Tyr Arg Thr Lys Tyr Thr His Lys Ser Arg Ala Phe Ser Glu Thr
            355                 360                 365 cca tcc ctg tat ctc cgg tgg ttg aac cag caa acc cgg tgg acc aag      1152
Pro Ser Leu Tyr Leu Arg Trp Leu Asn Gln Gln Thr Arg Trp Thr Lys
370                 375                 380 tcc tac ttc cga gag tgg ctg tat aat gcc cag tgg tgg cac aag cat      1200
Ser Tyr Phe Arg Glu Trp Leu Tyr Asn Ala Gln Trp Trp His Lys His
385                 390                 395                 400 cac atc tgg atg acc tat gag tct gtg gtg tcc ttc atc ttt ccc ttc      1248
His Ile Trp Met Thr Tyr Glu Ser Val Val Ser Phe Ile Phe Pro Phe
                405                 410                 415 ttc atc act gcc act gtt atc cgc ctc atc tat gcc ggc acc ata tgg      1296
Phe Ile Thr Ala Thr Val Ile Arg Leu Ile Tyr Ala Gly Thr Ile Trp
            420                 425                 430 aat gtt gtg tgg ctc ctc ctg tgc atc cag atc atg tct ctc ttc aaa      1344
Asn Val Val Trp Leu Leu Leu Cys Ile Gln Ile Met Ser Leu Phe Lys
        435                 440                 445 tcc atc tat gcc tgc tgg ctc cgc ggc aac ttc att atg ctc ctg atg      1392
Ser Ile Tyr Ala Cys Trp Leu Arg Gly Asn Phe Ile Met Leu Leu Met
450                 455                 460 tct ctc tac tcc atg ctg tac atg act ggg ctt ctg cca tcc aag tac      1440
Ser Leu Tyr Ser Met Leu Tyr Met Thr Gly Leu Leu Pro Ser Lys Tyr
465                 470                 475                 480 ttt gcc ttg ttg acc tta aac aag acc ggt tgg gga aca tct ggg cgc      1488
Phe Ala Leu Leu Thr Leu Asn Lys Thr Gly Trp Gly Thr Ser Gly Arg
                485                 490                 495 aag aag ata gta ggc aac tac atg cca ata ctg ccc ctg tcc ata tgg      1536
Lys Lys Ile Val Gly Asn Tyr Met Pro Ile Leu Pro Leu Ser Ile Trp
            500                 505                 510 gca gct gtt ctg tgt gga ggg gtg ggt tat agt atc tat atg gac tgt      1584
Ala Ala Val Leu Cys Gly Gly Val Gly Tyr Ser Ile Tyr Met Asp Cys
        515                 520                 525 caa aat gac tgg agc acc cct gaa aag caa aag gag atg tac cat cta      1632
Gln Asn Asp Trp Ser Thr Pro Glu Lys Gln Lys Glu Met Tyr His Leu
530                 535                 540 ttg tat ggg tgt gtg ggc tat gta atg tac tgg gta atc atg gct gtg      1680
Leu Tyr Gly Cys Val Gly Tyr Val Met Tyr Trp Val Ile Met Ala Val
545                 550                 555                 560 atg tac tgg gtc tgg gtg aag agg tgc tgc agg aag agg tcc caa act      1728
Met Tyr Trp Val Trp Val Lys Arg Cys Cys Arg Lys Arg Ser Gln Thr
                565                 570                 575 gtc acc ctg gtc cat gac att cct gat atg tgt gtt taa                  1767
Val Thr Leu Val His Asp Ile Pro Asp Met Cys Val
            580                 585

<210> SEQ ID NO 42
<211> LENGTH: 588
<212> TYPE: PRT
<213> ORGANISM: Xenopus laevis

<400> SEQUENCE: 42

Met Lys Glu Lys Ala Ala Glu Thr Met Glu Ile Pro Glu Gly Ile Pro
1               5                   10                  15

Lys Asp Leu Glu Pro Lys His Pro Thr Leu Trp Arg Ile Ile Tyr Tyr
            20                  25                  30

Ser Phe Gly Val Val Leu Leu Ala Thr Ile Thr Ala Ala Tyr Val Ala
        35                  40                  45

Glu Phe Gln Val Leu Lys His Glu Ala Ile Leu Phe Ser Leu Gly Leu
    50                  55                  60
```

```
Tyr Gly Leu Ala Met Leu Leu His Leu Met Met Gln Ser Leu Phe Ala
 65                  70                  75                  80

Phe Leu Glu Ile Arg Arg Val Asn Lys Ser Glu Leu Pro Cys Ser Phe
             85                  90                  95

Lys Lys Thr Val Ala Leu Thr Ile Ala Gly Tyr Gln Glu Asn Pro Glu
            100                 105                 110

Tyr Leu Ile Lys Cys Leu Glu Ser Cys Lys Tyr Val Lys Tyr Pro Lys
            115                 120                 125

Asp Lys Leu Lys Ile Ile Leu Val Ile Asp Gly Asn Thr Glu Asp Asp
            130                 135                 140

Ala Tyr Met Met Glu Met Phe Lys Asp Val Phe His Gly Glu Asp Val
145                 150                 155                 160

Gly Thr Tyr Val Trp Lys Gly Asn Tyr His Thr Val Lys Lys Pro Glu
                165                 170                 175

Glu Thr Asn Lys Gly Ser Cys Pro Glu Val Ser Lys Pro Leu Asn Glu
            180                 185                 190

Asp Glu Gly Ile Asn Met Val Glu Glu Leu Val Arg Asn Lys Arg Cys
            195                 200                 205

Val Cys Ile Met Gln Gln Trp Gly Gly Lys Arg Glu Val Met Tyr Thr
            210                 215                 220

Ala Phe Gln Ala Ile Gly Thr Ser Val Asp Tyr Val Gln Val Cys Asp
225                 230                 235                 240

Ser Asp Thr Lys Leu Asp Glu Leu Ala Thr Val Glu Met Val Lys Val
                245                 250                 255

Leu Glu Ser Asn Asp Met Tyr Gly Ala Val Gly Gly Asp Val Arg Ile
                260                 265                 270

Leu Asn Pro Tyr Asp Ser Phe Ile Ser Phe Met Ser Ser Leu Arg Tyr
                275                 280                 285

Trp Met Ala Phe Asn Val Glu Arg Ala Cys Gln Ser Tyr Phe Asp Cys
290                 295                 300

Val Ser Cys Ile Ser Gly Pro Leu Gly Met Tyr Arg Asn Asn Ile Leu
305                 310                 315                 320

Gln Val Phe Leu Glu Ala Trp Tyr Arg Gln Lys Phe Leu Gly Thr Tyr
                325                 330                 335

Cys Thr Leu Gly Asp Asp Arg His Leu Thr Asn Arg Val Leu Ser Met
            340                 345                 350

Gly Tyr Arg Thr Lys Tyr Thr His Lys Ser Arg Ala Phe Ser Glu Thr
            355                 360                 365

Pro Ser Leu Tyr Leu Arg Trp Leu Asn Gln Gln Thr Arg Trp Thr Lys
370                 375                 380

Ser Tyr Phe Arg Glu Trp Leu Tyr Asn Ala Gln Trp Trp His Lys His
385                 390                 395                 400

His Ile Trp Met Thr Tyr Glu Ser Val Val Ser Phe Ile Phe Pro Phe
                405                 410                 415

Phe Ile Thr Ala Thr Val Ile Arg Leu Ile Tyr Ala Gly Thr Ile Trp
                420                 425                 430

Asn Val Val Trp Leu Leu Cys Ile Gln Ile Met Ser Leu Phe Lys
                435                 440                 445

Ser Ile Tyr Ala Cys Trp Leu Arg Gly Asn Phe Ile Met Leu Leu Met
            450                 455                 460

Ser Leu Tyr Ser Met Leu Tyr Met Thr Gly Leu Leu Pro Ser Lys Tyr
465                 470                 475                 480

Phe Ala Leu Leu Thr Leu Asn Lys Thr Gly Trp Gly Thr Ser Gly Arg
```

```
                      485                 490                 495
Lys Lys Ile Val Gly Asn Tyr Met Pro Ile Leu Pro Leu Ser Ile Trp
                500                 505                 510

Ala Ala Val Leu Cys Gly Gly Val Gly Tyr Ser Ile Tyr Met Asp Cys
            515                 520                 525

Gln Asn Asp Trp Ser Thr Pro Glu Lys Gln Lys Glu Met Tyr His Leu
        530                 535                 540

Leu Tyr Gly Cys Val Gly Tyr Val Met Tyr Trp Val Ile Met Ala Val
545                 550                 555                 560

Met Tyr Trp Val Trp Val Lys Arg Cys Cys Arg Lys Arg Ser Gln Thr
                565                 570                 575

Val Thr Leu Val His Asp Ile Pro Asp Met Cys Val
                580                 585

<210> SEQ ID NO 43
<211> LENGTH: 1656
<212> TYPE: DNA
<213> ORGANISM: Xenopus laevis
<220> FEATURE:
<221> NAME/KEY: CDS
<222> LOCATION: (1)..(1656)

<400> SEQUENCE: 43
```

| | | |
|---|---|---|
| atg cac tgt gaa cgg ttt ata tgc atc ctg aga ata att ggg aca act<br>Met His Cys Glu Arg Phe Ile Cys Ile Leu Arg Ile Ile Gly Thr Thr<br>1               5                   10                  15 | | 48 |
| ctc ttc gga gtc tcc ttg tta ctt gga atc tca gct gct tat atc gtt<br>Leu Phe Gly Val Ser Leu Leu Leu Gly Ile Ser Ala Ala Tyr Ile Val<br>            20                  25                  30 | | 96 |
| ggt tac caa ttt atc caa aca gac aac tat tat ttc tca ttt gga ctc<br>Gly Tyr Gln Phe Ile Gln Thr Asp Asn Tyr Tyr Phe Ser Phe Gly Leu<br>        35                  40                  45 | | 144 |
| tat ggg gcg att tta gcc ctc cac ctt att atc caa agc ctt ttt gcc<br>Tyr Gly Ala Ile Leu Ala Leu His Leu Ile Ile Gln Ser Leu Phe Ala<br>    50                  55                  60 | | 192 |
| ttt ctg gaa cac cga aaa atg aaa cga tct cta gaa acc ccc att aaa<br>Phe Leu Glu His Arg Lys Met Lys Arg Ser Leu Glu Thr Pro Ile Lys<br>65                  70                  75                  80 | | 240 |
| ctg aat aaa tca gtt gcc cta tgt att gct gca tat caa gag gac gaa<br>Leu Asn Lys Ser Val Ala Leu Cys Ile Ala Ala Tyr Gln Glu Asp Glu<br>                85                  90                  95 | | 288 |
| gac tac tta cgg aaa tgt tta ctt tcg gtc aag cgc ttg acg tac cca<br>Asp Tyr Leu Arg Lys Cys Leu Leu Ser Val Lys Arg Leu Thr Tyr Pro<br>            100                 105                 110 | | 336 |
| gga atg aaa gtc atc atg gtg atc gat gga aac tcg gac gat gat ctc<br>Gly Met Lys Val Ile Met Val Ile Asp Gly Asn Ser Asp Asp Asp Leu<br>        115                 120                 125 | | 384 |
| tac atg atg aat atc ttt cgt gag att atg ggg aat gac agc tgc gcc<br>Tyr Met Met Asn Ile Phe Arg Glu Ile Met Gly Asn Asp Ser Cys Ala<br>    130                 135                 140 | | 432 |
| act tac gta tgg aaa aat aac ttc cac atg aaa ggc ccc aac gag acg<br>Thr Tyr Val Trp Lys Asn Asn Phe His Met Lys Gly Pro Asn Glu Thr<br>145                 150                 155                 160 | | 480 |
| gac gaa acg cac aga gag agc atg cag cac gta acg cag atg gtt ctc<br>Asp Glu Thr His Arg Glu Ser Met Gln His Val Thr Gln Met Val Leu<br>                165                 170                 175 | | 528 |
| tcc aat aga aac gtg tgc atc atg cag aaa tgg aat ggg aag aga gaa<br>Ser Asn Arg Asn Val Cys Ile Met Gln Lys Trp Asn Gly Lys Arg Glu<br>            180                 185                 190 | | 576 |
| gtc atg tac acc gcg ttc aag gca ctg ggg aga agt gtg gat tat gtg<br>                                                                                                                     | | 624 |

|  |  |  |  |  |  |  |  |  |  |  |  |  |  |
|---|---|---|---|---|---|---|---|---|---|---|---|---|---|
| Val | Met | Tyr | Thr | Ala | Phe | Lys | Ala | Leu | Gly | Arg | Ser | Val | Asp | Tyr | Val |
|  | 195 |  |  | 200 |  |  |  | 205 |  |  |

```
cag gta tgt gat tct gac aca gtg ctt gat ccg gcg tca tca gtg gag      672
Gln Val Cys Asp Ser Asp Thr Val Leu Asp Pro Ala Ser Ser Val Glu
210             215             220 atg gtc aaa gta ctg gag gaa gac atc atg gtt gga gga gtg ggt gga      720
Met Val Lys Val Leu Glu Glu Asp Ile Met Val Gly Gly Val Gly Gly
225             230             235             240 gat gtr cag att tta aac aag tac gac tca tgg att tcc ttc ctg agt      768
Asp Xaa Gln Ile Leu Asn Lys Tyr Asp Ser Trp Ile Ser Phe Leu Ser
                245             250             255 agc gtc aga tac tgg atg gcg ttt aac aty gag aga gca tgc cag tct      816
Ser Val Arg Tyr Trp Met Ala Phe Asn Xaa Glu Arg Ala Cys Gln Ser
        260             265             270 tac ttt ggc tgt gtg caa tgc att agc ggc ccg ttg ggg atg tac cgc      864
Tyr Phe Gly Cys Val Gln Cys Ile Ser Gly Pro Leu Gly Met Tyr Arg
            275             280             285 aat tcc ctt ctc cac gaa ttc att gaa gac tgg tac aac caa gaa ttt      912
Asn Ser Leu Leu His Glu Phe Ile Glu Asp Trp Tyr Asn Gln Glu Phe
    290             295             300 ttg ggt tcc cag tgc agt ttt ggg gat gac cgt cac cta acc aat cga      960
Leu Gly Ser Gln Cys Ser Phe Gly Asp Asp Arg His Leu Thr Asn Arg
305             310             315             320 gtt ttg agt ctg ggc tat gca acc aaa tac acg gcc aga tcc aaa tgc     1008
Val Leu Ser Leu Gly Tyr Ala Thr Lys Tyr Thr Ala Arg Ser Lys Cys
                325             330             335 ctt act gaa aca ccc acc gag tac ctg cgg tgg ctc aac cag caa acg     1056
Leu Thr Glu Thr Pro Thr Glu Tyr Leu Arg Trp Leu Asn Gln Gln Thr
            340             345             350 cga tgg agc aag tcc tac ttc cga gaa tgg ctg tac aat tca ttg tgg     1104
Arg Trp Ser Lys Ser Tyr Phe Arg Glu Trp Leu Tyr Asn Ser Leu Trp
        355             360             365 ttc cat aaa cat cac tta tgg atg acc tac gaa gct gtg att act gga     1152
Phe His Lys His His Leu Trp Met Thr Tyr Glu Ala Val Ile Thr Gly
    370             375             380 ttc ttt cct ttc ttc ctc atc gcc act gtc atc cag ctc ttc tac cgt     1200
Phe Phe Pro Phe Phe Leu Ile Ala Thr Val Ile Gln Leu Phe Tyr Arg
385             390             395             400 gga agg atc tgg aac atc ctc ctg ttc ttg ctg aca gta caa ctt gta     1248
Gly Arg Ile Trp Asn Ile Leu Leu Phe Leu Leu Thr Val Gln Leu Val
                405             410             415 ggc ctt atc aaa tct tcc ttt gct agt gcc ctc cga ggg aac ata gtc     1296
Gly Leu Ile Lys Ser Ser Phe Ala Ser Ala Leu Arg Gly Asn Ile Val
            420             425             430 atg gtc ttc atg tcc ttc tac tca gtg tta tac atg tcc agt tta cta     1344
Met Val Phe Met Ser Phe Tyr Ser Val Leu Tyr Met Ser Ser Leu Leu
        435             440             445 cct gcc aaa atg ttt gcc att gcc acc atc aac aag gca ggt tgg ggc     1392
Pro Ala Lys Met Phe Ala Ile Ala Thr Ile Asn Lys Ala Gly Trp Gly
    450             455             460 aca tca gga agg aag aca ata gtt gtg aat ttt ata gga ctg att cct     1440
Thr Ser Gly Arg Lys Thr Ile Val Val Asn Phe Ile Gly Leu Ile Pro
465             470             475             480 ata acc gtt tgg ttt aca att ctc ctt ggg ggc gtc tgc tac act att     1488
Ile Thr Val Trp Phe Thr Ile Leu Leu Gly Gly Val Cys Tyr Thr Ile
                485             490             495 tgg agg gaa aca aaa aag cca ttt tca gaa tct gaa aag ata gtt ctc     1536
Trp Arg Glu Thr Lys Lys Pro Phe Ser Glu Ser Glu Lys Ile Val Leu
            500             505             510 gcc gtt ggt gca ata ctt tac gca tgc tac tgg gtc atg ctt ttg act     1584
```

```
Ala Val Gly Ala Ile Leu Tyr Ala Cys Tyr Trp Val Met Leu Leu Thr
        515                 520                 525 atg tat gtt tct ctc gtc atg aar tgt ggc agg cgg aga aag gaa cca        1632
Met Tyr Val Ser Leu Val Met Lys Cys Gly Arg Arg Arg Lys Glu Pro
        530                 535                 540 caa cat gac ttg gtg ctt gct tga                                        1656
Gln His Asp Leu Val Leu Ala
545                 550

<210> SEQ ID NO 44
<211> LENGTH: 551
<212> TYPE: PRT
<213> ORGANISM: Xenopus laevis
<220> FEATURE:
<221> NAME/KEY: misc_feature
<222> LOCATION: (242)..(242)
<223> OTHER INFORMATION: The 'Xaa' at location 242 stands for Val.
<220> FEATURE:
<221> NAME/KEY: misc_feature
<222> LOCATION: (266)..(266)
<223> OTHER INFORMATION: The 'Xaa' at location 266 stands for Ile.

<400> SEQUENCE: 44

Met His Cys Glu Arg Phe Ile Cys Ile Leu Arg Ile Ile Gly Thr Thr
1               5                   10                  15

Leu Phe Gly Val Ser Leu Leu Leu Gly Ile Ser Ala Ala Tyr Ile Val
            20                  25                  30

Gly Tyr Gln Phe Ile Gln Thr Asp Asn Tyr Tyr Phe Ser Phe Gly Leu
        35                  40                  45

Tyr Gly Ala Ile Leu Ala Leu His Leu Ile Ile Gln Ser Leu Phe Ala
50                  55                  60

Phe Leu Glu His Arg Lys Met Lys Arg Ser Leu Glu Thr Pro Ile Lys
65                  70                  75                  80

Leu Asn Lys Ser Val Ala Leu Cys Ile Ala Ala Tyr Gln Glu Asp Glu
                85                  90                  95

Asp Tyr Leu Arg Lys Cys Leu Leu Ser Val Lys Arg Leu Thr Tyr Pro
            100                 105                 110

Gly Met Lys Val Ile Met Val Ile Asp Gly Asn Ser Asp Asp Asp Leu
        115                 120                 125

Tyr Met Met Asn Ile Phe Arg Glu Ile Met Gly Asn Asp Ser Cys Ala
130                 135                 140

Thr Tyr Val Trp Lys Asn Asn Phe His Met Lys Gly Pro Asn Glu Thr
145                 150                 155                 160

Asp Glu Thr His Arg Glu Ser Met Gln His Val Thr Gln Met Val Leu
                165                 170                 175

Ser Asn Arg Asn Val Cys Ile Met Gln Lys Trp Asn Gly Lys Arg Glu
            180                 185                 190

Val Met Tyr Thr Ala Phe Lys Ala Leu Gly Arg Ser Val Asp Tyr Val
        195                 200                 205

Gln Val Cys Asp Ser Asp Thr Val Leu Asp Pro Ala Ser Ser Val Glu
210                 215                 220

Met Val Lys Val Leu Glu Glu Asp Ile Met Val Gly Val Gly Gly Gly
225                 230                 235                 240

Asp Xaa Gln Ile Leu Asn Lys Tyr Asp Ser Trp Ile Ser Phe Leu Ser
                245                 250                 255

Ser Val Arg Tyr Trp Met Ala Phe Asn Xaa Glu Arg Ala Cys Gln Ser
            260                 265                 270

Tyr Phe Gly Cys Val Gln Cys Ile Ser Gly Pro Leu Gly Met Tyr Arg
        275                 280                 285
```

```
Asn Ser Leu Leu His Glu Phe Ile Glu Asp Trp Tyr Asn Gln Glu Phe
    290                 295                 300
Leu Gly Ser Gln Cys Ser Phe Gly Asp Asp Arg His Leu Thr Asn Arg
305                 310                 315                 320
Val Leu Ser Leu Gly Tyr Ala Thr Lys Tyr Thr Ala Arg Ser Lys Cys
                325                 330                 335
Leu Thr Glu Thr Pro Thr Glu Tyr Leu Arg Trp Leu Asn Gln Gln Thr
            340                 345                 350
Arg Trp Ser Lys Ser Tyr Phe Arg Glu Trp Leu Tyr Asn Ser Leu Trp
        355                 360                 365
Phe His Lys His His Leu Trp Met Thr Tyr Glu Ala Val Ile Thr Gly
370                 375                 380
Phe Phe Pro Phe Phe Leu Ile Ala Thr Val Ile Gln Leu Phe Tyr Arg
385                 390                 395                 400
Gly Arg Ile Trp Asn Ile Leu Leu Phe Leu Leu Thr Val Gln Leu Val
                405                 410                 415
Gly Leu Ile Lys Ser Ser Phe Ala Ser Ala Leu Arg Gly Asn Ile Val
            420                 425                 430
Met Val Phe Met Ser Phe Tyr Ser Val Leu Tyr Met Ser Ser Leu Leu
        435                 440                 445
Pro Ala Lys Met Phe Ala Ile Ala Thr Ile Asn Lys Ala Gly Trp Gly
450                 455                 460
Thr Ser Gly Arg Lys Thr Ile Val Val Asn Phe Ile Gly Leu Ile Pro
465                 470                 475                 480
Ile Thr Val Trp Phe Thr Ile Leu Leu Gly Gly Val Cys Tyr Thr Ile
                485                 490                 495
Trp Arg Glu Thr Lys Lys Pro Phe Ser Glu Ser Glu Lys Ile Val Leu
            500                 505                 510
Ala Val Gly Ala Ile Leu Tyr Ala Cys Tyr Trp Val Met Leu Leu Thr
        515                 520                 525
Met Tyr Val Ser Leu Val Met Lys Cys Gly Arg Arg Lys Glu Pro
530                 535                 540
Gln His Asp Leu Val Leu Ala
545                 550
```

<210> SEQ ID NO 45
<211> LENGTH: 1674
<212> TYPE: DNA
<213> ORGANISM: Xenopus laevis
<220> FEATURE:
<221> NAME/KEY: CDS
<222> LOCATION: (1)..(1674)
<300> PUBLICATION INFORMATION:
<308> DATABASE ACCESSION NUMBER: AY302252.1
<309> DATABASE ENTRY DATE: 2003-11-30
<313> RELEVANT RESIDUES IN SEQ ID NO: (102)..(1775)

<400> SEQUENCE: 45

```
atg cct ggg aag ttt cag acc ggc ctt agg gtg cta gcc act tgc ctc    48
Met Pro Gly Lys Phe Gln Thr Gly Leu Arg Val Leu Ala Thr Cys Leu
1               5                   10                  15 ttt gct ctg ctg gtg ttg ggg gcc atc ttg gtt gca tat gtg aca ggg    96
Phe Ala Leu Leu Val Leu Gly Gly Ile Leu Val Ala Tyr Val Thr Gly
            20                  25                  30 tac caa ttt att cat acc gat cgc cac cat ctc tca ttt ggc cta tac    144
Tyr Gln Phe Ile His Thr Asp Arg His His Leu Ser Phe Gly Leu Tyr
        35                  40                  45 gga gcc atc ctg ggt ctc cat tta ctc tct cag agc ctc ttt gct ttt    192
```

-continued

```
              Gly Ala Ile Leu Gly Leu His Leu Leu Ser Gln Ser Leu Phe Ala Phe
                  50                  55                  60 ttg gag cac agg aag atg cga gga ggt ggg cgg tgt cct tca gga aag      240
Leu Glu His Arg Lys Met Arg Gly Gly Gly Arg Cys Pro Ser Gly Lys
 65                  70                  75                  80 tcc aca gtg gtg ctt tgt att gca gca tat caa gag gac cca gag tac      288
Ser Thr Val Val Leu Cys Ile Ala Ala Tyr Gln Glu Asp Pro Glu Tyr
                 85                  90                  95 tta cgg aaa tgt ctg cga tca gtg cgc cgc ctc tca tat cct cac ctt      336
Leu Arg Lys Cys Leu Arg Ser Val Arg Arg Leu Ser Tyr Pro His Leu
            100                 105                 110 cgt gtg atc atg gtg gtg gat ggg aat aca gaa gag gac aga tat atg      384
Arg Val Ile Met Val Val Asp Gly Asn Thr Glu Glu Asp Arg Tyr Met
        115                 120                 125 atg gac ata ttc cga gag gtc atg gga tca gag gga acc tgc tgc tac      432
Met Asp Ile Phe Arg Glu Val Met Gly Ser Glu Gly Thr Cys Cys Tyr
    130                 135                 140 att tgg gac aaa aat tac cat gaa tca gag gag gga gga caa gag ggt      480
Ile Trp Asp Lys Asn Tyr His Glu Ser Glu Glu Gly Gly Gln Glu Gly
145                 150                 155                 160 gag agg gga gta cag gag atg gtg aag aac ttc cag tat gtc tgc atc      528
Glu Arg Gly Val Gln Glu Met Val Lys Asn Phe Gln Tyr Val Cys Ile
                165                 170                 175 atg cag aag tgg ggt gga aaa agg gaa gtc acg tat act gcg ttt cgt      576
Met Gln Lys Trp Gly Gly Lys Arg Glu Val Thr Tyr Thr Ala Phe Arg
            180                 185                 190 gca ctt gga gac agt gtg gct tat gtg cag gtc tgt gac tct gac act      624
Ala Leu Gly Asp Ser Val Ala Tyr Val Gln Val Cys Asp Ser Asp Thr
        195                 200                 205 gtg tta gac cca gct tgc acc gct gag atg ctg cgc att ttg gaa gaa      672
Val Leu Asp Pro Ala Cys Thr Ala Glu Met Leu Arg Ile Leu Glu Glu
    210                 215                 220 gat cct gaa gtg ggg gga gta ggt gga gat gtg cag atc ctg aat aag      720
Asp Pro Glu Val Gly Gly Val Gly Gly Asp Val Gln Ile Leu Asn Lys
225                 230                 235                 240 tac gaa tcg tgg atc tca ttt ctg agc agt ttc cgc tac tgg atg gca      768
Tyr Glu Ser Trp Ile Ser Phe Leu Ser Ser Phe Arg Tyr Trp Met Ala
                245                 250                 255 ttc aat gtg gaa cgg gcc tgc cag tcc tac ttt ggc tgt gtc cag tgc      816
Phe Asn Val Glu Arg Ala Cys Gln Ser Tyr Phe Gly Cys Val Gln Cys
            260                 265                 270 atc agt ggc cca ctg gga atg tat agg aac agt ctt ttg cag tac ttt      864
Ile Ser Gly Pro Leu Gly Met Tyr Arg Asn Ser Leu Leu Gln Tyr Phe
        275                 280                 285 tta gaa gat tgg tac cat caa aca ttt ttg ggg cag aag tgt agc ttt      912
Leu Glu Asp Trp Tyr His Gln Thr Phe Leu Gly Gln Lys Cys Ser Phe
    290                 295                 300 gga gat gac aga cat ctc acg aac cgt gta cta agc atg gga ttc cga      960
Gly Asp Asp Arg His Leu Thr Asn Arg Val Leu Ser Met Gly Phe Arg
305                 310                 315                 320 acg aag tat aca gct cgc tct cgt tgc ctg aca gag aca cca acg cgg     1008
Thr Lys Tyr Thr Ala Arg Ser Arg Cys Leu Thr Glu Thr Pro Thr Arg
                325                 330                 335 tat ttg cgc tgg ttg aac caa caa acg cgc tgg agc aaa tca tac ttc     1056
Tyr Leu Arg Trp Leu Asn Gln Gln Thr Arg Trp Ser Lys Ser Tyr Phe
            340                 345                 350 cgt gag tgg cta tac aat gca ctg tgg ttc cac aaa cac cac ctt tgg     1104
Arg Glu Trp Leu Tyr Asn Ala Leu Trp Phe His Lys His His Leu Trp
        355                 360                 365 atg acc tat gaa tct gtg gtt act ggc ttc ttt ccc ttc ttc ttg gtg     1152
```

```
gcc aca gtg gtt caa cta ttt tat cgt ggc cgt gtt tgg aat att ctt      1200
Ala Thr Val Val Gln Leu Phe Tyr Arg Gly Arg Val Trp Asn Ile Leu
385                 390                 395                 400 ctt ttt cta ttg acc gta cag ctt gtt ggt att ttg aag gca acc tat      1248
Leu Phe Leu Leu Thr Val Gln Leu Val Gly Ile Leu Lys Ala Thr Tyr
                405                 410                 415 gcc tgt atc ctt cga ggt aat gct gaa atg att ttc atg tca ctt tat      1296
Ala Cys Ile Leu Arg Gly Asn Ala Glu Met Ile Phe Met Ser Leu Tyr
            420                 425                 430 tca ctt ctc tac atg act agc ctt ctg cct gcc aaa ata ttc gca gtg      1344
Ser Leu Leu Tyr Met Thr Ser Leu Leu Pro Ala Lys Ile Phe Ala Val
        435                 440                 445 atc acc atc aaa aag tct ggc tgg ggg act tca ggg cgc agg aag ctg      1392
Ile Thr Ile Lys Lys Ser Gly Trp Gly Thr Ser Gly Arg Arg Lys Leu
    450                 455                 460 gtg gtg aat ttt atg ggt atg gtg ccc gtg tct gtc tgg ttt tgc att      1440
Val Val Asn Phe Met Gly Met Val Pro Val Ser Val Trp Phe Cys Ile
465                 470                 475                 480 ctg ctg gga gga tta gta tac aca gca tat tgt cag agt cat gat ccg      1488
Leu Leu Gly Gly Leu Val Tyr Thr Ala Tyr Cys Gln Ser His Asp Pro
                485                 490                 495 ttc acc gaa aca gaa ctg tta ttc ctg ttg aca ggt gcc atc tta tac      1536
Phe Thr Glu Thr Glu Leu Leu Phe Leu Leu Thr Gly Ala Ile Leu Tyr
            500                 505                 510 gga tgt tat tgg gtg gca ctt ctc agt tta tat ctt gct ttg att gcc      1584
Gly Cys Tyr Trp Val Ala Leu Leu Ser Leu Tyr Leu Ala Leu Ile Ala
        515                 520                 525 cgg cgg tgt ggg aag aga caa gag ctg tac aac tta gca ttg gag gaa      1632
Arg Arg Cys Gly Lys Arg Gln Glu Leu Tyr Asn Leu Ala Leu Glu Glu
    530                 535                 540 gtc tca gaa cca gag cca gct gcc aaa gca ata aag cct taa              1674
Val Ser Glu Pro Glu Pro Ala Ala Lys Ala Ile Lys Pro
545                 550                 555

<210> SEQ ID NO 46
<211> LENGTH: 557
<212> TYPE: PRT
<213> ORGANISM: Xenopus laevis

<400> SEQUENCE: 46

Met Pro Gly Lys Phe Gln Thr Gly Leu Arg Val Leu Ala Thr Cys Leu
1               5                   10                  15

Phe Ala Leu Leu Val Leu Gly Gly Ile Leu Val Ala Tyr Val Thr Gly
            20                  25                  30

Tyr Gln Phe Ile His Thr Asp Arg His His Leu Ser Phe Gly Leu Tyr
        35                  40                  45

Gly Ala Ile Leu Gly Leu His Leu Leu Ser Gln Ser Leu Phe Ala Phe
    50                  55                  60

Leu Glu His Arg Lys Met Arg Gly Gly Arg Cys Pro Ser Gly Lys
65                  70                  75                  80

Ser Thr Val Val Leu Cys Ile Ala Ala Tyr Gln Glu Asp Pro Glu Tyr
            85                  90                  95

Leu Arg Lys Cys Leu Arg Ser Val Arg Arg Leu Ser Tyr Pro His Leu
        100                 105                 110

Arg Val Ile Met Val Val Asp Gly Asn Thr Glu Glu Asp Arg Tyr Met
    115                 120                 125

Met Asp Ile Phe Arg Glu Val Met Gly Ser Glu Gly Thr Cys Cys Tyr
```

```
            130                 135                 140
Ile Trp Asp Lys Asn Tyr His Glu Ser Glu Glu Gly Gln Glu Gly
145                 150                 155                 160

Glu Arg Gly Val Gln Glu Met Val Lys Asn Phe Gln Tyr Val Cys Ile
                165                 170                 175

Met Gln Lys Trp Gly Gly Lys Arg Glu Val Thr Tyr Thr Ala Phe Arg
                180                 185                 190

Ala Leu Gly Asp Ser Val Ala Tyr Val Gln Val Cys Asp Ser Asp Thr
                195                 200                 205

Val Leu Asp Pro Ala Cys Thr Ala Glu Met Leu Arg Ile Leu Glu Glu
210                 215                 220

Asp Pro Glu Val Gly Val Gly Gly Asp Val Gln Ile Leu Asn Lys
225                 230                 235                 240

Tyr Glu Ser Trp Ile Ser Phe Leu Ser Ser Phe Arg Tyr Trp Met Ala
                245                 250                 255

Phe Asn Val Glu Arg Ala Cys Gln Ser Tyr Phe Gly Cys Val Gln Cys
                260                 265                 270

Ile Ser Gly Pro Leu Gly Met Tyr Arg Asn Ser Leu Leu Gln Tyr Phe
                275                 280                 285

Leu Glu Asp Trp Tyr His Gln Thr Phe Leu Gly Gln Lys Cys Ser Phe
                290                 295                 300

Gly Asp Asp Arg His Leu Thr Asn Arg Val Leu Ser Met Gly Phe Arg
305                 310                 315                 320

Thr Lys Tyr Thr Ala Arg Ser Arg Cys Leu Thr Glu Thr Pro Thr Arg
                325                 330                 335

Tyr Leu Arg Trp Leu Asn Gln Gln Thr Arg Trp Ser Lys Ser Tyr Phe
                340                 345                 350

Arg Glu Trp Leu Tyr Asn Ala Leu Trp Phe His Lys His His Leu Trp
                355                 360                 365

Met Thr Tyr Glu Ser Val Val Thr Gly Phe Phe Pro Phe Phe Leu Val
                370                 375                 380

Ala Thr Val Val Gln Leu Phe Tyr Arg Gly Arg Val Trp Asn Ile Leu
385                 390                 395                 400

Leu Phe Leu Leu Thr Val Gln Leu Val Gly Ile Leu Lys Ala Thr Tyr
                405                 410                 415

Ala Cys Ile Leu Arg Gly Asn Ala Glu Met Ile Phe Met Ser Leu Tyr
                420                 425                 430

Ser Leu Leu Tyr Met Thr Ser Leu Leu Pro Ala Lys Ile Phe Ala Val
                435                 440                 445

Ile Thr Ile Lys Lys Ser Gly Trp Gly Thr Ser Gly Arg Arg Lys Leu
450                 455                 460

Val Val Asn Phe Met Gly Met Val Pro Val Ser Val Trp Phe Cys Ile
465                 470                 475                 480

Leu Leu Gly Gly Leu Val Tyr Thr Ala Tyr Cys Gln Ser His Asp Pro
                485                 490                 495

Phe Thr Glu Thr Glu Leu Leu Phe Leu Leu Thr Gly Ala Ile Leu Tyr
                500                 505                 510

Gly Cys Tyr Trp Val Ala Leu Leu Ser Leu Tyr Leu Ala Leu Ile Ala
                515                 520                 525

Arg Arg Cys Gly Lys Arg Gln Glu Leu Tyr Asn Leu Ala Leu Glu Glu
                530                 535                 540

Val Ser Glu Pro Glu Pro Ala Ala Lys Ala Ile Lys Pro
545                 550                 555
```

<210> SEQ ID NO 47
<211> LENGTH: 1659
<212> TYPE: DNA
<213> ORGANISM: Danio rerio
<220> FEATURE:
<221> NAME/KEY: CDS
<222> LOCATION: (1)..(1659)
<300> PUBLICATION INFORMATION:
<308> DATABASE ACCESSION NUMBER: AF190742.1
<309> DATABASE ENTRY DATE: 2000-10-02
<313> RELEVANT RESIDUES IN SEQ ID NO: (34)..(1692)

<400> SEQUENCE: 47

| | | | | | | | | | | | | | | | | |
|---|---|---|---|---|---|---|---|---|---|---|---|---|---|---|---|---|
| atg | aga | tgt | gat | aaa | gcg | gtc | agc | tac | tta | agg | att | gtt | ggg | acg | aca | 48 |
| Met | Arg | Cys | Asp | Lys | Ala | Val | Ser | Tyr | Leu | Arg | Ile | Val | Gly | Thr | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctg | ttc | ggc | att | tca | ctg | ctt | gtg | gga | atc | tct | act | gct | tat | atc | atg | 96 |
| Leu | Phe | Gly | Ile | Ser | Leu | Leu | Val | Gly | Ile | Ser | Thr | Ala | Tyr | Ile | Met | |
| | | | 20 | | | | | 25 | | | | | 30 | | | |

| | | | | | | | | | | | | | | | | |
|---|---|---|---|---|---|---|---|---|---|---|---|---|---|---|---|---|
| ggg | tat | aag | ctt | gta | aca | act | ccg | ggc | aac | tat | ttg | tcc | ttt | ggt | ctt | 144 |
| Gly | Tyr | Lys | Leu | Val | Thr | Thr | Pro | Gly | Asn | Tyr | Leu | Ser | Phe | Gly | Leu | |
| | 35 | | | | | 40 | | | | | 45 | | | | | |

| | | | | | | | | | | | | | | | | |
|---|---|---|---|---|---|---|---|---|---|---|---|---|---|---|---|---|
| tat | gga | gca | att | ctt | gtc | atc | cac | ctc | atc | atc | caa | agt | gtg | ttt | gcc | 192 |
| Tyr | Gly | Ala | Ile | Leu | Val | Ile | His | Leu | Ile | Ile | Gln | Ser | Val | Phe | Ala | |
| 50 | | | | | 55 | | | | | 60 | | | | | | |

| | | | | | | | | | | | | | | | | |
|---|---|---|---|---|---|---|---|---|---|---|---|---|---|---|---|---|
| cta | ctg | gaa | cac | agg | aac | atg | aaa | cgc | tcc | ctg | gaa | aca | cca | atc | aaa | 240 |
| Leu | Leu | Glu | His | Arg | Asn | Met | Lys | Arg | Ser | Leu | Glu | Thr | Pro | Ile | Lys | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ctc | aac | aag | tca | ctg | gcc | cta | tgc | atc | gca | gcc | tat | cag | gaa | gac | ccc | 288 |
| Leu | Asn | Lys | Ser | Leu | Ala | Leu | Cys | Ile | Ala | Ala | Tyr | Gln | Glu | Asp | Pro | |
| | | | 85 | | | | | 90 | | | | | 95 | | | |

| | | | | | | | | | | | | | | | | |
|---|---|---|---|---|---|---|---|---|---|---|---|---|---|---|---|---|
| aac | tac | ctg | aga | aag | tgt | tta | ata | tca | gtg | aag | agg | ctc | acg | tat | ccg | 336 |
| Asn | Tyr | Leu | Arg | Lys | Cys | Leu | Ile | Ser | Val | Lys | Arg | Leu | Thr | Tyr | Pro | |
| | | 100 | | | | | 105 | | | | | 110 | | | | |

| | | | | | | | | | | | | | | | | |
|---|---|---|---|---|---|---|---|---|---|---|---|---|---|---|---|---|
| ggt | ata | aag | gtc | ata | atg | gtt | atc | gat | ggg | aac | aac | gat | gat | gac | tgc | 384 |
| Gly | Ile | Lys | Val | Ile | Met | Val | Ile | Asp | Gly | Asn | Asn | Asp | Asp | Asp | Cys | |
| | | 115 | | | | | 120 | | | | | 125 | | | | |

| | | | | | | | | | | | | | | | | |
|---|---|---|---|---|---|---|---|---|---|---|---|---|---|---|---|---|
| tac | atg | atg | gag | atc | ttt | cga | gaa | atc | atg | ggc | cgg | gac | aag | gca | gcc | 432 |
| Tyr | Met | Met | Glu | Ile | Phe | Arg | Glu | Ile | Met | Gly | Arg | Asp | Lys | Ala | Ala | |
| | 130 | | | | | 135 | | | | | 140 | | | | | |

| | | | | | | | | | | | | | | | | |
|---|---|---|---|---|---|---|---|---|---|---|---|---|---|---|---|---|
| acg | tac | att | tgg | aaa | agc | aac | tat | cac | cat | aga | gga | ccc | gaa | gaa | act | 480 |
| Thr | Tyr | Ile | Trp | Lys | Ser | Asn | Tyr | His | His | Arg | Gly | Pro | Glu | Glu | Thr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gaa | gaa | tca | tac | gca | aca | agc | ttg | cag | cat | gtt | tct | cac | ctg | gtt | ctc | 528 |
| Glu | Glu | Ser | Tyr | Ala | Thr | Ser | Leu | Gln | His | Val | Ser | His | Leu | Val | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| aat | aat | aag | tgt | gtg | tgc | atc | atg | cag | aag | tgg | ggc | ggg | aaa | aga | gag | 576 |
| Asn | Asn | Lys | Cys | Val | Cys | Ile | Met | Gln | Lys | Trp | Gly | Gly | Lys | Arg | Glu | |
| | | | 180 | | | | | 185 | | | | | 190 | | | |

| | | | | | | | | | | | | | | | | |
|---|---|---|---|---|---|---|---|---|---|---|---|---|---|---|---|---|
| gtc | atg | tac | acc | gcc | ttc | aaa | gcc | ctg | gga | aga | agt | gtt | gac | tat | gta | 624 |
| Val | Met | Tyr | Thr | Ala | Phe | Lys | Ala | Leu | Gly | Arg | Ser | Val | Asp | Tyr | Val | |
| | | 195 | | | | | 200 | | | | | 205 | | | | |

| | | | | | | | | | | | | | | | | |
|---|---|---|---|---|---|---|---|---|---|---|---|---|---|---|---|---|
| cag | gtt | tgt | gat | tca | gac | acc | atg | ctg | gac | ccg | gcc | tcc | tct | gta | gag | 672 |
| Gln | Val | Cys | Asp | Ser | Asp | Thr | Met | Leu | Asp | Pro | Ala | Ser | Ser | Val | Glu | |
| | 210 | | | | | 215 | | | | | 220 | | | | | |

| | | | | | | | | | | | | | | | | |
|---|---|---|---|---|---|---|---|---|---|---|---|---|---|---|---|---|
| atg | gtg | aag | gtt | cta | gaa | gaa | gat | ccc | aat | gtt | gga | gga | gta | ggt | gga | 720 |
| Met | Val | Lys | Val | Leu | Glu | Glu | Asp | Pro | Asn | Val | Gly | Gly | Val | Gly | Gly | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gat | gtg | cag | ata | ttg | aac | aaa | tat | gag | tcg | tgg | gtc | tcc | ttc | ctg | agc | 768 |
| Asp | Val | Gln | Ile | Leu | Asn | Lys | Tyr | Glu | Ser | Trp | Val | Ser | Phe | Leu | Ser | |
| | | | | 245 | | | | | 250 | | | | | 255 | | |

| | | | | | | | | | | | | | | | | |
|---|---|---|---|---|---|---|---|---|---|---|---|---|---|---|---|---|
| agc | gtg | agg | tat | tgg | atg | gcg | ttc | aac | att | gaa | aga | gcc | tgc | cag | tca | 816 |

```
Ser Val Arg Tyr Trp Met Ala Phe Asn Ile Glu Arg Ala Cys Gln Ser
            260                 265                 270 tat ttc ggg tgc gtt caa tgt atc agc gga ccc ttg gga atg tac agg      864
Tyr Phe Gly Cys Val Gln Cys Ile Ser Gly Pro Leu Gly Met Tyr Arg
        275                 280                 285 aac tcc ctc ctc cat gag ttc ctg gag gac tgg tat gat cag aca ttc      912
Asn Ser Leu Leu His Glu Phe Leu Glu Asp Trp Tyr Asp Gln Thr Phe
        290                 295                 300 atg gga agc cac tgc agt ttt ggc gat gac cgc cat ctg acc aat cga      960
Met Gly Ser His Cys Ser Phe Gly Asp Asp Arg His Leu Thr Asn Arg
305                 310                 315                 320 gta ctg agc ttg gga tat gcc acg aaa tac acc gcg cgc tcc aag tgc     1008
Val Leu Ser Leu Gly Tyr Ala Thr Lys Tyr Thr Ala Arg Ser Lys Cys
                325                 330                 335 ttg acc gag acg ccc att acc tac ctg cgc tgg ctc aac caa caa acc     1056
Leu Thr Glu Thr Pro Ile Thr Tyr Leu Arg Trp Leu Asn Gln Gln Thr
                340                 345                 350 cgc tgg agt aaa tcc tat ttc aga gag tgg ctt tac aac tcc ttg tgg     1104
Arg Trp Ser Lys Ser Tyr Phe Arg Glu Trp Leu Tyr Asn Ser Leu Trp
            355                 360                 365 ttc cac aag cac cac ttg tgg atg acc tac gag gcc gtc atc acc ggc     1152
Phe His Lys His His Leu Trp Met Thr Tyr Glu Ala Val Ile Thr Gly
370                 375                 380 ttc ttc ccg ttc ttc ctt atc gcc act gcc att caa ctg ttc tac cag     1200
Phe Phe Pro Phe Phe Leu Ile Ala Thr Ala Ile Gln Leu Phe Tyr Gln
385                 390                 395                 400 ggc agg atc tgg aat atc ctt ctg ttc ctg ctg atc gtc cag gtc gtg     1248
Gly Arg Ile Trp Asn Ile Leu Leu Phe Leu Leu Ile Val Gln Val Val
                405                 410                 415 gca ctc ata aag tcc tca ttt gcc agt tgc ctc cga ggc aac ata gtc     1296
Ala Leu Ile Lys Ser Ser Phe Ala Ser Cys Leu Arg Gly Asn Ile Val
                420                 425                 430 atg gtc ttc atg tca ttc tac tca gtg tta tac atg tca agt ctg cta     1344
Met Val Phe Met Ser Phe Tyr Ser Val Leu Tyr Met Ser Ser Leu Leu
            435                 440                 445 ccg gca aaa atg ttt gca ata gcc acc ata aac aaa tcc gga tgg gga     1392
Pro Ala Lys Met Phe Ala Ile Ala Thr Ile Asn Lys Ser Gly Trp Gly
450                 455                 460 acg tct gga agg aag acc gtg gtg gtg aac ttc atc gga ctc att cca     1440
Thr Ser Gly Arg Lys Thr Val Val Val Asn Phe Ile Gly Leu Ile Pro
465                 470                 475                 480 atc tca att tgg ttc act att ctt ttc gtt ggc att att tat acc ata     1488
Ile Ser Ile Trp Phe Thr Ile Leu Phe Val Gly Ile Ile Tyr Thr Ile
                485                 490                 495 atc caa gag acg cga aaa ccc ttt cct gaa tcc gaa aag gtg gtt ttg     1536
Ile Gln Glu Thr Arg Lys Pro Phe Pro Glu Ser Glu Lys Val Val Leu
                500                 505                 510 ata att ggc gca atc gtt tat atc agc tac tgg gtt gtg ttt ttg act     1584
Ile Ile Gly Ala Ile Val Tyr Ile Ser Tyr Trp Val Val Phe Leu Thr
            515                 520                 525 ttg tac gct gtc ctc att atg aag tgt ggc aag agg aag aaa gga cag     1632
Leu Tyr Ala Val Leu Ile Met Lys Cys Gly Lys Arg Lys Lys Gly Gln
530                 535                 540 cag tat gac atg gtt ctt gac gta tag                                  1659
Gln Tyr Asp Met Val Leu Asp Val
545                 550

<210> SEQ ID NO 48
<211> LENGTH: 552
<212> TYPE: PRT
<213> ORGANISM: Danio rerio
```

<400> SEQUENCE: 48

```
Met Arg Cys Asp Lys Ala Val Ser Tyr Leu Arg Ile Val Gly Thr Thr
1               5                   10                  15
Leu Phe Gly Ile Ser Leu Leu Val Gly Ile Ser Thr Ala Tyr Ile Met
            20                  25                  30
Gly Tyr Lys Leu Val Thr Thr Pro Gly Asn Tyr Leu Ser Phe Gly Leu
        35                  40                  45
Tyr Gly Ala Ile Leu Val Ile His Leu Ile Gln Ser Val Phe Ala
50                  55                  60
Leu Leu Glu His Arg Asn Met Lys Arg Ser Leu Glu Thr Pro Ile Lys
65                  70                  75                  80
Leu Asn Lys Ser Leu Ala Leu Cys Ile Ala Ala Tyr Gln Glu Asp Pro
                85                  90                  95
Asn Tyr Leu Arg Lys Cys Leu Ile Ser Val Lys Arg Leu Thr Tyr Pro
            100                 105                 110
Gly Ile Lys Val Ile Met Val Ile Asp Gly Asn Asn Asp Asp Asp Cys
        115                 120                 125
Tyr Met Met Glu Ile Phe Arg Glu Ile Met Gly Arg Asp Lys Ala Ala
130                 135                 140
Thr Tyr Ile Trp Lys Ser Asn Tyr His His Arg Gly Pro Glu Glu Thr
145                 150                 155                 160
Glu Glu Ser Tyr Ala Thr Ser Leu Gln His Val Ser His Leu Val Leu
                165                 170                 175
Asn Asn Lys Cys Val Cys Ile Met Gln Lys Trp Gly Gly Lys Arg Glu
            180                 185                 190
Val Met Tyr Thr Ala Phe Lys Ala Leu Gly Arg Ser Val Asp Tyr Val
        195                 200                 205
Gln Val Cys Asp Ser Asp Thr Met Leu Asp Pro Ala Ser Ser Val Glu
210                 215                 220
Met Val Lys Val Leu Glu Glu Asp Pro Asn Val Gly Gly Val Gly Gly
225                 230                 235                 240
Asp Val Gln Ile Leu Asn Lys Tyr Glu Ser Trp Val Ser Phe Leu Ser
                245                 250                 255
Ser Val Arg Tyr Trp Met Ala Phe Asn Ile Glu Arg Ala Cys Gln Ser
            260                 265                 270
Tyr Phe Gly Cys Val Gln Cys Ile Ser Gly Pro Leu Gly Met Tyr Arg
        275                 280                 285
Asn Ser Leu Leu His Glu Phe Leu Glu Asp Trp Tyr Asp Gln Thr Phe
290                 295                 300
Met Gly Ser His Cys Ser Phe Gly Asp Asp Arg His Leu Thr Asn Arg
305                 310                 315                 320
Val Leu Ser Leu Gly Tyr Ala Thr Lys Tyr Thr Ala Arg Ser Lys Cys
                325                 330                 335
Leu Thr Glu Thr Pro Ile Thr Tyr Leu Arg Trp Leu Asn Gln Gln Thr
            340                 345                 350
Arg Trp Ser Lys Ser Tyr Phe Arg Glu Trp Leu Tyr Asn Ser Leu Trp
        355                 360                 365
Phe His Lys His His Leu Trp Met Thr Tyr Glu Ala Val Ile Thr Gly
370                 375                 380
Phe Phe Pro Phe Phe Leu Ile Ala Thr Ala Ile Gln Leu Phe Tyr Gln
385                 390                 395                 400
Gly Arg Ile Trp Asn Ile Leu Leu Phe Leu Leu Ile Val Gln Val Val
                405                 410                 415
```

```
Ala Leu Ile Lys Ser Ser Phe Ala Ser Cys Leu Arg Gly Asn Ile Val
            420                 425                 430

Met Val Phe Met Ser Phe Tyr Ser Val Leu Tyr Met Ser Ser Leu Leu
            435                 440                 445

Pro Ala Lys Met Phe Ala Ile Ala Thr Ile Asn Lys Ser Gly Trp Gly
            450                 455                 460

Thr Ser Gly Arg Lys Thr Val Val Asn Phe Ile Gly Leu Ile Pro
465                 470                 475                 480

Ile Ser Ile Trp Phe Thr Ile Leu Phe Val Gly Ile Ile Tyr Thr Ile
                485                 490                 495

Ile Gln Glu Thr Arg Lys Pro Phe Pro Glu Ser Glu Lys Val Val Leu
            500                 505                 510

Ile Ile Gly Ala Ile Val Tyr Ile Ser Tyr Trp Val Val Phe Leu Thr
            515                 520                 525

Leu Tyr Ala Val Leu Ile Met Lys Cys Gly Lys Arg Lys Lys Gly Gln
            530                 535                 540

Gln Tyr Asp Met Val Leu Asp Val
545                 550
```

<210> SEQ ID NO 49
<211> LENGTH: 2994
<212> TYPE: DNA
<213> ORGANISM: Danio rerio
<220> FEATURE:
<221> NAME/KEY: CDS
<222> LOCATION: (1)..(633)
<220> FEATURE:
<221> NAME/KEY: CDS
<222> LOCATION: (1059)..(1160)
<220> FEATURE:
<221> NAME/KEY: misc_feature
<222> LOCATION: (1425)..(1425)
<223> OTHER INFORMATION: 1425 = any
<220> FEATURE:
<221> NAME/KEY: misc_feature
<222> LOCATION: (1481)..(1481)
<223> OTHER INFORMATION: 1481= any
<220> FEATURE:
<221> NAME/KEY: misc_feature
<222> LOCATION: (1632)..(1632)
<223> OTHER INFORMATION: 1632 = any
<220> FEATURE:
<221> NAME/KEY: misc_feature
<222> LOCATION: (1834)..(1834)
<223> OTHER INFORMATION: 1834 = any
<220> FEATURE:
<221> NAME/KEY: CDS
<222> LOCATION: (2065)..(2991)
<220> FEATURE:
<221> NAME/KEY: misc_feature
<222> LOCATION: (2295)..(2295)
<223> OTHER INFORMATION: 2295 = any

<400> SEQUENCE: 49

```
atg ccc tct cgc ttt ggc act gcg gtg cgg atc ttc atc acc acc tta      48
Met Pro Ser Arg Phe Gly Thr Ala Val Arg Ile Phe Ile Thr Thr Leu
1               5                   10                  15 ttt gca gca gtg gtg ctt ttc gca atc cta cta gcc tat gtg aca ggt      96
Phe Ala Ala Val Val Leu Phe Ala Ile Leu Leu Ala Tyr Val Thr Gly
                20                  25                  30 tac cag ttc atc cac aca gag cag cac cat ctg tct ttt ggc ttg tac     144
Tyr Gln Phe Ile His Thr Glu Gln His His Leu Ser Phe Gly Leu Tyr
            35                  40                  45 ggt gca ttt cta tcc ctc cac ctt ctc ctg cag agt ctc ttc gcc tac     192
Gly Ala Phe Leu Ser Leu His Leu Leu Leu Gln Ser Leu Phe Ala Tyr
        50                  55                  60
```

```
ctg gag cac aga caa atg cga ggc ccc tcc aga ccg cag cac ctg cgc      240
Leu Glu His Arg Gln Met Arg Gly Pro Ser Arg Pro Gln His Leu Arg
 65                  70                  75                  80 cgc act gtg gcc ctc tgc att gca gcc tat cag gaa gat cca gac tac      288
Arg Thr Val Ala Leu Cys Ile Ala Ala Tyr Gln Glu Asp Pro Asp Tyr
                     85                  90                  95 ctt cgc aag tgt ctg cgg agt tcg cgc att tct ttt ccc ggg ctg aaa      336
Leu Arg Lys Cys Leu Arg Ser Ser Arg Ile Ser Phe Pro Gly Leu Lys
                100                 105                 110 gtg gtg ttg gtg gtg gat ggc aat cgg cag gag gat gcc tac atg atg      384
Val Val Leu Val Val Asp Gly Asn Arg Gln Glu Asp Ala Tyr Met Met
            115                 120                 125 gat atc ttc cag gag gtg atg ggg gga gtg gag cag aca ggc tgt gtg      432
Asp Ile Phe Gln Glu Val Met Gly Gly Val Glu Gln Thr Gly Cys Val
        130                 135                 140 gtg tgg aaa ggg aat tac cac agt aac ggg gat gga gga gga gga gga      480
Val Trp Lys Gly Asn Tyr His Ser Asn Gly Asp Gly Gly Gly Gly Gly
145                 150                 155                 160 ggg aaa ggc tcg gtg cat gcc gaa gag gct gca cga gtg gcc aga gtg      528
Gly Lys Gly Ser Val His Ala Glu Glu Ala Ala Arg Val Ala Arg Val
                165                 170                 175 gtg cgg agc tgc cgt tac tcc tgc atc atg cag gaa tgg ggt ggc aag      576
Val Arg Ser Cys Arg Tyr Ser Cys Ile Met Gln Glu Trp Gly Gly Lys
                180                 185                 190 agg gaa gtg atg tat aca gcc ttc aaa gca ctt gga gat aca gtg gat      624
Arg Glu Val Met Tyr Thr Ala Phe Lys Ala Leu Gly Asp Thr Val Asp
            195                 200                 205 tac atg cag gtaagtctaa acctcattta acaaccaaaa aaaaaaatcg              673
Tyr Met Gln
        210 gaaacatacc tctatgcttt tgatcttgt tactctttt tttatgccta caattaacca      733 acggttcata ctctagtcat ctcaatgtcc ctgtaatctg aatccttgca acactaaggt    793 caaaggtcag tcctttaaat tcacctgtag ttccgagcac acctgtgtgc tgtcatcaac    853 tattcattgt ttcggcgtat aatgtgtatg ttcagaaaca gaaatgacct tgaaacatct    913 gtgaacctct ctttacaaca gtccttgcat tgttcacaca gtgattgtta acatgagcct    973 taccttctgg aaattagtca atatttgtat acgagttagt gaggaagtct tccaagtaag    1033 tatctcttgc tttgtttgtt tgcag gta tgt gat tca gac act gta ctt gat     1085
                              Val Cys Asp Ser Asp Thr Val Leu Asp
                                              215                 220 cca gca tgc act att gag atg ttg aag att cta gag gag gat cct gat      1133
Pro Ala Cys Thr Ile Glu Met Leu Lys Ile Leu Glu Glu Asp Pro Asp
                225                 230                 235 gtg gga gga gtt gga gga gat gtt cag gtaataattt taaggcaatt            1180
Val Gly Gly Val Gly Gly Asp Val Gln
240                 245 tgtaaatatg tagaaacatt tcaacaaatt aatttgagag gattacattt gatctcatag    1240
atatatacat tagatatcgc ctggcctatt gtctattgga cggaatccaa agccagagat    1300
atacacatat atctatgatc gggagttttc ctggatgtta gtatgtaatt ttttttttct    1360
aattacgaaa attataattt tacatcactt ttctacattg atggatcagt caccgaacgg    1420
gcatncctga caaaaagctt gtgttgtgt gtacagaaat gtactattca ccctccctat     1480
naaatttgat ctaatcatgt cctgaaacac agctcctctc ctgctttcac ttctcatact    1540
gacggaggga gcgattcgtt tgtgaatgaa tccccggaac gactctttca ctaacgttag    1600
ccgacaataa tacgagtttc tggcagcgca gnatctcgtt gtcatatttc ttttgcattg    1660
```

```
tttgctgatt ttattcaaca aaactagcat aagccgagtg tttaatgcga gttggagctg    1720
ctttgcctta tatggtgaat gcagtaagtg actgttatca tcaataacgt tacctgatta    1780
gcacaaaagt tcagaacata caaaaacaga aaaaaacgta atattaccta tganatgttc    1840
tgcctttgtg ctttgttttc tttgtttgct cgttactaca accgtagaca gcgctaaagt    1900
cccgcatctt cacgtaataa cactgtcttg actagtgcgg ttgaatgaca ttctcctggg    1960
agcactgtac caatgtggct gtgctattga cgcatgctca gggtccctat gcgatatcta    2020
gtgtatatat ctatgatttg ttctctgttc attgtttcct tcag att ctg aac aag    2076
                                              Ile Leu Asn Lys tat gac tcc tgg atc tcc ttc ctg agc agt gtc cgc tat tgg atg gcc    2124
Tyr Asp Ser Trp Ile Ser Phe Leu Ser Ser Val Arg Tyr Trp Met Ala
250             255                 260                 265 ttc aat gtg gag cgg gcc tgc cag tct tat ttc gga tgt gtg cag tgc    2172
Phe Asn Val Glu Arg Ala Cys Gln Ser Tyr Phe Gly Cys Val Gln Cys
                270                 275                 280 atc agt gga cct cta gga atg tac cgt aac tct ctc ctt cag cag ttc    2220
Ile Ser Gly Pro Leu Gly Met Tyr Arg Asn Ser Leu Leu Gln Gln Phe
                285                 290                 295 tta gag ccc tgg tac cac cag acc ttc cta gga agc aag tgc agt ttt    2268
Leu Glu Pro Trp Tyr His Gln Thr Phe Leu Gly Ser Lys Cys Ser Phe
            300                 305                 310 ggt gat gat cga cat ctc acc aac cgn gtc ctt agc ttt ggc ttc aaa    2316
Gly Asp Asp Arg His Leu Thr Asn Arg Val Leu Ser Phe Gly Phe Lys
            315                 320                 325 acc aag ttc acg gca cgc tct caa tgc cag acc gag acc cca aca caa    2364
Thr Lys Phe Thr Ala Arg Ser Gln Cys Gln Thr Glu Thr Pro Thr Gln
330             335                 340                 345 tac ctg cgt tgg ctc aat cag cag acc cgc tgg agc aag tct tac ttt    2412
Tyr Leu Arg Trp Leu Asn Gln Gln Thr Arg Trp Ser Lys Ser Tyr Phe
                350                 355                 360 cga gag tgg ctc tac aat gct ctt tgg ttc cac aag cac agc ctg tgg    2460
Arg Glu Trp Leu Tyr Asn Ala Leu Trp Phe His Lys His Ser Leu Trp
                365                 370                 375 atg acc tat gaa tct gtg gtt act ggg ttc ttc ccc ttc ttt ctg gtg    2508
Met Thr Tyr Glu Ser Val Val Thr Gly Phe Phe Pro Phe Phe Leu Val
                380                 385                 390 gct aca gtc atc cac ctg ttc tac aga ggc cgg ttg tgg aac atc tta    2556
Ala Thr Val Ile His Leu Phe Tyr Arg Gly Arg Leu Trp Asn Ile Leu
            395                 400                 405 ctc ttc ttg ttg acg gtc cag ctg gtg ggt atg gtg aag gcc acc tac    2604
Leu Phe Leu Leu Thr Val Gln Leu Val Gly Met Val Lys Ala Thr Tyr
410             415                 420                 425 gcc tgc ttc ctg cgg ggc agc ctt gtc atg atc ttc atg tca ctc tac    2652
Ala Cys Phe Leu Arg Gly Ser Leu Val Met Ile Phe Met Ser Leu Tyr
                430                 435                 440 tca ctg ctc tac atg tca agc ctg ctc cct gct aag atc ttt gcc ctg    2700
Ser Leu Leu Tyr Met Ser Ser Leu Leu Pro Ala Lys Ile Phe Ala Leu
            445                 450                 455 ctg act att aac aaa gca gga tgg ggc aca tca ggc agg aaa aag atg    2748
Leu Thr Ile Asn Lys Ala Gly Trp Gly Thr Ser Gly Arg Lys Lys Met
            460                 465                 470 gta gta aac ctt att gga gct gtg cct gtt act gtg tgg aca gcc att    2796
Val Val Asn Leu Ile Gly Ala Val Pro Val Thr Val Trp Thr Ala Ile
            475                 480                 485 ctg ctt ggt gga gtg gtt tac acc att tac tgc gag gtt caa gaa cct    2844
Leu Leu Gly Gly Val Val Tyr Thr Ile Tyr Cys Glu Val Gln Glu Pro
490                 495                 500                 505
```

| | | |
|---|---|---|
| ttt acc gcg act gag aag gct ctt ctt atc gca ggc acc att gtc tat<br>Phe Thr Ala Thr Glu Lys Ala Leu Leu Ile Ala Gly Thr Ile Val Tyr<br>510                          515                       520 | | 2892 |
| gcc tct tac tgg ctt ata ctc ctg gtg ctc tac ctg gcc ata gtg gcc<br>Ala Ser Tyr Trp Leu Ile Leu Leu Val Leu Tyr Leu Ala Ile Val Ala<br>           525                       530                     535 | | 2940 |
| aaa cgt tgt aac aaa aga gaa gaa cag ttc cac ctt tcc tat gcc gaa<br>Lys Arg Cys Asn Lys Arg Glu Glu Gln Phe His Leu Ser Tyr Ala Glu<br>540                          545                       550 | | 2988 |
| gcc tag<br>Ala | | 2994 |

```
<210> SEQ ID NO 50
<211> LENGTH: 554
<212> TYPE: PRT
<213> ORGANISM: Danio rerio

<400> SEQUENCE: 50
```

Met Pro Ser Arg Phe Gly Thr Ala Val Arg Ile Phe Ile Thr Thr Leu
1                   5                      10                 15

Phe Ala Ala Val Val Leu Phe Ala Ile Leu Leu Ala Tyr Val Thr Gly
                 20                      25                      30

Tyr Gln Phe Ile His Thr Glu Gln His His Leu Ser Phe Gly Leu Tyr
               35                     40                     45

Gly Ala Phe Leu Ser Leu His Leu Leu Leu Gln Ser Leu Phe Ala Tyr
 50                      55                      60

Leu Glu His Arg Gln Met Arg Gly Pro Ser Arg Pro Gln His Leu Arg
65                  70                     75                 80

Arg Thr Val Ala Leu Cys Ile Ala Ala Tyr Gln Glu Asp Pro Asp Tyr
                 85                     90                     95

Leu Arg Lys Cys Leu Arg Ser Ser Arg Ile Ser Phe Pro Gly Leu Lys
               100                   105                 110

Val Val Leu Val Val Asp Gly Asn Arg Gln Glu Asp Ala Tyr Met Met
           115                   120                 125

Asp Ile Phe Gln Glu Val Met Gly Gly Val Glu Gln Thr Gly Cys Val
130                 135                   140

Val Trp Lys Gly Asn Tyr His Ser Asn Gly Asp Gly Gly Gly Gly Gly
145                 150                   155                 160

Gly Lys Gly Ser Val His Ala Glu Glu Ala Ala Arg Val Ala Arg Val
               165                   170                 175

Val Arg Ser Cys Arg Tyr Ser Cys Ile Met Gln Glu Trp Gly Gly Lys
           180                   185                 190

Arg Glu Val Met Tyr Thr Ala Phe Lys Ala Leu Gly Asp Thr Val Asp
           195                   200                 205

Tyr Met Gln Val Cys Asp Ser Asp Thr Val Leu Asp Pro Ala Cys Thr
210                 215                   220

Ile Glu Met Leu Lys Ile Leu Glu Glu Asp Pro Asp Val Gly Gly Val
225                 230                   235                 240

Gly Gly Asp Val Gln Ile Leu Asn Lys Tyr Asp Ser Trp Ile Ser Phe
           245                   250                 255

Leu Ser Ser Val Arg Tyr Trp Met Ala Phe Asn Val Glu Arg Ala Cys
           260                   265                 270

Gln Ser Tyr Phe Gly Cys Val Gln Cys Ile Ser Gly Pro Leu Gly Met
           275                   280                 285

Tyr Arg Asn Ser Leu Leu Gln Gln Phe Leu Glu Pro Trp Tyr His Gln
           290                   295                 300

-continued

```
Thr Phe Leu Gly Ser Lys Cys Ser Phe Gly Asp Asp Arg His Leu Thr
305                 310                 315                 320

Asn Arg Val Leu Ser Phe Gly Phe Lys Thr Lys Phe Thr Ala Arg Ser
                325                 330                 335

Gln Cys Gln Thr Glu Thr Pro Thr Gln Tyr Leu Arg Trp Leu Asn Gln
            340                 345                 350

Gln Thr Arg Trp Ser Lys Ser Tyr Phe Arg Glu Trp Leu Tyr Asn Ala
        355                 360                 365

Leu Trp Phe His Lys His Ser Leu Trp Met Thr Tyr Glu Ser Val Val
    370                 375                 380

Thr Gly Phe Phe Pro Phe Phe Leu Val Ala Thr Val Ile His Leu Phe
385                 390                 395                 400

Tyr Arg Gly Arg Leu Trp Asn Ile Leu Leu Phe Leu Leu Thr Val Gln
                405                 410                 415

Leu Val Gly Met Val Lys Ala Thr Tyr Ala Cys Phe Leu Arg Gly Ser
            420                 425                 430

Leu Val Met Ile Phe Met Ser Leu Tyr Ser Leu Leu Tyr Met Ser Ser
        435                 440                 445

Leu Leu Pro Ala Lys Ile Phe Ala Leu Leu Thr Ile Asn Lys Ala Gly
    450                 455                 460

Trp Gly Thr Ser Gly Arg Lys Lys Met Val Val Asn Leu Ile Gly Ala
465                 470                 475                 480

Val Pro Val Thr Val Trp Thr Ala Ile Leu Leu Gly Gly Val Val Tyr
                485                 490                 495

Thr Ile Tyr Cys Glu Val Gln Glu Pro Phe Thr Ala Thr Glu Lys Ala
            500                 505                 510

Leu Leu Ile Ala Gly Thr Ile Val Tyr Ala Ser Tyr Trp Leu Ile Leu
        515                 520                 525

Leu Val Leu Tyr Leu Ala Ile Val Ala Lys Arg Cys Asn Lys Arg Glu
    530                 535                 540

Glu Gln Phe His Leu Ser Tyr Ala Glu Ala
545                 550

<210> SEQ ID NO 51
<211> LENGTH: 2919
<212> TYPE: DNA
<213> ORGANISM: Pasteurella multocida
<220> FEATURE:
<221> NAME/KEY: CDS
<222> LOCATION: (1)..(2919)
<300> PUBLICATION INFORMATION:
<308> DATABASE ACCESSION NUMBER: AF036004.2
<309> DATABASE ENTRY DATE: 1998-04-15
<313> RELEVANT RESIDUES IN SEQ ID NO: (1)..(2919)

<400> SEQUENCE: 51 atg aat aca tta tca caa gca ata aaa gca tat aac agc aat gac tat       48
Met Asn Thr Leu Ser Gln Ala Ile Lys Ala Tyr Asn Ser Asn Asp Tyr
1               5                   10                  15 caa tta gca ctc aaa tta ttt gaa aag tcg gcg gaa atc tat gga cgg       96
Gln Leu Ala Leu Lys Leu Phe Glu Lys Ser Ala Glu Ile Tyr Gly Arg
            20                  25                  30 aaa att gtt gaa ttt caa att acc aaa tgc aaa gaa aaa ctc tca gca      144
Lys Ile Val Glu Phe Gln Ile Thr Lys Cys Lys Glu Lys Leu Ser Ala
        35                  40                  45 cat cct tct gtt aat tca gca cat ctt tct gta aat aaa gaa gaa aaa      192
His Pro Ser Val Asn Ser Ala His Leu Ser Val Asn Lys Glu Glu Lys
    50                  55                  60 gtc aat gtt tgc gat agt ccg tta gat att gca aca caa ctg tta ctt      240
```

-continued

| | | |
|---|---|---|
| Val Asn Val Cys Asp Ser Pro Leu Asp Ile Ala Thr Gln Leu Leu Leu<br>65     70       75      80 | | |
| tcc aac gta aaa aaa tta gta ctt tct gac tcg gaa aaa aac acg tta<br>Ser Asn Val Lys Lys Leu Val Leu Ser Asp Ser Glu Lys Asn Thr Leu<br>      85       90       95 | | 288 |
| aaa aat aaa tgg aaa ttg ctc act gag aag aaa tct gaa aat gcg gag<br>Lys Asn Lys Trp Lys Leu Leu Thr Glu Lys Lys Ser Glu Asn Ala Glu<br>    100       105      110 | | 336 |
| gta aga gcg gtc gcc ctt gta cca aaa gat ttt ccc aaa gat ctg gtt<br>Val Arg Ala Val Ala Leu Val Pro Lys Asp Phe Pro Lys Asp Leu Val<br>      115       120      125 | | 384 |
| tta gcg cct tta cct gat cat gtt aat gat ttt aca tgg tac aaa aag<br>Leu Ala Pro Leu Pro Asp His Val Asn Asp Phe Thr Trp Tyr Lys Lys<br>130        135       140 | | 432 |
| cga aag aaa aga ctt ggc ata aaa cct gaa cat caa cat gtt ggt ctt<br>Arg Lys Lys Arg Leu Gly Ile Lys Pro Glu His Gln His Val Gly Leu<br>145        150       155      160 | | 480 |
| tct att atc gtt aca aca ttc aat cga cca gca att tta tcg att aca<br>Ser Ile Ile Val Thr Thr Phe Asn Arg Pro Ala Ile Leu Ser Ile Thr<br>        165       170      175 | | 528 |
| tta gcc tgt tta gta aac caa aaa aca cat tac ccg ttt gaa gtt atc<br>Leu Ala Cys Leu Val Asn Gln Lys Thr His Tyr Pro Phe Glu Val Ile<br>    180       185      190 | | 576 |
| gtg aca gat gat ggt agt cag gaa gat cta tca ccg atc att cgc caa<br>Val Thr Asp Asp Gly Ser Gln Glu Asp Leu Ser Pro Ile Ile Arg Gln<br>      195       200      205 | | 624 |
| tat gaa aat aaa ttg gat att cgc tac gtc aga caa aaa gat aac ggt<br>Tyr Glu Asn Lys Leu Asp Ile Arg Tyr Val Arg Gln Lys Asp Asn Gly<br>210        215       220 | | 672 |
| ttt caa gcc agt gcc gct cgg aat atg gga tta cgc tta gca aaa tat<br>Phe Gln Ala Ser Ala Ala Arg Asn Met Gly Leu Arg Leu Ala Lys Tyr<br>225        230       235      240 | | 720 |
| gac ttt att ggc tta ctc gac tgt gat atg gcg cca aat cca tta tgg<br>Asp Phe Ile Gly Leu Leu Asp Cys Asp Met Ala Pro Asn Pro Leu Trp<br>        245       250      255 | | 768 |
| gtt cat tct tat gtt gca gag cta tta gaa gat gat gat tta aca atc<br>Val His Ser Tyr Val Ala Glu Leu Leu Glu Asp Asp Asp Leu Thr Ile<br>    260       265      270 | | 816 |
| att ggt cca aga aaa tac atc gat aca caa cat att gac cca aaa gac<br>Ile Gly Pro Arg Lys Tyr Ile Asp Thr Gln His Ile Asp Pro Lys Asp<br>      275       280      285 | | 864 |
| ttc tta aat aac gcg agt ttg ctt gaa tca tta cca gaa gtg aaa acc<br>Phe Leu Asn Asn Ala Ser Leu Leu Glu Ser Leu Pro Glu Val Lys Thr<br>290        295       300 | | 912 |
| aat aat agt gtt gcc gca aaa ggg gaa gga aca gtt tct ctg gat tgg<br>Asn Asn Ser Val Ala Ala Lys Gly Glu Gly Thr Val Ser Leu Asp Trp<br>305        310       315      320 | | 960 |
| cgc tta gaa caa ttc gaa aaa aca gaa aat ctc cgc tta tcc gat tcg<br>Arg Leu Glu Gln Phe Glu Lys Thr Glu Asn Leu Arg Leu Ser Asp Ser<br>        325       330      335 | | 1008 |
| cct ttc cgt ttt ttt gcg gcg ggt aat gtt gct ttc gct aaa aaa tgg<br>Pro Phe Arg Phe Phe Ala Ala Gly Asn Val Ala Phe Ala Lys Lys Trp<br>    340       345      350 | | 1056 |
| cta aat aaa tcc ggt ttc ttt gat gag gaa ttt aat cac tgg ggt gga<br>Leu Asn Lys Ser Gly Phe Phe Asp Glu Glu Phe Asn His Trp Gly Gly<br>      355       360      365 | | 1104 |
| gaa gat gtg gaa ttt gga tat cgc tta ttc cgt tac ggt agt ttc ttt<br>Glu Asp Val Glu Phe Gly Tyr Arg Leu Phe Arg Tyr Gly Ser Phe Phe<br>370        375       380 | | 1152 |
| aaa act att gat ggc att atg gcc tac cat caa gag cca cca ggt aaa | | 1200 |

```
                                    -continued

Lys Thr Ile Asp Gly Ile Met Ala Tyr His Gln Glu Pro Pro Gly Lys
385                 390                 395                 400 gaa aat gaa acc gat cgt gaa gcg gga aaa aat att acg ctc gat att    1248
Glu Asn Glu Thr Asp Arg Glu Ala Gly Lys Asn Ile Thr Leu Asp Ile
                405                 410                 415 atg aga gaa aag gtc cct tat atc tat aga aaa ctt tta cca ata gaa    1296
Met Arg Glu Lys Val Pro Tyr Ile Tyr Arg Lys Leu Leu Pro Ile Glu
            420                 425                 430 gat tcg cat atc aat aga gta cct tta gtt tca att tat atc cca gct    1344
Asp Ser His Ile Asn Arg Val Pro Leu Val Ser Ile Tyr Ile Pro Ala
        435                 440                 445 tat aac tgt gca aac tat att caa cgt tgc gta gat agt gca ctg aat    1392
Tyr Asn Cys Ala Asn Tyr Ile Gln Arg Cys Val Asp Ser Ala Leu Asn
    450                 455                 460 cag act gtt gtt gat ctc gag gtt tgt att tgt aac gat ggt tca aca    1440
Gln Thr Val Val Asp Leu Glu Val Cys Ile Cys Asn Asp Gly Ser Thr
465                 470                 475                 480 gat aat acc tta gaa gtg atc aat aag ctt tat ggt aat aat cct agg    1488
Asp Asn Thr Leu Glu Val Ile Asn Lys Leu Tyr Gly Asn Asn Pro Arg
                485                 490                 495 gta cgc atc atg tct aaa cca aat ggc gga ata gcc tca gca tca aat    1536
Val Arg Ile Met Ser Lys Pro Asn Gly Gly Ile Ala Ser Ala Ser Asn
            500                 505                 510 gca gcc gtt tct ttt gct aaa ggt tat tac att ggg cag tta gat tca    1584
Ala Ala Val Ser Phe Ala Lys Gly Tyr Tyr Ile Gly Gln Leu Asp Ser
        515                 520                 525 gat gat tat ctt gag cct gat gca gtt gaa ctg tgt tta aaa gaa ttt    1632
Asp Asp Tyr Leu Glu Pro Asp Ala Val Glu Leu Cys Leu Lys Glu Phe
    530                 535                 540 tta aaa gat aaa acg cta gct tgt gtt tat acc act aat aga aac gtc    1680
Leu Lys Asp Lys Thr Leu Ala Cys Val Tyr Thr Thr Asn Arg Asn Val
545                 550                 555                 560 aat ccg gat ggt agc tta atc gct aat ggt tac aat tgg cca gaa ttt    1728
Asn Pro Asp Gly Ser Leu Ile Ala Asn Gly Tyr Asn Trp Pro Glu Phe
                565                 570                 575 tca cga gaa aaa ctc aca acg gct atg att gct cac cac ttt aga atg    1776
Ser Arg Glu Lys Leu Thr Thr Ala Met Ile Ala His His Phe Arg Met
            580                 585                 590 ttc acg att aga gct tgg cat tta act gat gga ttc aat gaa aaa att    1824
Phe Thr Ile Arg Ala Trp His Leu Thr Asp Gly Phe Asn Glu Lys Ile
        595                 600                 605 gaa aat gcc gta gac tat gac atg ttc ctc aaa ctc agt gaa gtt gga    1872
Glu Asn Ala Val Asp Tyr Asp Met Phe Leu Lys Leu Ser Glu Val Gly
    610                 615                 620 aaa ttt aaa cat ctt aat aaa atc tgc tat aac cgt gta tta cat ggt    1920
Lys Phe Lys His Leu Asn Lys Ile Cys Tyr Asn Arg Val Leu His Gly
625                 630                 635                 640 gat aac aca tca att aag aaa ctt ggc att caa aag aaa aac cat ttt    1968
Asp Asn Thr Ser Ile Lys Lys Leu Gly Ile Gln Lys Lys Asn His Phe
                645                 650                 655 gtt gta gtc aat cag tca tta aat aga caa ggc ata act tat tat aat    2016
Val Val Val Asn Gln Ser Leu Asn Arg Gln Gly Ile Thr Tyr Tyr Asn
            660                 665                 670 tat gac gaa ttt gat gat tta gat gaa agt aga aag tat att ttc aat    2064
Tyr Asp Glu Phe Asp Asp Leu Asp Glu Ser Arg Lys Tyr Ile Phe Asn
        675                 680                 685 aaa acc gct gaa tat caa gaa gag att gat atc tta aaa gat att aaa    2112
Lys Thr Ala Glu Tyr Gln Glu Glu Ile Asp Ile Leu Lys Asp Ile Lys
    690                 695                 700 atc atc cag aat aaa gat gcc aaa atc gca gtc agt att ttt tat ccc    2160
```

```
Ile Ile Gln Asn Lys Asp Ala Lys Ile Ala Val Ser Ile Phe Tyr Pro
705                 710                 715                 720 aat aca tta aac ggc tta gtg aaa aaa cta aac aat att att gaa tat       2208
Asn Thr Leu Asn Gly Leu Val Lys Lys Leu Asn Asn Ile Ile Glu Tyr
                725                 730                 735 aat aaa aat ata ttc gtt att gtt cta cat gtt gat aag aat cat ctt       2256
Asn Lys Asn Ile Phe Val Ile Val Leu His Val Asp Lys Asn His Leu
            740                 745                 750 aca cca gat atc aaa aaa gaa ata cta gcc ttc tat cat aaa cat caa       2304
Thr Pro Asp Ile Lys Lys Glu Ile Leu Ala Phe Tyr His Lys His Gln
        755                 760                 765 gtg aat att tta cta aat aat gat atc tca tat tac acg agt aat aga       2352
Val Asn Ile Leu Leu Asn Asn Asp Ile Ser Tyr Tyr Thr Ser Asn Arg
    770                 775                 780 tta ata aaa act gag gcg cat tta agt aat att aat aaa tta agt cag       2400
Leu Ile Lys Thr Glu Ala His Leu Ser Asn Ile Asn Lys Leu Ser Gln
785                 790                 795                 800 tta aat cta aat tgt gaa tac atc att ttt gat aat cat gac agc cta       2448
Leu Asn Leu Asn Cys Glu Tyr Ile Ile Phe Asp Asn His Asp Ser Leu
                805                 810                 815 ttc gtt aaa aat gac agc tat gct tat atg aaa aaa tat gat gtc ggc       2496
Phe Val Lys Asn Asp Ser Tyr Ala Tyr Met Lys Lys Tyr Asp Val Gly
            820                 825                 830 atg aat ttc tca gca tta aca cat gat tgg atc gag aaa atc aat gcg       2544
Met Asn Phe Ser Ala Leu Thr His Asp Trp Ile Glu Lys Ile Asn Ala
        835                 840                 845 cat cca cca ttt aaa aag ctc att aaa act tat ttt aat gac aat gac       2592
His Pro Pro Phe Lys Lys Leu Ile Lys Thr Tyr Phe Asn Asp Asn Asp
    850                 855                 860 tta aaa agt atg aat gtg aaa ggg gca tca caa ggt atg ttt atg acg       2640
Leu Lys Ser Met Asn Val Lys Gly Ala Ser Gln Gly Met Phe Met Thr
865                 870                 875                 880 tat gcg cta gcg cat gag ctt ctg acg att att aaa gaa gtc atc aca       2688
Tyr Ala Leu Ala His Glu Leu Leu Thr Ile Ile Lys Glu Val Ile Thr
                885                 890                 895 tct tgc cag tca att gat agt gtg cca gaa tat aac act gag gat att       2736
Ser Cys Gln Ser Ile Asp Ser Val Pro Glu Tyr Asn Thr Glu Asp Ile
            900                 905                 910 tgg ttc caa ttt gca ctt tta atc tta gaa aag aaa acc ggc cat gta       2784
Trp Phe Gln Phe Ala Leu Leu Ile Leu Glu Lys Lys Thr Gly His Val
        915                 920                 925 ttt aat aaa aca tcg acc ctg act tat atg cct tgg gaa cga aaa tta       2832
Phe Asn Lys Thr Ser Thr Leu Thr Tyr Met Pro Trp Glu Arg Lys Leu
    930                 935                 940 caa tgg aca aat gaa caa att gaa agt gca aaa aga gga gaa aat ata       2880
Gln Trp Thr Asn Glu Gln Ile Glu Ser Ala Lys Arg Gly Glu Asn Ile
945                 950                 955                 960 cct gtt aac aag ttc att att aat agt ata act cta taa                   2919
Pro Val Asn Lys Phe Ile Ile Asn Ser Ile Thr Leu
                965                 970

<210> SEQ ID NO 52
<211> LENGTH: 972
<212> TYPE: PRT
<213> ORGANISM: Pasteurella multocida

<400> SEQUENCE: 52

Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

```
Lys Ile Val Glu Phe Gln Ile Thr Lys Cys Lys Glu Lys Leu Ser Ala
             35                  40                  45

His Pro Ser Val Asn Ser Ala His Leu Ser Val Asn Lys Glu Glu Lys
         50                  55                  60

Val Asn Val Cys Asp Ser Pro Leu Asp Ile Ala Thr Gln Leu Leu Leu
 65                  70                  75                  80

Ser Asn Val Lys Lys Leu Val Leu Ser Asp Ser Glu Lys Asn Thr Leu
                 85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
            115                 120                 125

Leu Ala Pro Leu Pro Asp His Val Asn Asp Phe Thr Trp Tyr Lys Lys
            130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
            180                 185                 190

Val Thr Asp Asp Gly Ser Gln Glu Asp Leu Ser Pro Ile Ile Arg Gln
            195                 200                 205

Tyr Glu Asn Lys Leu Asp Ile Arg Tyr Val Arg Gln Lys Asp Asn Gly
            210                 215                 220

Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
                245                 250                 255

Val His Ser Tyr Val Ala Glu Leu Leu Glu Asp Asp Asp Leu Thr Ile
            260                 265                 270

Ile Gly Pro Arg Lys Tyr Ile Asp Thr Gln His Ile Asp Pro Lys Asp
            275                 280                 285

Phe Leu Asn Asn Ala Ser Leu Leu Glu Ser Leu Pro Glu Val Lys Thr
            290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
            340                 345                 350

Leu Asn Lys Ser Gly Phe Phe Asp Glu Glu Phe Asn His Trp Gly Gly
            355                 360                 365

Glu Asp Val Glu Phe Gly Tyr Arg Leu Phe Arg Tyr Gly Ser Phe Phe
            370                 375                 380

Lys Thr Ile Asp Gly Ile Met Ala Tyr His Gln Glu Pro Pro Gly Lys
385                 390                 395                 400

Glu Asn Glu Thr Asp Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
            420                 425                 430

Asp Ser His Ile Asn Arg Val Pro Leu Val Ser Ile Tyr Ile Pro Ala
            435                 440                 445

Tyr Asn Cys Ala Asn Tyr Ile Gln Arg Cys Val Asp Ser Ala Leu Asn
```

-continued

```
            450             455             460
Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
                485                 490                 495

Val Arg Ile Met Ser Lys Pro Asn Gly Gly Ile Ala Ser Ala Ser Asn
            500                 505                 510

Ala Ala Val Ser Phe Ala Lys Gly Tyr Tyr Ile Gly Gln Leu Asp Ser
                515                 520                 525

Asp Asp Tyr Leu Glu Pro Asp Ala Val Glu Leu Cys Leu Lys Glu Phe
            530                 535                 540

Leu Lys Asp Lys Thr Leu Ala Cys Val Tyr Thr Thr Asn Arg Asn Val
545                 550                 555                 560

Asn Pro Asp Gly Ser Leu Ile Ala Asn Gly Tyr Asn Trp Pro Glu Phe
                565                 570                 575

Ser Arg Glu Lys Leu Thr Thr Ala Met Ile Ala His His Phe Arg Met
            580                 585                 590

Phe Thr Ile Arg Ala Trp His Leu Thr Asp Gly Phe Asn Glu Lys Ile
        595                 600                 605

Glu Asn Ala Val Asp Tyr Asp Met Phe Leu Lys Leu Ser Glu Val Gly
610                 615                 620

Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
                645                 650                 655

Val Val Val Asn Gln Ser Leu Asn Arg Gln Gly Ile Thr Tyr Tyr Asn
                660                 665                 670

Tyr Asp Glu Phe Asp Asp Leu Asp Glu Ser Arg Lys Tyr Ile Phe Asn
        675                 680                 685

Lys Thr Ala Glu Tyr Gln Glu Glu Ile Asp Ile Leu Lys Asp Ile Lys
            690                 695                 700

Ile Ile Gln Asn Lys Asp Ala Lys Ile Ala Val Ser Ile Phe Tyr Pro
705                 710                 715                 720

Asn Thr Leu Asn Gly Leu Val Lys Lys Leu Asn Asn Ile Ile Glu Tyr
                725                 730                 735

Asn Lys Asn Ile Phe Val Ile Val Leu His Val Asp Lys Asn His Leu
                740                 745                 750

Thr Pro Asp Ile Lys Lys Glu Ile Leu Ala Phe Tyr His Lys His Gln
            755                 760                 765

Val Asn Ile Leu Leu Asn Asn Asp Ile Ser Tyr Tyr Thr Ser Asn Arg
770                 775                 780

Leu Ile Lys Thr Glu Ala His Leu Ser Asn Ile Asn Lys Leu Ser Gln
785                 790                 795                 800

Leu Asn Leu Asn Cys Glu Tyr Ile Ile Phe Asp Asn His Asp Ser Leu
                805                 810                 815

Phe Val Lys Asn Asp Ser Tyr Ala Tyr Met Lys Lys Tyr Asp Val Gly
                820                 825                 830

Met Asn Phe Ser Ala Leu Thr His Asp Trp Ile Glu Lys Ile Asn Ala
            835                 840                 845

His Pro Pro Phe Lys Lys Leu Ile Lys Thr Tyr Phe Asn Asp Asn Asp
        850                 855                 860

Leu Lys Ser Met Asn Val Lys Gly Ala Ser Gln Gly Met Phe Met Thr
865                 870                 875                 880
```

```
Tyr Ala Leu Ala His Glu Leu Leu Thr Ile Ile Lys Glu Val Ile Thr
                885                 890                 895

Ser Cys Gln Ser Ile Asp Ser Val Pro Glu Tyr Asn Thr Glu Asp Ile
            900                 905                 910

Trp Phe Gln Phe Ala Leu Leu Ile Leu Glu Lys Lys Thr Gly His Val
        915                 920                 925

Phe Asn Lys Thr Ser Thr Leu Thr Tyr Met Pro Trp Glu Arg Lys Leu
    930                 935                 940

Gln Trp Thr Asn Glu Gln Ile Glu Ser Ala Lys Arg Gly Glu Asn Ile
945                 950                 955                 960

Pro Val Asn Lys Phe Ile Ile Asn Ser Ile Thr Leu
                965                 970

<210> SEQ ID NO 53
<211> LENGTH: 1260
<212> TYPE: DNA
<213> ORGANISM: Streptococcus pyogenes
<220> FEATURE:
<221> NAME/KEY: CDS
<222> LOCATION: (1)..(1260)
<300> PUBLICATION INFORMATION:
<308> DATABASE ACCESSION NUMBER: L21187.1
<309> DATABASE ENTRY DATE: 1993-07-23
<313> RELEVANT RESIDUES IN SEQ ID NO: (79)..(1338)

<400> SEQUENCE: 53 gtg cct att ttt aaa aaa act tta att gtt tta tcc ttt att ttt ttg      48
Met Pro Ile Phe Lys Lys Thr Leu Ile Val Leu Ser Phe Ile Phe Leu
1               5                  10                  15 ata tct atc ttg att tat cta aat atg tat cta ttt gga aca tca act      96
Ile Ser Ile Leu Ile Tyr Leu Asn Met Tyr Leu Phe Gly Thr Ser Thr
            20                  25                  30 gta gga att tat gga gta ata tta ata acc tat cta gtt atc aaa ctt     144
Val Gly Ile Tyr Gly Val Ile Leu Ile Thr Tyr Leu Val Ile Lys Leu
        35                  40                  45 gga tta tct ttc ctt tat gag cca ttt aaa gga aag cca cat gac tat     192
Gly Leu Ser Phe Leu Tyr Glu Pro Phe Lys Gly Lys Pro His Asp Tyr
    50                  55                  60 aaa gtt gct gct gta att cct tct tat aat gaa gat gcc gag tca tta     240
Lys Val Ala Ala Val Ile Pro Ser Tyr Asn Glu Asp Ala Glu Ser Leu
65                  70                  75                  80 tta gaa aca ctt aaa agt gtg tta gca cag acc tat ccg tta tca gaa     288
Leu Glu Thr Leu Lys Ser Val Leu Ala Gln Thr Tyr Pro Leu Ser Glu
                85                  90                  95 att tat att gtt gat gat ggg agt tca aac aca gat gca ata caa tta     336
Ile Tyr Ile Val Asp Asp Gly Ser Ser Asn Thr Asp Ala Ile Gln Leu
            100                 105                 110 att gaa gag tat gta aat aga gaa gtg gat att tgt cga aac gtt atc     384
Ile Glu Glu Tyr Val Asn Arg Glu Val Asp Ile Cys Arg Asn Val Ile
        115                 120                 125 gtt cac cgt tcc ctt gtc aat aaa gga aaa cgc cat gct caa gcg tgg     432
Val His Arg Ser Leu Val Asn Lys Gly Lys Arg His Ala Gln Ala Trp
    130                 135                 140 gca ttt gaa aga tct gac gct gac gtt ttt tta acc gta gat tca gat     480
Ala Phe Glu Arg Ser Asp Ala Asp Val Phe Leu Thr Val Asp Ser Asp
145                 150                 155                 160 act tat atc tat cca aat gcc tta gaa gaa ctc cta aaa agc ttc aat     528
Thr Tyr Ile Tyr Pro Asn Ala Leu Glu Glu Leu Leu Lys Ser Phe Asn
                165                 170                 175 gat gag aca gtt tat gct gca aca gga cat ttg aat gct aga aac aga     576
Asp Glu Thr Val Tyr Ala Ala Thr Gly His Leu Asn Ala Arg Asn Arg
            180                 185                 190
```

```
caa act aat cta tta acg cga ctt aca gat atc cgt tac gat aat gcc      624
Gln Thr Asn Leu Leu Thr Arg Leu Thr Asp Ile Arg Tyr Asp Asn Ala
            195                 200                 205 ttt ggg gtg gag cgt gct gct caa tca tta aca ggt aat att tta gtt      672
Phe Gly Met Glu Arg Ala Ala Gln Ser Leu Thr Gly Asn Ile Leu Val
210                 215                 220 tgc tca gga cca ttg agt att tat cga cgt gaa gtg att att cct aac      720
Cys Ser Gly Pro Leu Ser Ile Tyr Arg Arg Glu Met Ile Ile Pro Asn
225                 230                 235                 240 tta gag cgc tat aaa aat caa aca ttc cta ggt tta cct gtt agc att      768
Leu Glu Arg Tyr Lys Asn Gln Thr Phe Leu Gly Leu Pro Val Ser Ile
            245                 250                 255 ggg gat gat cga tgt tta aca aat tat gct att gat tta gga cgc act      816
Gly Asp Asp Arg Cys Leu Thr Asn Tyr Ala Ile Asp Leu Gly Arg Thr
                260                 265                 270 gtc tac caa tca aca gct aga tgt gat act gat gta cct ttc caa tta      864
Val Tyr Gln Ser Thr Ala Arg Cys Asp Thr Asp Val Pro Phe Gln Leu
            275                 280                 285 aaa agt tat tta aag caa caa aat cga tgg aat aaa tct ttt ttt aga      912
Lys Ser Tyr Leu Lys Gln Gln Asn Arg Trp Asn Lys Ser Phe Phe Arg
290                 295                 300 gaa tct att att tct gtt aaa aaa att ctt tct aat ccc atc gtt gcc      960
Glu Ser Ile Ile Ser Val Lys Lys Ile Leu Ser Asn Pro Ile Val Ala
305                 310                 315                 320 tta tgg act att ttc gaa gtc gtt atg ttt atg atg ttg att gtc gca     1008
Leu Trp Thr Ile Phe Glu Val Val Met Phe Met Met Leu Ile Val Ala
            325                 330                 335 att ggg aat ctt ttg ttt aat caa gct att caa tta gac ctt att aaa     1056
Ile Gly Asn Leu Leu Phe Asn Gln Ala Ile Gln Leu Asp Leu Ile Lys
                340                 345                 350 ctt ttt gcc ttt tta tcc atc atc ttt atc gtt gct tta tgt cgt aat     1104
Leu Phe Ala Phe Leu Ser Ile Ile Phe Ile Val Ala Leu Cys Arg Asn
            355                 360                 365 gtt cat tat atg gtc aaa cat cct gct agt ttt ttg tta tct cct ctg     1152
Val His Tyr Met Val Lys His Pro Ala Ser Phe Leu Leu Ser Pro Leu
370                 375                 380 tat gga ata tta cac ttg ttt gtc tta cag ccc cta aaa ctt tat tct     1200
Tyr Gly Ile Leu His Leu Phe Val Leu Gln Pro Leu Lys Leu Tyr Ser
385                 390                 395                 400 tta tgc acc att aaa aat acg gaa tgg gga aca cgt aaa aag gtc act     1248
Leu Cys Thr Ile Lys Asn Thr Glu Trp Gly Thr Arg Lys Lys Val Thr
            405                 410                 415 att ttt aaa taa                                                     1260
Ile Phe Lys <210> SEQ ID NO 54
<211> LENGTH: 419
<212> TYPE: PRT
<213> ORGANISM: Streptococcus pyogenes

<400> SEQUENCE: 54

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Lys Pro His Asp Tyr
    50                  55                  60
```

```
Lys Val Ala Ala Val Ile Pro Ser Tyr Asn Glu Asp Ala Glu Ser Leu
 65                  70                  75                  80

Leu Glu Thr Leu Lys Ser Met Leu Ala Gln Thr Tyr Pro Leu Ser Glu
                 85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Met Asp Ile Cys Arg Asn Val Ile
        115                 120                 125

Val His Arg Ser Leu Val Asn Lys Gly Lys Arg His Ala Gln Ala Trp
130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Met Glu Arg Ala Ala Gln Ser Leu Thr Gly Asn Ile Leu Val
210                 215                 220

Cys Ser Gly Pro Leu Ser Ile Tyr Arg Arg Glu Met Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 55
<211> LENGTH: 1254
<212> TYPE: DNA
<213> ORGANISM: Streptococcus equi
<220> FEATURE:
<221> NAME/KEY: CDS
<222> LOCATION: (1)..(1254)
<300> PUBLICATION INFORMATION:
<308> DATABASE ACCESSION NUMBER: AF347022.1
<309> DATABASE ENTRY DATE: 2002-11-13
<313> RELEVANT RESIDUES IN SEQ ID NO: (531)..(1784)
```

<400> SEQUENCE: 55

```
atg aga aca tta aaa aac ctc ata act gtt gtg gcc ttt agt att ttt    48
Met Arg Thr Leu Lys Asn Leu Ile Thr Val Val Ala Phe Ser Ile Phe
1               5                  10                  15 tgg gta ctg ttg att tac gtc aat gtt tat ctc ttt ggt gct aaa gga    96
Trp Val Leu Leu Ile Tyr Val Asn Val Tyr Leu Phe Gly Ala Lys Gly
            20                  25                  30 agc ttg tca att tat ggc ttt ttg ctg ata gct tac cta tta gtc aaa   144
Ser Leu Ser Ile Tyr Gly Phe Leu Leu Ile Ala Tyr Leu Leu Val Lys
        35                  40                  45 atg tcc tta tcc ttt ttt tac aag cca ttt aag gga agg gct ggg caa   192
Met Ser Leu Ser Phe Phe Tyr Lys Pro Phe Lys Gly Arg Ala Gly Gln
    50                  55                  60 tat aag gtt gca gcc att att ccc tct tat aac gaa gat gct gag tca   240
Tyr Lys Val Ala Ala Ile Ile Pro Ser Tyr Asn Glu Asp Ala Glu Ser
65                  70                  75                  80 ttg cta gag acc tta aaa agt gtt cag cag caa acc tat ccc cta gca   288
Leu Leu Glu Thr Leu Lys Ser Val Gln Gln Gln Thr Tyr Pro Leu Ala
                85                  90                  95 gaa att tat gtt gtt gac gat gga agt gct gat gag aca ggt att aag   336
Glu Ile Tyr Val Val Asp Asp Gly Ser Ala Asp Glu Thr Gly Ile Lys
            100                 105                 110 cgc att gaa gac tat gtg cgt gac act ggt gac cta tca agc aat gtc   384
Arg Ile Glu Asp Tyr Val Arg Asp Thr Gly Asp Leu Ser Ser Asn Val
        115                 120                 125 att gtt cac cgg tca gaa aaa aat caa gga aag cgt cat gca cag gcc   432
Ile Val His Arg Ser Glu Lys Asn Gln Gly Lys Arg His Ala Gln Ala
    130                 135                 140 tgg gcc ttt gaa aga tca gac gct gat gtc ttt ttg acc gtt gac tca   480
Trp Ala Phe Glu Arg Ser Asp Ala Asp Val Phe Leu Thr Val Asp Ser
145                 150                 155                 160 gat act tat atc tac cct gat gct tta gag gag ttg tta aaa acc ttt   528
Asp Thr Tyr Ile Tyr Pro Asp Ala Leu Glu Glu Leu Leu Lys Thr Phe
                165                 170                 175 aat gac cca act gtt ttt gct gcg acg ggt cac ctt aat gtc aga aat   576
Asn Asp Pro Thr Val Phe Ala Ala Thr Gly His Leu Asn Val Arg Asn
            180                 185                 190 aga caa acc aat ctc tta aca cgc ttg aca gat att cgc tat gat aat   624
Arg Gln Thr Asn Leu Leu Thr Arg Leu Thr Asp Ile Arg Tyr Asp Asn
        195                 200                 205 gct ttt ggc gtt gaa cga gct gcc caa tcc gtt aca ggt aat att ctc   672
Ala Phe Gly Val Glu Arg Ala Ala Gln Ser Val Thr Gly Asn Ile Leu
    210                 215                 220 gtt tgc tca ggc ccg ctt agc gtt tac aga cgc gag gtg gtt gtt cct   720
Val Cys Ser Gly Pro Leu Ser Val Tyr Arg Arg Glu Val Val Val Pro
225                 230                 235                 240 aac ata gat aga tac atc aac cag acc ttc ctg ggt att cct gta agt   768
Asn Ile Asp Arg Tyr Ile Asn Gln Thr Phe Leu Gly Ile Pro Val Ser
                245                 250                 255 atc ggt gat gac agg tgc ttg acc aac tat gca act gat tta gga aag   816
Ile Gly Asp Asp Arg Cys Leu Thr Asn Tyr Ala Thr Asp Leu Gly Lys
            260                 265                 270 act gtt tat caa tcc act gct aaa tgt att aca gat gtt cct gac aag   864
Thr Val Tyr Gln Ser Thr Ala Lys Cys Ile Thr Asp Val Pro Asp Lys
        275                 280                 285 atg tct act tac ttg aag cag caa aac cgc tgg aac aag tcc ttc ttt   912
Met Ser Thr Tyr Leu Lys Gln Gln Asn Arg Trp Asn Lys Ser Phe Phe
    290                 295                 300 aga gag tcc att att tct gtt aag aaa atc atg aac aat cct ttt gta   960
```

```
Arg Glu Ser Ile Ile Ser Val Lys Lys Ile Met Asn Asn Pro Phe Val
305                 310                 315                 320 gcc cta tgg acc ata ctt gag gtg tct atg ttt atg atg ctt gtt tat        1008
Ala Leu Trp Thr Ile Leu Glu Val Ser Met Phe Met Met Leu Val Tyr
                325                 330                 335 tct gtg gtg gat ttc ttt gta gac aat gtc aga gaa ttt gat tgg ctc        1056
Ser Val Val Asp Phe Phe Val Asp Asn Val Arg Glu Phe Asp Trp Leu
            340                 345                 350 agg gtt ttg gcc ttt ctg gtg att atc ttc att gtt gct ctt tgt cgt        1104
Arg Val Leu Ala Phe Leu Val Ile Ile Phe Ile Val Ala Leu Cys Arg
        355                 360                 365 aat att cac tat atg ctt aag cac ccg ctg tcc ttc ttg tta tct ccg        1152
Asn Ile His Tyr Met Leu Lys His Pro Leu Ser Phe Leu Leu Ser Pro
    370                 375                 380 ttt tat ggg gta ctg cat ttg ttt gtc cta cag ccc ttg aaa ttg tat        1200
Phe Tyr Gly Val Leu His Leu Phe Val Leu Gln Pro Leu Lys Leu Tyr
385                 390                 395                 400 tct ctt ttt act att aga aat gct gac tgg gga aca cgt aaa aaa tta        1248
Ser Leu Phe Thr Ile Arg Asn Ala Asp Trp Gly Thr Arg Lys Lys Leu
                405                 410                 415 tta taa                                                                 1254
Leu <210> SEQ ID NO 56
<211> LENGTH: 417
<212> TYPE: PRT
<213> ORGANISM: Streptococcus equi

<400> SEQUENCE: 56

Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
    50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Thr Tyr Pro Leu Ala
                85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
        115                 120                 125

Ile Val His Arg Ser Glu Lys Asn Gln Gly Lys Arg His Ala Gln Ala
    130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
    210                 215                 220
```

-continued

```
Val Cys Ser Gly Pro Leu Ser Val Tyr Arg Arg Glu Val Val Pro
225                 230                 235                 240

Asn Ile Asp Arg Tyr Ile Asn Gln Thr Phe Leu Gly Ile Pro Val Ser
            245                 250                 255

Ile Gly Asp Asp Arg Cys Leu Thr Asn Tyr Ala Thr Asp Leu Gly Lys
        260                 265                 270

Thr Val Tyr Gln Ser Thr Ala Lys Cys Ile Thr Asp Val Pro Asp Lys
    275                 280                 285

Met Ser Thr Tyr Leu Lys Gln Gln Asn Arg Trp Asn Lys Ser Phe Phe
290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
                325                 330                 335

Ser Val Val Asp Phe Phe Val Asp Asn Val Arg Glu Phe Asp Trp Leu
            340                 345                 350

Arg Val Leu Ala Phe Leu Val Ile Ile Phe Ile Val Ala Leu Cys Arg
        355                 360                 365

Asn Ile His Tyr Met Leu Lys His Pro Leu Ser Phe Leu Leu Ser Pro
370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu
```

<210> SEQ ID NO 57
<211> LENGTH: 1254
<212> TYPE: DNA
<213> ORGANISM: Streptococcus uberis
<220> FEATURE:
<221> NAME/KEY: CDS
<222> LOCATION: (1)..(1254)
<300> PUBLICATION INFORMATION:
<308> DATABASE ACCESSION NUMBER: AJ242946.2
<309> DATABASE ENTRY DATE: 1999-07-07
<313> RELEVANT RESIDUES IN SEQ ID NO: (23)..(1276)

<400> SEQUENCE: 57

```
atg gaa aaa cta aaa aat ctc att aca ttt atg act ttt att ttc ctg      48
Met Glu Lys Leu Lys Asn Leu Ile Thr Phe Met Thr Phe Ile Phe Leu
1               5                   10                  15 tgg ctc ata att att ggg ctt aat gtt ttt gta ttt gga act aaa gga      96
Trp Leu Ile Ile Ile Gly Leu Asn Val Phe Val Phe Gly Thr Lys Gly
            20                  25                  30 agt cta aca gtg tat ggg att att cta tta acc tat ttg tcg ata aaa     144
Ser Leu Thr Val Tyr Gly Ile Ile Leu Leu Thr Tyr Leu Ser Ile Lys
        35                  40                  45 atg gga tta tct ttt ttt tat cgt ccc tat aaa gga agt gta ggt caa     192
Met Gly Leu Ser Phe Phe Tyr Arg Pro Tyr Lys Gly Ser Val Gly Gln
    50                  55                  60 tat aag gta gca gct att atc cca tct tat aat gag gat ggt gtc ggt     240
Tyr Lys Val Ala Ala Ile Ile Pro Ser Tyr Asn Glu Asp Gly Val Gly
65                  70                  75                  80 tta cta gaa act cta aag agt gtt caa aaa caa aca tat cca att gca     288
Leu Leu Glu Thr Leu Lys Ser Val Gln Lys Gln Thr Tyr Pro Ile Ala
                85                  90                  95 gaa att ttc gta att gac gat ggg tca gta gat aaa aca ggt ata aaa     336
Glu Ile Phe Val Ile Asp Asp Gly Ser Val Asp Lys Thr Gly Ile Lys
                100                 105                 110
```

```
ttg gtc gaa gac tat gtg aag tta aat ggc ttt gga gac caa gtt atc      384
Leu Val Glu Asp Tyr Val Lys Leu Asn Gly Phe Gly Asp Gln Val Ile
        115                 120                 125 gtt cat cag atg cct gaa aat gtt ggt aaa aga cat gct cag gct tgg      432
Val His Gln Met Pro Glu Asn Val Gly Lys Arg His Ala Gln Ala Trp
130                 135                 140 gca ttt gaa agg tct gat gct gat gtt ttc tta aca gtg gat tca gat      480
Ala Phe Glu Arg Ser Asp Ala Asp Val Phe Leu Thr Val Asp Ser Asp
145                 150                 155                 160 acc tac atc tat cct gat gct ctt gaa gaa tta tta aag aca ttt aat      528
Thr Tyr Ile Tyr Pro Asp Ala Leu Glu Glu Leu Leu Lys Thr Phe Asn
                165                 170                 175 gat cca gag gtc tac gct gca act ggt cat tta aat gca aga aat aga      576
Asp Pro Glu Val Tyr Ala Ala Thr Gly His Leu Asn Ala Arg Asn Arg
            180                 185                 190 caa act aat ctc tta act aga ctg act gat att cgt tac gat aat gca      624
Gln Thr Asn Leu Leu Thr Arg Leu Thr Asp Ile Arg Tyr Asp Asn Ala
        195                 200                 205 ttt ggt gta gaa cgt gct gct cag tct gtt acg gga aat att ttg gtt      672
Phe Gly Val Glu Arg Ala Ala Gln Ser Val Thr Gly Asn Ile Leu Val
210                 215                 220 tgt tcc gga cct tta agt att tat aga cgt tcc gtc ggt att cca aat      720
Cys Ser Gly Pro Leu Ser Ile Tyr Arg Arg Ser Val Gly Ile Pro Asn
225                 230                 235                 240 ctt gaa cgc tat acc tca caa aca ttt ctt ggt gtc cct gta agc ata      768
Leu Glu Arg Tyr Thr Ser Gln Thr Phe Leu Gly Val Pro Val Ser Ile
                245                 250                 255 ggg gat gac cgt tgt ttg aca aat tat gca act gat ttg gga aaa acg      816
Gly Asp Asp Arg Cys Leu Thr Asn Tyr Ala Thr Asp Leu Gly Lys Thr
            260                 265                 270 gtt tat cag tca act gca aga tgt gat act gac gtt cca gat aag ttt      864
Val Tyr Gln Ser Thr Ala Arg Cys Asp Thr Asp Val Pro Asp Lys Phe
        275                 280                 285 aag gtt ttc atc aaa caa caa aat cgt tgg aat aag tca ttt ttt agg      912
Lys Val Phe Ile Lys Gln Gln Asn Arg Trp Asn Lys Ser Phe Phe Arg
290                 295                 300 gag tct att atc tct gtt aag aag tta tta gcc aca cca agt gtt gct      960
Glu Ser Ile Ile Ser Val Lys Lys Leu Leu Ala Thr Pro Ser Val Ala
305                 310                 315                 320 gtt tgg act att aca gaa gtt tcc atg ttc atc atg cta gtt tat tct     1008
Val Trp Thr Ile Thr Glu Val Ser Met Phe Ile Met Leu Val Tyr Ser
                325                 330                 335 atc ttt agc tta ttg ata gga gag gct caa gaa ttt aat ctc ata aaa     1056
Ile Phe Ser Leu Leu Ile Gly Glu Ala Gln Glu Phe Asn Leu Ile Lys
            340                 345                 350 ctg gtt gct ttt tta gtt att att ttc ata gta gct ctt tgt aga aat     1104
Leu Val Ala Phe Leu Val Ile Ile Phe Ile Val Ala Leu Cys Arg Asn
        355                 360                 365 gtt cat tac atg gtt aag cat cca ttt gct ttt tta ttg tca ccg ttt     1152
Val His Tyr Met Val Lys His Pro Phe Ala Phe Leu Leu Ser Pro Phe
370                 375                 380 tat gga ttg ata cat cta ttc gtt ttg caa cct ctt aag ata tat tcg     1200
Tyr Gly Leu Ile His Leu Phe Val Leu Gln Pro Leu Lys Ile Tyr Ser
385                 390                 395                 400 tta ttt act ata aga aat gct aca tgg gga act cgt aaa aag aca agt     1248
Leu Phe Thr Ile Arg Asn Ala Thr Trp Gly Thr Arg Lys Lys Thr Ser
                405                 410                 415 aaa taa                                                              1254
Lys
```

```
<210> SEQ ID NO 58
<211> LENGTH: 417
<212> TYPE: PRT
<213> ORGANISM: Streptococcus uberis

<400> SEQUENCE: 58

Met Glu Lys Leu Lys Asn Leu Ile Thr Phe Met Thr Phe Ile Phe Leu
1               5                   10                  15

Trp Leu Ile Ile Ile Gly Leu Asn Val Phe Val Phe Gly Thr Lys Gly
            20                  25                  30

Ser Leu Thr Val Tyr Gly Ile Ile Leu Leu Thr Tyr Leu Ser Ile Lys
        35                  40                  45

Met Gly Leu Ser Phe Phe Tyr Arg Pro Tyr Lys Gly Ser Val Gly Gln
    50                  55                  60

Tyr Lys Val Ala Ala Ile Ile Pro Ser Tyr Asn Glu Asp Gly Val Gly
65                  70                  75                  80

Leu Leu Glu Thr Leu Lys Ser Val Gln Lys Gln Thr Tyr Pro Ile Ala
                85                  90                  95

Glu Ile Phe Val Ile Asp Asp Gly Ser Val Asp Lys Thr Gly Ile Lys
            100                 105                 110

Leu Val Glu Asp Tyr Val Lys Leu Asn Gly Phe Gly Asp Gln Val Ile
        115                 120                 125

Val His Gln Met Pro Glu Asn Val Gly Lys Arg His Ala Gln Ala Trp
    130                 135                 140

Ala Phe Glu Arg Ser Asp Ala Asp Val Phe Leu Thr Val Asp Ser Asp
145                 150                 155                 160

Thr Tyr Ile Tyr Pro Asp Ala Leu Glu Glu Leu Leu Lys Thr Phe Asn
                165                 170                 175

Asp Pro Glu Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Val Thr Gly Asn Ile Leu Val
    210                 215                 220

Cys Ser Gly Pro Leu Ser Ile Tyr Arg Arg Ser Val Gly Ile Pro Asn
225                 230                 235                 240

Leu Glu Arg Tyr Thr Ser Gln Thr Phe Leu Gly Val Pro Val Ser Ile
                245                 250                 255

Gly Asp Asp Arg Cys Leu Thr Asn Tyr Ala Thr Asp Leu Gly Lys Thr
            260                 265                 270

Val Tyr Gln Ser Thr Ala Arg Cys Asp Thr Asp Val Pro Asp Lys Phe
        275                 280                 285

Lys Val Phe Ile Lys Gln Gln Asn Arg Trp Asn Lys Ser Phe Phe Arg
    290                 295                 300

Glu Ser Ile Ile Ser Val Lys Lys Leu Leu Ala Thr Pro Ser Val Ala
305                 310                 315                 320

Val Trp Thr Ile Thr Glu Val Ser Met Phe Ile Met Leu Val Tyr Ser
                325                 330                 335

Ile Phe Ser Leu Leu Ile Gly Glu Ala Gln Glu Phe Asn Leu Ile Lys
            340                 345                 350

Leu Val Ala Phe Leu Val Ile Ile Phe Ile Val Ala Leu Cys Arg Asn
        355                 360                 365

Val His Tyr Met Val Lys His Pro Phe Ala Phe Leu Leu Ser Pro Phe
    370                 375                 380
```

```
                                                              -continued

Tyr Gly Leu Ile His Leu Phe Val Leu Gln Pro Leu Lys Ile Tyr Ser
385                 390                 395                 400

Leu Phe Thr Ile Arg Asn Ala Thr Trp Gly Thr Arg Lys Lys Thr Ser
                405                 410                 415

Lys

<210> SEQ ID NO 59
<211> LENGTH: 1254
<212> TYPE: DNA
<213> ORGANISM: Streptococcus equisimilis
<220> FEATURE:
<221> NAME/KEY: CDS
<222> LOCATION: (1)..(1254)
<300> PUBLICATION INFORMATION:
<308> DATABASE ACCESSION NUMBER: AF023876.1
<309> DATABASE ENTRY DATE: 1997-12-04
<313> RELEVANT RESIDUES IN SEQ ID NO: (1)..(1254)

<400> SEQUENCE: 59 atg aga aca tta aaa aac ctc ata act gtt gtg gcc ttt agt att ttt         48
Met Arg Thr Leu Lys Asn Leu Ile Thr Val Val Ala Phe Ser Ile Phe
1               5                   10                  15 tgg gta ctg ttg att tac gtc aat gtt tat ctc ttt ggt gct aaa gga         96
Trp Val Leu Leu Ile Tyr Val Asn Val Tyr Leu Phe Gly Ala Lys Gly
            20                  25                  30 agc ttg tca att tat ggc ttt ttg ctg ata gct tac cta tta gtc aaa        144
Ser Leu Ser Ile Tyr Gly Phe Leu Leu Ile Ala Tyr Leu Leu Val Lys
        35                  40                  45 atg tcc tta tcc ttt ttt tac aag cca ttt aag gga agg gct ggg caa        192
Met Ser Leu Ser Phe Phe Tyr Lys Pro Phe Lys Gly Arg Ala Gly Gln
50                  55                  60 tat aag gtt gca gcc att att ccc tct tat aac gaa gat gct gag tca        240
Tyr Lys Val Ala Ala Ile Ile Pro Ser Tyr Asn Glu Asp Ala Glu Ser
65                  70                  75                  80 ttg cta gag acc tta aaa agt gtt cag cag caa acc tat ccc cta gca        288
Leu Leu Glu Thr Leu Lys Ser Val Gln Gln Gln Thr Tyr Pro Leu Ala
                85                  90                  95 gaa att tat gtt gtt gac gat gga agt gct gat gag aca ggt att aag        336
Glu Ile Tyr Val Val Asp Asp Gly Ser Ala Asp Glu Thr Gly Ile Lys
            100                 105                 110 cgc att gaa gac tat gtg cgt gac act ggt gac cta tca agc aat gtc        384
Arg Ile Glu Asp Tyr Val Arg Asp Thr Gly Asp Leu Ser Ser Asn Val
        115                 120                 125 att gtt cat cgg tca gag aaa aat caa gga aag cgt cat gca cag gcc        432
Ile Val His Arg Ser Glu Lys Asn Gln Gly Lys Arg His Ala Gln Ala
130                 135                 140 tgg gcc ttt gaa aga tca gac gct gat gtc ttt ttg acc gtt gac tca        480
Trp Ala Phe Glu Arg Ser Asp Ala Asp Val Phe Leu Thr Val Asp Ser
145                 150                 155                 160 gat act tat atc tac cct gat gct tta gag gag ttg tta aaa acc ttt        528
Asp Thr Tyr Ile Tyr Pro Asp Ala Leu Glu Glu Leu Leu Lys Thr Phe
                165                 170                 175 aat gac cca act gtt ttt gct gcg acg ggt cac ctt aat gtc aga aat        576
Asn Asp Pro Thr Val Phe Ala Ala Thr Gly His Leu Asn Val Arg Asn
            180                 185                 190 aga caa acc aat ctc tta aca cgc ttg aca gat att cgc tat gat aat        624
Arg Gln Thr Asn Leu Leu Thr Arg Leu Thr Asp Ile Arg Tyr Asp Asn
        195                 200                 205 gct ttt ggc gtt gaa cga gct gcc caa tcc gtt aca ggt aat atc ctt        672
Ala Phe Gly Val Glu Arg Ala Ala Gln Ser Val Thr Gly Asn Ile Leu
210                 215                 220 gtt tgc tca ggt ccg ctt agc gtt tac aga cgc gag gtg gtt gtt cct        720
```

```
Val Cys Ser Gly Pro Leu Ser Val Tyr Arg Arg Glu Val Val Pro
225                 230                 235                 240 aac ata gat aga tac atc aac cag acc ttc ctg ggt att cct gta agt      768
Asn Ile Asp Arg Tyr Ile Asn Gln Thr Phe Leu Gly Ile Pro Val Ser
                245                 250                 255 att ggt gat gac agg tgc ttg acc aac tat gca act gat tta gga aag      816
Ile Gly Asp Asp Arg Cys Leu Thr Asn Tyr Ala Thr Asp Leu Gly Lys
            260                 265                 270 act gtt tat caa tcc act gct aaa tgt att aca gat gtt cct gac aag      864
Thr Val Tyr Gln Ser Thr Ala Lys Cys Ile Thr Asp Val Pro Asp Lys
        275                 280                 285 atg tct act tac ttg aag cag caa aac cgc tgg aac aag tcc ttc ttt      912
Met Ser Thr Tyr Leu Lys Gln Gln Asn Arg Trp Asn Lys Ser Phe Phe
    290                 295                 300 aga gag tcc att att tct gtt aag aaa atc atg aac aat cct ttt gta      960
Arg Glu Ser Ile Ile Ser Val Lys Lys Ile Met Asn Asn Pro Phe Val
305                 310                 315                 320 gcc cta tgg acc ata ctt gag gtg tct atg ttt atg atg ctt gtt tat     1008
Ala Leu Trp Thr Ile Leu Glu Val Ser Met Phe Met Met Leu Val Tyr
                325                 330                 335 tct gtg gtg gat ttc ttt gta ggc aat gtc aga gaa ttt gat tgg ctc     1056
Ser Val Val Asp Phe Phe Val Gly Asn Val Arg Glu Phe Asp Trp Leu
            340                 345                 350 agg gtt tta gcc ttt ctg gtg att atc ttc att gtt gcc ctg tgt cgg     1104
Arg Val Leu Ala Phe Leu Val Ile Ile Phe Ile Val Ala Leu Cys Arg
        355                 360                 365 aac att cat tac atg ctt aag cac ccg ctg tcc ttc ttg tta tct ccg     1152
Asn Ile His Tyr Met Leu Lys His Pro Leu Ser Phe Leu Leu Ser Pro
    370                 375                 380 ttt tat ggg gtg ctg cat ttg ttt gtc cta cag ccc ttg aaa tta tat     1200
Phe Tyr Gly Val Leu His Leu Phe Val Leu Gln Pro Leu Lys Leu Tyr
385                 390                 395                 400 tct ctt ttt act att aga aat gct gac tgg gga aca cgt aaa aaa tta     1248
Ser Leu Phe Thr Ile Arg Asn Ala Asp Trp Gly Thr Arg Lys Lys Leu
                405                 410                 415 tta taa                                                             1254
Leu

<210> SEQ ID NO 60
<211> LENGTH: 417
<212> TYPE: PRT
<213> ORGANISM: Streptococcus equisimilis

<400> SEQUENCE: 60

Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
    50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
```

```
                    115                 120                 125
Ile Val His Arg Ser Glu Lys Asn Gln Gly Lys Arg His Ala Gln Ala
130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Lys Thr Phe
                165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
    210                 215                 220

Val Cys Ser Gly Pro Leu Ser Val Tyr Arg Arg Glu Val Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Cys Leu Thr Asn Tyr Ala Thr Asp Leu Gly Lys
            260                 265                 270

Thr Val Tyr Gln Ser Thr Ala Lys Cys Ile Thr Asp Val Pro Asp Lys
        275                 280                 285

Met Ser Thr Tyr Leu Lys Gln Gln Asn Arg Trp Asn Lys Ser Phe Phe
    290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
                325                 330                 335

Ser Val Val Asp Phe Phe Val Gly Asn Val Arg Glu Phe Asp Trp Leu
            340                 345                 350

Arg Val Leu Ala Phe Leu Val Ile Ile Phe Ile Val Ala Leu Cys Arg
        355                 360                 365

Asn Ile His Tyr Met Leu Lys His Pro Leu Ser Phe Leu Leu Ser Pro
    370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu

<210> SEQ ID NO 61
<211> LENGTH: 1248
<212> TYPE: DNA
<213> ORGANISM: Sulfolobus tokodaii str. 7
<220> FEATURE:
<221> NAME/KEY: CDS
<222> LOCATION: (1)..(1248)
<300> PUBLICATION INFORMATION:
<308> DATABASE ACCESSION NUMBER: AP000988
<309> DATABASE ENTRY DATE: 2001-09-17
<313> RELEVANT RESIDUES IN SEQ ID NO: (173392)..(174639)

<400> SEQUENCE: 61 gtg gtg att atg ttt cac tta ttt cac gga gtc tca tat ttc att tat      48
Met Met Ile Met Phe His Leu Phe His Gly Val Ser Tyr Phe Ile Tyr
1               5                   10                  15 tct ctt tca ttc aca att ata act att ctt tat ttc ttt ttg aat tca      96
Ser Leu Ser Phe Thr Ile Ile Thr Ile Leu Tyr Phe Phe Leu Asn Ser
            20                  25                  30
```

| | | | | | | | | | | | | | | | |
|---|---|---|---|---|---|---|---|---|---|---|---|---|---|---|---|
| ttt | ttt | gca | gta | ata | agt | aat | aat | aga | aaa | act | caa | cac | tca | agt | ttt | 144 |
| Phe | Phe | Ala | Val | Ile | Ser | Asn | Asn | Arg | Lys | Thr | Gln | His | Ser | Ser | Phe | |
| | | 35 | | | | 40 | | | | 45 | | | | | | |

| tat | aat | ctc | tct | gat | ctt | aca | gtt | gtg | ata | cca | gtt | tat | aag | gag | gaa | 192 |
| Tyr | Asn | Leu | Ser | Asp | Leu | Thr | Val | Met | Ile | Pro | Val | Tyr | Lys | Glu | Glu | |
| 50 | | | | | 55 | | | | | 60 | | | | | | |

| ata | gat | att | ttt | gaa | aaa | gtg | ata | agg | act | tta | tat | gac | aca | agg | tta | 240 |
| Ile | Asp | Ile | Phe | Glu | Lys | Met | Ile | Arg | Thr | Leu | Tyr | Asp | Thr | Arg | Leu | |
| 65 | | | | | 70 | | | | | 75 | | | | | 80 | |

| gaa | ttt | att | gtt | gta | ggg | gat | agt | gtt | cta | gaa | cca | tac | aaa | tca | att | 288 |
| Glu | Phe | Ile | Val | Val | Gly | Asp | Ser | Val | Leu | Glu | Pro | Tyr | Lys | Ser | Ile | |
| | | | | 85 | | | | | 90 | | | | | 95 | | |

| acg | gaa | aga | tat | ggt | ggt | aaa | ttt | att | tat | atg | cgt | gaa | cat | aag | ggg | 336 |
| Thr | Glu | Arg | Tyr | Gly | Gly | Lys | Phe | Ile | Tyr | Met | Arg | Glu | His | Lys | Gly | |
| | | | 100 | | | | | 105 | | | | | 110 | | | |

| aaa | aga | tac | gcg | tta | gcc | gag | gga | gtt | aag | tat | gta | aga | tct | cct | cta | 384 |
| Lys | Arg | Tyr | Ala | Leu | Ala | Glu | Gly | Val | Lys | Tyr | Val | Arg | Ser | Pro | Leu | |
| | | 115 | | | | | 120 | | | | | 125 | | | | |

| gtg | atg | ttt | cta | gat | agt | gat | acg | att | att | tat | aaa | gac | tct | ata | cta | 432 |
| Met | Met | Phe | Leu | Asp | Ser | Asp | Thr | Ile | Ile | Tyr | Lys | Asp | Ser | Ile | Leu | |
| 130 | | | | | 135 | | | | | 140 | | | | | | |

| aag | atg | tta | agt | gtt | ttt | gat | gag | tca | gta | ggt | gga | gta | ggg | cca | aat | 480 |
| Lys | Met | Leu | Ser | Val | Phe | Asp | Glu | Ser | Val | Gly | Gly | Val | Gly | Pro | Asn | |
| 145 | | | | | 150 | | | | | 155 | | | | | 160 | |

| att | aga | att | atg | tat | gac | gag | aaa | aat | aaa | tat | gca | tat | tat | tat | ggt | 528 |
| Ile | Arg | Ile | Met | Tyr | Asp | Glu | Lys | Asn | Lys | Tyr | Ala | Tyr | Tyr | Tyr | Gly | |
| | | | | 165 | | | | | 170 | | | | | 175 | | |

| gaa | ttc | ttt | gag | aga | ata | agt | gag | ata | gta | aac | agg | gcg | gta | aac | tat | 576 |
| Glu | Phe | Phe | Glu | Arg | Ile | Ser | Glu | Ile | Val | Asn | Arg | Ala | Val | Asn | Tyr | |
| | | | 180 | | | | | 185 | | | | | 190 | | | |

| ttt | gga | agt | gct | ata | ata | tta | agt | gga | caa | tgt | gta | ata | tat | agg | acc | 624 |
| Phe | Gly | Ser | Ala | Ile | Ile | Leu | Ser | Gly | Gln | Cys | Val | Ile | Tyr | Arg | Thr | |
| | | 195 | | | | | 200 | | | | | 205 | | | | |

| gaa | ctc | gta | aaa | cca | tat | ata | tta | tct | aaa | gag | ttt | tta | gag | ccg | aaa | 672 |
| Glu | Leu | Val | Lys | Pro | Tyr | Ile | Leu | Ser | Lys | Glu | Phe | Leu | Glu | Pro | Lys | |
| | 210 | | | | | 215 | | | | | 220 | | | | | |

| atg | ttt | gga | aga | cca | att | aaa | att | tcc | gat | gat | aga | gat | tta | acc | gat | 720 |
| Met | Phe | Gly | Arg | Pro | Ile | Lys | Ile | Ser | Asp | Asp | Arg | Asp | Leu | Thr | Asp | |
| 225 | | | | | 230 | | | | | 235 | | | | | 240 | |

| ttt | gtt | ata | aaa | aaa | ggg | tat | agg | gct | gta | aaa | gtc | ttt | gat | gca | gtg | 768 |
| Phe | Val | Ile | Lys | Lys | Gly | Tyr | Arg | Ala | Val | Lys | Val | Phe | Asp | Ala | Met | |
| | | | | 245 | | | | | 250 | | | | | 255 | | |

| gca | tat | aca | aaa | ccc | cct | aga | gac | ata | aaa | atg | ttt | acg | aaa | caa | gta | 816 |
| Ala | Tyr | Thr | Lys | Pro | Pro | Arg | Asp | Ile | Lys | Met | Phe | Thr | Lys | Gln | Val | |
| | | | 260 | | | | | 265 | | | | | 270 | | | |

| act | aga | tgg | aca | aga | gca | aat | tat | ctt | aat | ttt | ata | agg | gag | ata | gct | 864 |
| Thr | Arg | Trp | Thr | Arg | Ala | Asn | Tyr | Leu | Asn | Phe | Ile | Arg | Glu | Ile | Ala | |
| | | 275 | | | | | 280 | | | | | 285 | | | | |

| gac | ggt | agt | ata | agt | aaa | agg | ggt | tca | tta | tac | gtt | ttt | aat | atg | ata | 912 |
| Asp | Gly | Ser | Ile | Ser | Lys | Arg | Gly | Ser | Leu | Tyr | Val | Phe | Asn | Met | Ile | |
| | 290 | | | | | 295 | | | | | 300 | | | | | |

| tac | acc | aat | ctg | tta | cca | tta | ttt | acg | ctc | ttg | ttc | ctt | tat | atg | agt | 960 |
| Tyr | Thr | Asn | Leu | Leu | Pro | Leu | Phe | Thr | Leu | Leu | Phe | Leu | Tyr | Met | Ser | |
| 305 | | | | | 310 | | | | | 315 | | | | | 320 | |

| ttc | act | aga | att | ctt | aag | atc | tat | tcc | tca | att | aat | gta | att | aat | act | 1008 |
| Phe | Thr | Arg | Ile | Leu | Lys | Ile | Tyr | Ser | Ser | Ile | Asn | Val | Ile | Asn | Thr | |
| | | | | 325 | | | | | 330 | | | | | 335 | | |

| aag | ctc | tta | tta | cta | ttg | tat | ctg | cca | acc | cgt | tac | cat | tcc | gac | ttc | 1056 |
| Lys | Leu | Leu | Leu | Leu | Leu | Tyr | Leu | Pro | Thr | Arg | Tyr | His | Ser | Asp | Phe | |
| | | | 340 | | | | | 345 | | | | | 350 | | | |

```
ttt atc ttt tat tta ttc ttg cat tac gga gga ttt ata gct ata ata    1104
Phe Ile Phe Tyr Leu Phe Leu His Tyr Gly Gly Phe Ile Ala Ile Ile
        355                 360                 365 ccc ttt gta atg acc atg att tat tta att cca gaa gat aaa ttg aaa    1152
Pro Phe Val Met Thr Met Ile Tyr Leu Ile Pro Glu Asp Lys Leu Lys
370                 375                 380 act cta ata tac ggt tct atc gca cta gca gtg caa tat att gct tcc    1200
Thr Leu Ile Tyr Gly Ser Ile Ala Leu Ala Met Gln Tyr Ile Ala Ser
385                 390                 395                 400 cta tat gct atg ata act ttc tgg tgg caa gat tgg tta act aga taa    1248
Leu Tyr Ala Met Ile Thr Phe Trp Trp Gln Asp Trp Leu Thr Arg
                405                 410                 415

<210> SEQ ID NO 62
<211> LENGTH: 415
<212> TYPE: PRT
<213> ORGANISM: Sulfolobus tokodaii str. 7

<400> SEQUENCE: 62

Met Met Ile Met Phe His Leu Phe His Gly Val Ser Tyr Phe Ile Tyr
1               5                   10                  15

Ser Leu Ser Phe Thr Ile Ile Thr Ile Leu Tyr Phe Phe Leu Asn Ser
            20                  25                  30

Phe Phe Ala Val Ile Ser Asn Asn Arg Lys Thr Gln His Ser Ser Phe
        35                  40                  45

Tyr Asn Leu Ser Asp Leu Thr Val Met Ile Pro Val Tyr Lys Glu Glu
    50                  55                  60

Ile Asp Ile Phe Glu Lys Met Ile Arg Thr Leu Tyr Asp Thr Arg Leu
65                  70                  75                  80

Glu Phe Ile Val Val Gly Asp Ser Val Leu Pro Tyr Lys Ser Ile
                85                  90                  95

Thr Glu Arg Tyr Gly Gly Lys Phe Ile Tyr Met Arg Glu His Lys Gly
            100                 105                 110

Lys Arg Tyr Ala Leu Ala Glu Gly Val Lys Tyr Val Arg Ser Pro Leu
        115                 120                 125

Met Met Phe Leu Asp Ser Asp Thr Ile Ile Tyr Lys Asp Ser Ile Leu
    130                 135                 140

Lys Met Leu Ser Val Phe Asp Glu Ser Val Gly Gly Val Gly Pro Asn
145                 150                 155                 160

Ile Arg Ile Met Tyr Asp Glu Lys Asn Lys Tyr Ala Tyr Tyr Gly
                165                 170                 175

Glu Phe Phe Glu Arg Ile Ser Glu Ile Val Asn Arg Ala Val Asn Tyr
            180                 185                 190

Phe Gly Ser Ala Ile Ile Leu Ser Gly Gln Cys Val Ile Tyr Arg Thr
        195                 200                 205

Glu Leu Val Lys Pro Tyr Ile Leu Ser Lys Glu Phe Leu Glu Pro Lys
    210                 215                 220

Met Phe Gly Arg Pro Ile Lys Ile Ser Asp Asp Arg Asp Leu Thr Asp
225                 230                 235                 240

Phe Val Ile Lys Lys Gly Tyr Arg Ala Val Lys Val Phe Asp Ala Met
                245                 250                 255

Ala Tyr Thr Lys Pro Pro Arg Asp Ile Lys Met Phe Thr Lys Gln Val
            260                 265                 270

Thr Arg Trp Thr Arg Ala Asn Tyr Leu Asn Phe Ile Arg Glu Ile Ala
        275                 280                 285

Asp Gly Ser Ile Ser Lys Arg Gly Ser Leu Tyr Val Phe Asn Met Ile
```

```
                290                 295                 300
Tyr Thr Asn Leu Leu Pro Leu Phe Thr Leu Leu Phe Leu Tyr Met Ser
305                 310                 315                 320

Phe Thr Arg Ile Leu Lys Ile Tyr Ser Ser Ile Asn Val Ile Asn Thr
                325                 330                 335

Lys Leu Leu Leu Leu Leu Tyr Leu Pro Thr Arg Tyr His Ser Asp Phe
                340                 345                 350

Phe Ile Phe Tyr Leu Phe Leu His Tyr Gly Gly Phe Ile Ala Ile Ile
                355                 360                 365

Pro Phe Val Met Thr Met Ile Tyr Leu Ile Pro Glu Asp Lys Leu Lys
                370                 375                 380

Thr Leu Ile Tyr Gly Ser Ile Ala Leu Ala Met Gln Tyr Ile Ala Ser
385                 390                 395                 400

Leu Tyr Ala Met Ile Thr Phe Trp Trp Gln Asp Trp Leu Thr Arg
                405                 410                 415

<210> SEQ ID NO 63
<211> LENGTH: 48
<212> TYPE: DNA
<213> ORGANISM: Artificial sequence
<220> FEATURE:
<223> OTHER INFORMATION: Oligonucleotide

<400> SEQUENCE: 63
tcgacaggcc tggatcctta attaaactag tctcgaggag ctcggtac                   48

<210> SEQ ID NO 64
<211> LENGTH: 40
<212> TYPE: DNA
<213> ORGANISM: Artificial sequence
<220> FEATURE:
<223> OTHER INFORMATION: Oligonucleotide

<400> SEQUENCE: 64
cgagctcctc gagactagtt taattaagga tccaggcctg                            40

<210> SEQ ID NO 65
<211> LENGTH: 53
<212> TYPE: DNA
<213> ORGANISM: Artificial sequence
<220> FEATURE:
<223> OTHER INFORMATION: Oligonucleotide

<400> SEQUENCE: 65
gagctcctag gctcgagtta acactagtaa gcttaattaa gatatcattt aca             53

<210> SEQ ID NO 66
<211> LENGTH: 60
<212> TYPE: DNA
<213> ORGANISM: Artificial sequence
<220> FEATURE:
<223> OTHER INFORMATION: Oligonucleotide

<400> SEQUENCE: 66
aattgtaaat gatatcttaa ttaagcttac tagtgttaac tcgagcctag gagctctgca      60

<210> SEQ ID NO 67
<211> LENGTH: 37
<212> TYPE: DNA
<213> ORGANISM: Artificial sequence
<220> FEATURE:
<223> OTHER INFORMATION: Oligonucleotide

<400> SEQUENCE: 67
```

```
aattgtaaat gatatcttaa ttaagcttac tagtgtt                            37

<210> SEQ ID NO 68
<211> LENGTH: 33
<212> TYPE: DNA
<213> ORGANISM: Artificial sequence
<220> FEATURE:
<223> OTHER INFORMATION: Oligonucleotide

<400> SEQUENCE: 68
aacactagta agcttaatta agatatcatt tac                               33
```